(12) United States Patent
Dong et al.

(10) Patent No.: US 8,563,000 B2
(45) Date of Patent: Oct. 22, 2013

(54) MELANOCORTIN RECEPTOR LIGANDS MODIFIED WITH HYDANTOIN

(75) Inventors: Zheng Xin Dong, Holliston, MA (US); Daniel B. Deoliveira, Bellingham, MA (US); Jeanne Mary Comstock, West Boylston, MA (US)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 544 days.

(21) Appl. No.: 12/602,010

(22) PCT Filed: May 23, 2008

(86) PCT No.: PCT/US2008/006675
§ 371 (c)(1),
(2), (4) Date: Nov. 25, 2009

(87) PCT Pub. No.: WO2008/147556
PCT Pub. Date: Dec. 4, 2008

(65) Prior Publication Data
US 2010/0184646 A1    Jul. 22, 2010

Related U.S. Application Data

(60) Provisional application No. 60/931,784, filed on May 25, 2007.

(51) Int. Cl.
| | | |
|---|---|---|
| *A61K 39/00* | (2006.01) |
| *A61K 38/12* | (2006.01) |
| *A61P 29/00* | (2006.01) |
| *A61P 1/00* | (2006.01) |
| *A61P 19/02* | (2006.01) |
| *A61P 3/00* | (2006.01) |
| *A61P 35/00* | (2006.01) |
| *A61P 37/00* | (2006.01) |
| *A61P 11/00* | (2006.01) |
| *A61P 25/00* | (2006.01) |
| *C07K 7/06* | (2006.01) |

(52) U.S. Cl.
USPC ........ 424/185.1; 514/10.7; 530/329; 530/328

(58) Field of Classification Search
None
See application file for complete search history.

(56) References Cited

U.S. PATENT DOCUMENTS

| 6,951,916 B2 | 10/2005 | Mazur et al. |
| 2002/0143141 A1 | 10/2002 | Chen et al. |

FOREIGN PATENT DOCUMENTS

| WO | 02/00654 | 1/2002 |
| WO | 02/08227 | 1/2002 |
| WO | 2005/000339 A2 | 1/2005 |
| WO | 2005/019212 A1 | 3/2005 |
| WO | 2005/060985 A1 | 7/2005 |
| WO | 2007/008704 | 1/2007 |

OTHER PUBLICATIONS

Haskell-Luevano, Peptides, 17, 6, 1996.*
Mayer, Journal of Medicinal Chemistry, 48, 9, 2005.*
Stilz, Journal of Medicinal Chemistry, 44, 2001.*
Xiao, J. Org. Chem., 62, 1997.*
Haskell-Luevano, C. et al., "Truncation studies of a-melanotropin peptides identify tripeptide analogues exhibiting prolonged agonist activity", Peptides, 1996, 17:995-1002.
Navarro, W. et al., "Effects of Melanocortin Receptor Activation and Blockade on Ethanol Intake: A Possible Role for the Melanocortin-4 Receptor," Alcohol Clin Exp Res., 2005, p. 949-957, 29(6).

* cited by examiner

*Primary Examiner* — Robert A Wax
*Assistant Examiner* — William Craigo
(74) *Attorney, Agent, or Firm* — Pamela C. Ball

(57) ABSTRACT

The present invention relates to peptide ligands of the melanocortin receptors, in particular the melanocortin-4 receptor, and as such, are useful in the treatment of disorders responsive to the activation of this receptor, such as obesity, diabetes mellitus and sexual dysfunction.

19 Claims, 7 Drawing Sheets

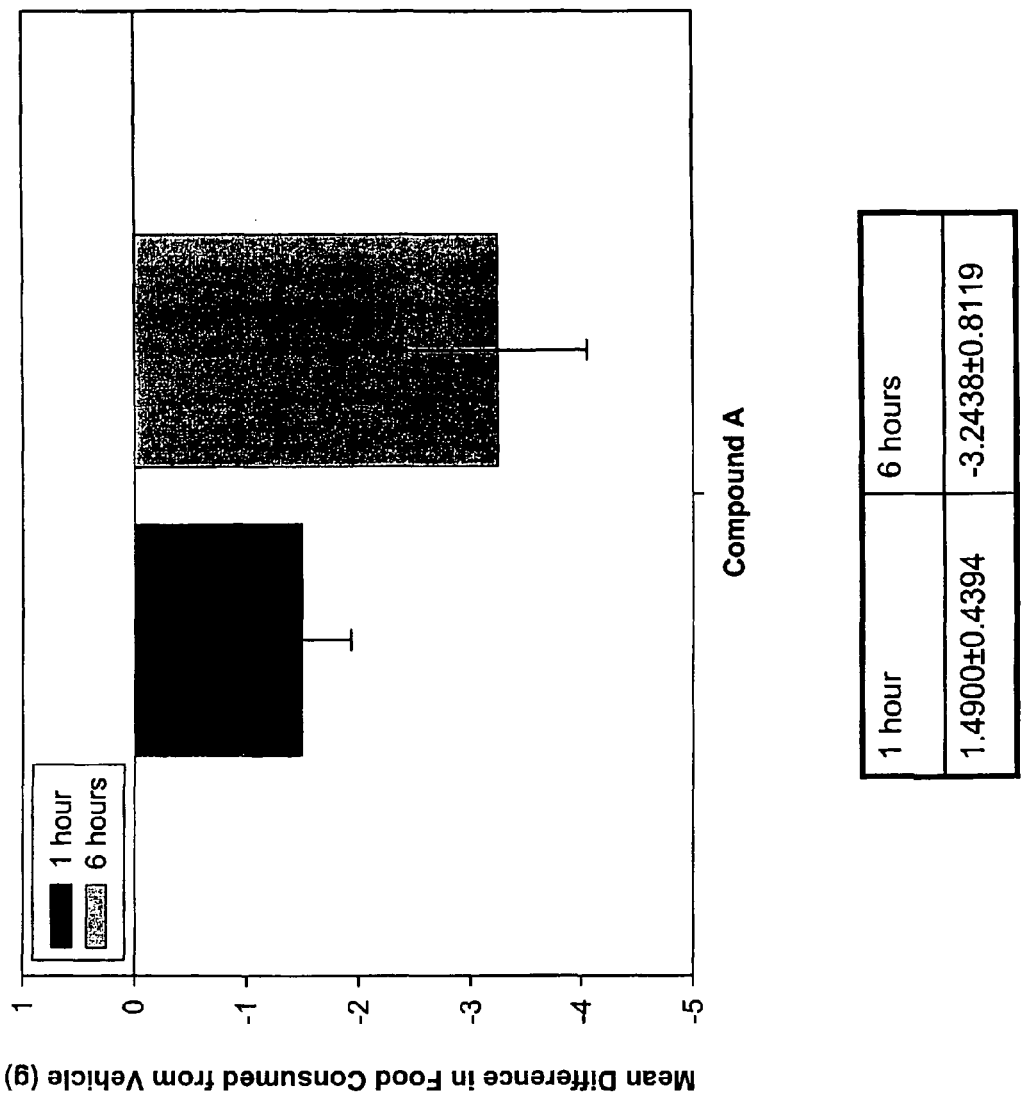

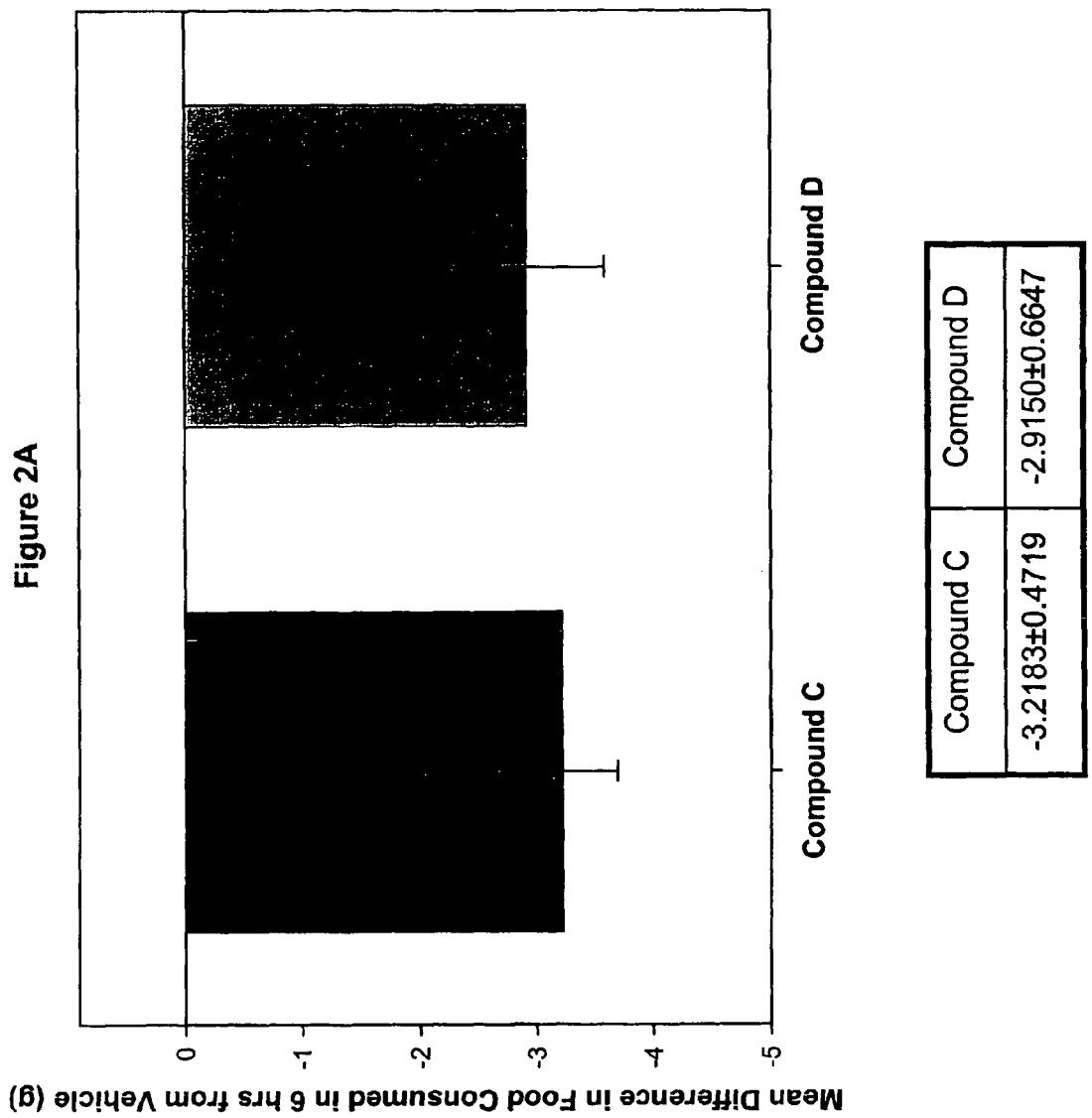

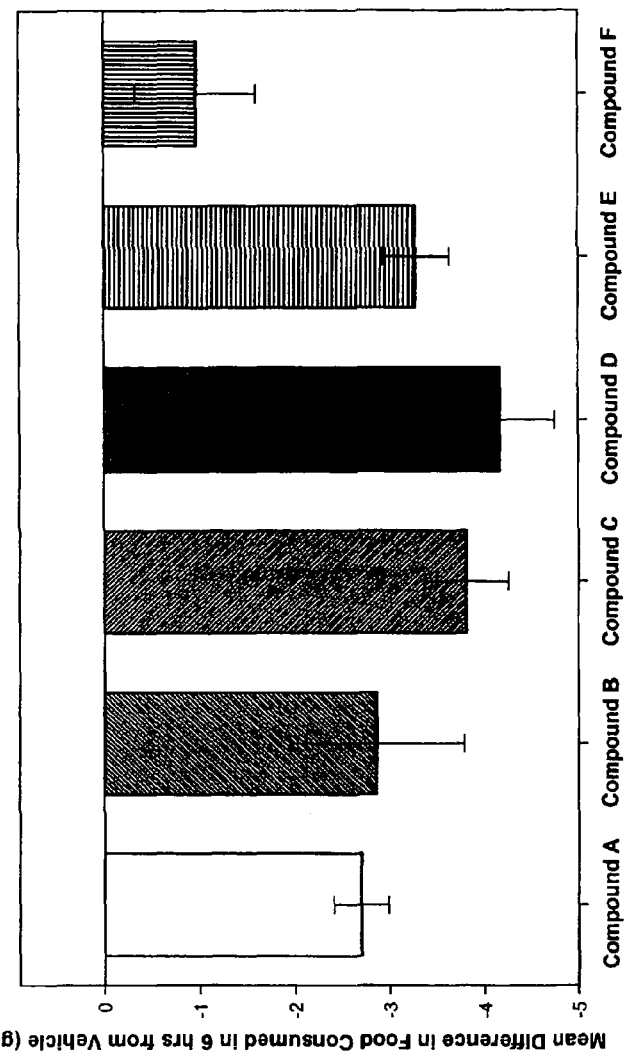

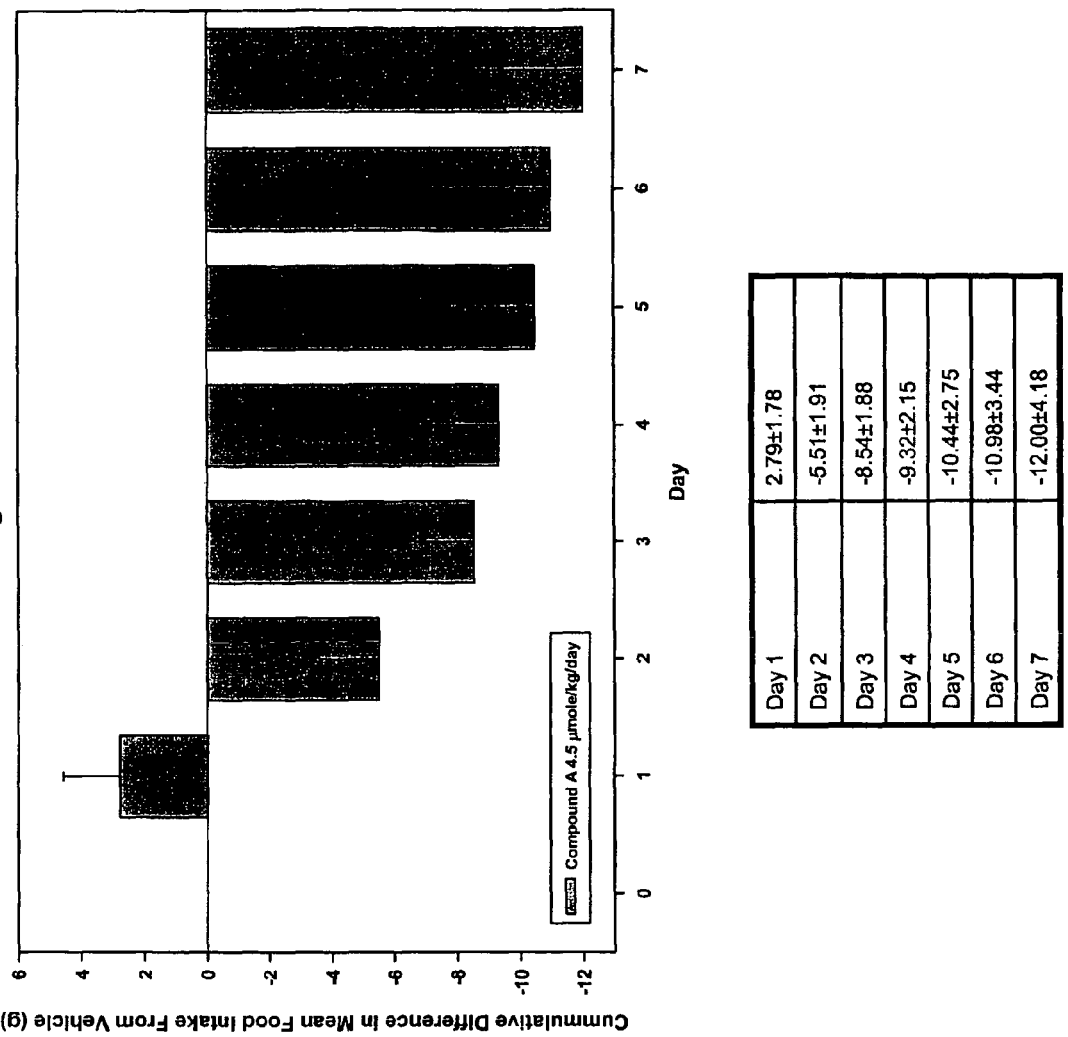

| | Compound A |
|---|---|
| Day 1 | -0.43±0.86 |
| Day 2 | -6.68±1.09 |
| Day 3 | -7.31±1.08 |
| Day 4 | -7.69±1.66 |
| Day 5 | -9.10±2.03 |
| Day 6 | -10.09±2.23 |
| Day 7 | -10.46±2.84 |

| | Compound C |
|---|---|
| Day 1 | -1.69±0.78 |
| Day 2 | -12.71±2.57 |
| Day 3 | -17.94±3.14 |
| Day 4 | -19.86±3.61 |
| Day 5 | -22.61±3.61 |
| Day 6 | -24.93±4.33 |
| Day 7 | -25.86±4.23 |

| | Compound D |
|---|---|
| Day 1 | -1.65±0.79 |
| Day 2 | -9.73±1.55 |
| Day 3 | -13.31±1.91 |
| Day 4 | -15.39±2.12 |
| Day 5 | -17.84±2.34 |
| Day 6 | -19.64±2.10 |
| Day 7 | -20.46±2.48 |

| | Compound A |
|---|---|
| Day 1 | 4.34±1.29 |
| Day 2 | 5.09±1.18 |
| Day 3 | 8.55±1.74 |
| Day 4 | 6.34±1.67 |
| Day 5 | 4.16±1.83 |
| Day 6 | 5.49±1.56 |
| Day 7 | 5.60±2.39 |

| | Compound C |
|---|---|
| Day 1 | 2.70±2.34 |
| Day 2 | -3.21±3.64 |
| Day 3 | -2.48±3.22 |
| Day 4 | -6.13±2.78 |
| Day 5 | -9.48±2.66 |
| Day 6 | -9.95±2.83 |
| Day 7 | -10.18±2.86 |

| | Compound D |
|---|---|
| Day 1 | 1.75±1.54 |
| Day 2 | -0.08±1.61 |
| Day 3 | 2.28±1.62 |
| Day 4 | -1.75±1.76 |
| Day 5 | -4.15±1.88 |
| Day 6 | -3.18±2.35 |
| Day 7 | -1.38±4.05 |

MELANOCORTIN RECEPTOR LIGANDS MODIFIED WITH HYDANTOIN

This application is a United States national stage filing under 35 U.S.C. §371 of international (PCT) application no. PCT/US2008/006675, filed May 23, 2008, and designating the US, which claims priority to U.S. provisional application No. 60/931,784, filed May 25, 2007.

FIELD OF THE INVENTION

The present invention relates to a series of new melanocortin receptor ligands useful in treating diseases responsive to modulation of such receptors. The invention also relates to pharmaceutical compositions comprising such peptide analogs and to their use in the prevention or treatment of conditions affected by such receptors.

BACKGROUND OF THE INVENTION

Melanocortins are a family of regulatory peptides which are formed by post-translational processing of pro-hormone pro-opiomelanocortin (POMC; 131 amino acids in length). POMC is processed into three classes of hormones; the melanocortins, including but not limited to α-MSH (melanocyte stimulating hormone), β-MSH and γ-MSH, adrenocorticotropin hormone (ACTH), various endorphins (e.g. lipotropin) (Cone, R. D. et al., *Recent Prog. Horm. Res.*, 51:287-317 (1996); and Cone, R. D. et al., *Ann. N.Y. Acad. Sci.*, 31:342-63 (1993)) and their peptide fragments. Melanocortins have been found in a wide variety of normal human tissues including the brain, adrenal, skin, testis, spleen, kidney, ovary, lung, thyroid, liver, colon, small intestine and pancreas (Tatro, J. B. et al., *Endocrinol.*, 121:1900-7 (1987); Mountjoy, K. G. et al., *Science*, 257:1248-51 (1992); Chhajlani, V. et al., *FEBS Lett.*, 309:417-20 (1992); Gantz, I. et al., *J. Biol. Chem.*, 268:8246-50 (1993) and Gantz, I. et al., *J. Biol. Chem.*, 268:15174-9 (1993)).

Melanocortin peptides have been shown to exhibit a wide variety of physiological activities including the control of behavior and memory, affecting neurotrophic and antipyretic properties, as well as affecting the modulation of the immune system. Aside from their well known effects on adrenal cortical functions (adrenocorticotropic hormone, ACTH) and on melanocytes (melanocyte stimulating hormone, MSH), melanocortins have also been shown to control the cardiovascular system, analgesia, thermoregulation and the release of other neurohumoral agents including prolactin, luteinizing hormone and biogenic amines (De Wied, D. et al., *Methods Achiev. Exp. Pathol.*, 15:167-199 (1991); De Wied, D. et al., *Physiol. Rev.*, 62:977-1059 (1982); Guber, K. A. et al., *Am. J. Physiol.* 257:R681-R94 (1989); Walker, J. M. et al., *Science*, 210:1247-9 (1980); Murphy, M. T. et al., *Science*, 221:192-3 (1983); Ellerkmann, E. et al., *Endocrinol.*, 130:133-8 (1992) and Versteeg, D. H. G. et al., *Life Sci.*, 38:835-40 (1986)).

It has also been shown that binding sites for melanocortins are distributed in many different tissue types including lachrymal and submandibular glands, pancreas, adipose, bladder, duodenum, spleen, brain and gonadal tissues as well as malignant melanoma tumors. Five melanocortin receptors (MC-R) have been characterized to date. These include melanocyte-specific receptor (MC1-R), corticoadrenal-specific ACTH receptor (MC2-R), melacortin-3 (MC3-R), melanocortin-4 (MC4-R) and melanocortin-5 receptor (MC5-R). All of the melanocortin receptors respond to the peptide hormone class of melanocyte stimulating hormones (MSH) (Cone, R. D. et al., *Ann. N.Y. Acad. Sci.*, 680:342-63 (1993); and Cone, R. D. et al., *Recent Prog. Horm. Res.*, 51:287-318 (1996)).

MC1-R, known in the art as Melanocyte Stimulating Hormone Receptor (MSH-R), Melanotropin Receptor or Melanocortin-1 Receptor, is a 315 amino acid transmembrane protein belonging to the family of G-Protein coupled receptors. MC1-R is a receptor for both MSH and ACTH. The activity of MC1-R is mediated by G-proteins which activate adenylate cyclase. MC1-R receptors are found in melanocytes and corticoadrenal tissue as well as various other tissues such as adrenal gland, leukocytes, lung, lymph node, ovary, testis, pituitary, placenta, spleen and uterus. MC2-R, also called Adrenocorticotropic Hormone Receptor (ACTH-R), is a 297 amino acid transmembrane protein found in melanocytes and the corticoadrenal tissue. MC2-R mediates the corticotrophic effect of ACTH. In humans, MC3-R is a 360 amino acid transmembrane protein found in brain tissue; in mice and rats MC3-R is a 323 amino acid transmembrane protein. MC4-R is a 332 amino acid transmembrane protein which is also expressed in brain as well as placental and gut tissues. MC5-R is a 325 amino acid transmembrane protein expressed in the adrenals, stomach, lung and spleen and very low levels in the brain. MC5-R is also expressed in the three layers of adrenal cortex, predominantly in the aldosterone-producing zona glomerulosa cells.

The five known melanocortin receptors differ, however, in their functions. For example, MC1-R is a G-protein coupled receptor that regulates pigmentation in response to α-MSH, a potent agonist of MC1-R. Agonism of the MC1-R receptor results in stimulation of the melanocytes which causes eumelanin and increases the risk for cancer of the skin. Agonism of MC1-R can also have neurological effects. Stimulation of MC2-R activity can result in carcinoma of adrenal tissue. Recent pharmacological confirmation has established that central MC4-R receptors are the prime mediators of the anorexic and orexigenic effects reported for melanocortin agonists and antagonists, respectively. The effects of agonism of the MC3-R and MC5-R are not yet known.

There has been great interest in melanocortin (MC-R) receptors as targets for the design of novel therapeutics to treat disorders of body weight such as obesity and cachexia. Both genetic and pharmacological evidence points toward central MC4-R receptors as the principal target (Giraudo, S. Q. et al., *Brain Res.*, 809:302-6 (1998); Farooqi, I. S. et al., *N.E. J. Med.*, 348:1085-95 (2003); MacNeil, D. J. et al., *Euro. J. Pharm.*, 44:141-57 (2002); MacNeil, D. J. et al., *Euro. J. Pharm.*, 450:93-109 (2002); Kask, A. et al., *NeuroReport*, 10:707-11 (1999); Huszer, D. et al., *Cell*, 131-41 (1997); Klebig, M. L. et al., *Proc. Natl. Acad. Sci.*, 92:4728-32 (1995); Karbon, E. et al., Abstr. 19th Ann. Winter Neuropeptide Conf., (1998); Fan, W. et al., *Nature*, 385:165-8 (1997); Seely, R. J., *Nature*, 390:349 (1997); Comuzzie, A. G., *Nat. Gen.*, 15:273-6 (1997); Chagnon, Y. C., *Mol. Med.*, 3(10): 663-73 (1997); WO 97/47316 (Lee et al., 1997); and Shutter, J. R., *Gen. & Dev.*, 11:593-602 (1997)). Stimulation of the MC-4 receptor by its endogenous ligand, αMSH, produces a satiety signal. It is believed that by providing potent MC-4 receptor agonists, appetite might be suppressed and weight loss achieved.

The current progress with receptor-selective agonists and antagonists evidences the therapeutic potential of melanocortin receptor activation, particularly MC4-R.

Agonist, antagonist or other ligand compounds activating one or more melanocortin receptor would be useful for treating a wide variety of indications in a subject in need thereof or at risk thereof including acute and chronic inflammatory diseases such as general inflammation (U.S. Pat. No. 6,613,874

(Mazur et al., 2003); and Catania, A. et al., *Pharm. Rev.*, 56:1-29 (2004)), inflammatory bowel disease (U.S. Pat. No. 6,713,487 (Yu et al., 2004)); and Catania, A. et al., *Pharm. Rev.*, 56:1-29 (2004)), brain inflammation (Catania, A. et al., *Pharm. Rev.*, 56:1-29 (2004)), sepsis (U.S. Pat. No. 6,613,874 (Mazur et al., 2003); U.S. Pat. No. 6,713,487 (Yu et al., 2004); and Catania, A. et al., *Pharm. Rev.*, 56:1-29 (2004)) and septic shock (U.S. Pat. No. 6,613,874 (Mazur et al., 2003); and Catania, A. et al., *Pharm. Rev.*, 56:1-29 (2004)), diseases with an autoimmune component such as rheumatoid arthritis (U.S. Pat. No. 6,713,487 (Yu et al., 2004); and Catania, A. et al., *Pharm. Rev.*, 56:1-29 (2004)), gouty arthritis (Catania, A. et al., *Pharm. Rev.*, 56:1-29 (2004); and Getting, S. J. et al., *Curr. Opin. Investig. Drugs*, 2:1064-9 (2001)), and multiple sclerosis (U.S. Pat. No. 6,713,487 (Yu et al., 2004)), metabolic diseases and medical conditions accompanied by weight gain such as obesity (U.S. Pat. No. 6,613,874 (Mazur et al., 2003); U.S. Pat. No. 6,600,015 (Chen et al., 2003); Fehm, H. L. et al., *J. Clin. Endo. & Metab.*, 86:1144-8 (2001); Hansen, M. J. et al., *Brain Res.*, 1039:137-45 (2005); Ye, Z. et al., *Peptides*, 26:2017-25 (2005); Farooqi, I. S. et al., *N.E. J Med.*, 348:1085-95 (2003); MacNeil, D. J. et al., *Eu. J. Pharm.*, 44:141-57 (2002); MacNeil, D. J. et al., *Euro. J. Pharm.*, 450:93-109 (2002); Kask, A. et al., *NeuroReport*, 10:707-11 (1999); Schwartz, M. W., *J. Clin. Invest.*, 108:963-4 (2001); Gura, T., *Science*, 287:1738-40 (2000); Raffin-Sanson, M. L., *Euro. J. Endo.*, 144:207-8 (2001); and Hamilton, B. S. et al., *Obesity Res.*, 10:182-7 (2002)), feeding disorders (U.S. Pat. No. 6,720,324 (Marzabadi et al., 2004); Fehm, H. L. et al., *J. Clin. Endo. & Metab.*, 86:1144-8 (2001); and Pontillo, J. et al., *Bioorganic & Med. Chem. Ltrs.*, 15:2541-6 (2005)) and Prader-Willi Syndrome (GE, Y. et al., *Brain Res.*, 957:42-5 (2002)), metabolic diseases and medical conditions accompanied by weight loss such as anorexia (U.S. Pat. No. 6,613,874 (Mazur et al., 2003); and Wisse, B. R. et al., *Endocrinology*, 142:3292-301 (2001)), bulimia (U.S. Pat. No. 6,720,324 (Marzabadi et al., 2004)), AIDS wasting (Marsilje, T. H. et al., *Bioorg. Med. Chem. Lett.*, 14:3721-5 (2004); and Markison, S. et al., *Endocrinology*, 146:2766-73 (2005)), cachexia (U.S. Pat. No. 6,613,874 (Mazur et al., 2003); Lechan, R. M. et al., *Endocrinology*, 142:3288-91 (2001); and Pontillo, J. et al., *Bioorganic & Med. Chem. Ltrs.*, 15:2541-6 (2005)), cancer cachexia (U.S. Pat. No. 6,639,123 (Van der Ploeg et al., 2003)) and wasting in frail elderly (U.S. Pat. No. 6,639,123 (Van der Ploeg et al., 2003)), diabetes (U.S. Pat. No. 6,713,487 (Yu et al., 2004)) and diabetalogical related conditions and complications of diabetes such as retinopathy (U.S. Pat. No. 6,525,019 (D'Amato, 2003), neoplastic proliferation (U.S. Pat. No. 6,713,487 (Yu et al., 2004)) such as skin cancer (Sturm, R. A., *Melanoma Res.*, 12:405-16 (2002); and Bastiens, M. T. et al., *Am. J. Hum. Genet.*, 68:884-94 (2001)), and prostate cancer (Luscombe, C. J. et al., *British J. Cancer*, 85:1504-9 (2001)), reproductive or sexual medical conditions such as endometriosis (U.S. Pat. No. 6,713,487 (Yu et al., 2004)) and uterine bleeding in women (U.S. Pat. No. 6,613,874 (Mazur et al., 2003)), sexual dysfunction (U.S. Pat. No. 6,720,324 (Marzabadi et al., 2004); Van der Ploeg, L. H. T. et al., PNAS, 99:11381-6 (2002), Molinoff, P. B. et al., *Ann. N.Y. Acad. Sci.*, 994:96-102 (2003), and Hopps, C. V. et al., *B.J.U. Int'l.*, 92:534-8 (2003)), erectile dysfunction ((U.S. Pat. No. 6,613,874 (Mazur et al., 2003); Diamond, L. E. et al., *Urology*, 65:755-9 (2005); Wessells, H. et al., *Int'l. J. Impotence Res.*, 12:S74-9 (2000); Andersson, K-E. et al., *Int'l. J. Impotence Res.*, 14:S82-S92 (2002); Bertolini, A. et. al., *Sexual Behavior: Pharmacology and Biochemistry*, Raven Press, NY, p 247-57 (1975); Wessells, H. et al., *Neuroscience*, 118:755-62 (2003); Wessells, H. et al., *Urology*, 56:641-6 (2000); Shadiack, A. M. et al., *Soc. for Neuroscience Abst*, (2003); Wessells, H. et al., *J. Urology*, 160:389-93 (1998); Rosen, R. C. et al., *Int'l. J. Impotence Res.*, 16:135-42 (2004); and Wessells, H. et al., *Peptides*, 26:1972-7 (2005)) and decreased sexual response in females (U.S. Pat. No. 6,713,487 (Yu et al., 2004); and Fourcroy, J. L., *Drugs*, 63:1445-57 (2003)), diseases or conditions resulting from treatment or insult to the organism such as organ transplant rejection (U.S. Pat. No. 6,713,487 (Yu et al., 2004); and Catania, A. et al., *Pharm. Rev.*, 56:1-29 (2004)), ischemia and reperfusion injury (Mioni, C. et al., *Euro. J. Pharm.*, 477:227-34 (2003); and Catania, A. et al., *Pharm. Rev.*, 56:1-29 (2004)), treatment of spinal cord injury and to accelerate wound healing (Sharma H. S. et al., *Acta. Nerochir. Suppl.*, 86:399-405 (2003); Sharma H. S., *Ann. N.Y. Acad. Sci.*, 1053: 407-21 (2005); and U.S. Pat. No. 6,525,019 (D'Amato, 2003)), as well as weight loss caused by chemotherapy, radiation therapy, temporary or permanent immobilization (Harris, R. B. et al., *Physiol. Behav.*, 73:599-608 (2001)) or dialysis, cardiovascular diseases or conditions such as hemorrhagic shock (Catania, A. et al., *Pharm. Rev.*, 56:1-29 (2004)), cardiogenic shock (U.S. Pat. No. 6,613,874 (Mazur et al., 2003)), hypovolemic shock (U.S. Pat. No. 6,613,874 (Mazur et al., 2003)), cardiovascular disorders (U.S. Pat. No. 6,613,874 (Mazur et al., 2003)) and cardiac cachexia (Markison, S. et al., *Endocrinology*, 146: 2766-73 (2005)), pulmonary diseases or conditions such as acute respiratory distress syndrome (U.S. Pat. No. 6,350,430 (Dooley et al., 2002); and Catania, A. et al., *Pharm. Rev.*, 56:1-29 (2004)), chronic obstructive pulmonary disease (U.S. Pat. No. 6,713,487 (Yu et al., 2004)), asthma (U.S. Pat. No. 6,713,487 (Yu et al., 2004)) and pulmonary fibrosis, to enhance immune tolerance (Luger, T. A. et al., *Pathobiology*, 67:318-21 (1999)) and to combat assaults to the immune system such as those associated with certain allergies (U.S. Pat. No. 6,713,487 (Yu et al., 2004)) or organ transplant rejection (U.S. Pat. No. 6,713,487 (Yu et al., 2004)); and Catania, A. et al., *Pharm. Rev.*, 56:1-29 (2004)), treatment of dermatological diseases and conditions such as psoriasis (U.S. Pat. No. 6,713,487 (Yu et al., 2004)), skin pigmentation depletion (U.S. Pat. No. 6,713,487 (Yu et al., 2004); and Ye, Z. et al., *Peptides*, 26:2017-25 (2005)), acne (Hatta, N. et al., *J. Invest. Dermatol.*, 116:564-70 (2001); and Bohm, M. et al., *J. Invest. Dermatol.*, 118:533-9 (2002)), keloid formation (U.S. Pat. No. 6,525,019 (D'Amato, 2003)) and skin cancer (Sturm, R. A., *Melanoma Res.*, 12:405-16 (2002); and Bastiens, M. T. et al., *Am. J. Hum. Genet.*, 68:884-94 (2001)), behavioral, central nervous system or neuronal conditions and disorders such as anxiety (U.S. Pat. No. 6,720,324 (Marzabadi et al., 2003); and Pontillo, J. et al., *Bioorganic & Med. Chem. Ltrs.*, 15:2541-6 (2005)), depression (Chaki, S. et al., *Peptides*, 26:1952-64 (2005), Bednarek, M. A. et al., *Expert Opinion Ther. Patents*, 14:327-36 (2004); and U.S. Pat. No. 6,720,324 (Marzabadi et al., 2003)), memory and memory dysfunction (U.S. Pat. No. 6,613,874 (Mazur et al., 2003); and Voisey, J. et al., *Curr. Drug Targets*, 4:586-97 (2003)), modulating pain perception (U.S. Pat. No. 6,613,874 (Mazur et al., 2003); Bertolini, A. et al., *J. Endocrinol. Invest.*, 4:241-51 (1981); and Vrinten, D. et al., *J. Neuroscience*, 20:8131-7 (2000)) and treating neuropathic pain (Pontillo, J. et al., *Bioorganic & Med. Chem. Ltrs.*, 15:2541-6 (2005)), conditions and diseases associated with alcohol consumption, alcohol abuse and/or alcoholism (WO 05/060985 (Marsh et al., 2005); and Navarro, M. et al., *Alcohol Clin. Exp. Res.*, 29:949-57 (2005)), and renal conditions or diseases such as the treatment of renal cachexia (Markison, S. et al., Endocrinology, 146: 2766-73 (2005)) or natriuresis (U.S. Pat. No. 6,613,874 (Mazur et al., 2003)).

Ligand compounds activating one or more melanocortin receptor would be useful for modulating a wide variety of normalizing or homeostatic activities in a subject in need thereof including thyroxin release (U.S. Pat. No. 6,613,874 (Mazur et al., 2003)), aldosterone synthesis and release (U.S. Pat. No. 6,613,874 (Mazur et al., 2003)), body temperature (U.S. Pat. No. 6,613,874 (Mazur et al., 2003)), blood pressure (U.S. Pat. No. 6,613,874 (Mazur et al., 2003)), heart rate (U.S. Pat. No. 6,613,874 (Mazur et al., 2003)), vascular tone (U.S. Pat. No. 6,613,874 (Mazur et al., 2003)), brain blood flow (U.S. Pat. No. 6,613,874 (Mazur et al., 2003)), blood glucose levels (U.S. Pat. No. 6,613,874 (Mazur et al., 2003)), bone metabolism, bone formation or development (Dumont, L. M. et al., *Peptides,* 26:1929-35 (2005)), ovarian weight (U.S. Pat. No. 6,613,874 (Mazur et al., 2003)), placental development (U.S. Pat. No. 6,613,874 (Mazur et al., 2003)), prolactin and FSH secretion (U.S. Pat. No. 6,613,874 (Mazur et al., 2003)), intrauterine fetal growth (U.S. Pat. No. 6,613,874 (Mazur et al., 2003)), parturition (U.S. Pat. No. 6,613,874 (Mazur et al., 2003)), spermatogenesis (U.S. Pat. No. 6,613,874 (Mazur et al., 2003)), sebum and pheromone secretion (U.S. Pat. No. 6,613,874 (Mazur et al., 2003)), neuroprotection (U.S. Pat. No. 6,639,123 (Van der Ploeg et al., 2003)) and nerve growth (U.S. Pat. No. 6,613,874 (Mazur et al., 2003)) as well as modulating motivation (U.S. Pat. No. 6,613,874 (Mazur et al., 2003)), learning (U.S. Pat. No. 6,613,874 (Mazur et al., 2003)) and other behaviors (U.S. Pat. No. 6,613,874 (Mazur et al., 2003)).

Hydantoin ($C_3H_2N_2O_2$), also known as glycolyl urea or by its IUPAC name imidazole-2,4(3H, 5H)-dione, is a crystalline, heterocyclic organic compound which can be thought of as a cyclic "double-condensation reaction" product of glycolic acid and urea or allantoin, an oxidation product ($C_4H_6N_4O_3$) of uric acid that is the metabolic end product of vertebrate purine oxidation. Hydantoin which has the following chemical structure:

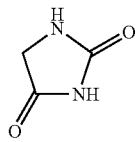

and is similar to imidazolidine, the hydrogen-saturated analogue of imidazole except that it has carbonyl groups in the $2^{nd}$ and $4^{th}$ positions in the ring. It has a molecular weight of 100.076 g/mol, is slightly soluble in water and has a melting point of 216-224° C. Hydantoin and its derivatives have antibacterial, antifungal, antiprotozoal and anthelmintic properties. Hydantoin has traditionally been an ingredient in anticonvulsants used in the treatment of seizures associated with epilepsy. It is believed that hydantoins depress abnormal neuronal discharges in the central nervous system. Phenyloin, another anticonvulsant synthesized from hydantoin, is used as a skeletal muscle relaxant and for the treatment of severe trigeminal neuralgia.

Applicants have discovered a class of compounds that have a high affinity for the melanocortin receptors, particularly selective for the MC-4 subtype relative to the other receptor subtype, especially the MC-5 subtype. Specifically, Applicants discovered that peptides modified with hydantoin exhibited increased affinity for the MC-4 receptor subtype. It is therefore an objective of this invention to provide chemical compounds that activate or antagonize the MC-4 receptor subtype. It is a further an objective of the present invention to provide ligands for the melanocortin receptors which exhibit greater stability and selectivity for melanocortin receptors than native melanocortin receptor ligands. Yet another objective of the invention is to provide means for the administration of said compounds for the treatment of various ailments and/or conditions associated with either the over or the under production of melanocortin peptides.

SUMMARY OF THE INVENTION

Applicants have discovered a novel class of cyclic peptide analogs Modified with a hydantoin moiety that are ligands for the melanocortin receptors and are selective for the MC-4 receptor subtype. One of the unique structural features of this new class is the use of unnatural or synthetic amino acid residues in the N-terminal region. Such substitutions contribute not only to the selectivity of the compound, but also the binding affinity at the targeted receptor. These new compounds bind to the MC-4 receptor with low nanomolar affinity and exhibit a prolonged plasma half-life compared to α-MSH. Studies using male, Sprague-Dawley rats indicate that these new compounds effectively suppress food intake and induce body weight loss.

In particular, the present invention is directed to compounds according to formula (I), (II) or (III), and pharmaceutically acceptable salts, hydrates, solvates or prodrugs thereof, useful as modulators of one or more melanocortin receptors. The invention also covers uses thereof, particularly as medicinal agents in the treatment of certain, identifiable diseases and/or conditions. According to a first aspect, the invention provides a compound of formula (I), pharmaceutically-acceptable salts, hydrates, solvates and/or prodrugs thereof

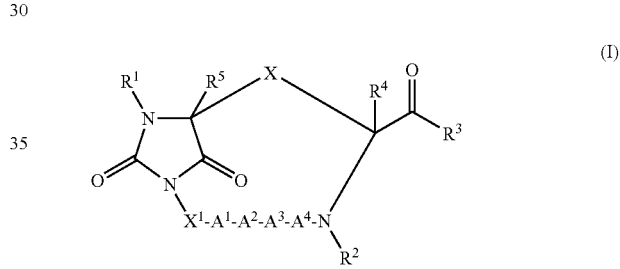

(I)

wherein the hydantoin moiety is formed from fusing the amino group of $X^1$, i.e.,

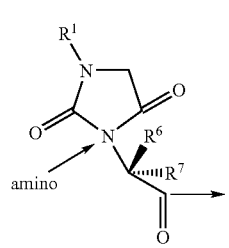

with the amino and carboxyl groups of one of the amino acids comprising X,

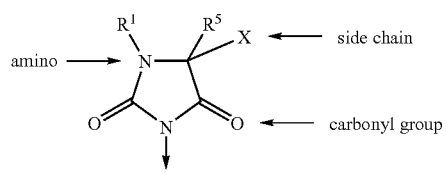

together with a carbonyl group, i.e.,

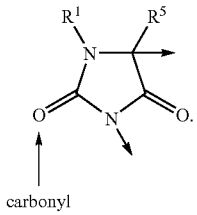
carbonyl

In the shorthand used by the Applicants to identify an embodiment of formula (I), for example cyclo[Hydantoin(C(O)-(Cys-D-Ala))-His-D-Phe-Arg-Trp-Cys]-NH$_2$, (SEQ ID NO:1) "Hydantoin(C(O)-(AA$^1$-AA$^2$)" refers to the amino acids which form the hydantoin structure. In the aforementioned embodiment, "C(O)" refers to the carbonyl group situated between the two nitrogens of the imidazolinyl heterocyclic ring. The first listed amino acid "AA" in the given example is Cys, contributes both its N-terminal amino and C-terminal carboxyl groups to form the highlighted section of the hydantoin moiety as indicated below

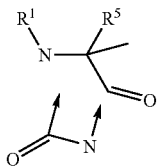

(the section of the hydantoin moiety not part of AA$^1$ has been broken away). In the illustrative example, AA$^2$ is D-Ala wherein its N-terminal amino comprises part of the hydantoin structure, as indicated in bold below,

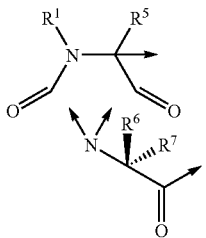

R$^7$ is methyl and R$^6$ is a hydrogen.

In the preferred embodiment of the compounds according to formula (I), hereinafter referred to as Group I compounds, X is selected from the group consisting of —CH$_2$—S—S—CH$_2$—, —C(CH$_3$)$_2$—S—S—CH$_2$—, —CH$_2$—S—S—C(CH$_3$)$_2$—, —C(CH$_3$)$_2$—S—S—C(CH$_3$)$_2$—, —(CH$_2$)$_2$—S—S—CH$_2$—, —CH$_2$—S—S—(CH$_2$)$_2$—, —(CH$_2$)$_2$—S—S—(CH$_2$)$_2$—, —C(CH$_3$)$_2$—S—S—(CH$_2$)$_2$—, —(CH$_2$)$_2$—S—S—C(CH$_3$)$_2$—, —(CH$_2$)$_r$—C(O)—NR$^8$—(CH$_2$)$_t$— and —(CH$_2$)$_r$—NR$^8$—C(O)—(CH$_2$)$_t$—;

R$^1$ and R$^2$ each is, independently, H, (C$_1$-C$_{10}$)alkyl or substituted (C$_1$-C$_{10}$)alkyl;

R$^3$ is —OH or —NH$_2$;

R$^4$ and R$^5$ each is, independently, H, (C$_1$-C$_{10}$)alkyl or substituted (C$_1$-C$_{10}$)alkyl;

X$^1$ is

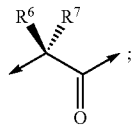

A$^1$ is His, 2-Pal, 3-Pal, 4-Pal, (X$^1$, X$^2$, X$^3$, X$^4$, X$^5$)Phe, Taz, 2-Thi, 3-Thi or is deleted;

A$^2$ is D-Bal, D-1-Nal, D-2-Nal, D-Phe or D-(X$^1$, X$^2$, X$^3$, X$^4$, X$^5$)Phe;

A$^3$ is Arg, hArg, Dab, Dap, Lys or Orn;

A$^4$ is Bal, 1-Nal, 2-Nal, (X$^1$, X$^2$, X$^3$, X$^4$, X$^5$)Phe or Trp;

R$^6$ and R$^7$ each is, independently for each occurrence thereof, H, (C$_1$-C$_{10}$)alkyl, (C$_1$-C$_{10}$)heteroalkyl, aryl(C$_1$-C$_5$)alkyl, substituted (C$_1$-C$_{10}$)alkyl, substituted (C$_1$-C$_{10}$)heteroalkyl or substituted aryl(C$_1$-C$_5$)alkyl provided that R$^6$ and R$^7$ may be joined together to form a ring;

R$^8$ is H, (C$_1$-C$_{10}$)alkyl or substituted (C$_1$-C$_{10}$)alkyl;

r is, independently for each occurrence thereof, 1, 2, 3, 4 or 5; and t is, independently for each occurrence thereof, 1 or 2.

A preferred compound of the above formula, hereafter referred to as Group I(A) compounds, is where X is selected from the group consisting of —CH$_2$—S—S—CH$_2$— and —(CH$_2$)$_2$—S—S—CH$_2$—;

r is, independently for each occurrence thereof, 1, 2, 3, 4 or 5;

t is, independently for each occurrence thereof, 1 or 2;

R$^1$, R$^2$, R$^4$ and R$^5$ each is H;

X$^1$ is selected from the group consisting of

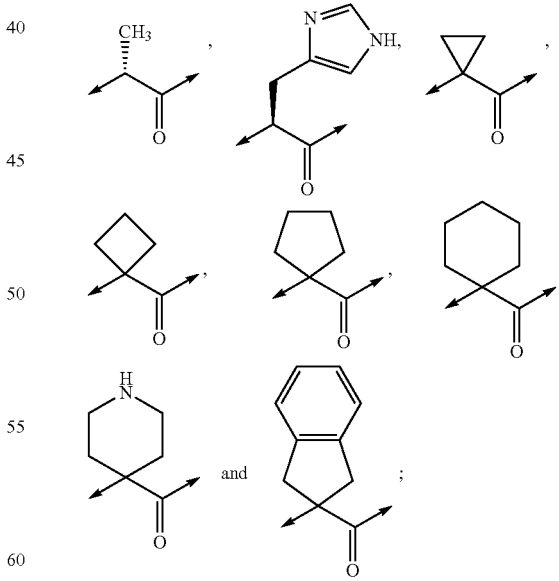

A$^1$ is His or deleted;

A$^2$ is D-1-Nal, D-2-Nal or D-Phe;

A$^3$ is Arg; and

A$^4$ is Bal, 1-Nal, 2-Nal or Trp.

A preferred Group IA compound, hereafter referred to as a Group I(B) compound, is where X¹ is

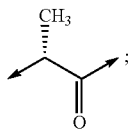

A² is D-Phe or D-2-Nal; and

A⁴ Trp;

Representative embodiments of the Group IB class of compounds, hereafter referred to as Group I(C) compounds, are as follows:

```
                                                (SEQ ID NO: 1)
cyclo[Hydantoin(C(O)-(Cys-D-Ala))-His-D-Phe-Arg-
Trp-Cys]-NH₂;

(SEQ ID NO: 2)
cyclo[Hydantoin(C(O)-(hCys-D-Ala))-His-D-Phe-Arg-
Trp-Cys]-NH₂;

(SEQ ID NO: 1)
cyclo[Hydantoin(C(O)-(Cys-D-Ala))-His-D-2-Nal-Arg-
Trp-Cys]-NH₂;
or
                                                (SEQ ID NO: 2)
cyclo[Hydantoin(C(O)-(hCys-D-Ala))-His-D-2-Nal-
Arg-Trp-Cys]-NH₂;
``` with the compound cyclo[Hydantoin(C(O)-(Cys-D-Ala))-His-D-Phe-Arg-Trp-Cys]-NH₂ (SEQ ID NO:1) or a pharmaceutically acceptable salt thereof, the most preferred of this group.

In another aspect of the instant application, the invention is directed to a class of compounds hereafter referred to as Group I(D) compounds wherein X is selected from the group consisting of —(CH₂)$_t$—C(O)—NR⁶—(CH₂)$_r$— and —(CH₂)$_r$—NR⁶—C(O)—(CH₂)$_t$—.

r is, independently for each occurrence thereof, 1, 2, 3, 4 or 5;

t is, independently for each occurrence thereof, 1 or 2;

R¹, R², R⁴ and R⁵ each is H;

R³ is NH₂;

X¹ is selected from the group consisting of

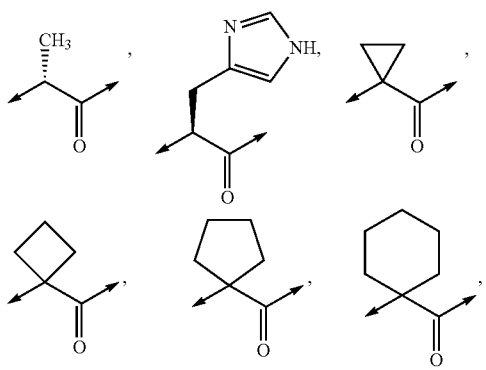

A¹ is His or deleted;

A² is D-1-Nal, D-2-Nal or D-Phe;

A³ is Arg; and

A⁴ is Bal, 1-Nal, 2-Nal or Trp;

or a pharmaceutically acceptable salt thereof.

A subclass of the Group II compounds, the Group I(E) compounds are those in which X is —(CH₂)$_t$—C(O)—NR⁶—(CH₂)$_r$—;

t is 1; and r is 1;

X¹ is selected from the group consisting of:

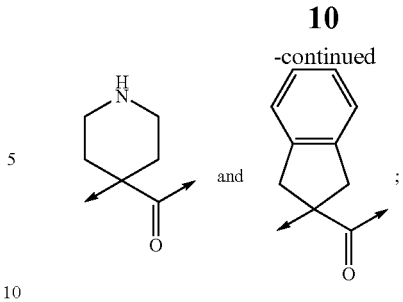

A¹ is His;

A² is D-Phe;

A³ is Arg; and

A⁴ is Bal, 1-Nal, 2-Nal or Trp or pharmaceutically acceptable salts thereof.

A preferred subclass of the Group IIA compounds, hereinafter referred to as Group I(F) compounds, are those compounds according to formula (I) wherein X¹ is and R⁶ is a methyl, ethyl, propyl or butyl, preferably either a methyl or propyl; or a pharmaceutically acceptable salt thereof. Specific examples, classified as Group I(G) compounds, include:

```
                                            (SEQ ID NO: 3)
cyclo[Hydantoin(C(O)-(Asp-D-Ala))-His-D-Phe-Arg-
Trp-Lys]-NH₂;

(SEQ ID NO: 4)
cyclo[Hydantoin(C(O)-(Asp-D-Ala))-His-D-Phe-Arg-
Trp-Orn]-NH₂;

(SEQ ID NO: 4)
cyclo[Hydantoin(C(O)-(Asp-D-Ala))-His-D-Phe-Arg-
Trp-Dab]-NH₂;
or (SEQ ID NO: 4)
cyclo[Hydantoin(C(O)-(Asp-D-Ala))-His-D-Phe-Arg-
Trp-Dap]-NH₂;
``` preferably, cyclo[Hydantoin(C(O)-(Asp-D-Ala))-His-D-Phe-Arg-Trp-Orn]-NH₂; (SEQ ID NO:4) or cyclo[Hydantoin(C(O)-(Asp-D-Ala))-His-D-Phe-Arg-Trp-Dap]-NH₂; (SEQ ID NO:4) or pharmaceutically acceptable salts thereof.

In another subclass of Group I,
X¹ is

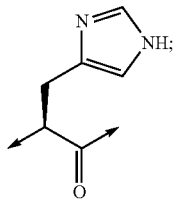

A² is D-2-Nal or D-Phe;

R⁶ is methyl, ethyl, propyl or butyl, preferably propyl; or pharmaceutically acceptable salts thereof, which are referred to as Group I(H) compounds which include the following Group I(I) compounds: cyclo[Hydantoin(C(O)-(Asp-His))-D-2-Nal-Arg-Trp-Lys]-NH₂; (SEQ ID NO:5) or cyclo[Hydantoin(C(O)-(Asp-His))-D-Phe-Arg-Trp-Lys]-NH₂; (SEQ ID NO:5) or pharmaceutically acceptable salts thereof.

In the preferred Group ID compounds, A² is D-2-Nal (Group I(J)) as found in example, cyclo[Hydantoin(C(O)-(Asp-His))-D-2-Nal-Arg-Trp-Lys]-NH₂ (SEQ ID NO:5) (Group I(K)) or a pharmaceutically acceptable salt thereof.

In yet another subclass of the Group I compounds, known as the Group I(L) compounds,
X¹ is selected from the group consisting of:

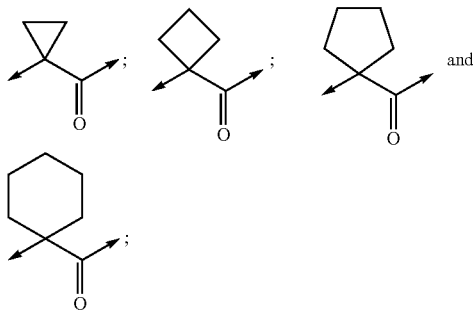

A² is D-2-Nal or D-Phe; and

R⁶ is methyl, ethyl, propyl or butyl, preferably a propyl; or a pharmaceutically acceptable salt thereof. Specific examples of the Group IH compounds, or the Group I(M) compounds are as follows:

```
                                            (SEQ ID NO: 6)
cyclo[Hydantoin(C(O)-(Asp-A3c))-D-Phe-Arg-Trp-
Lys]-NH₂;

(SEQ ID NO: 7)
cyclo[Hydantoin(C(O)-(Asp-A5c))-D-Phe-Arg-Trp-
Lys]-NH₂;

(SEQ ID NO: 8)
cyclo[Hydantoin(C(O)-(Asp-A6c))-D-Phe-Arg-Trp-
Lys]-NH₂;

(SEQ ID NO: 6)
cyclo[Hydantoin(C(O)-(Asp-A3c))-D-2-Nal-Arg-Trp-
Lys]-NH₂;

(SEQ ID NO: 7)
cyclo[Hydantoin(C(O)-(Asp-A5c))-D-2-Nal-Arg-Trp-
Lys]-NH₂;
or (SEQ ID NO: 8)
cyclo[Hydantoin(C(O)-(Asp-A6c))-D-2-Nal-Arg-Trp-
Lys]-NH₂;
``` or a pharmaceutically acceptable salts thereof. Even more preferred are those wherein A² is D-2-Nal and R⁶ is a methyl, ethyl, propyl or butyl, preferably a propyl; or a pharmaceutically acceptable salt thereof (the Group I(N) class) which include the following Group I(O) examples:

```
                                            (SEQ ID NO: 6)
cyclo[Hydantoin(C(O)-(Asp-A3c))-D-2-Nal-Arg-Trp-
Lys]-NH₂;

(SEQ ID NO: 7)
cyclo[Hydantoin(C(O)-(Asp-A5c))-D-2-Nal-Arg-Trp-
Lys]-NH₂;
or (SEQ ID NO: 8)
cyclo[Hydantoin(C(O)-(Asp-A6c))-D-2-Nal-Arg-Trp-
Lys]-NH₂;
``` or a pharmaceutically acceptable salt thereof.

In another subgroup (Group I(P)) of the Group I compounds,
X¹ is selected from the group consisting of:

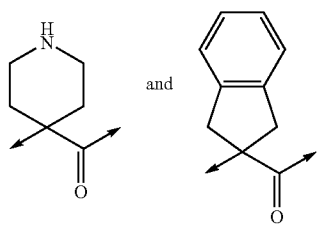

A² is D-2-Nal or D-Phe;

R⁶ is methyl, ethyl, propyl or butyl, preferably a propyl;

or a pharmaceutically acceptable salt thereof. The following Group I(O) compounds are preferred examples:

```
                                             (SEQ ID NO: 9)
cyclo[Hydantoin(C(O)-(Asp-Aic))-D-Phe-Arg-Trp-
Lys]-NH₂;

(SEQ ID NO: 10)
cyclo[Hydantoin(C(O)-(Asp-Apc))-D-Phe-Arg-Trp-
Lys]-NH₂;

(SEQ ID NO: 9)
cyclo[Hydantoin(C(O)-(Asp-Aic))-D-2-Nal-Arg-Trp-
Lys]-NH₂;
or
                                             (SEQ ID NO: 10)
cyclo[Hydantoin(C(O)-(Asp-Apc))-D-2-Nal-Arg-Trp-
Lys]-NH₂;
``` or a pharmaceutically acceptable salt thereof, with those compounds having D-2-Nal at $A^2$ and $R^6$ a methyl (Group I(R)) as found in cyclo[Hydantoin-(C(O)-(Asp-Aic))-D-2-Nal-Arg-Trp-Lys]-NH₂; (SEQ ID NO:9) and cyclo[Hydantoin-(C(O)-(Asp-Apc))-D-2-Nal-Arg-Trp-Lys]-NH₂ (SEQ ID NO:10) (Group I(S)) being most preferred of this subclass.

In yet another embodiment of the formula (I) compounds (the Group I(T) class), $X$ is —$(CH_2)_t$—C(O)—NR⁶—$(CH_2)_r$—;

t is 1; and r is 2;

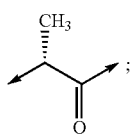

$X^1$ is $A^1$ is His;

$A^2$ is D-Phe;

$A^3$ is Arg;

$A^4$ is Trp; and $R^6$ is methyl, ethyl, propyl or butyl;

or a pharmaceutically acceptable salts thereof. Specific examples (Group I(U)) include,

```
                                             (SEQ ID NO: 11)
cyclo[Hydantoin(C(O)-(Glu-D-Ala))-His-D-Phe-Arg-
Trp-Orn]-NH₂;

(SEQ ID NO: 11)
cyclo[Hydantoin(C(O)-(Glu-D-Ala))-His-D-Phe-Arg-
Trp-Dab]-NH₂;
or
                                             (SEQ ID NO: 11)
cyclo[Hydantoin(C(O)-(Glu-D-Ala))-His-D-Phe-Arg-
Trp-Dap]-NH₂,
``` or a pharmaceutically acceptable salt thereof, particularly cyclo[Hydantoin(C(O)-(Glu-D-Ala))-His-D-Phe-Arg-Trp-Dap]-NH₂ (SEQ ID NO:11) (Group I(V)); or a pharmaceutically acceptable salt thereof.

In another subclass (Group I(W)),

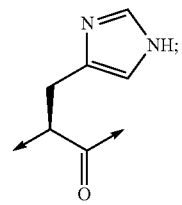

$X^1$ is $A^1$ is deleted;

$A^2$ is D-Phe;

$A^3$ is Arg; and $R^6$ is methyl, ethyl, propyl or butyl;

or a pharmaceutically acceptable salt thereof with cyclo[Hydantoin(C(O)-(Glu-His))-D-Phe-Arg-Trp-Dap]-NH₂ (SEQ ID NO:12) (Group I(X)), or a pharmaceutically acceptable salt thereof, being preferred.

A pharmaceutically acceptable salt of a compound of formula (I) may readily be prepared by mixing together solutions of a compound of formula (I) and the desired acid or base, as appropriate. The salt may precipitate from solution and be collected by filtration or may be recovered by evaporation of the solvent.

According to a first aspect, the invention provides a compound of formula (II), pharmaceutically-acceptable salts, hydrates, solvates and/or prodrugs thereof.

(II)

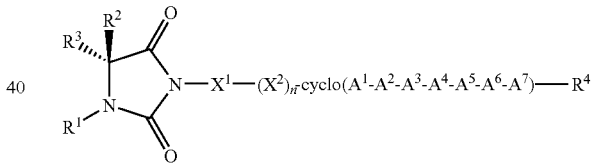

wherein the hydantoin moiety is formed from fusing the amino group of $X^1$, i.e.,

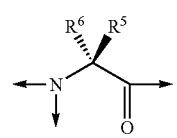

with the following

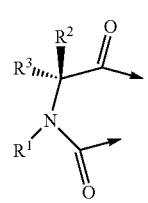

to form the hydantoin structure as follows:

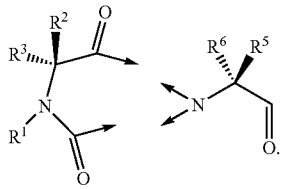

In the preferred embodiment of the compounds according to formula (II), hereinafter referred to as Group II compounds,
$X^1$ is

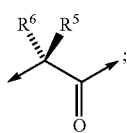

$X^2$ is

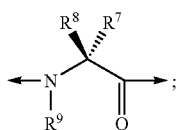

$A^1$ is Asp, Cys, D-Cys, Dab, Dap, Glu, Lys, Orn, Pen or D-Pen;
$A^2$ is an L- or D-amino acid;
$A^3$ is His, 2-Pal, 3-Pal, 4-Pal, $(X^1, X^2, X^3, X^4, X^5)$Phe, Taz, 2-Thi or 3-Thi;
$A^4$ is D-Bal, D-1-Nal, D-2-Nal, D-Phe or D-$(X^1, X^2, X^3, X^4, X^5)$Phe;
$A^5$ is Arg, hArg, Dab, Dap, Lys or Orn;
$A^6$ is Bal, 1-Nal, 2-Nal, $(X^1, X^2, X^3, X^4, X^5)$Phe or Trp;
$A^7$ is Asp, Cys, D-Cys, Dab, Dap, Glu, Lys, Orn, Pen or D-Pen;
$R^1$ is H, $(C_1-C_{10})$alkyl or substituted $(C_1-C_{10})$alkyl;
$R^2$ and $R^3$ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl$(C_1-C_5)$alkyl or $R^2$ and $R^3$ may be fused together form a cyclic moiety;
$R^4$ is $CO_2H$ or $C(O)NH_2$;
$R^5$ and $R^6$ each is, independently, H, $(C_1-C_{10})$heteroalkyl, aryl$(C_1-C_5)$alkyl, substituted $(C_1-C_{10})$alkyl, substituted $(C_1-C_{10})$heteroalkyl or substituted aryl$(C_1-C_5)$alkyl or $R^5$ and $R^6$ may be fused together form a cyclic moiety;
$R^7$ and $R^8$ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl$(C_1-C_6)$alkyl; or $R^7$ and $R^8$ may be fused together form a cyclic moiety;
$R^9$ is H, $(C_1-C_{10})$alkyl or substituted $(C_1-C_{10})$alkyl; and
n is, independently for each occurrence thereof, 1, 2, 3, 4, 5, 6 or 7;
or a pharmaceutically acceptable salt thereof.

A preferred class of compounds according to formula (II), hereafter referred to as Group II(A) examples, are those compounds wherein $A^2$ is D-Ala, Asn, Asp, Gln or Glu;
$R^5$ and $R^6$ each is, independently, H, $(C_1-C_{10})$alkyl, $(C_1-C_{10})$heteroalkyl, substituted $(C_1-C_{10})$alkyl or substituted $(C_1-C_{10})$heteroalkyl or $R^5$ and $R^6$ may be fused together form a cyclic moiety; and
$R^7$ and $R^8$ each is, independently, H, $(C_1-C_{10})$alkyl, $(C_1-C_{10})$heteroalkyl, substituted $(C_1-C_{10})$alkyl or substituted $(C_1-C_{10})$heteroalkyl;
or a pharmaceutically acceptable salt thereof.
$R^1$, $R^2$, $R^3$, and $R^9$, each is, independently, H; and
$R^4$ is $C(O)NH_2$;
$A^1$ is Cys;
$A^2$ is D-Ala or Glu;
$A^3$ is His;
$A^4$ is D-2-Nal or D-Phe;
$A^5$ is Arg;
$A^6$ is Trp; and
$A^7$ is Cys or Pen;
or pharmaceutically acceptable salts thereof.

A preferred subclass of the Group IIA compounds (Group II(B)), are those having
$R^1$, $R^2$, $R^3$, and $R^9$, each is, independently, H;
$R^4$ is $C(O)NH_2$;
$R^5$ and $R^6$ each is, independently, H, methyl, n-propyl, isopropyl, n-butyl, isobutyl, sec-butyl, tert-butyl or $(CH_2)$—NH—C(N)—$NH_2$; $R^7$ is H;
$R^8$ is methyl;
$R^9$ is H;
or pharmaceutically acceptable salts thereof. Preferred Group IIB compounds (Group II(C)) include:

```
                                                    (SEQ ID NO: 13)
Hydantoin(C(O)-(Arg-Gly))-cyclo(Cys-Glu-His-D-Phe-Arg-Trp-Cys)-
NH2;

(SEQ ID NO: 14)
Hydantoin(C(O)-(Nle-Gly))-cyclo(Cys-Glu-His-D-Phe-Arg-Trp-Cys)-
NH2;

(SEQ ID NO: 15)
Hydantoin(C(O)-(Gly-Gly))-cyclo(Cys-Glu-His-D-Phe-Arg-Trp-Cys)-
NH2;

(SEQ ID NO: 16)
Hydantoin(C(O)-(Nle-Gly))-cyclo(Cys-D-Ala-His-D-Phe-Arg-Trp-Cys)-
NH2;

(SEQ ID NO: 17)
Hydantoin(C(O)-(Gly-Gly))-cyclo(Cys-D-Ala-His-D-Phe-Arg-Trp-Cys)-
NH2;

(SEQ ID NO: 18)
Hydantoin(C(O)-(Nle-Gly))-cyclo(Cys-D-Ala-His-D-Phe-Arg-Trp-Pen)-
NH2;
```

-continued

Hydantoin(C(O)-(Gly-Gly))-cyclo(Cys-D-Ala-His-D-Phe-Arg-Trp-Pen)-NH$_2$;  (SEQ ID NO: 19)

Hydantoin(C(O)-(Ala-Gly))-cyclo(Cys-D-Ala-His-D-Phe-Arg-Trp-Cys)-NH$_2$;  (SEQ ID NO: 20)

Hydantoin(C(O)-(D-Ala-Gly))-cyclo(Cys-D-Ala-His-D-Phe-Arg-Trp-Cys)-NH$_2$;  (SEQ ID NO: 21)

Hydantoin(C(O)-(Aib-Gly))-cyclo(Cys-D-Ala-His-D-Phe-Arg-Trp-Cys)-NH$_2$;  (SEQ ID NO: 22)

Hydantoin(C(O)-(Val-Gly))-cyclo(Cys-D-Ala-His-D-Phe-Arg-Trp-Cys)-NH$_2$;  (SEQ ID NO: 23)

Hydantoin(C(O)-(Ile-Gly))-cyclo(Cys-D-Ala-His-D-Phe-Arg-Trp-Cys)-NH$_2$;  (SEQ ID NO: 24)

Hydantoin(C(O)-(Leu-Gly))-cyclo(Cys-D-Ala-His-D-Phe-Arg-Trp-Cys)-NH$_2$;  (SEQ ID NO: 25)

Hydantoin(C(O)-(Gly-Gly))-cyclo(Cys-Glu-His-D-2-Nal-Arg-Trp-Cys)-NH$_2$;  (SEQ ID NO: 15)

Hydantoin(C(O)-(Nle-Gly))-cyclo(Cys-Glu-His-D-2-Nal-Arg-Trp-Cys)-NH$_2$;  (SEQ ID NO: 14)

Hydantoin(C(O)-(D-Arg-Gly))-cyclo(Cys-Glu-His-D-Phe-Arg-Trp-Cys)-NH$_2$;  (SEQ ID NO: 26)

Hydantoin(C(O)-(Arg-Gly))-cyclo(Cys-Glu-His-D-Phe-Arg-Trp-Cys)-NH$_2$;  (SEQ ID NO: 13)

Hydantoin(C(O)-(D-Arg-Gly))-cyclo(Cys-D-Ala-His-D-Phe-Arg-Trp-Cys)-NH$_2$;  (SEQ ID NO: 27)

Hydantoin(C(O)-(Arg-Gly))-cyclo(Cys-D-Ala-His-D-Phe-Arg-Trp-Cys)-NH$_2$;  (SEQ ID NO: 28)

Hydantoin(C(O)-(D-Arg-Gly))-cyclo(Cys-D-Ala-His-D-2-Nal-Arg-Trp-Cys)-NH$_2$;  (SEQ ID NO: 27)
or Hydantoin(C(O)-(Arg-Gly))-cyclo(Cys-D-Ala-His-D-2-Nal-Arg-Trp-Cys)-NH$_2$;  (SEQ ID NO: 28)

or a pharmaceutically acceptable salts thereof.

Even more preferred (Group II(D)) are Group IIC compounds wherein A$^4$ is D-Phe, such as found in the following examples (Group II(E)):

Hydantoin(C(O)-(Nle-Gly))-cyclo(Cys-Glu-His-D-Phe-Arg-Trp-Cys)-NH$_2$;  (SEQ ID NO: 14)

Hydantoin(C(O)-(Gly-Gly))-cyclo(Cys-Glu-His-D-Phe-Arg-Trp-Cys)-NH$_2$;  (SEQ ID NO: 15)

Hydantoin(C(O)-(Nle-Gly))-cyclo(Cys-D-Ala-His-D-Phe-Arg-Trp-Cys)-NH$_2$;  (SEQ ID NO: 16)

-continued (SEQ ID NO: 17)
Hydantoin(C(O)-(Gly-Gly))-cyclo(Cys-D-Ala-His-D-Phe-Arg-Trp-Cys)-NH$_2$;

(SEQ ID NO: 18)
Hydantoin(C(O)-(Nle-Gly))-cyclo(Cys-D-Ala-His-D-Phe-Arg-Trp-Pen)-NH$_2$;

(SEQ ID NO: 19)
Hydantoin(C(O)-(Gly-Gly))-cyclo(Cys-D-Ala-His-D-Phe-Arg-Trp-Pen)-NH$_2$;

(SEQ ID NO: 20)
Hydantoin(C(O)-(Ala-Gly))-cyclo(Cys-D-Ala-His-D-Phe-Arg-Trp-Cys)-NH$_2$;

(SEQ ID NO: 21)
Hydantoin(C(O)-(D-Ala-Gly))-cyclo(Cys-D-Ala-His-D-Phe-Arg-Trp-Cys)-NH$_2$;

(SEQ ID NO: 22)
Hydantoin(C(O)-(Aib-Gly))-cyclo(Cys-D-Ala-His-D-Phe-Arg-Trp-Cys)-NH$_2$;

(SEQ ID NO: 23)
Hydantoin(C(O)-(Val-Gly))-cyclo(Cys-D-Ala-His-D-Phe-Arg-Trp-Cys)-NH$_2$;

(SEQ ID NO: 24)
Hydantoin(C(O)-(Ile-Gly))-cyclo(Cys-D-Ala-His-D-Phe-Arg-Trp-Cys)-NH$_2$;

(SEQ ID NO: 25)
Hydantoin(C(O)-(Leu-Gly))-cyclo(Cys-D-Ala-His-D-Phe-Arg-Trp-Cys)-NH$_2$;

(SEQ ID NO: 26)
Hydantoin(C(O)-(D-Arg-Gly))-cyclo(Cys-Glu-His-D-Phe-Arg-Trp-Cys)-NH$_2$;

(SEQ ID NO: 13)
Hydantoin(C(O)-(Arg-Gly))-cyclo(Cys-Glu-His-D-Phe-Arg-Trp-Cys)-NH$_2$;

(SEQ ID NO: 28)
Hydantoin(C(O)-(Arg-Gly))-cyclo(Cys-D-Ala-His-D-Phe-Arg-Trp-Cys)-NH$_2$;
or (SEQ ID NO: 27)
Hydantoin(C(O)-(D-Arg-Gly))-cyclo(Cys-D-Ala-His-D-Phe-Arg-Trp-Cys)-NH$_2$;

or a pharmaceutically acceptable salts thereof, particularly Hydantoin(C(O)-(Arg-Gly))-cyclo(Cys-Glu-His-D-Phe-Arg-Trp-Cys)-NH$_2$ (SEQ ID NO:13) (Group II(F)) or a pharmaceutically acceptable salt thereof.

A second preferred formula (II) subclass (Group II(G)) are those compounds wherein
$R^1$, $R^2$, $R^3$, and $R^9$, each is, independently, H; and
$R^4$ is C(O)NH$_2$;
$R^5$ and $R^6$ each is, independently, H, methyl, isopropyl, isobutyl or are fused together to form cyclohexyl or CH$_2$-cyclohexyl;
$R^7$ is H;
$R^8$ is n-propyl;
$R^9$ is H;
$A^1$ is Cys;
$A^2$ is D-Ala or Glu;
$A^3$ is H is;
$A^4$ is D-2-Nal or D-Phe;
$A^5$ is Arg;
$A^6$ is Trp; and
$A^7$ is Cys or Pen;
or a pharmaceutically acceptable salts thereof. Examples from the subclass, referred to as the Group II(H) compounds, include the following:

(SEQ ID NO: 29)
Hydantoin(C(O)-(Ala-Nle))-cyclo(Cys-Glu-His-D-Phe-Arg-Trp-Cys)-NH$_2$;

(SEQ ID NO: 30)
Hydantoin(C(O)-(Val-Nle))-cyclo(Cys-Glu-His-D-Phe-Arg-Trp-Cys)-NH$_2$;

(SEQ ID NO: 31)
Hydantoin(C(O)-(Gly-Nle))-cyclo(Cys-Glu-His-D-Phe-Arg-Trp-Cys)-NH$_2$;

(SEQ ID NO: 32)
Hydantoin(C(O)-(A6c-Nle))-cyclo(Cys-D-Ala-His-D-Phe-Arg-Trp-Cys)-NH$_2$;

(SEQ ID NO: 33)
Hydantoin(C(O)-(Gly-Nle))-cyclo(Cys-D-Ala-His-D-Phe-Arg-Trp-Cys)-NH$_2$;

(SEQ ID NO: 34)
Hydantoin(C(O)-(Ala-Nle))-cyclo(Cys-D-Ala-His-D-Phe-Arg-Trp-Cys)-NH$_2$;

(SEQ ID NO: 35)
Hydantoin(C(O)-(D-Ala-Nle))-cyclo(Cys-D-Ala-His-D-Phe-Arg-Trp-Cys)-NH$_2$;

(SEQ ID NO: 36)
Hydantoin(C(O)-(Val-Nle))-cyclo(Cys-D-Ala-His-D-Phe-Arg-Trp-Cys)-NH$_2$;

(SEQ ID NO: 37)
Hydantoin(C(O)-(Leu-Nle))-cyclo(Cys-D-Ala-His-D-Phe-Arg-Trp-Cys)-NH$_2$;

(SEQ ID NO: 38)
Hydantoin(C(O)-(Cha-Nle))-cyclo(Cys-D-Ala-His-D-Phe-Arg-Trp-Cys)-NH$_2$;
or (SEQ ID NO: 39)
Hydantoin(C(O)-(Aib-Nle))-cyclo(Cys-D-Ala-His-D-Phe-Arg-Trp-Cys)-NH$_2$;

or pharmaceutically acceptable salts thereof. More preferred Group III(H) compounds (hereafter Group II(I)) are those examples wherein
  $A^2$ is D-Ala;
  $A^4$ D-Phe; and
  $A^7$ is Cys;
or pharmaceutically acceptable salts thereof. Specific compounds from this preferred class (Group II(J)) include:

(SEQ ID NO: 32)
Hydantoin(C(O)-(A6c-Nle))-cyclo(Cys-D-Ala-His-D-Phe-Arg-Trp-Cys)-NH$_2$;

(SEQ ID NO: 35)
Hydantoin(C(O)-(D-Ala-Nle))-cyclo(Cys-D-Ala-His-D-Phe-Arg-Trp-Cys)-NH$_2$;

(SEQ ID NO: 36)
Hydantoin(C(O)-(Val-Nle))-cyclo(Cys-D-Ala-His-D-Phe-Arg-Trp-Cys)-NH$_2$;

(SEQ ID NO: 37)
Hydantoin(C(O)-(Leu-Nle))-cyclo(Cys-D-Ala-His-D-Phe-Arg-Trp-Cys)-NH$_2$;

(SEQ ID NO: 38)
Hydantoin(C(O)-(Cha-Nle))-cyclo(Cys-D-Ala-His-D-Phe-Arg-Trp-Cys)-NH$_2$;
or (SEQ ID NO: 39)
Hydantoin(C(O)-(Aib-Nle))-cyclo(Cys-D-Ala-His-D-Phe-Arg-Trp-Cys)-NH$_2$;

or pharmaceutically acceptable salts thereof.

A third preferred subclass of compounds according to formula (II) are the Group II(K) class having the following requirements:

$A^1$ is Cys;
$A^2$ is D-Ala or Glu;
$A^3$ is His;
$A^4$ is D-2-Nal or D-Phe;
$A^5$ is Arg;
$A^6$ is Trp; and
$A^7$ is Cys or Pen;
$R^1$, $R^2$, $R^3$, $R^6$, $R^7$ and $R^9$, each is, independently, H;
$R^8$ is (CH$_2$)$_3$—NH—C(N)—NH$_2$;
provided that either $R^4$ is C(O)NH$_2$ and $R^5$ is H or $R^5$ is C(O)NH$_2$ and $R^4$ is H; or pharmaceutically acceptable salts thereof. Preferred Group II(L) compounds that fall within this subclass include:

(SEQ ID NO: 40)
Hydantoin(C(O)-(Gly-Arg))-cyclo(Cys-Glu-His-D-Phe-Arg-Trp-Cys)-NH$_2$;

(SEQ ID NO: 40)
Hydantoin(C(O)-(Gly-Arg))-cyclo(Cys-Glu-His-D-2-Nal-Arg-Trp-Cys)-NH$_2$;

(SEQ ID NO: 41)
Hydantoin(C(O)-(Gly-Arg))-cyclo(Cys-D-Ala-His-D-Phe-Arg-Trp-Cys)-NH$_2$;

(SEQ ID NO: 41)
Hydantoin(C(O)-(Gly-Arg))-cyclo(Cys-D-Ala-His-D-2-Nal-Arg-Trp-Cys)-NH$_2$;

(SEQ ID NO: 42)
Hydantoin(C(O)-(Gly-D-Arg))-cyclo(Cys-Glu-His-D-Phe-Arg-Trp-Cys)-NH$_2$;

(SEQ ID NO: 42)
Hydantoin(C(O)-(Gly-D-Arg))-cyclo(Cys-Glu-His-D-Phe-Arg-Trp-Cys)-NH$_2$;

```
                                                (SEQ ID NO: 43)
Hydantoin(C(O)-(Gly-D-Arg))-cyclo(Cys-D-Ala-His-D-
Phe-Arg-Trp-Cys)-NH2;
and (SEQ ID NO: 43)
Hydantoin(C(O)-(Gly-D-Arg))-cyclo(Cys-D-Ala-His-D-
2-Nal-Arg-Trp-Cys)-NH2;
``` or pharmaceutically acceptable salts thereof.

Even more preferred (the Group II(M) subclass) are those Compounds of Group II wherein $A^4$ is D-Phe as found in the following preferred examples (Group II(N)):

```
                                                (SEQ ID NO: 40)
Hydantoin(C(O)-(Gly-Arg))-cyclo(Cys-Glu-His-D-Phe-
Arg-Trp-Cys)-NH2;

(SEQ ID NO: 41)
Hydantoin(C(O)-(Gly-Arg))-cyclo(Cys-D-Ala-His-D-
Phe-Arg-Trp-Cys)-NH2;

(SEQ ID NO: 42)
Hydantoin(C(O)-(Gly-D-Arg))-cyclo(Cys-Glu-His-D-
Phe-Arg-Trp-Cys)-NH2;
and (SEQ ID NO: 43)
Hydantoin(C(O)-(Gly-D-Arg))-cyclo(Cys-D-Ala-His-D-
Phe-Arg-Trp-Cys)-NH2;
``` or pharmaceutically acceptable salts thereof.

Yet another preferred embodiment of formula (II), known as Group II(O), is Hydantoin(C(O)-(Nle-Ala))-cyclo(Cys-Glu-His-D-Phe-Arg-Trp-Cys)-NH2; (SEQ ID NO:44) or a pharmaceutically acceptable salt thereof.

A pharmaceutically acceptable salt of a compound of formula (II) may readily be prepared by mixing together solutions of a compound of formula (II) and the desired acid or base, as appropriate. The salt may precipitate from solution and be collected by filtration or may be recovered by evaporation of the solvent.

The present invention also relates to a class of cyclic peptide analogs that are ligands for the melanocortin receptors having a structure according to formula (III) as depicted below:

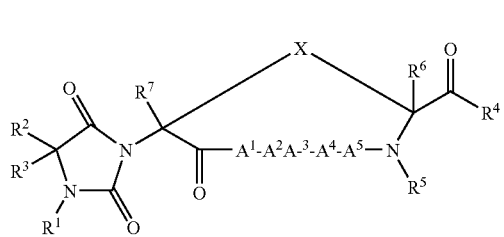

(III)

wherein the hydantoin moiety is formed from fusing the amino group of one of the amino acids that make up X, i.e., "$AA^2$"

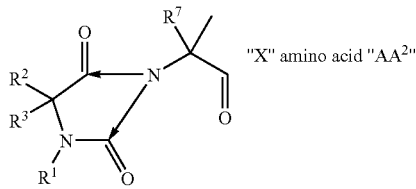

with a second amino acid, i.e., "$AA^1$" making up X,

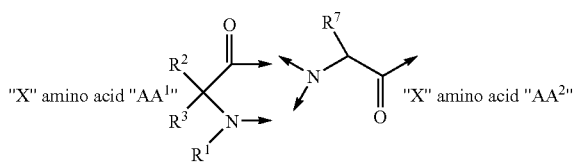

together with a carbonyl group, i.e., C(O), as follows:

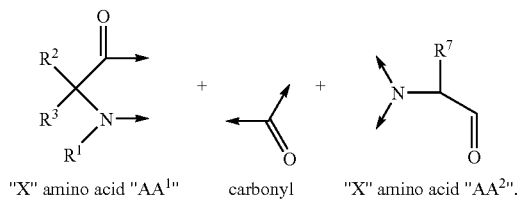

In the shorthand used to identify an embodiment of formula (III), such as cyclo[Hydantoin(C(O)-(Ala-Cys))-D-Ala-His-D-Phe-Arg-Trp-Cys]-NH2, (SEQ ID NO:45) "Hydantoin(C(O)-($AA^1$-$AA^2$)" identifies the amino acids forming the hydantoin structure. The carbonyl group situated between the two nitrogens of the imidazolinyl heterocyclic ring is indicated as "C(O)". "$AA^1$" is part of the hydantoin structure with either $R^2$ or $R^3$ (depending on the stereoisomerism of the example) being the side chain while the other is the hydrogen found on the α-carbon. "$AA^2$" is the amino acid that contributes its N-terminal to the hydantoin structure. For the given example, cyclo[Hydantoin(C(O)-(Ala-Cys))-D-Ala-His-D-Phe-Arg-Trp-Cys]-NH2, (SEQ ID NO:45) the hydantoin is formed as follows:

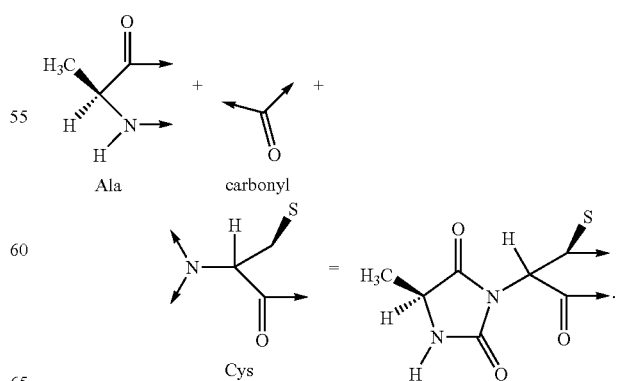

As for the variables of formula (III),

X is selected from the group consisting of —CH$_2$—S—S—CH$_2$—, —C(CH$_3$)$_2$—S—S—CH$_2$—, —CH$_2$—S—S—C(CH$_3$)$_2$—, —C(CH$_3$)$_2$—S—S—C(CH$_3$)$_2$—, —(CH$_2$)$_2$—S—S—CH$_2$—, —CH$_2$—S—S—(CH$_2$)$_2$—, —(CH$_2$)$_2$—S—S—(CH$_2$)$_2$—, —C(CH$_3$)$_2$—S—S—(CH$_2$)$_2$—, —(CH$_2$)$_2$—S—S—C(CH$_3$)$_2$—, —(CH$_2$)$_t$—C(O)—NR$^8$—(CH$_2$)$_r$— and —(CH$_2$)$_r$—NR$^8$—C(O)—(CH$_2$)$_t$—;

R$^1$ and R$^5$ each is, independently, H, (C$_1$-C$_{10}$)alkyl or substituted (C$_1$-C$_{10}$)alkyl;

R$^4$ is —OH or —NH$_2$;

R$^6$ and R$^7$ each is, independently, H, (C$_1$-C$_{10}$)alkyl or substituted (C$_1$-C$_{10}$)alkyl;

R$^2$ and R$^3$ each is, independently, H, (C$_1$-C$_{10}$)alkyl, (C$_1$-C$_{10}$)heteroalkyl, aryl(C$_1$-C$_5$)alkyl, substituted (C$_1$-C$_{10}$)alkyl, substituted (C$_1$-C$_{10}$)heteroalkyl or substituted aryl(C$_1$-C$_5$)alkyl or R$^2$ and R$^3$ may be fused together to form a ring;

A$^1$ is an L- or D-amino acid or deleted;

A$^2$ is His, 2-Pal, 3-Pal, 4-Pal, (X$^1$, X$^2$, X$^3$, X$^4$, X$^5$)Phe, Taz, 2-Thi or 3-Thi;

A$^3$ is D-Bal, D-1-Nal, D-2-Nal, D-Phe or D-(X$^1$, X$^2$, X$^3$, X$^4$, X$^5$)Phe;

A$^4$ is Arg, hArg, Dab, Dap, Lys or Orn;

A$^5$ is Bal, 1-Nal, 2-Nal, (X$^1$, X$^2$, X$^3$, X$^4$, X$^5$)Phe or Trp;

r is, independently for each occurrence thereof, 1, 2, 3, 4 or 5; and t is, independently for each occurrence thereof, 1 or 2;

or pharmaceutically acceptable salts thereof.

In the preferred embodiment of the compounds according to formula (III), hereinafter referred to as Group III compounds, A$^1$ is Ala, D-Ala, Asn, Asp, Gln, Glu or Gly; or a pharmaceutically acceptable salt thereof.

In another preferred embodiment (the Group III(A) subclass),

X is selected from the group consisting of —CH$_2$—S—S—CH$_2$—, —C(CH$_3$)$_2$—S—S—CH$_2$— and (CH$_2$)$_2$—S—S—CH$_2$—;

A$^1$ is D-Ala or Glu;

A$^2$ is His;

A$^3$ is D-Phe;

A$^4$ is Arg;

A$^5$ is Trp;

R$^1$, R$^5$, R$^6$ and R$^7$, each is, independently, H;

R$^2$ and R$^3$ each is, independently, H, (C$_1$-C$_{10}$)alkyl, (C$_1$-C$_{10}$)heteroalkyl, substituted (C$_1$-C$_{10}$)alkyl or substituted (C$_1$-C$_{10}$)heteroalkyl or R$^2$ and R$^3$ may be fused together form a cyclic moiety; and R$^4$ is NH$_2$;

or a pharmaceutically acceptable salt thereof.

In an even more preferred subgroup of Group III(A) (the Group III(B) subclass), R$^2$ and R$^3$ each is, independently, H, methyl, n-propyl, isopropyl, n-butyl, isobutyl, sec-butyl, tert-butyl or (CH$_2$)—NH—C(N)—NH$_2$; or a pharmaceutically acceptable salt thereof. Specific examples of Group III(B), are the Group III(C) compounds:

```
                                                    (SEQ ID NO: 46)
cyclo[Hydantoin(C(O)-(Nle-Cys))-D-Ala-His-D-Phe-Arg-Trp-Cys]-
NH2;

(SEQ ID NO: 45)
cyclo[Hydantoin(C(O)-(Ala-Cys))-D-Ala-His-D-Phe-Arg-Trp-Cys]-
NH2;

(SEQ ID NO: 47)
cyclo[Hydantoin(C(O)-(D-Ala-Cys))-D-Ala-His-D-Phe-Arg-Trp-Cys]-
NH2;

(SEQ ID NO: 48)
cyclo[Hydantoin(C(O)-(Aib-Cys))-D-Ala-His-D-Phe-Arg-Trp-Cys]-
NH2;

(SEQ ID NO: 49)
cyclo[Hydantoin(C(O)-(Val-Cys))-D-Ala-His-D-Phe-Arg-Trp-Cys]-
NH2;

(SEQ ID NO: 50)
cyclo[Hydantoin(C(O)-(Abu-Cys))-D-Ala-His-D-Phe-Arg-Trp-Cys]-
NH2;

(SEQ ID NO: 51)
cyclo[Hydantoin(C(O)-(Leu-Cys))-D-Ala-His-D-Phe-Arg-Trp-Cys]-
NH2;

(SEQ ID NO: 52)
cyclo[Hydantoin(C(O)-(Ile-Cys))-D-Ala-His-D-Phe-Arg-Trp-Cys]-NH2;

(SEQ ID NO: 53)
cyclo[Hydantoin(C(O)-(Cha-Cys))-D-Ala-His-D-Phe-Arg-Trp-Cys]-
NH2;

(SEQ ID NO: 54)
cyclo[Hydantoin(C(O)-(A6c-Cys))-D-Ala-His-D-Phe-Arg-Trp-Cys]-
NH2;

(SEQ ID NO: 55)
cyclo[Hydantoin(C(O)-(Phe-Cys))-D-Ala-His-D-Phe-Arg-Trp-Cys]-
NH2;
```

```
                                                     (SEQ ID NO: 56)
cyclo[Hydantoin(C(O)-(Gly-Cys))-D-Ala-His-D-Phe-Arg-Trp-Cys]-NH2;
or (SEQ ID NO: 57)
cyclo[Hydantoin(C(O)-(Gly-Cys))-Glu-His-D-Phe-Arg-Trp-Cys]-NH2;
``` or pharmaceutically acceptable salts thereof.

In another subclass of Group III, $R^2$ and $R^3$ each is, independently, H, methyl, isopropyl, isobutyl, sec-butyl or may be fused together to form a cyclohexyl (hereafter the Group III(D) subclass); or pharmaceutically acceptable salts thereof, of which the following are preferred examples thereof (Group III(E)):

```
                                                     (SEQ ID NO: 48)
cyclo[Hydantoin(C(O)-(Aib-Cys))-D-Ala-His-D-Phe-
Arg-Trp-Cys]-NH2;

(SEQ ID NO: 49)
cyclo[Hydantoin(C(O)-(Val-Cys))-D-Ala-His-D-Phe-
Arg-Trp-Cys]-NH2;

(SEQ ID NO: 51)
cyclo[Hydantoin(C(O)-(Leu-Cys))-D-Ala-His-D-Phe-
Arg-Trp-Cys]-NH2;

(SEQ ID NO: 52)
cyclo[Hydantoin(C(O)-(Ile-Cys))-D-Ala-His-D-Phe-
Arg-Trp-Cys]-NH2;

(SEQ ID NO: 54)
cyclo[Hydantoin(C(O)-(A6c-Cys))-D-Ala-His-D-Phe-
Arg-Trp-Cys]-NH2;
or (SEQ ID NO: 57)
cyclo[Hydantoin(C(O)-(Gly-Cys))-Glu-His-D-Phe-Arg-
Trp-Cys]-NH2;
``` or pharmaceutically acceptable salts thereof.

In yet another preferred subclass of Group III, hereafter Group III(F), $A^1$ is Glu and $R^2$ and $R^3$ each is, independently, H, or pharmaceutically acceptable salts thereof with the following compound (Group III(G)) cyclo[Hydantoin(C(O)-(Gly-Cys))-Glu-His-D-Phe-Arg-Trp-Cys]-NH2; (SEQ ID NO:57) or a pharmaceutically acceptable salt thereof, a preferred example thereof.

A pharmaceutically acceptable salt of a compound of formula (III) may readily be prepared by mixing together solutions of a compound of formula (III) and the desired acid or base, as appropriate. The salt may precipitate from solution and be collected by filtration or may be recovered by evaporation of the solvent.

For the avoidance of doubt, unless otherwise indicated, the term substituted means substituted by one or more defined groups. In the case where groups may be selected from a number of alternative groups, the selected groups may be the same or different. For the avoidance of doubt, the term independently means that where more than one substituent is selected from a number of possible substituents, those substituents may be the same or different.

The pharmaceutically acceptable salts of the compounds of the invention which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically acceptable metal salts, in particular non-toxic alkali and alkaline earth metal salts, with bases. Examples include the sodium, potassium, aluminum, calcium, magnesium, zinc and diethanolamine salts (Berge, S. M. et al., *J. Pharm. Sci.*, 66:1-19 (1977); Gould, P. L., *Int'l J. Pharmaceutics*, 33:201-17 (1986); and Bighley, L. D. et al., *Encyclo. Pharma. Tech.*, Marcel Dekker Inc, New York, 13:453-97 (1996).

The pharmaceutically acceptable solvates of the compounds of the invention include the hydrates thereof. Also included within the scope of the invention and various salts of the invention are polymorphs thereof. Hereinafter, compounds their pharmaceutically acceptable salts, their solvates or polymorphs, defined in any aspect of the invention (except intermediate compounds in chemical processes) are referred to as "compounds of the invention".

The compounds of the invention may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

In another aspect, the present invention provides a pharmaceutical composition comprising an effective amount of a compound of formula (I) (which hereinafter will include formulae I(A) to I(X)), formula (II) (which hereinafter will include formulae II(A) to II(P)), or formula (III), (which hereinafter will include formulae III(A) to IIII(G)), or pharmaceutically acceptable salts thereof together with a pharmaceutically acceptable carrier or diluent.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, wherein said compound is a melanocortin receptor agonist or antagonist.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, wherein said compound is a selective melanocortin-4 receptor agonist.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, wherein said compound is a selective melanocortin-4 receptor agonist with a functional activity characterized by an $EC_{50}$ at least 15-fold more selective for the human melanocortin-4 receptor than for the human melanocortin-1 receptor, the human melanocortin-3 receptor and the human melanocortin-5 receptor.

In yet another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, wherein said compound is a selective melanocortin-4 receptor agonist with a functional activity characterized by an $EC_{50}$ at least 17-fold more selective for the human melanocortin-4 receptor than for the human melanocortin-3 receptor, an $EC_{50}$ at least 90-fold more selective for the human melanocortin-4 receptor than for the human melanocortin-3 receptor, an $EC_{50}$ at least 200-fold more selective for the human melanocortin-4 receptor than for the human melanocortin-5 receptor, or an $EC_{50}$ at least 3000-fold more selective for the human melanocortin-4 receptor than for the human melanocortin-5 receptor.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating an acute or chronic inflammatory disease or medical condition such as general inflammation, inflammatory bowel disease, brain inflammation, sepsis and septic shock.

In another aspect, the present invention provides a pharmaceutical composition comprising an effective amount of a compound formula (I), formula (II) or formula (III), or a pharmaceutically acceptable salt thereof, and a pharmaceutically acceptable carrier or diluent, useful for treating a disease or medical condition with an autoimmune component such as rheumatoid arthritis, gouty arthritis and multiple sclerosis.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a metabolic disease or medical condition accompanied by weight gain such as obesity, feeding disorders and Prader-Willi Syndrome. In a further aspect, the disease or condition treated is obesity. In yet a further aspect, the disease or condition treated is a feeding disorder.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for decreasing food intake, for decreasing body weight, or a combination thereof.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for decreasing food intake without compromising body weight. In yet another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for decreasing food consumption while increasing body weight.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a metabolic disease or medical condition accompanied by weight loss such as anorexia, bulimia, AIDS wasting, cachexia, cancer cachexia and wasting in frail elderly. In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for increasing food intake, for increasing body weight, or a combination thereof.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a neoplastic disease or medical condition such as skin cancer and cancer cachexia.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a reproductive or sexual medical condition such as endometriosis, uterine bleeding, sexual dysfunction, erectile dysfunction and decreased sexual response in females.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a disease or medical condition resulting from treatment or insult to an organism such as organ transplant rejection, ischemia and reperfusion injury, wounding and spinal cord injury, and weight loss due to a medical procedure selected from the group consisting of chemotherapy, radiation therapy, temporary or permanent immobilization and dialysis.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a cardiovascular disease or medical condition such as hemorrhagic shock, cardiogenic shock, hypovolemic shock, cardiovascular disorders and cardiac cachexia.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a pulmonary disease or medical condition such as acute respiratory distress syndrome, pulmonary fibrosis, chronic obstructive pulmonary disease and asthma.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for enhancing immune tolerance and treating allergies.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a dermatological disease or medical condition such as psoriasis, skin pigmentation depletion, acne and keloid formation.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a behavioral or central nervous system or neuronal disease or medical condition such as anxiety, depression, memory dysfunction and neuropathic pain.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for treating a renal disease or medical condition such as renal cachexia and natriuresis.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for modulating ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection and nerve growth.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for modulating bone metabolism, bone formation and bone development.

In another aspect, the present invention provides a pharmaceutical composition comprising an effective amount of a compound of formula (I), formula (II) or formula (III), or a pharmaceutically acceptable salt thereof, and a pharmaceutically acceptable carrier or diluent, useful for inhibiting alcohol consumption, for reducing alcohol consumption, for treating alcoholism, or for overcoming alcohol abuse. In a further aspect, the compound of the composition useful for inhibiting alcohol consumption, for reducing alcohol consumption, for treating alcoholism, or for treating alcohol abuse is a selective melanocortin-4 receptor agonist. In yet a further aspect, the compound of the composition useful for inhibiting alcohol consumption is a selective melanocortin-4 receptor agonist, or a pharmaceutically acceptable salt thereof, with a functional activity characterized by an $EC_{50}$ at least 15-fold more selective for the human melanocortin-4 receptor than for the human melanocortin-1 receptor, the human melanocortin-3 receptor and the human melanocortin-5 receptor. In yet another aspect, the compound of the composition useful for inhibiting alcohol consumption is a selective melanocortin-4 receptor agonist, or a pharmaceutically acceptable salt thereof, with a functional activity characterized by an $EC_{50}$ at least 17-fold more selective for the human melanocortin-4 receptor than for the human melanocortin-3 receptor, an $EC_{50}$ at least 90-fold more selective for the human melanocortin-4 receptor than for the human melanocortin-3 receptor, an $EC_{50}$ at least 200-fold more selective for the human melanocortin-4 receptor than for the human melanocortin-5 receptor, or an $EC_{50}$ at least 3000-fold more selective for the human melanocortin-4 receptor than for the human melanocortin-5 receptor.

In another aspect, the present invention provides the use of a therapeutically effective amount of a melanocortin-4 receptor agonist compound of formula (I), formula (II) or formula (III), or a pharmaceutically acceptable salt thereof, for the manufacture of a medicament useful for inhibiting alcohol consumption, for reducing alcohol consumption, for treating alcoholism, or for treating alcohol abuse in a subject in need of such treatment.

In yet another aspect, the present invention provides a method of eliciting an agonist or an antagonist effect from a melanocortin receptor in a subject in need thereof which comprises administering to said subject an effective amount of a compound of formula (I), formula (II) or formula (III), or a pharmaceutically acceptable salt thereof.

In another aspect, the present invention provides a method of eliciting an agonist or an antagonist effect from a melanocortin receptor in a subject in need thereof which comprises administering to said subject an effective amount of a compound of formula (I), formula (II) or formula (III), or a pharmaceutically acceptable salt thereof, wherein said compound is a selective melanocortin-4 receptor agonist.

In another aspect, the present invention provides a method of eliciting an agonist or an antagonist effect from a melanocortin receptor in a subject in need thereof which comprises administering to said subject an effective amount of a compound of formula (I), formula (II) or formula (III), or a pharmaceutically acceptable salt thereof, wherein said compound is a selective melanocortin-4 receptor agonist with a functional activity characterized by an $EC_{50}$ at least 15-fold more selective for the human melanocortin-4 receptor than for the human melanocortin-1 receptor, the human melanocortin-3 receptor and the human melanocortin-5 receptor.

In yet another aspect, the present invention provides a method of eliciting an agonist or an antagonist effect from a melanocortin receptor in a subject in need thereof which comprises administering to said subject an effective amount of a compound of formula (I), formula (II) or formula (III), or a pharmaceutically acceptable salt thereof, wherein said compound is a selective melanocortin-4 receptor agonist with a functional activity characterized by an $EC_{50}$ at least 17-fold more selective for the human melanocortin-4 receptor than for the human melanocortin-3 receptor, an $EC_{50}$ at least 90-fold more selective for the human melanocortin-4 receptor than for the human melanocortin-3 receptor, an $EC_{50}$ at least 200-fold more selective for the human melanocortin-4 receptor than for the human melanocortin-5 receptor, or an $EC_{50}$ at least 3000-fold more selective for the human melanocortin-4 receptor than for the human melanocortin-5 receptor.

In another aspect, the present invention provides a method of treating an acute or chronic inflammatory disease or medical condition such as general inflammation, inflammatory bowel disease, brain inflammation, sepsis and septic shock by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a disease or medical condition with an autoimmune component such as rheumatoid arthritis, gouty arthritis and multiple sclerosis by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a metabolic disease or medical condition accompanied by weight gain such as obesity, feeding disorders and Prader-Willi Syndrome by eliciting an agonist or antagonist effect from a melanocortin receptor by administering an effective amount of a compound of formula (I), formula (II) or formula (III), or a pharmaceutically acceptable salt thereof.

In a further aspect of the foregoing method, the disease or condition treated is obesity. In yet a further aspect of the foregoing method, the disease or condition treated is a feeding disorder.

In another aspect, the present invention provides a method of decreasing food intake, decreasing body weight, or a combination thereof, by eliciting an agonist or antagonist effect from a melanocortin receptor by administering an effective amount of a compound of formula (I), formula (II) or formula (III), or a pharmaceutically acceptable salt thereof.

In another, the present invention provides a method of decreasing food intake without compromising body weight by eliciting an agonist or antagonist effect from a melanocortin receptor by administering an effective amount of a compound of formula (I), formula (II) or formula (III), or a pharmaceutically acceptable salt thereof. In yet another aspect of the foregoing method, the present invention provides a method of decreasing food intake while increasing body weight by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of increasing food intake, increasing body weight or a combination thereof, by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a metabolic disease or medical condition accompanied by weight loss such as anorexia, bulimia, AIDS wasting, cachexia, cancer cachexia and wasting in frail elderly by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a neoplastic disease or medical condition such as skin cancer and cancer cachexia by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a reproductive or sexual medical condition such as endometriosis, uterine bleeding, sexual dysfunction, erectile dysfunction and decreased sexual response in females by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a disease or medical condition resulting from treatment or insult to an organism such as organ transplant rejection, ischemia and reperfusion injury, wounding and spinal cord injury, and weight loss due to a medical procedure selected from the group consisting of chemotherapy, radiation therapy, temporary or permanent immobilization and dialysis by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a cardiovascular disease or medical condition such as hemorrhagic shock, cardiogenic shock, hypovolemic shock, cardiovascular disorders and cardiac cachexia by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a pulmonary disease or medical condition such as acute respiratory distress syndrome, pulmonary fibrosis, chronic obstructive pulmonary disease and asthma by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of enhancing immune tolerance or treating allergies by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating dermatological disease or medical condition such as psoriasis, skin pigmentation depletion, acne and keloid formation by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a behavioral or central nervous system or neuronal disease or medical condition such as anxiety, depression, memory dysfunction and neuropathic pain by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of treating a renal disease or medical condition such as renal cachexia and natriuresis by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of modulating a normalizing or homeostatic activity such as ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection and nerve growth by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of modulating a normalizing or homeostatic activity such as bone metabolism, bone formation and bone development by eliciting an agonist or antagonist effect from a melanocortin receptor by administering an effective amount of a compound of formula (I), formula (II) or formula (III), or a pharmaceutically acceptable salt thereof.

In another aspect, the present invention provides a method of inhibiting alcohol consumption, for reducing alcohol consumption, for treating alcoholism, or for treating alcohol abuse by eliciting an agonist or antagonist effect from a melanocortin receptor by administering an effective amount of a compound of formula (I), formula (II) or formula (III), or a pharmaceutically acceptable salt thereof. In a further aspect of the foregoing method, the compound is a selective melanocortin-4 receptor agonist. In yet a further aspect of the immediately foregoing method, the compound of the composition useful for inhibiting alcohol consumption is a selective melanocortin-4 receptor agonist, or a pharmaceutically acceptable salt thereof, with a functional activity characterized by an $EC_{50}$ at least 15-fold more selective for the human melanocortin-4 receptor than for the human melanocortin-1 receptor, the human melanocortin-3 receptor and the human melanocortin-5 receptor. In yet another aspect of the foregoing method, the compound of the composition useful for inhibiting alcohol consumption is a selective melanocortin-4 receptor agonist, or a pharmaceutically acceptable salt thereof, with a functional activity characterized by an $EC_{50}$ at least 17-fold more selective for the human melanocortin-4 receptor than for the human melanocortin-3 receptor, an $EC_{50}$ at least 90-fold more selective for the human melanocortin-4 receptor than for the human melanocortin-3 receptor, an $EC_{50}$ at least 200-fold more selective for the human melanocortin-4 receptor than for the human melanocortin-5 receptor, or an $EC_{50}$ at least 3000-fold more selective for the human melanocortin-4 receptor than for the human melanocortin-5 receptor.

In a further aspect, the present invention provides the use of a therapeutically effective amount of a melanocortin-4 receptor agonist or antagonist compound according to formula (I), formula (II) or formula (III), or a pharmaceutically acceptable salt thereof, for the manufacture of a medicament useful to treat a disease and/or medical condition selected from the group consisting of acute and chronic inflammatory diseases such as general inflammation, inflammatory bowel disease, brain inflammation, sepsis and septic shock; diseases with an autoimmune component such as rheumatoid arthritis, gouty arthritis and multiple sclerosis; metabolic diseases and medical disorders accompanied by weight gain such as obesity, feeding disorders and Prader-Willi Syndrome; metabolic diseases and medical disorders accompanied by weight loss such as anorexia, bulimia, AIDS wasting, cachexia, cancer cachexia and wasting in frail elderly; diabetes, diabetalogical related conditions and complications of diabetes such as retinopathy; neoplastic proliferation such as skin cancer and prostate cancer; reproductive or sexual medical conditions such as endometriosis and uterine bleeding in women, sexual dysfunction, erectile dysfunction and decreased sexual response in females; diseases or conditions resulting from treatment or insult to the organism such as organ transplant rejection, ischemia and reperfusion injury, spinal cord injury and wounding, as well as weight loss caused chemotherapy, radiation therapy, temporary or permanent immobilization or dialysis; cardiovascular diseases or conditions such as hemorrhagic shock, cardiogenic shock, hypovolemic shock, cardiovascular disorders and cardiac cachexia; pulmonary diseases or conditions such as acute respiratory distress syndrome, chronic obstructive pulmonary disease, asthma and pulmonary fibrosis; to enhance immune tolerance and to combat assaults to the immune system such as those associated with certain allergies or organ transplant rejection; treatment of dermatological diseases and conditions such as psoriasis, skin pigmentation depletion, acne, keloid formation and skin cancer; behavioral, central nervous system and neuronal disorders such as anxiety, depression, memory dysfunction, and neuropathic pain; and renal conditions or diseases such as the treatment of renal cachexia and natriuresis.

In a further aspect, the present invention provides the use of a therapeutically effective amount of a melanocortin-4 receptor agonist or antagonist compound according to formula (I), formula (II) or formula (III), or a pharmaceutically acceptable salt thereof, for the manufacture of a medicament useful to modulate normalizing or homeostatic activities such as ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection, nerve growth, bone metabolism, bone formation and bone development.

It will be appreciated that therapeutic interventions addressing both normal physiological and pathophysiological processes which utilize the melanocortin receptors are also contemplated.

Additional objects, advantages, and features of the present invention will become apparent from the following description and appended claims, taken in conjunction with the accompanying figures.

The compounds of formula (I), formula (II) and formula (III) are ligands for at least one of the melanocortin receptors (MC1-R, MC2-R, MC3-R, MC4-R and MC5-R), preferably MC4-R, and a selection thereof were tested for their ability to act as a ligand in the in vitro assay described below.

BRIEF DESCRIPTION OF THE DRAWINGS

FIG. 1: Cumulative mean food intake difference from vehicle in rats at 1 hour and 4 hours after administration of various concentrations of Compound A.

FIG. 2A. Cumulative mean food intake difference from vehicle in rats after administration of various concentrations of Compounds C and D.

FIG. 2B. Cumulative mean food intake difference from vehicle in rats after administration of various concentrations of Compounds A, B, C, D, E and F.

FIG. 3A. Cumulative mean food intake difference from vehicle in rats after administration of 4.5 μmole/Kg/day of Compound A.

Figure 3B:
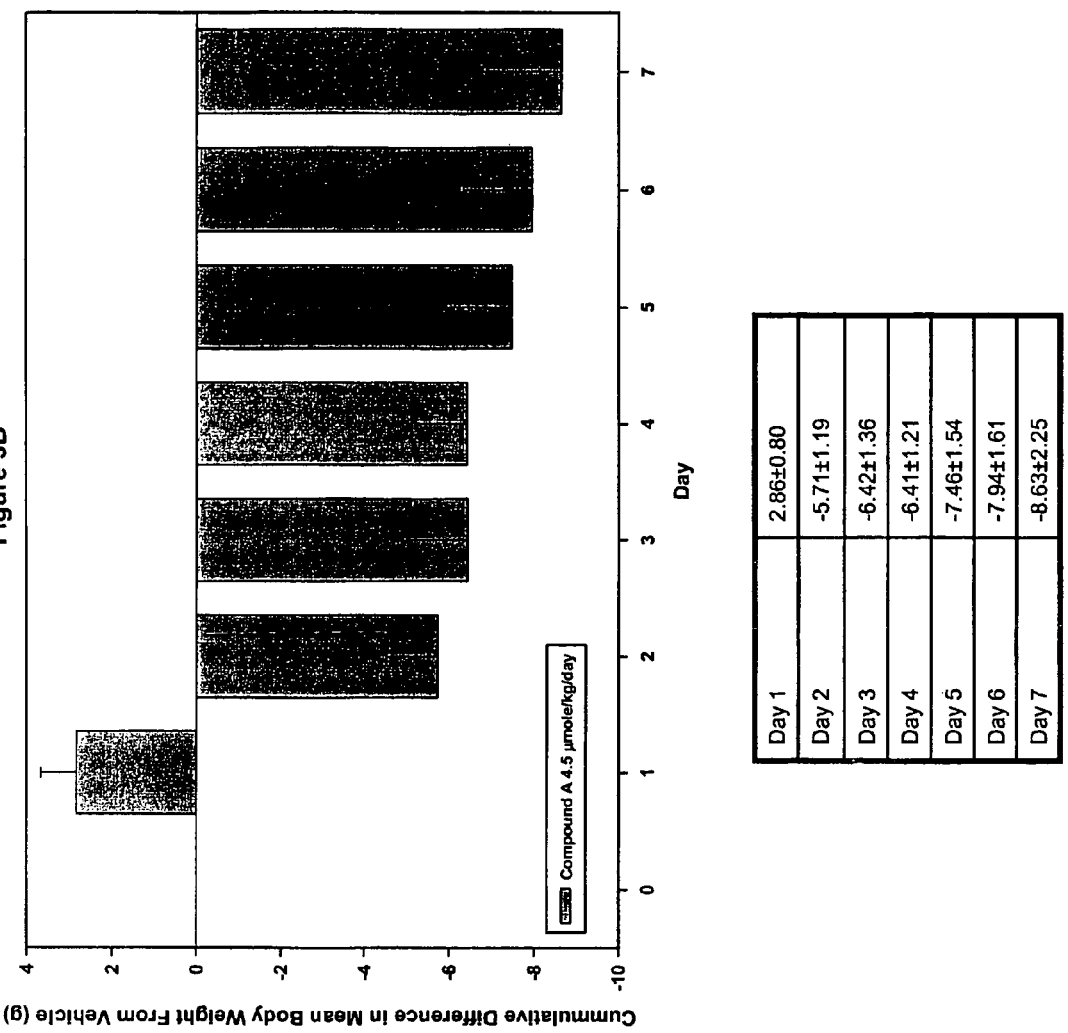
FIG. 3B. Cumulative mean body weight difference from vehicle in rats after administration of 4.5 μmole/Kg/day of Compound A.
Figure 4A:
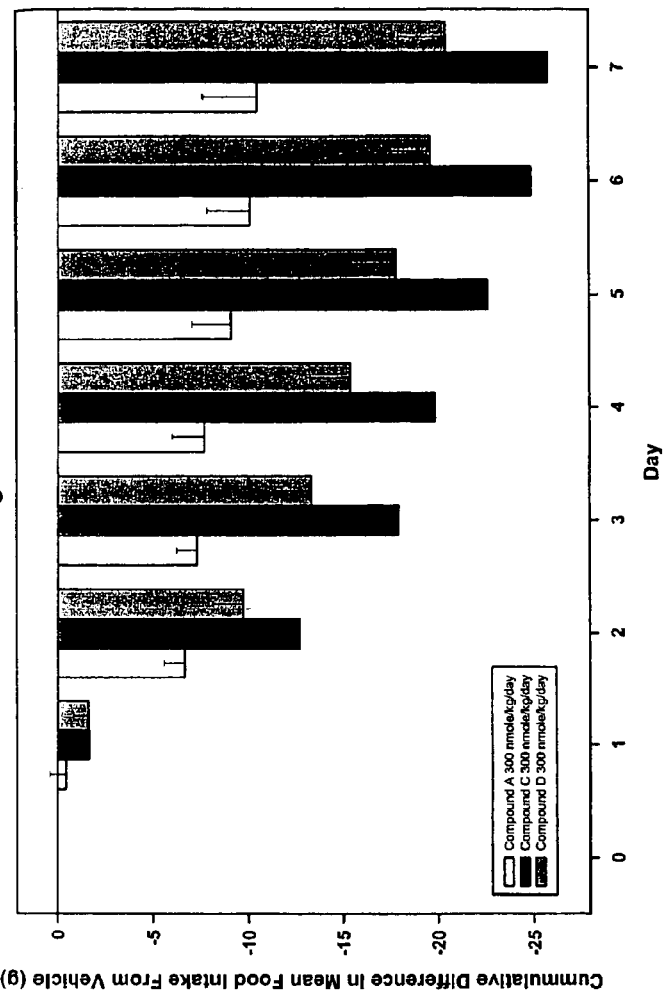
FIG. 4A. Cumulative mean food intake difference from vehicle in rats after administration of 300 ηmole/Kg/day of Compounds A, C and D.
Figure 4B:
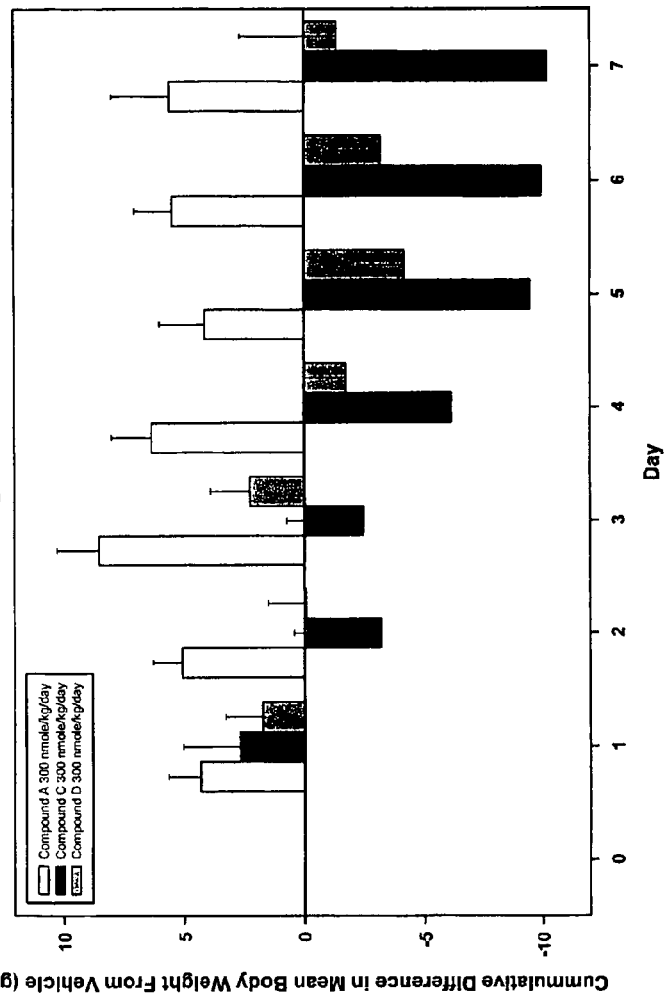
FIG. 4B. Cumulative mean body weight difference from vehicle in rats after administration of 300 ηmole/Kg/day of Compounds A, C and D.

LEGEND for FIG. 1 to FIG. 4B:

| Letter Code | Compound Formula |
| --- | --- |
| A | cyclo[Hydantoin(C(O)-(Glu-D-Ala))-His-D-Phe-Arg-Trp-Dap]-NH$_2$ (SEQ ID NO: 11) |
| B | Hydantoin(C(O)-(D-Arg-Gly))-c(Cys-Glu-His-D-Phe-Arg-Trp-Cys)-NH$_2$ (SEQ ID NO: 26) |

| Letter Code | Compound Formula |
|---|---|
| C | Hydantoin(C(O)-(Arg-Gly))-c(Cys-Glu-His-D-Phe-Arg-Trp-Cys)-NH$_2$ (SEQ ID NO: 13) |
| D | Hydantoin(C(O)-(Gly-D-Arg))-c(Cys-Glu-His-D-Phe-Arg-Trp-Cys)-NH$_2$ (SEQ ID NO: 42) |
| E | Hydantoin(C(O)-(Gly-Arg))-c(Cys-Glu-His-D-Phe-Arg-Trp-Cys)-NH$_2$ (SEQ ID NO: 40) |
| F | Hydantoin(C(O)-(Nle-Gly))-c(Cys-Glu-His-D-Phe-Arg-Trp-Cys)-NH$_2$ (SEQ ID NO: 14) |

DETAILED DESCRIPTION OF THE INVENTION

Definitions of Terms, Abbreviations and Acronyms

The following are definitions of terms used in this specification. The initial definition provided for a group or term herein applies to that group or term throughout the present specification, individually or as part of another group, unless otherwise indicated. Unless defined otherwise, all technical and scientific terms used herein have the same meaning as commonly understood by one of ordinary skill in the art to which this invention belongs.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When a subscript is used with reference to an alkyl or other group, the subscript refers to the number of carbon atoms that the group may contain.

The term "substituted alkyl" refers to an alkyl group as defined above having one, two or three substituents selected from the group consisting of halo, amino, cyano, keto (=O), —OR$_a$, —SR$_a$, NR$_a$R$_b$, —(C=O)R$_a$, —CO$_2$R$_a$, —C(=O)NR$_a$R$_b$, —NR$_a$C(=O)R$_b$, NR$_a$CO$_2$R$_b$, —OC(=O)R$_a$, —OC(=O)NR$_a$R$_b$, —NR$_c$C(=O)NR$_a$R$_b$, NR$_a$SO$_2$R$_d$, SO$_2$R$_d$, SO$_3$R$_d$, cycloalkyl, aryl, heteroaryl, or heterocycle, wherein the groups R$_a$, R$_b$, and R$_c$ are selected from hydrogen, (C$_1$-C$_6$)alkyl, aryl, heteroaryl, heterocycle, cycloalkyl, or (C$_1$-C$_6$)alkyl substituted with halogen, hydroxy, methoxy, nitro, amino, cyano, —(C=O)H, —CO$_2$H, —(C=O)alkyl, —CO$_2$alkyl, —NH(alkyl), —NH(cycloalkyl), —N(alkyl)$_2$, carboxy, acyl, —C(=O)H, —C(=O)phenyl, —CO$_2$-alkyl, cycloalkyl, —(C=O)NH$_2$, —(C=O)NH(alkyl), —(C=O)NH(cycloalkyl), —(C=O)N(alkyl)$_2$, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, —NH—CH$_2$-carboxy, —NH—CH$_2$—CO$_2$-alkyl, phenyl, benzyl, phenylethyl, or phenyloxy. The group R$_d$ may be selected from the same groups as R$_a$, R$_b$ and R$_c$ but is not hydrogen. Alternatively, the groups R$_a$ and R$_b$ may together form a heterocyclo or heteroaryl ring. It should be understood that when a substituted alkyl group is substituted with an aryl, cycloalkyl, heteroaryl, or heterocyclo, such rings are as defined below and thus may have one to three substituents as set forth below in the definitions for these terms.

When the term "alkyl" is used as a suffix following another specifically named group, e.g., arylalkyl or heteroarylalkyl, the term defines, with more specificity, at least one of the substituents that the substituted alkyl will contain. For example, arylalkyl refers to an aryl bonded through an alkyl, or in other words, a substituted alkyl group having from 1 to 12 carbon atoms and at least one substituent that is aryl (e.g., benzyl or biphenyl). "Lower arylalkyl" refers to substituted alkyl groups having 1 to 4 carbon atoms and at least one aryl substituent.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred. A substituted alkenyl or alkynyl will contain one, two, or three substituents as defined above for alkyl groups.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1 to 8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above. Substituted alkylene, alkenylene, and alkynylene groups may have substituents as defined above for substituted alkyl groups.

The term "alkoxy" refers to the group OR$_e$ wherein R$_e$ is alkyl, substituted alkyl, alkenyl, substituted alkenyl, alkynyl, substituted alkynyl, heterocycle, or cycloalkyl. Thus, an alkoxy includes such groups as methoxy, ethoxy, cyclopropyloxy, pyrrolidinyloxy, and so forth. The term "aryloxy" refers to the groups O(aryl) or O(heteroaryl), wherein aryl and heteroaryl are as defined below.

The term "alkylthio" refers to an alkyl or substituted alkyl group as defined above bonded through one or more sulfur (—S—) atoms, e.g., —S (alkyl) or —S (alkyl-R$_a$).

The term "alkylamino" refers to an alkyl or substituted alkyl group as defined above bonded through one or more nitrogen (—NR$_f$—) groups, wherein R$_f$ is hydrogen, alkyl, substituted alkyl, or cycloalkyl.

The term "acyl" refers to an alkyl or substituted alkyl group as defined above bonded through one or more carbonyl {—C(=O)—} groups. When the term acyl is used in conjunction with another group, as in acylamino, this refers to the carbonyl group {—C(=O)} linked to the second named group. Thus, acylamino refers to —C(=O)NH$_2$, substituted acylamino refers to the group —C(=O)NRR, and acylaryl refers to —C(=O)(aryl).

The term "aminoacyl" refers to the group NR$_f$C(=O)R$_g$, wherein R$_g$ is hydrogen, alkyl, or substituted alkyl, and R$_f$ is as defined above for alkylamino groups.

The term "halo" or "halogen" refers to chloro, bromo, fluoro and iodo. Unless otherwise indicated, any haloalkyl, haloalkoxy or haloalkylthio group contains one or more halo atoms which halo atoms may be the same or different.

The term "carboxy" when used alone refers to the group $CO_2H$. Carboxyalkyl refers to the group $CO_2R$, wherein R is alkyl or substituted alkyl.

The term "sulphonyl" refers to a sulphoxide group (i.e., $-S(O)_{1-2}-$) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., $-SO_2$-alkyl), or bivalent (e.g., $-SO_2$-alkylene, etc.)

The term "cycloalkyl" refers to substituted and unsubstituted monocyclic or bicyclic hydrocarbon groups of 3 to 9 carbon atoms which are, respectively, fully saturated or partially unsaturated, including a fused aryl ring, for example, an indan. A cycloalkyl group may be substituted by one or more (such as one to three) substituents selected from alkyl, substituted alkyl, aminoalkyl, halogen, cyano, nitro, trifluoromethyl, hydroxy, alkoxy, alkylamino, sulphonyl, $-SO_2$(aryl), $-CO_2H$, $-CO_2$-alkyl, $-C(=O)H$, keto, $-C(=O)-(CH_2)_{1-2}NH_2$, $-C(=O)-(CH_2)_{1-2}NH$(alkyl), $-C(=O)-(CH_2)_{1-2}N$(alkyl)$_2$, acyl, aryl, heterocycle, heteroaryl, or another cycloalkyl ring of 3 to 7 carbon atoms. The term "cycloalkylene" refers to a cycloalkyl forming a link or spacer between two other groups, i.e., a cycloalkylene is a cycloalkyl that is bonded to at least two other groups. The term cycloalkyl includes saturated or partially unsaturated carbocyclic rings having a carbon-carbon bridge of three to four carbon atoms or having a benzene ring joined thereto. When the cycloalkyl group is substituted with a further ring, said further ring may have one to two substituents selected from $R_k$, wherein $R_k$ is lower alkyl, hydroxy, lower alkoxy, amino, halogen, cyano, trifluoromethyl, trifluoromethoxy, nitro, and lower alkyl substituted with one to two hydroxy, lower alkoxy, amino, halogen, cyano, trifluoromethyl, trifluoromethoxy, and/or nitro.

The term "aryl" refers to substituted and unsubstituted phenyl, 1-naphthyl and 2-naphthyl, with phenyl being preferred. The aryl may have zero, one, two or three substituents selected from the group consisting of alkyl, substituted alkyl, alkoxy, alkylthio, halo, hydroxy, nitro, cyano, amino, trifluoromethyl, trifluoromethoxy, sulphonyl, $-SO_2$(aryl), $-NH$(alkyl), $-NH$(cycloalkyl), $-N$(alkyl)$_2$, carboxy, acyl, $-C(=O)H$, $-C(=O)$phenyl, $-CO_2$-alkyl, cycloalkyl, $-C(=O)NH_2$, $-C(=O)NH$(alkyl), $-C(=O)NH$(cycloalkyl), $-C(=O)N$(alkyl)$_2$, $-NH-CH_2$-carboxy, $-NH-CH_2CO_2$-alkyl, $-C(=O)-(CH_2)_{1-2}NH_2$, $-C(=O)-(CH_2)_{1-2}NH$(alkyl), $-C(=O)-(CH_2)_{1-2}N$(alkyl)$_2$, phenyl, benzyl, phenylethyl, phenyloxy, phenylthio, heterocyclo, heteroaryl, or a $(C_3-C_7)$cycloalkyl ring. The term "arylene" refers to an aryl as defined above forming a link or spacer between two other groups, i.e., an arylene is an aryl that is bonded to at least two other groups. When the aryl group is substituted with a further ring, said further ring may have one to two substituents selected from $R_k$, wherein $R_k$ is defined as above.

The term "heterocyclo" or "heterocycle" refers to substituted and unsubstituted non-aromatic 3-to 7-membered monocyclic groups, 7-to 11-membered bicyclic groups, and 10-to 15-membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain one, two or three substituents selected from the group consisting of halo, amino, cyano, alkyl, substituted alkyl, trifluoromethyl, trifluoromethoxy, sulphonyl, $-SO_2$(aryl), $-NH$(alkyl), $-NH$(cycloalkyl), $-N$(alkyl)$_2$, alkoxy, alkylthio, hydroxy, nitro, phenyl, benzyl, phenylethyl, phenyloxy, phenylthio, carboxy, $-CO_2$-alkyl, cycloalkyl, $-C(=O)H$, acyl, $-C(=O)NH_2$, $-C(=O)NH$(alkyl), $-C(=O)NH$(cycloalkyl), $-C(=O)N$(alkyl)$_2$, $-NH-CH_2$-carboxy, $-NH-CH_2CO_2$-alkyl, $-C(=O)-(CH_2)_{1-2}NH_2$, $-C(=O)-(CH_2)_{1-2}NH$(alkyl), $-C(=O)-(CH_2)_{1-2}N$(alkyl)$_2$, heterocyclo, heteroaryl, a $(C_3-C_7)$cycloalkyl ring, keto, $=N-OH$, $=N-O$-lower alkyl, or a five or six-membered ketal, i.e., 1,3-dioxolane or 1,3-dioxane. When the heterocyclo group is substituted with a further ring, said further ring may have one to two substituents selected from $R_k$, wherein $R_k$ is defined as above. Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11-to 14-membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, amino, cyano, alkyl, substituted alkyl, trifluoromethyl, trifluoromethoxy, sulphonyl, $-SO_2$(aryl), $-NH$(alkyl), $-NH$(cycloalkyl), $-N$(alkyl)$_2$, alkoxy, alkylthio, hydroxy, nitro, phenyl, benzyl, phenylethyl, phenyloxy, phenylthio, carboxy, cycloalkyl, $-C(=O)H$, acyl, $-C(=O)NH_2$, $-C(=O)NH$(alkyl), $-C(=O)NH$(cycloalkyl), $-C(=O)N$(alkyl)$_2$, $-NH-CH_2$-carboxy, $-NH-CH_2CO_2$-alkyl, $-C(=O)-(CH_2)_{1-2}NH_2$, $-C(=O)-(CH_2)_{1-2}NH$(alkyl), $-C(=O)-(CH_2)_{1-2}N$(alkyl)$_2$, heterocylco, heteroaryl, or a $(C_3-C_7)$cycloalkyl ring. The heterocyclo ring may have a sulfur heteroatom that is substituted with one or more oxygen (=O) atoms. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like. Exemplary tricyclic heteroaryl groups include carbazolyl, benzidolyl, phenanthrollinyl, acridinyl, phenanthridinyl, xanthenyl and the like.

When reference is made herein to a particularly-named heterocyclic or heteroaryl group, such as azetidinyl, imidazolyl, piperazinyl, and so forth, the named ring may optionally contain one or more (preferably one to three) substituents selected from the substituents recited above for heteroaryl and heterocyclo groups, as appropriate.

When reference is made to a particularly-named group having at least one heterocyclo, heteroaryl, or carbocyclic ring "joined" thereto, it is meant that two substituents attached to the same, adjacent, or non-adjacent atoms of the particularly-named group may join to form a second or third ring (i.e., the further ring may be fused, bridged or attached in a spiro fashion). Each ring of these bicyclic or tricyclic groups may be optionally substituted, wherein the substituents are selected from those recited above for cycloalkyl, aryl, heterocyclo and heteroaryl groups. Thus, an imidazole having at least one ring joined thereto may include an aryl-fused imidazole such as benzimidazole having one or more (preferably one to three substituents), to an heteroaryl-fused imidazole such as a pyridoimidazole having one or more (preferably one to three) substituents, and so forth.

Additionally, one skilled in the field may make appropriate substitutions for the various groups of compounds of formula (I), (II) or (III) herein without departing from the spirit and scope of the invention. Throughout the specification, groups and substituents thereof may be chosen to provide stable moieties and compounds.

The compounds of formula (I), (II) or (III) form salts which are also within the scope of this invention. Reference to a compound of any one of formula (I), (II) or (III) herein is understood to include reference to salts thereof, unless otherwise indicated. The term "salt(s)", as employed herein, denotes acidic and/or basic salts formed with inorganic and/or organic acids and bases. In addition, when a compound of any one of formula (I), (II) or (III) contains both a basic moiety, such as but not limited to an amine or a pyridine or imidazole ring, and an acidic moiety, such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also contemplated as within the scope of the invention, e.g., they may be useful in isolation or purification steps which may be employed during preparation. Salts of the compounds of any one of formula (I), (II) or (III) may be formed, for example, by reacting a compound of formula (I), (II) or (III) with an amount of acid or base, such as an equivalent amount, in a medium such as one in which the salt precipitates or in an aqueous medium followed by lyophilization.

The compounds of any one of formula (I), (II) or (III) which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of any one of formula (I), (II) or (III) which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)pethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of this invention are also contemplated herein. The term "prodrug", as employed herein, denotes a compound which, upon administration to a subject, undergoes chemical conversion by metabolic or chemical processes to yield a compound of any one of formula (I), (II) or (III), and/or a salt and/or solvate thereof. Solvates of the compounds of formula (I), (II) or (III) are preferably hydrates.

Compounds of any one of formula (I), (II) or (III) and salts thereof may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. The nomenclature used to define the peptides is that typically used in the art wherein the amino group at the N-terminus appears to the left and the carboxyl group at the C-terminus appears to the right.

The term "amino acid" refers to naturally occurring and synthetic amino acids, as well as amino acid analogs and amino acid mimetics that function in a manner similar to the naturally occurring amino acids. Unless otherwise indicated, with the exception of the N-terminal amino acid, all abbreviations (e.g. Ala) of amino acids in this disclosure stand for the structure of
—NH—C(R)(R')—CO—, wherein R and R' each is, independently, hydrogen or the side chain of an amino acid (e.g., R=CH$_3$ and R'=H for Ala), or R and R' may be joined to form a ring system. For the N-terminal amino acid, the abbreviation stands for the structure of:

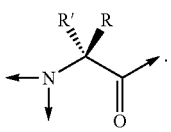

Naturally occurring amino acids are those encoded by the genetic code, as well as those amino acids that are later modified. The term "amino acid analog" refers to a compound that has the same basic chemical structure as a naturally occurring amino acid, i.e., an α-carbon that is bound to a hydrogen, a carboxyl group, an amino group, and an R group, e.g., homoserine and norleucine. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission.

| Nomenclature and Abbreviations | |
|---|---|
| Symbol | Meaning |
| Abu | α-aminobutyric acid |
| Acc | 1-amino-1-cyclo (C$_3$—C$_9$) alkyl carboxylic acid such as: |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Aha | 7-aminoheptanoic acid |
| Ahx | 6-aminohexanoic acid |
| Aib | α-aminoisobutyric acid |
| Aic | 2-aminoindan-2-carboxylic acid |
| Ala or A | alanine |
| β-Ala | beta-alanine |

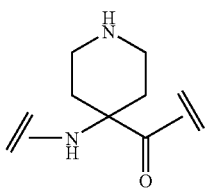

| | |
|---|---|
| Apc | denotes the structure: |
| Apn | 5-aminopentanoic acid (HN—(CH$_2$)$_4$—C(O)) |
| Arg or R | arginine |

-continued

| Nomenclature and Abbreviations | |
|---|---|
| Symbol | Meaning |
| hArg | homoarginine |
| Asn or N | asparagine |
| Asp or D | aspartic acid |
| Bal | 3-benzothienylalanine |
| Bip | 4,4'-biphenylalanine, represented by the structure |

| | |
|---|---|
| Bpa | 4-benzoylphenylalanine |
| 4-Br-Phe | 4-bromo-phenylalanine |
| Cha | β-cyclohexylalanine |
| hCha | homo-cyclohexylalanine |
| Chg | cyclohexylglycine |
| Cys or C | cysteine |
| hCys | homocysteine |
| Dab | 2,4-diaminobutyric acid |
| Dap | 2,3-diaminopropionic acid |
| Dip | β,β-diphenylalanine |
| Doc | 8-amino-3,6-dioxaoctanoic acid with the structure of: |

| | |
|---|---|
| 2-Fua | β-(2-furyl)-alanine |
| Gaba | 4-aminobutyric acid |
| Gln or Q | glutamine |
| Glu or E | glutamic acid |
| Gly or G | glycine |
| His or H | histidine |
| 3-Hyp | trans-3-hydroxy-L-proline, i.e., (2S, 3S)-3-hydroxypyrrolidine-2-carboxylic acid |
| 4-Hyp | 4-hydroxyproline, i.e., (2S, 4R)-4-hydroxypyrrolidine-2-carboxylic acid |
| Ile or I | isoleucine |
| Leu or L | leucine |
| hLeu | homoleucine |
| Lys or K | lysine |
| Met or M | methionine |
| β-hMet | β-homomethionine |
| 1-Nal | β-(1-naphthyl)alanine: |
| 2-Nal | β-(2-naphthyl)alanine |
| Nip | nipecotic acid |
| Nle | norleucine |
| Oic | octahydroindole-2-carboxylic acid |
| Orn | ornithine |
| 2-Pal | β-(2-pyridyl)alanine |
| 3-Pal | β-(3-pyridyl)alanine |
| 4-Pal | β-(4-pyridyl)alanine |
| Pen | penicillamine |
| Phe or F | phenylalanine |
| hPhe | homophenylalanine |
| Pro or P | proline |
| hPro | homoproline |
| Ser or S | serine |
| Tle | tert-Leucine |
| Taz | β-(4-thiazolyl)alanine |
| 2-Thi | β-(2-thienyl)alanine |
| 3-Thi | β-(3-thienyl)alanine |
| Thr or T | threonine |

Nomenclature and Abbreviations

| Symbol | Meaning |
| --- | --- |
| Trp or W | tryptophan |
| Tyr or Y | tyrosine |
| D-(Et)Tyr | has a structure of |
| | 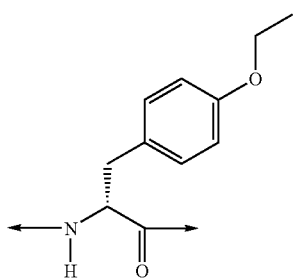 |
| Val or V | valine |

The letter "D" preceding the above three-letter abbreviations, e.g. as in "D-Nal" or "D-Phe", denotes the D-form of the amino acid. The letter "L" preceding an amino acid three-letter abbreviation denotes the natural L-form of the amino acid. For purposes of this disclosure, unless otherwise indicated, absence of a "D" or "L" designation indicates that the abbreviation refers to the L-form. Where the common single-letter abbreviation is used, capitalization refers to the L-form and small letter designation refers to the D-form, unless otherwise indicated.

The designation "NH$_2$" in e.g., Ac-Nle-c(Cys-D-Ala-His-D-Phe-Arg-Trp-Cys)-NH$_2$, (SEQ ID NO:58) indicates that the C-terminus of the peptide is amidated. Ac-Nle-c(Cys-D-Ala-His-D-Phe-Arg-Trp-Cys), (SEQ ID NO:59) or alternatively Ac-Nle-c(Cys-D-Ala-His-D-Phe-Arg-Trp-Cys)-OH, (SEQ ID NO:60) indicates that the C-terminus is the free acid.

"-c(Cys-Cys)-" or "-cyclo(Cys-Cys)-" denotes the structure:

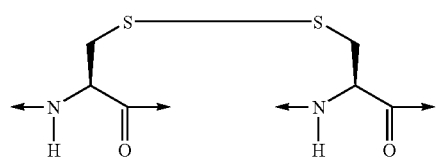

"-c(Cys-Pen)-" or "-cyclo(Cys-Pen)-" denotes the structure:

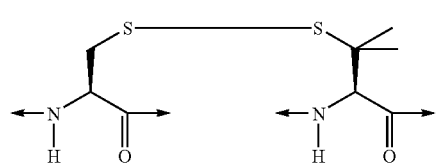

"-c(Asp-Lys)-" or "-cyclo(Asp-Lys)-" denotes the structure:

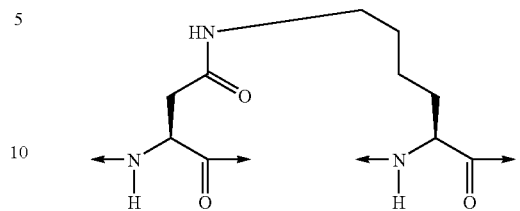

Applicants have devised the following shorthand used in naming the specific embodiments and/or species:

"HydantoinC(O)-(Aa-Ab)" denotes the structure:

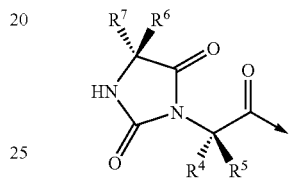

wherein amino acid "A$^a$" has the structure:

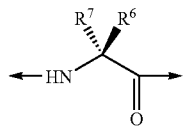

and
amino acid "A$^b$" the structure:

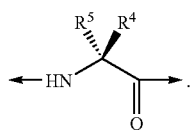

For example, a compound represented as "cyclo[Hydantoin(C(O)-(Cys-Ab))-A$^1$-A$^2$-A$^3$-A$^4$-Cys]-" would have the following the structure:

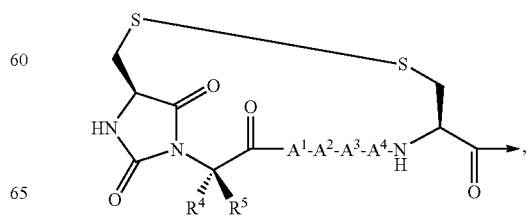

whereas a compound represented as "cyclo[Hydantoin(C(O)-(A$^b$-Cys))-A$^1$-A$^2$-A$^3$-A$^4$-Cys]-" would have the structure:

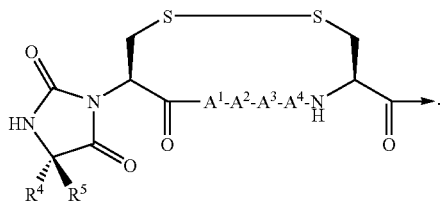

For further guidance, "cyclo[Hydantoin(C(O)-(Asp-A$^b$))-A$^1$-A$^2$-A$^3$-A$^4$-Lys]" represents the following compound:

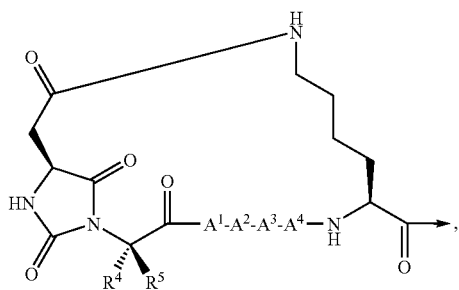

whereas "cyclo[Hydantoin(C(O)-(Dap-Ab))-A$^1$-A$^2$-A$^3$-A$^4$-Asp]-" has the following formula:

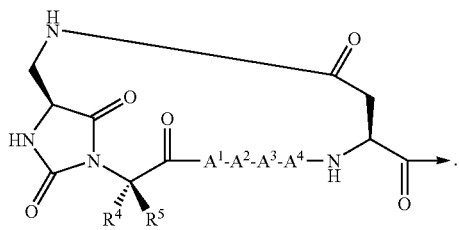

As used herein, "MC-3 agonist", "MC-4 agonist" "MC-5 agonist" refers to a compound with affinity for the MC-3 receptor, MC-4 receptor or MC-5 receptor, respectively, that results in measurable biological activity in cells, tissues, or organisms which contain the MC-3, MC-4 or MC-5 receptor. Assays which demonstrate MC-3/MC-4/MC-5 agonistic activity of compounds are well known in the art.

As used herein, "MC-3 antagonist", "MC-4 antagonist" and "MC-5 antagonist" refer to compounds with affinity for the MC-3 receptor, MC-4 receptor or MC-5 receptor, respectively, and blocks stimulation by a known MC agonist. Assays used to determine MC-3/MC-4/MC-5 antagonistic activity of a compound are known by one skilled in the art.

As used herein, "MC-3 receptor", "MC-4 receptor" and "MC-5 receptor" mean the known MC-3, MC-4 and MC-5 receptors, their splice variants, and un-described receptors. MC-3 receptors are described by Gantz et al., supra (human MC-3); Desarnaud et al., supra (mouse MC-3); and Reyfuss, L. et al., "Identification of a Receptor for Gamma Melanotropin and Other Proopiomelanocortin Peptides in the Hypothalamus and Limbic System", Proc. Natl. Acad. Sci. USA, 90:8856-60 (1993). MC-4 receptors are described by Gantz et al., supra (human MC-4); Alvaro, J. D. et al., "Morphine Down-Regulates Melanocortin-4 Receptor Expression in Brain Regions that Mediate Opiate Addiction", Mol-Pharmacol., 50(3):583-91 (1996); and Takeuchi, S. et al., "Melanocortin Receptor Genes in the Chicken-Tissue Distributions", Gen-Comp-Endocrinol., 112(2):220-31 (1998)

As used herein, "measurable" means the biologic effect is both reproducible and significantly different from the baseline variability of the assay.

A "pharmaceutically-acceptable salt" is a cationic salt formed at any acidic (carboxylic acid) group, or an anionic salt formed at any basic (e.g., amino) group and are known in the art, as described in WO 87/05297 (Johnston et al., 1987), incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there is none. For example, a chiral tartrate salt may be prepared from the compounds of the invention, and this definition includes such chiral salts. The skilled artisan is able to prepare any number of salts given the knowledge in the art. Furthermore, the skilled artisan may prefer one salt to another for reasons of solubility, stability, formulation ease and the like. Determination and optimization of such salts is within the purview of the skilled artisan's practice.

The phrase "specifically (or selectively) binds" to melanocortin receptor when referring to a protein or peptide, refers to a binding reaction that is determinative of the presence of the protein in a heterogeneous population of proteins and other biologics. Thus, under designated immunoassay conditions, the specified peptides bind to a particular melanocortin receptor at a greater rate than the background and do not substantially bind in a significant amount to other proteins present in the sample. Typically, a specific or selective reaction will be at least twice background signal or noise and more typically more than 10 to 100 times background.

As used herein, "selective" means having an activation preference for a specific receptor over other receptors which can be quantified based upon whole cell, tissue, or organism assays which demonstrate receptor activity, such as the cAMP enzyme immunoassay (EIA) system. A compound's selectivity is determined from a comparison of its EC$_{50}$ values at the relevant receptors being referenced. As used herein, use of the term "selective over the other MC receptors" means selective with respect to all other MC-R receptors. For example, a compound having an EC$_{50}$ of 8 nM at the MC-4 receptor and an EC$_{50}$ of >80 nM at the MC-1, MC-2, MC-3 and MC-5 receptors has a selectivity ratio for the MC-4 receptor over the other MC receptors of at least 1:10. Additionally, it will be recognized that selectivity may also refer to one of the MC-1, MC-2 or MC-5 receptors individually. For example, a compound having an $EC_{50}$ of 8 nM at the MC-4 receptor and an $EC_{50}$ of 80 nM at the MC-1 receptor has a selectivity ratio for the MC-4 receptor over the MC-1 receptor of 1:10. Such a compound is selective over the MC-1 receptor, regardless of its $EC_{50}$ value for MC-2 or MC-5.

As used herein, the terms "treat", "treating" and "treatment" include palliative, curative and prophylactic treatment.
Methods of Preparation The peptides of this invention can be prepared by standard solid phase peptide synthesis. See, e.g., Stewart, J. M., et al., Solid Phase Synthesis, (Pierce Chemical Co., 2d ed. 1984). Starting materials are commercially available or can be readily prepared by one of ordinary skill in the art using known methods. Solvents, temperatures, pressures and other reaction conditions may readily be selected by one of ordinary skill in the art.

The substituents $R^2$ and $R^3$ of the above generic formula may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBT.

When $R^1$ is —$NH_2$, the synthesis of the peptide starts with an Fmoc-amino acid which is coupled to the Rink Amide MBHA resin. If $R^1$ is —OH, the synthesis of the peptide starts with a Fmoc-amino acid which is coupled to Wang resin.

In the synthesis of a peptide of this invention containing A6c and/or Aib, the coupling time is 2 hours for these residues and the residue immediately following them.

The indicated steps may be varied to increase yield of desired product. The skilled artisan will recognize the judicious choice of reactants, solvents, and temperatures is an important component in any successful synthesis. Determination of optimal conditions is routine, thus the skilled artisan can make a variety of compounds using the guidance of the below descriptions.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions both electrophilic and nucleophilic, etherification, esterification and saponification and the like.

The skilled artisan will also readily appreciate that certain reactions are best carried out when potentially reactive functionalities on the molecule are masked or protected, thus avoiding any undesirable side reactions and/or increasing the yield of the reaction. It is recognized that it is preferable to use a protecting group for any reactive functionality such as a carboxyl, hydroxyl and the like. This is standard practice, well within the normal practice of the skilled artisan. These reactions are found in the literature and are also well within the scope of the skilled artisan.

Certain abbreviations used during the description of the synthesis of the representative examples that follow are defined as follows:

| | |
|---|---|
| Ac: | acyl group, i.e. $CH_3C(=O)$— |
| Boc: | tert-butyloxycarbonyl |
| Bzl: | benzyl |
| DCM: | dichloromethane |
| DIC: | N,N-diisopropylcarbodiimide |
| DIPEA: | diisopropylethyl amine |
| Dmab: | 4-{N-(1-(4,4-dimethyl-2,6-dioxocyclohexylidene)-3-methylbutyl)-amino} benzyl |
| DMAP: | 4-(dimethylamino)pyridine |
| DMF | dimethylformamide |
| DNP: | 2,4-dinitrophenyl |
| DTT: | dithiothrietol |
| Fm: | fluorenylmethyl |
| Fmoc: | fluorenylmethyloxycarbonyl |
| For: | formyl |
| HATU: | O-(7-azabenzothiazol-1-yl)-N,N,N',N'-tetramethyluronium-hexafluorophosphate |
| HBTU: | 2-(1H-benzotriazole-1-yl)-1,1,3,3-tetramethyluronium hexafluorophosphate |
| cHex: | cyclohexyl |
| HOAT: | O-(7-azabenzotriazol-1-yl)-1,1,3,3-tetramethyluronium hexafluorophosphate |
| HOBT: | 1-hydroxy-benzotriazole hydrate |
| MBHA: | 4-methylbenzhydrylamine |
| Mmt: | 4-methoxytrityl |
| Mtt: | N-e-4-methyltrityl |
| NMP: | N-methylpyrrolidone |
| ODmab: | 4{N-[1-(4,4-dimethyl-2,6-dioxo-cyclohexylidene)-3-methylbutyl]-amino}benzyloxy |
| O-tBu: | oxy-tert-butyl |
| Pbf: | 2,2,4,6,7-pentamethyldihydrobenzofuran-5-sulfonyl |
| PyAoP: | 7-azabenzotriazol-1-yloxytris(pyrrolidino)phosphonium-hexafluorophosphate |
| PyBroP: | bromo-tris-pyrrolidino-phosphonium hexafluorophosphate |
| tBu: | tert-butyl |
| TIS: | triisopropylsilane |
| TOS: | tosyl |
| Trt: | trityl |
| TFA: | trifluoroacetic acid |
| TFFH: | tramethylfluoroforamidinium hexafluorophosphate |
| Z: | benzyloxycarbonyl |

Representative examples for synthesizing representative compounds of the present invention are disclosed in Examples 1-5. The described methods for making a peptide of this invention employ methods that are well-known to those skilled in the art. Other methods are also known to those skilled in the art. The examples are provided for the purpose of illustration and are not meant to limit the scope of the present invention in any manner.

EXAMPLE 1 cyclo[Hydantoin(C(O)-(Cys-D-Ala))-His-D-Phe-Arg-Trp-Cys]-NH$_2$ (SEQ ID NO:1)

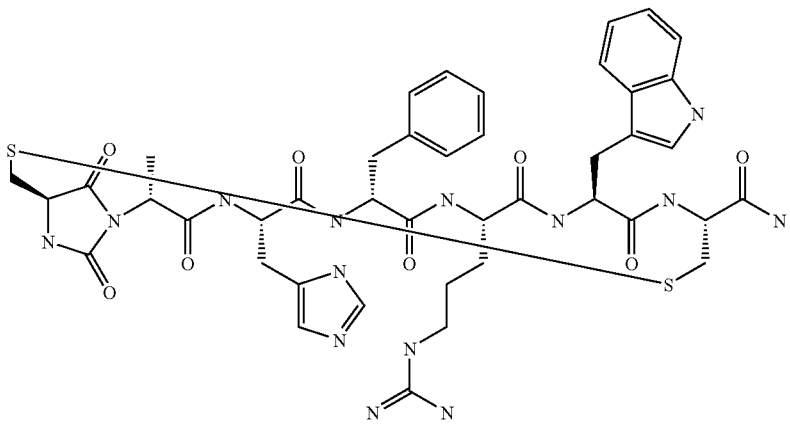

The hydantoin containing, cyclic peptide amide, cyclo[Hydantoin(C(O)-(Cys-D-Ala))-His-D-Phe-Arg-Trp-Cys]-NH$_2$ (SEQ ID NO:1) was assembled using Fmoc-chemistry on an Apex peptide synthesizer (AAPPTEC; Louisville, Ky., USA). To begin, 135 mg of 0.78 mmol/g (0.105 mmoles) Rink Amide MBHA resin (Novabiochem; San Diego, Calif., USA) was placed in a reaction well and pre-swollen in 1.5 mL of dimethylformamide (DMF) prior to synthesis. Cycle 1: The resin was treated with two 1.5 mL portions of 25% piperidine in DMF for 5 minutes and 25 minutes respectively, followed by 4 washes of 1.5 mL DMF; each wash consisting of adding 1.5 mL of solvent, mixing for 1 minute and then emptying for 1 minute. Amino acids stocks were prepared in N-methylpyrrollidinone (NMP) as 0.45 M solutions containing 0.45M N-hydroxybenzotriazole (HOBT). Diisopropylcarbodiimde (DIC) was prepared as a 1.3 M solution in NMP. To the de-blocked resin was added 1.45 mL (0.7 mmoles) of the first amino acid, Fmoc-cysteine(Trt)-OH (Novabiochem; San Diego, Calif., USA), along with 0.5 mL (0.65 mmoles) of DIC. After one hour of constant mixing the reagents were drained from the resin and the coupling step repeated. Following amino acid acylation, the resin was washed with two 1.5 mL aliquots of DMF; each washing lasting 1 minute in duration. The process of assembling the peptide (deblock/wash/acylate/wash) was repeated for cycles 2-7 which were conducted with the identical procedure described for cycle 1. In particular, the following amino acids were used, Cycle 2: Fmoc-Trp(Boc)-OH (Genzyme; Cambridge, Mass., USA); Cycle 3: Fmoc-Arg(Pbf)-OH (Novabiochem; San Diego, Calif., USA); Cycle 4: Fmoc-D-Phe-OH (Genzyme; Cambridge, Mass., USA); Cycle 5: Fmoc-His(Trt)-OH (Novabiochem; San Diego, Calif., USA); Cycle 6: Fmoc-D-Ala-OH (Genzyme; Cambridge, Mass., USA); and Cycle 7: Fmoc-Cys(Trt)-OH, (Novabiochem; San Diego, Calif., USA). The N-terminal Fmoc was removed with 25% piperidine in DMF which was followed by four 1.5 mL DMF washes lasting 1 minute per washing.

The peptide-resin was conditioned with several milliliters of 1,4-dioxane/water (9:1), drained, and then treated with 5.6 mL (80 eq) of 1.5M diisopropylethyl amine (DIPEA) in dioxane/water(9:1) followed by 1 mL of 0.32 M (3.0 eq) of phenylchloroformate in dioxane/water(9:1). The solution was mixed for 1 hour, drained and washed with dioxane/water several times followed by ethyl ether several times. The resin was then treated with 0.5 M DIPEA in DMF and mixed for two hours. The resin was again washed with dioxane/water followed by an ethyl ether.

To the resulting peptide-resin, 5 mL of the following reagent was added: 2% triisopropylsilane (TIS), 5% water, 5% (w/v) dithiothrieitol (DTT), 88% trifluoroacetic acid (TFA); and the mixture was allowed to blend for 3.5 hours. The filtrate that formed was collected into 40 mL of cold anhydrous ethyl ether. The precipitate was pelleted for 10 minutes at 3500 RPM in a refrigerated centrifuge. The ether was decanted and the peptide re-suspended in fresh ether. The ether workup was performed a total of 3 times. Following the last ether wash, the peptide was allowed to air dry to remove any residual ether.

The peptide was dissolved in 10% acetonitrile and analyzed by mass spectrometry and reverse-phase HPLC employing a 30×4.6 cm C18 column (Vydac; Hesperia, Calif., USA) with a gradient of 2-60% acetonitrile (0.1% TFA) over 30 minutes. This analysis identified a product with >42% purity with the remainder being primarily the non-hydantoin containing product. Mass analysis employing electrospray ionization identified a main product containing a mass of 947.42 da which corresponds to the desired reduced product. The crude product (~95 mg) was diluted to a concentration of 2 mg/mL in 5% acetic acid. To this solution 0.5 M iodine/methanol was added drop wise with vigorous stirring until a pale yellow color was achieved. The solution was vigorously stirred for another 10 minutes. Excess iodine was then quenched by adding 1.0 M sodium thiosulfate under continuous mixing until the mixture was rendered colorless. The peptide was re-examined by mass spectrometry analysis and HPLC. Mass spectrometry analysis identified a main species with a mass of 944.44, suggesting successful oxidation of the peptide. The peptide solution was concentrated to ~10 mL using a centrifugal evaporator and then purified on a preparative HPLC equipped with a C18 column using a similar elution gradient. The purified product was re-analyzed by HPLC for purity (>95%) and mass spectrometry (945.1 da) and subsequently lyophilized. Following lyophillization 13.6 mg of purified product was obtained representing a 13.7% yield.

EXAMPLE 2 cyclo[Hydantoin(C(O)-(Glu-D-Ala))-His-D-Phe-Arg-Trp-Dap]-NH$_2$ (SEQ ID NO:11)

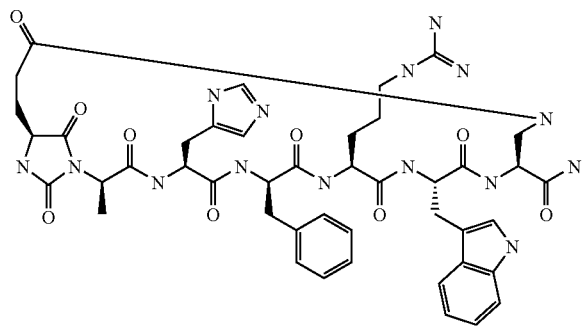 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CNC(=O)CC[C@@H]2NC(=O)N1C2=O]

The hydantoin-containing, peptide lactam cyclo[Hydantoin(C(O)-(Glu-D-Ala))-His-D-Phe-Arg-Trp-Dap]-NH$_2$ (SEQ ID NO:11) was assembled using Fmoc-chemistry on an Apex peptide synthesizer (AAPPTEC; Louisville, Ky., USA). To start, 135 mg of 0.78 mmol/g (0.105 mmoles) Rink Amide MBHA resin (Novabiochem; San Diego, Calif., USA) was placed in a reaction well and pre-swollen in 1.5 mL of dimethylformamide (DMF). Cycle 1: The resin was treated with two 1.5 mL portions of 25% piperidine in DMF for 5 and 10 minutes, respectively, followed by 4 washes of 1.5 mL DMF; each wash consisting of adding 1.5 mL of solvent, mixing for 1 minute then emptying for 1 minute. Amino acids stocks were prepared in N-methylpyrrollidinone (NMP) as 0.45 M solutions containing 0.45 M N-hydroxybenzotriazole (HOBT). Diisopropylcarbodiimide (DIC) was prepared as a 1.3 M solution in NMP. To the de-blocked resin, 1.45 mL of the first amino acid (0.62 mmoles), i.e., Fmoc-Dap(Mtt)-OH (Novabiochem; San Diego, Calif., USA), was added together with 0.5 mL (0.62 mmoles) of DIC. After one hour of constant mixing, the reagents were drained off and the coupling step repeated. Following amino acid acylation, the resin was washed with two 1.5 mL aliquots of DMF for 1 minute per wash. The process of assembling the peptide (deblock/wash/acylate/wash) was repeated for cycles 2-7 which were identical to cycle 1, as described above. The following amino acids were used, respectively for the cycles as indicated: Cycle 2: Fmoc-trp(Boc)-OH (Genzyme; Cambridge, Mass., USA); Cycle 3: Fmoc-Arg(Pbf)-OH (Genzyme; Cambridge, Mass., USA); Cycle 4: Fmoc-D-Phe-OH (Novabiochem; San Diego, Calif., USA): Cycle 5: Fmoc-His(Trt)-OH (Genzyme; Cambridge, Mass., USA); Cycle 6: Fmoc-D-Ala-OH, (Genzyme; Cambridge, Mass., USA); and Cycle 7: Fmoc-Glu(O-2-PhiPr)-OH (Bachem, King of Prussia, Pa.). The N-terminal Fmoc was removed with 25% piperidine in DMF followed by four, 1 minute washings with 1.5 mL DMF then three, 1 minute washings with dichloromethane (DCM).

The resin was conditioned with 80 eq of 1.5 M diisopropylethylamine (DIPEA) in DCM followed by 2.0 eq of p-nitrophenylchloroformate in DCM. The solution was mixed for 2 hours, drained and washed with DMF several times. The resin was then treated with 10 eq of DIPEA in DMF and mixed for 30 minutes. The resin was washed with DMF and thereafter with DCM.

The Mtt (methyltrityl) side-chain protecting group of diaminopropionic acid (Dap) as well as the O-2-PhiPr (0-2-phenylisopropyl) side-chain protecting group of glutamic acid (Glu) were both removed after 10 washes of 5 mL of 5% triisopropylsilane (TIS) and 1% trifluoroacetic acid (TFA) in DCM for 3-5 minutes each. Following the last wash, the resin was again washed first with DCM and then twice with DMF. The resin was treated twice with DIPEA (10 eq) in DMF for 2 minute treatments followed by 4 washes with DMF. An aliquot of resin (<1 mg) gave a positive Kaiser test (positive control: dark blue color). The resin was then treated with the 10 eq 0.5 M HOBT, 10 eq of 0.5 M PyAop, 20 eq of 2 M DIPEA and 0.5 eq of 0.45 M DMAP for 8 hours with constant stirring. A follow-up Kaiser test was slightly positive indicating incomplete lactam formation. A second round of lactam forming conditions was employed using 10 eq of 0.5 M HOAT, 2 eq of 0.5 M HATU, 20 eq of 1 M DIPEA, and 0.5 eq of 0.45 M DMAP with constant stirring for 4 hours. A follow-up Kaiser test was negative (no visible blue color) for the presence of a free amine. The resin was washed once with DMF then three times with DCM.

Approximately 5 mL of the following reagent was added to the resin: 2% TIS, 5% water, 5% (w/v) dithiothrieitol (DTT) and 88% TFA; which was allowed to mix for 3.5 hours. The filtrate was collected into 40 mL of cold anhydrous ethyl ether. The precipitate was pelleted for 10 minutes at 3500 RPM in a refrigerated centrifuge. The ether was decanted and the peptide re-suspended in fresh ether. The ether workup was performed a total of 3 times. Following the last ether wash, the peptide was allowed to air dry to remove residual ether. The resulting peptide was dissolved in 10% acetonitrile and analyzed by mass spectrometry. A single product with a mass of 938.7 da was identified, corresponding to the desired hydantoin-lactam peptide-product. The crude product (~90 mg) was purified on a preparative HPLC equipped with a C$_{18}$ column using a suitable elution gradient. The purified product was re-analyzed by HPLC for purity (>95%) and lyophilized resulting in 24 mg of product obtained representing a yield of 25%.

EXAMPLE 3 cyclo[Hydantoin(C(O)-(Gly-Cys))-Glu-His-D-Phe-Arg-Trp-Cys]-NH$_2$ (SEC/ID NO:57)

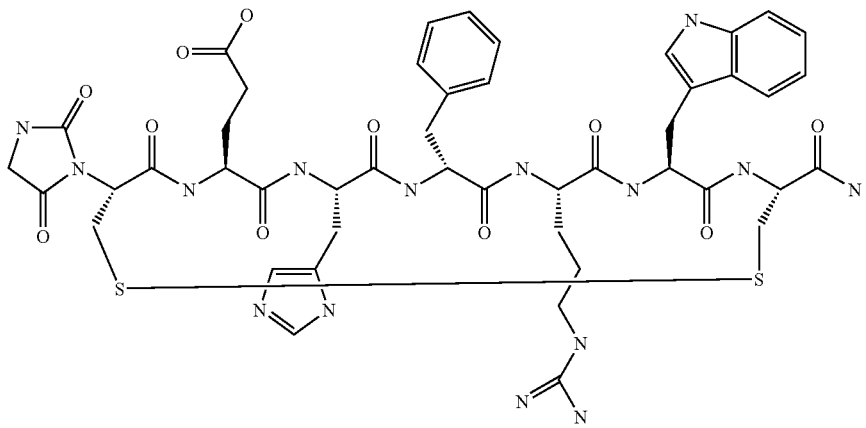 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](N2C(=O)CNC2=O)CSSC[C@@H](C(N)=O)NC(=O)[C@H](Cc2c[nH]c3ccccc23)NC1=O]

The hydantoin containing cyclic peptide amide cyclo[Hydantoin(C(O)-(Gly-Cys))-Glu-His-D-Phe-Arg-Trp-Cys]-NH$_2$ (SEQ ID NO:57) was assembled using Fmoc-chemistry on an Apex peptide synthesizer (AAPPTEC, Louisville, Ky., USA). Prior to the commencement of the synthesis, 220 mg of 0.91 mmol/g (0.20 mmoles) Rink Amide MBHA resin (Polymer Laboratories, Amherst, Mass., USA) was placed in a reaction well and pre-swollen in 3.0 mL of dimethylformamide (DMF). Cycle 1: The resin was treated with two 3 mL portions of 25% piperidine in DMF for 5 and 10 minutes intervals, respectively, which were followed by 4 washes of 3 mL DMF; each wash consisting of introducing 3 mL of solvent, mixing for 1 minute and emptying for 1 minute. Amino acids stocks were prepared in N-methylpyrrollidinone (NMP) as 0.45 M solutions containing 0.45 M N-hydroxybenzotriazole (HOBT). HBTU [2-(1H-benzo-triazole-1-yl)-1,1,3,3-tetramethyluronium hexafluorophosphate] was prepared as a 0.45 M solution in NMP and diisopropylethylamine (DIPEA) was prepared as a 2.73 M solution in NMP. To the de-blocked resin, 2 mL of the first amino acid (0.9 mmoles), Fmoc-Cys(Trt)-OH (Novabiochem; San Diego, Calif., USA) was added along with 2 mL (0.9 mmoles) of HBTU and 1.5 mL (4.1 mmoles) of DIPEA. After one hour of constant mixing, the reagents were drained off and the coupling step repeated. Following amino acid acylation, the resin wash washed with two 3 mL aliquots of DMF for 1 minute intervals. The process of assembling the peptide (deblock/wash/acylate/wash) was repeated for cycles 2-8 which were identical cycle 1 as described above. The following amino acids were used: Cycle 2: Fmoc-Trp(Boc)-OH (Genzyme; Cambridge, Mass., USA); Cycle 3: Fmoc-Arg(Pbf)-OH (Novabiochem; San Diego, Calif., USA); Cycle 4: Fmoc-D-Phe-OH (Genzyme; Cambridge, Mass., USA); Cycle 5: Fmoc-His(Trt)-OH (Novabiochem; San Diego, Calif., USA); Cycle 6: Fmoc-Glu-OH (Genzyme; Cambridge, Mass., USA); Cycle 7: Fmoc-Cys(Trt)-OH, (Novabiochem; San Diego, Calif., USA); and Cycle 8: Fmoc-Gly-OH (Novabiochem; San Diego, Calif., USA). The N-terminal Fmoc was removed with 25% piperidine in DMF as discussed previously followed by four, 1 minute washes of 3 mL DMF.

The resin was conditioned with 80 eq of 1.5M DIPEA in dichloromethane (DCM) followed by the addition of 1.1 eq of p-nitrophenylchloroformate in DCM. The solution was mixed for 2 hours, drained and washed with DMF several times. The resin was then treated with 10 eq of DIPEA in DMF and mixed for 30 minutes. The resin was again washed with DMF followed by a DCM wash.

To the resin, 5 mL of the following reagent was added and allowed to mix for 3½ hours: 2% triisopropylsilane (TIS), 5% water, 5% (w/v) dithiothrieitol (DTT) and 88% trifluoroacetic acid (TFA). The filtrate that formed was collected into 40 mL of cold anhydrous ethyl ether. The precipitate was pelleted for 10 minutes at 3500 RPM in a refrigerated centrifuge. The ether was decanted and the collected peptide was re-suspended in fresh ether. The ether workup was performed 3 times. Following the last ether wash, the peptide was air dried to remove residual ether.

The dried peptide was dissolved in 10% acetonitrile and analyzed by mass spectrometry and reverse-phase HPLC analysis using a 30×4.6 cm C$_{18}$ column (Vydac; Hesperia, Calif., USA) with a gradient of 2-60% acetonitrile (0.1% TFA) for a period of 30 minutes. The HPLC analysis identified a product that was 30% pure. The non-hydantoin containing product accounted for the remaining percentage. Mass analysis employing electrospray ionization identified a main product containing a mass of 1062 da corresponding to the desired reduced product. The crude product (~200 mg) was diluted to a concentration of 2 mg/mL in 5% acetic acid. To this solution, 0.5 M iodine/methanol was added drop-wise with vigorous stirring until a pale yellow color was achieved. The solution was vigorously stirred for another 10 minutes. Excess iodine was then quenched by adding 1.0 M sodium thiosulfate under continuous mixing until the mixture was rendered colorless. The peptide was re-examined by mass spectrometry analysis and HPLC. Mass spectrometry analysis identified a main species with mass of 1060.4 da suggesting successful oxidation of the peptide. The peptide solution was concentrated to ~10 mL using a centrifugal evaporator and then purified on a preparative HPLC equipped with a C18 column using a similar elution gradient. The purified product was re-analyzed by HPLC for purity (>95%) and mass spectrometry (1059.7 da) and subsequently lyophilized. Following lyophillization, 16.8 mg of purified product was collected; a 7.9% yield.

EXAMPLE 4

Hydantoin(C(O)-(Gly-D-Arg))-cyclo(Cys-Glu-His-D-Phe-Arg-Trp-Cys)-NH$_2$ (SEQ ID NO:42)

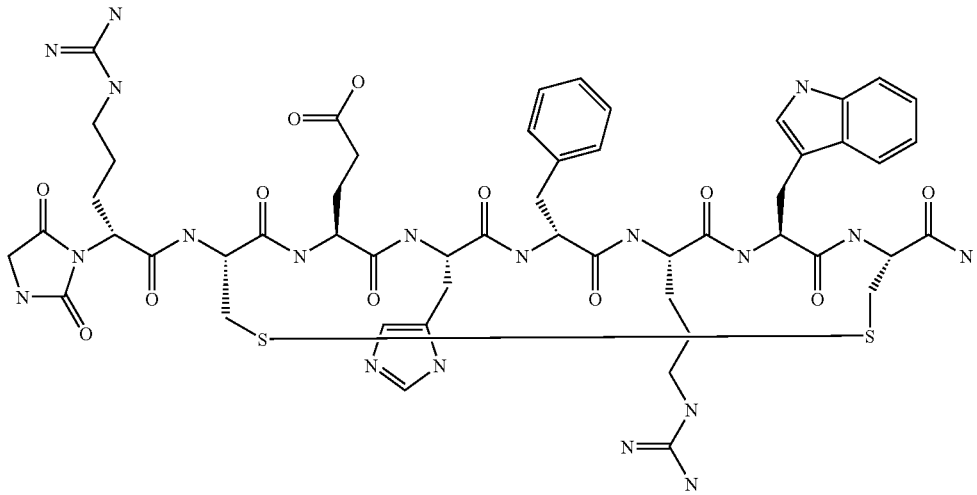 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)[C@@H](CCCNC(=N)N)N2C(=O)CNC2=O)CSSC[C@@H](C(N)=O)NC(=O)[C@H](Cc2c[nH]c3ccccc23)NC1=O]

The hydantoin containing, cyclic peptide amide, Hydantoin(C(O)-(Gly-D-Arg))-cyclo(Cys-Glu-His-D-Phe-Arg-Trp-Cys)-NH$_2$, (SEQ ID NO:42) was assembled using Fmoc-chemistry on an Apex peptide synthesizer (APAPPTEC; Louisville, Ky., USA). Prior to the commencement of the synthesis of the titled compound, 220 mg of 0.91 mmol/g (0.20 mmoles) Rink Amide MBHA resin (Polymer Laboratories, Amherst, Mass., USA) was placed in a reaction well to pre-swell in 3.0 mL of dimethylformamide (DMF). Cycle 1: The resin was treated with two 3 mL portions of 25% piperidine in DMF for 5 and 10 minutes intervals, respectively, which were followed by 4 washes of 3 mL DMF; each wash consisting of the steps of adding 3 mL of solvent, mixing for 1 minute and then emptying for 1 minute. Amino acids stocks were prepared in N-methylpyrrollidinone (NMP) as 0.45 M solutions containing 0.45 M N-hydroxybenzotriazole (HOBT). HBTU [2-(1H-benzo-triazole-1-yl)-1,1,3,3-tetramethyluronium hexafluorophosphate] was prepared as a 0.45 M solution in NMP. Diisopropylethylamine (DIPEA) was prepared as a 2.73 M solution in NMP. To the de-blocked resin, 2 mL of the first amino acid (0.9 mmoles), i.e., Fmoc-Cys(Trt)-OH (Novabiochem; San Diego, Calif., USA) was added along with 2 mL (0.9 mmoles) of HBTU and 1.5 mL (4.1 mmoles) of DIPEA. After one hour of constant mixing, the reagents were drained off and the coupling step repeated. Following the amino acid acylation process, the resin wash washed with two 3 mL aliquots of DMF for 1 minute periods. The peptide assembly process, i.e., de-blocking, washing, acylating and washing as described above for cycle 1, was repeated for cycles 2-9. In each particular cycle, the following amino acids were used, as indicated: Cycle 2: Fmoc-Trp (Boc)-OH (Genzyme; Cambridge, Mass., USA); Cycle 3: Fmoc-Arg(Pbf)-OH (Novabiochem; San Diego, Calif., USA); Cycle 4: Fmoc-D-Phe-OH (Genzyme; Cambridge, Mass., USA); Cycle 5: Fmoc-His(Trt)-OH (Novabiochem; San Diego, Calif., USA); Cycle 6: Fmoc-Glu-OH (Genzyme; Cambridge, Mass., USA); Cycle 7: Fmoc-Cys(Trt)-OH, (Novabiochem; San Diego, Calif., USA); Cycle 8: Fmoc-D-Arg(Pbf)-OH (Genzyme; Cambridge, Mass., USA); and Cycle 9: Fmoc-Gly-OH (Novabiochem; San Diego, Calif., USA). The N-terminal Fmoc protecting group was removed with a solution of 25% piperidine in DMF, as previous described, followed by four 3 mL DMF washes lasting 1 minute each.

The resin was conditioned with 80 eq of 1.5 M DIPEA in dichloromethane (DCM) followed by the addition of 1.1 eq of p-nitrophenylchloroformate in DCM. The reaction was mixed for 2 hours, the solvent was drained off and the resulting product was washed with DMF several times. The resin was treated with 10 eq of DIPEA in DMF and mixed for approximately 30 minutes. The resin was washed with DMF followed by DCM.

To the resin, 5 mL of the following reagent was added: 2% triisopropylsilane (TIS), 5% water, 5% (w/v) dithiothrieitol (DTT) and 88% trifluoroacetic acid (TFA). The solution was mixed for 3.5 hours. The filtrate was collected into 40 mL of cold anhydrous ethyl ether. The precipitate was pelleted for 10 minutes at 3500 RPM in a refrigerated centrifuge. The ether was decanted and the peptide was re-suspended in fresh ether. The ether workup was repeated 3 additional times. Following the last ether wash, the peptide air dried to remove residual ether.

The peptide was dissolved in 10% acetonitrile and analyzed by mass spectrometry and reverse-phase HPLC using a 30×4.6 cm C$_{18}$ column (Vydac; Hesperia, Calif., USA) with a gradient of 2-60% acetonitrile (0.1% TFA) over a 30 minute period. The described analysis indicated that the resulting product was ~30% pure, the remainder being primarily non-hydantoin containing product. Mass spectral analysis by electrospray ionization, indicated the mass of the main product to be 1218 da which was consistent with the expected, reduced product. The crude product (~200 mg) was diluted to a concentration of 2 mg/mL in 5% acetic acid. To this solution, a 0.5 M iodine/methanol mixture was added drop-wise with vigorous stirring until a pale yellow color was achieved. The solution was stirred vigorously for 10 minutes. Excess iodine was quenched by adding 1.0 M sodium thiosulfate, under continuous mixing, to the mixture until rendered colorless. The peptide was re-examined by mass spectrometry analysis and HPLC. The mass spectrometry analysis identified a main species with a mass of 1216.4 da suggesting the successful oxidation of the peptide. The peptide solution was concentrated to ~10 mL using a centrifugal evaporator and purified on a preparative HPLC equipped with a C18 column using a similar elution gradient. The purified product was re-analyzed by HPLC for purity (>95%) and mass spectrometry (1216.4 da) and subsequently lyophilized. Following lyophillization, 18.4 mg of purified product was obtained representing a 7.5% yield.

EXAMPLE 5

Hydantoin(C(O)-(Arg-Gly))-cyclo(Cys-Glu-His-D-Phe-Arg-Trp-Cys)-NH$_2$ (SEQ ID NO:13)

(Novabiochem; San Diego, Calif., USA); cycle 6: Fmoc-Glu(OtBu)-OH (Genzyme; Cambridge, Mass., USA) cycle 7: Fmoc-Cys(Trt)-OH, (Novabiochem; San Diego, Calif., USA); cycle 8: Fmoc-Gly-OH (Novabiochem; San Diego, Calif., USA); and cycle 9: Fmoc-Arg(Pbf)-OH (Genzyme; Cambridge, Mass., USA). The N-terminal Fmoc-protecting group was removed with a solution of 25% piperidine in DMF followed by four 1 minute washes with 3.0 mL DMF. The resin was washed four times with 3.0 mL DCM; each washing

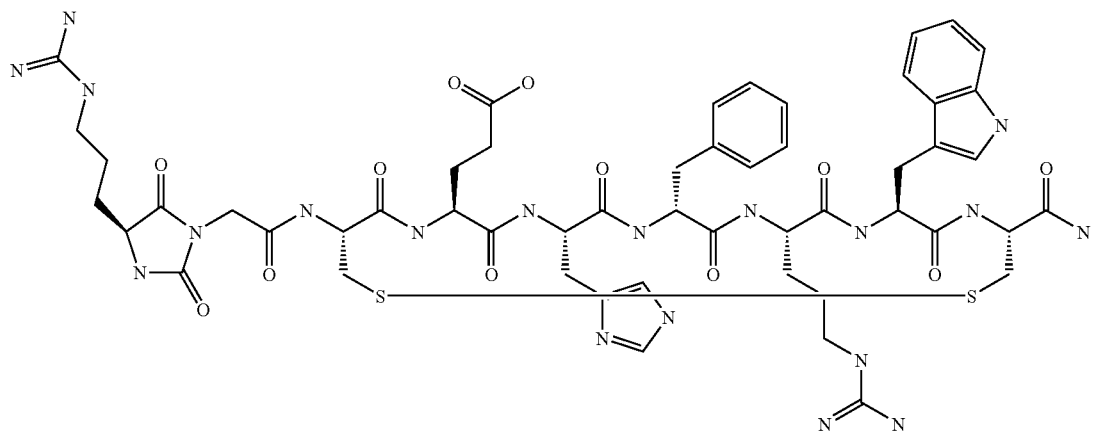 [SMILES: N=C(N)NCCC[C@@H]1NC(=O)[C@@H](Cc2ccccc2)NC(=O)[C@H](Cc2c[nH]cn2)NC(=O)[C@H](CCC(=O)O)NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC1=O]

The peptide, Hydantoin(C(O)-(Arg-Gly))-cyclo(Cys-Glu-His-D-Phe-Arg-Trp-Cys)-NH$_2$ (SEQ ID NO:13) was assembled using Fmoc-chemistry on an Apex peptide synthesizer (AAPPTEC; Louisville, Ky., USA). In ten separate reaction wells of the synthesizer, a 270 mg of 0.74 mmol/g (0.20 mmoles) Rink Amide MBHA resin (Novabiochem; San Diego, Calif., USA) aliquot was and pre-swollen in 3.0 mL of dimethylformamide (DMF). Cycle 1: The resin was treated with two 3.0 mL portions of 25% piperidine in DMF for 5 and 10 minutes intervals, respectively, followed by 4 washes of 3.0 mL DMF. Each wash consisted of adding 3.0 mL of solvent, mixing for 1 minute and emptying for 1 minute. Amino acids stocks were prepared in N-methylpyrrollidinone (NMP) as 0.45 M solutions containing 0.45 M N-hydroxybenzotriazole (HOBT). Diisopropylcarbodiimde (DIC) was prepared as a 0.5 M solution in NMP. To the de-blocked resin, 2.25 mL of the first amino acid (1.0 mmoles), i.e., Fmoc Cys(Trt)-OH (Novabiochem; San Diego, Calif., USA), was added along with 2.0 mL (1.0 mmoles) of DIC. After one hour of constant mixing, the reagents were drained and the coupling step repeated. Following amino acid acylation, the resin was washed with two 3.0 mL aliquots of DMF each wash lasting 1 minute. The above-described process steps for the cycle 1, i.e., de-blocking, washing, acylating and washing, were repeated for cycles 2-9 with the following amino acids: cycle 2: Fmoc-Trp(Boc)-OH (Genzyme; Cambridge, Mass., USA); cycle 3: Fmoc-Arg(Pbf)-OH (Novabiochem; San Diego, Calif., USA); cycle 4: Fmoc-D-Phe-OH (Genzyme; Cambridge, Mass., USA); cycle 5: Fmoc-His(Trt)-OH lasting approximately 1 minute in duration. The resins from each of the 10 wells were combined. A small aliquot of the combined resin was obtained and the peptide attached thereto was de-protected and cleaved off so that the integrity of the main-chain assembly of the linear peptide could be determined by HPLC and MS analysis.

The peptide-resin was transferred to a 500 mL reaction vessel equipped with a filter frit at the bottom. The resin was conditioned with several deciliters of DMF for several minutes which was drained off. A solution comprising 45 mL (86 eq) of 3.8 M diisopropylethylamine (DIPEA) in dichloromethane (DCM) was then added followed by drop-wise addition of 15.5 mL of 0.3 M (2.3 eq) of phenylchloroformate in DCM. The reaction vessel was gently mixed on an orbital shaker for 3 hours with gentle nitrogen bubbling. DCM was added periodically during the 3 hours of mixing to replace DCM lost due to evaporation. The liquid portion was then drained off. The resin was washed with DMF several times and treated for 10 minutes with a solution of 10 eq DIPEA in DMF which was later drained off. The base treatment (DIPEA) formed the hydantoin moiety with the concomitant liberation of p-nitrophenol, evident by the presence of yellow colored solvent. The 10 minute base treatment was repeated until there was no longer evidence of p-nitrophenol being released. The resin was washed with DMF followed by DCM.

To the resulting hydantoin-peptidyl resin, 80 mL of the following reagent was added: 6% triisopropylsilane (TIS), 2% water, 5% (w/v) dithiothrieitol (DTT) and 87% trifluoroacetic acid (TFA) which was allowed to mix for 4.5 hours. A filtrate was collected into 1000 mL of cold anhydrous ethyl ether which was pelleted for 30 minutes in a refrigerated centrifuge at 4200 RPM. The ether was decanted. The peptide was re-suspended in fresh ether and subjected to a second centrifugation. The ether was decanted and the peptide air dried to remove residual ether.

The peptide was dissolved in 10% acetonitrile for analysis by mass spectrometry and reverse-phase HPLC, which was performed in a 30 minute period with UV detection at 220 nm using a Luna C18(2), 56100A 250×4.6 mm column (Phenomenex; Torrance, Calif., USA) having a gradient of 2-80% acetonitrile (0.1% TFA). This analysis identified a single major product that was more than 70% pure. The non-hydantoin containing product accounted for the remainder of the product. Mass was analyzed with electrospray ionization techniques identifying ions of 407.2, 610.0 and 1218.4 corresponding to the MH+3, MH+2 and MH+1 ions, respectively, of mass 1218.4 da which was consistent with the desired linear product. The crude product (~2.4 g) was diluted to a concentration of 2 mg/mL in 5% acetic acid. To this solution, 0.5 M iodine/methanol was added drop-wise with vigorous stirring until a pale yellow color was observed. The solution was stirred vigorously for 10 minutes. Excess iodine was quenched by adding 1.0 M sodium thiosulfate drop-wise with continuous mixing until the mixture was observed to be colorless. The peptide was re-examined by mass spectrometry which identified the main species having a mass of 1216.4 da evidencing the successful oxidation of the peptide to the disulfide product. The peptide solution was concentrated to ~500 mL using a centrifugal evaporator and then purified on a preparative HPLC equipped with a Luna C18(2), 5 ⊕ 100Å250×21.2 mm preparative HPLC column (Phenomenex; Torrance, Calif., USA) having an elution gradient of 10-50% acetonirile (0.1% TFA) over 40 minutes with UV detection at 290 nm. The purified product was re-analyzed by HPLC for purity (>99%). Additional mass spectrometry analysis indicated a product with a mass of 1216.2 da consistent with the calculated molecular weight of the desired peptide 1216.4 da. Following lyophillization, 334 mg of purified product was obtained representing a 14% yield.

Additional compounds may be synthesized using the guidance of the examples as detailed above, including, but not limited to, the following compounds:

cyclo[Hydantoin(C(O)-(Asp-His))-D-2-Nal-Arg-Trp-Lys]-NH$_2$, (SEQ ID NO:5) which has the following structure:

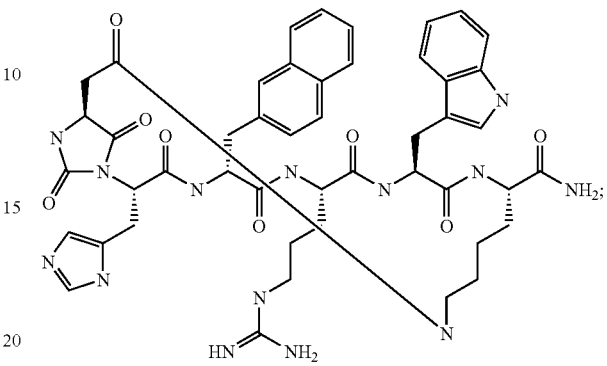

cyclo[Hydantoin(C(O)-(Glu-His))-D-Phe-Arg-Trp-Lys]NH$_2$, (SEQ ID NO:61) which has the following structure:

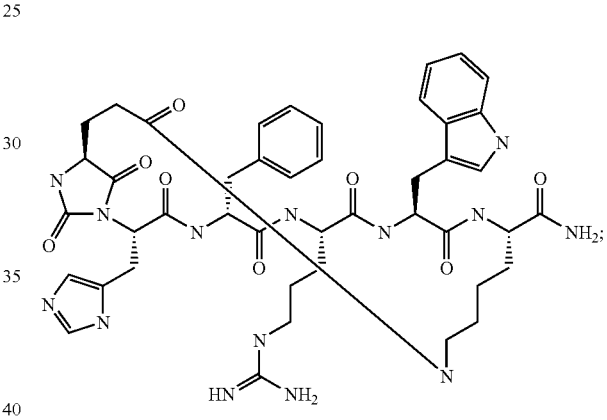

cyclo[Hydantoin(C(O)-(Cys-D-Ala)-His-D-Phe-Arg-Trp-Cys]-NH$_2$, (SEQ ID NO:1) which has the following structure:

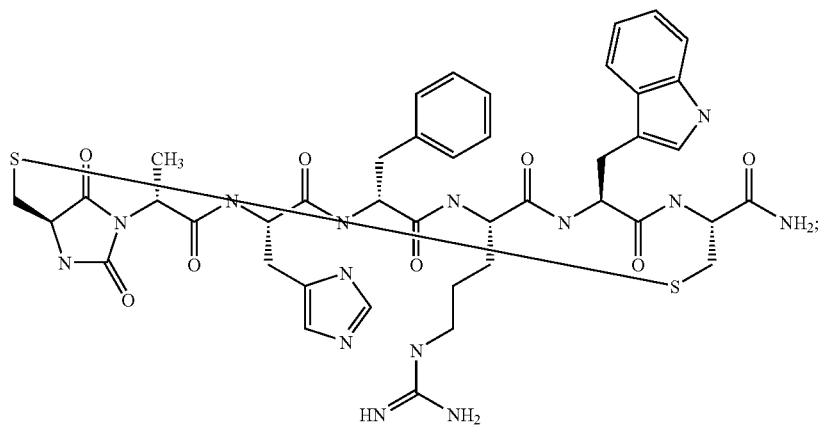 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CSSC[C@@H]2NC(=O)N1C2=O]

cyclo[Hydantoin(C( ))-(Asp-His))-D-Phe-Arg-Trp-Lys]-NH$_2$, (SEQ ID NO:5) which has the following structure:

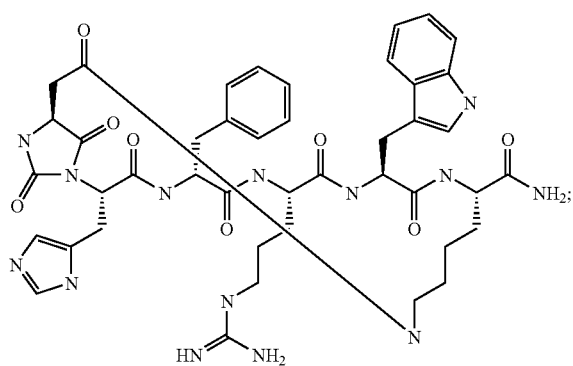 [SMILES: N=C(N)NCCC[C@@H]1NC(=O)[C@@H](Cc2ccccc2)NC(=O)[C@H](Cc2cnc[nH]2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-A6c))-D-Phe-Arg-Trp-Lys]-NH$_2$, (SEQ ID NO:8) which has the following structure:

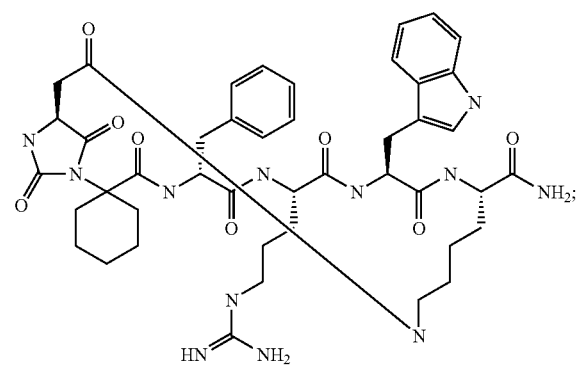

cyclo[Hydantoin(C(O)-(Asp-Aic))-D-Phe-Arg-Trp-Lys]-NH$_2$, (SEQ ID NO:9) which has the following structure:

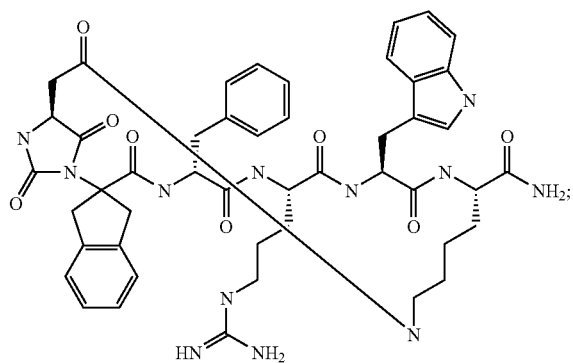 [SMILES: N=C(N)NCCC[C@@H]1NC(=O)[C@@H](Cc2ccccc2)NC(=O)C2(Cc3ccccc3C2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-Apc))-D-Phe-Arg-Trp-Lys]-NH$_2$, (SEQ ID NO:10) which has the following structure:

cyclo[Hydantoin(C(O)-(Asp-A5c))-D-Phe-Arg-Trp-Lys]-NH$_2$, (SEQ ID NO:7) which has the following structure:

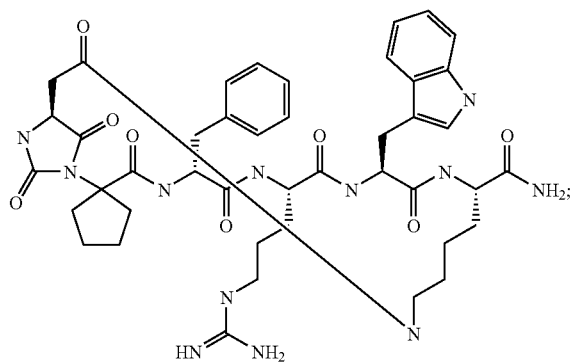 [SMILES: N=C(N)NCCC[C@@H]1NC(=O)[C@@H](Cc2ccccc2)NC(=O)C2(CCCC2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-A3c))-D-Phe-Arg-Trp-Lys]-NH$_2$, (SEQ ID NO:6) which has the following structure:

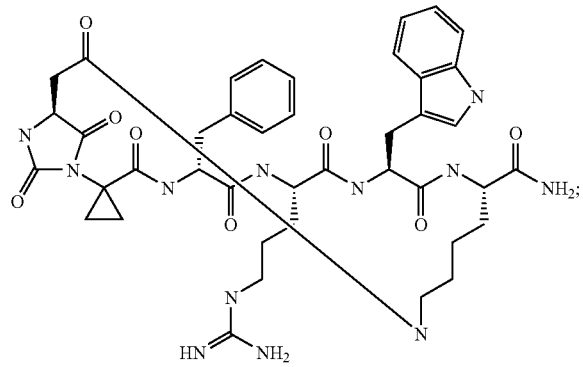 [SMILES: N=C(N)NCCC[C@@H]1NC(=O)[C@@H](Cc2ccccc2)NC(=O)C2(CC2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-Aic))-D-2-Nal-Arg-Trp-Lys]-NH$_2$, (SEQ ID NO:9) which has the following structure:

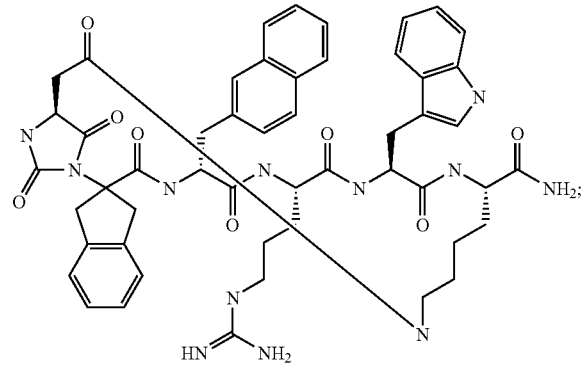 [SMILES: N=C(N)NCCC[C@@H]1NC(=O)[C@@H](Cc2ccc3ccccc3c2)NC(=O)C2(Cc3ccccc3C2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-A5c))-D-2-Nal-Arg-Trp-Lys]-NH$_2$, (SEQ ID NO:7) which has the following structure:

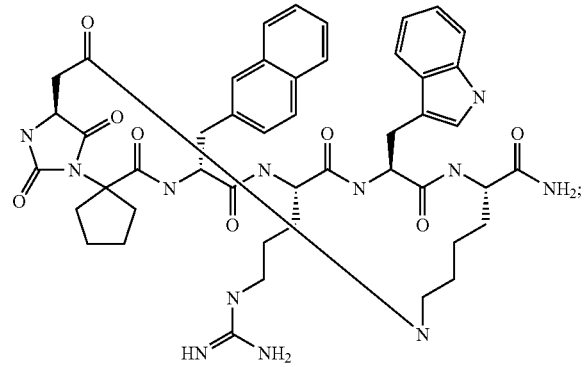 [SMILES: N=C(N)NCCC[C@@H]1NC(=O)[C@@H](Cc2ccc3ccccc3c2)NC(=O)C2(CCCC2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-A6c))-D-2-Nal-Arg-Trp-Lys]-NH$_2$, (SEQ ID NO:8) which has the following structure:

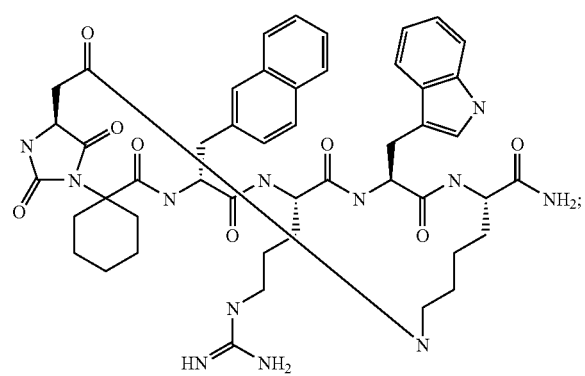 [SMILES: N=C(N)NCCC[C@@H]1NC(=O)[C@@H](Cc2ccc3ccccc3c2)NC(=O)C2(CCCCC2)N2C(=O)N[C@@H](CC(=O)NCCCC[C@@H](C(N)=O)NC(=O)[C@H](Cc3c[nH]c4ccccc34)NC1=O)C2=O]

cyclo[Hydantoin(C(O)-(Asp-Apc))-D-2-Nal-Arg-Trp-Lys]-NH$_2$, (SEQ ID NO:10) which has the following structure:

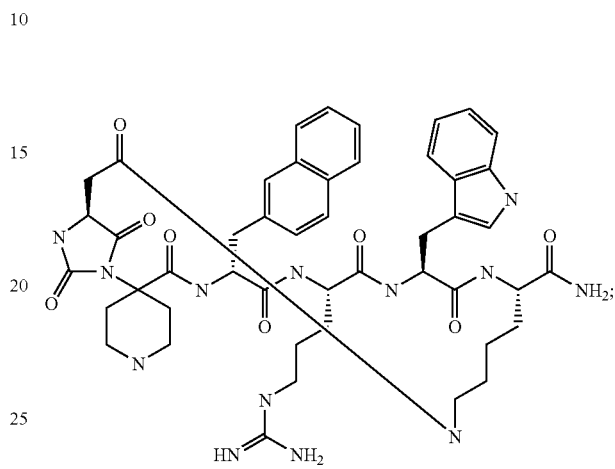

cyclo[Hydantoin(C(O)-(Asp-A3c))-D-2-Nal-Arg-Trp-Lys]-NH$_2$, (SEQ ID NO:6) which has the following structure:

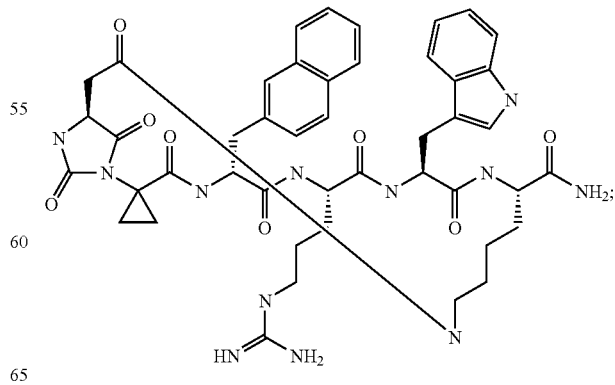

cyclo[Hydantoin(C)(O)-(hCys-D-Ala))-His-D-Phe-Arg-Trp-Cys]-NH₂, (SEQ ID NO:2) which has the following structure:
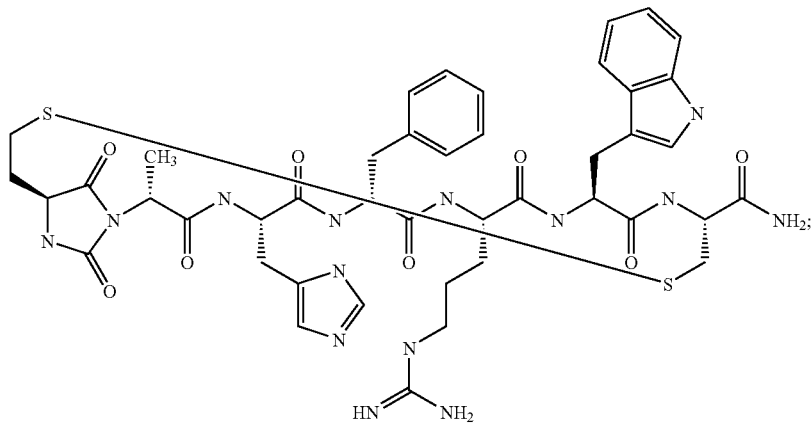 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CSSCC[C@@H]2NC(=O)N1C2=O]
[Hydantoin(C(O)-(Nle-Gly))-cyclo(Cys-Glu-His-D-Phe-Arg-Trp-Cys)]-NH₂, (SEQ ID NO:62) which has the following structure:
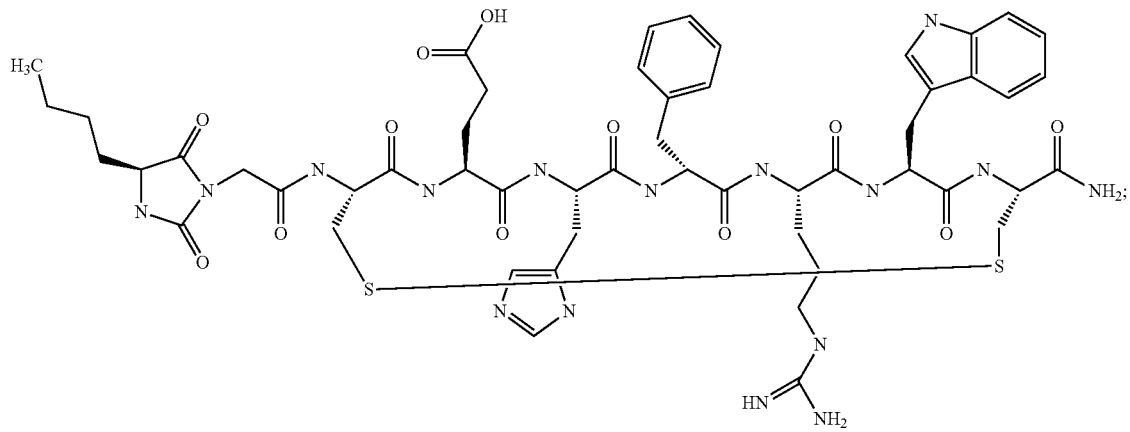 [SMILES: CCCC[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@H](CCC(=O)O)NC2=O)C1=O]
[Hydantoin(C(O)-(Gly-Gly))-cyclo(Cys-Glu-His-D-Phe-Arg-Trp-Cys)]—NH₂, (SEQ ID NO:63) which has the following structure:
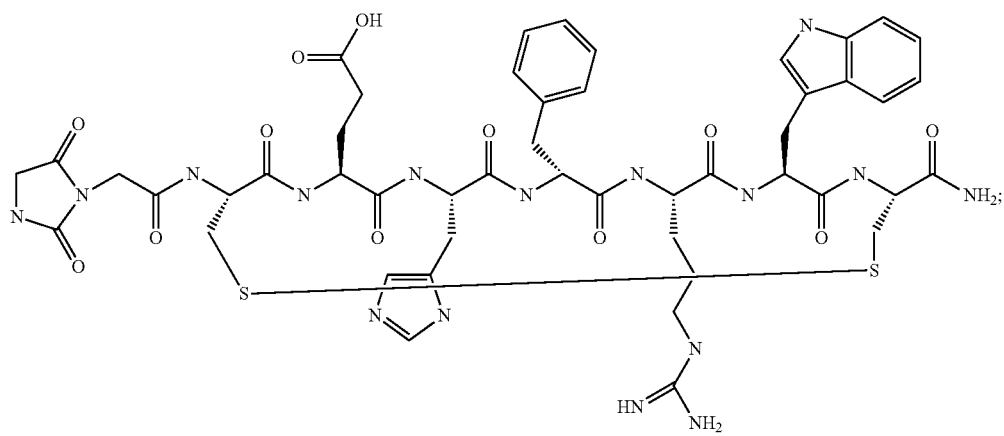 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)CN2C(=O)CNC2=O)CSSC[C@@H](C(N)=O)NC(=O)[C@H](Cc2c[nH]c3ccccc23)NC1=O]

[Hydantoin(C(O)-(Ala-Nle))-cyclo(Cys-Glu-His-D-Phe-Arg-Trp-Cys)]—NH$_2$, (SEQ ID NO:64) having which has the following structure:
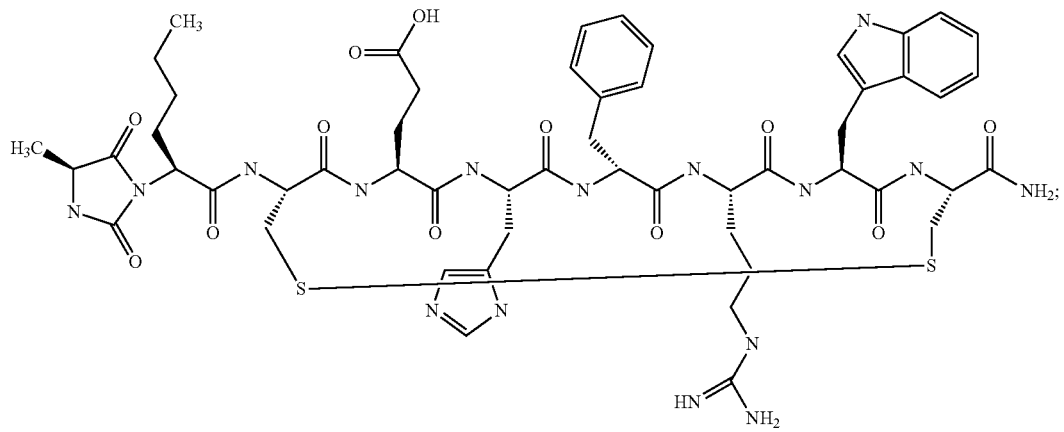 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@H](CCC(=O)O)NC1=O)N1C(=O)N[C@@H](C)C1=O]
[Hydantoin(C(O)-(Val-Nle))-cyclo(Cys-Glu-His-D-Phe-Arg-Trp-Cys)]-NH$_2$, (SEQ ID NO:65) which has the following structure:
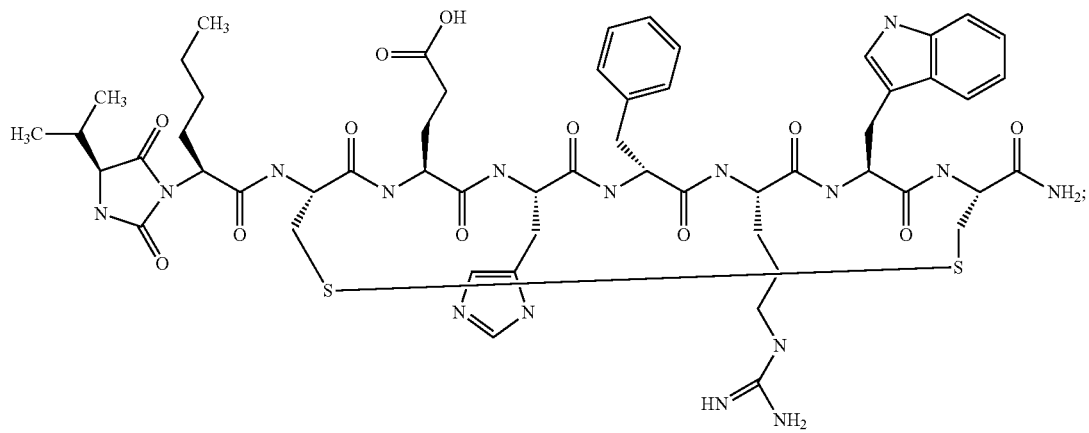 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@H](CCC(=O)O)NC1=O)N1C(=O)N[C@@H](C(C)C)C1=O]
[Hydantoin(C(O)-(Nle-Ala))-cyclo(Cys-Glu-His-D-Phe-Arg-Trp-Cys)]—NH$_2$, (SEQ ID NO:66) which has the following structure:
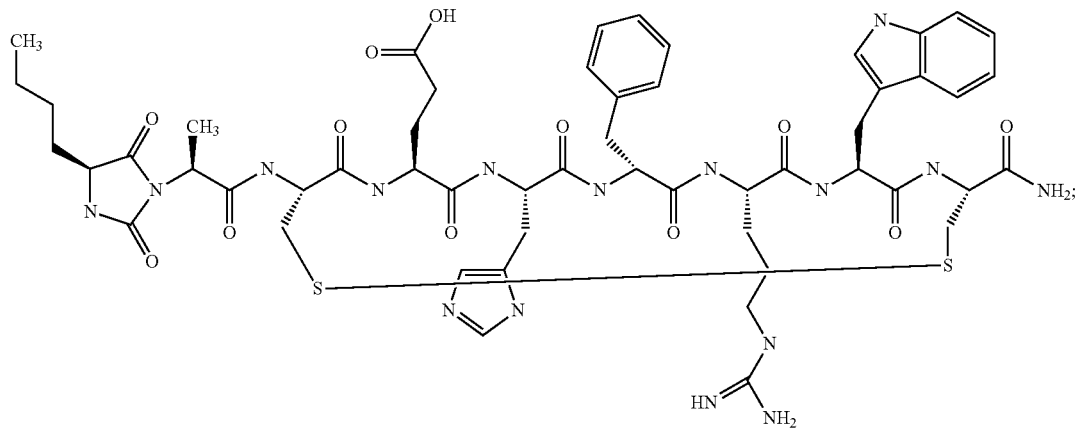 [SMILES: CCCC[C@@H]1NC(=O)N([C@@H](C)C(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@H](CCC(=O)O)NC2=O)C1=O]

[Hydantoin(C(O)-(Gly-Nle))-cyclo(Cys-Glu-His-D-Phe-Arg-Trp-Cys)]—NH$_2$, (SEQ ID NO:67) which has the following structure:
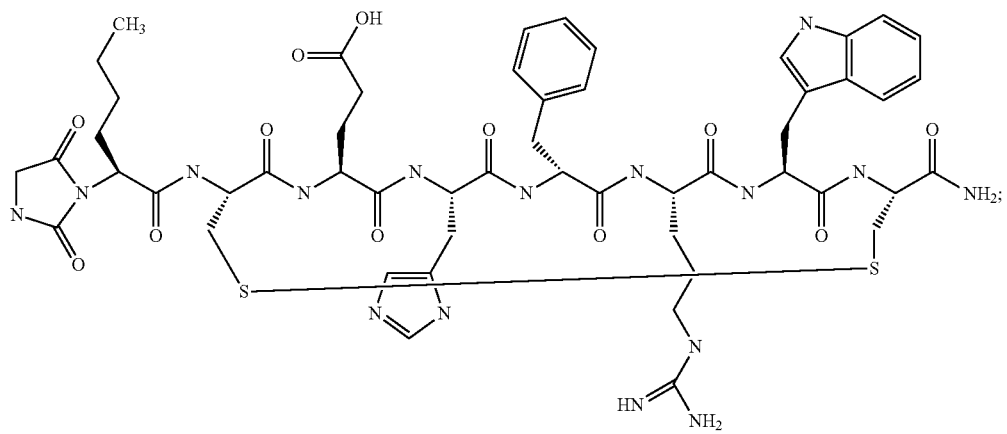 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@H](CCC(=O)O)NC1=O)N1C(=O)CNC1=O]
cyclo[Hydantoin(C(O)-(Cys-D-Ala))-His-D-2-Nal-Arg-Trp-Cys)]-NH$_2$, (SEQ ID NO:1) which has the following structure:
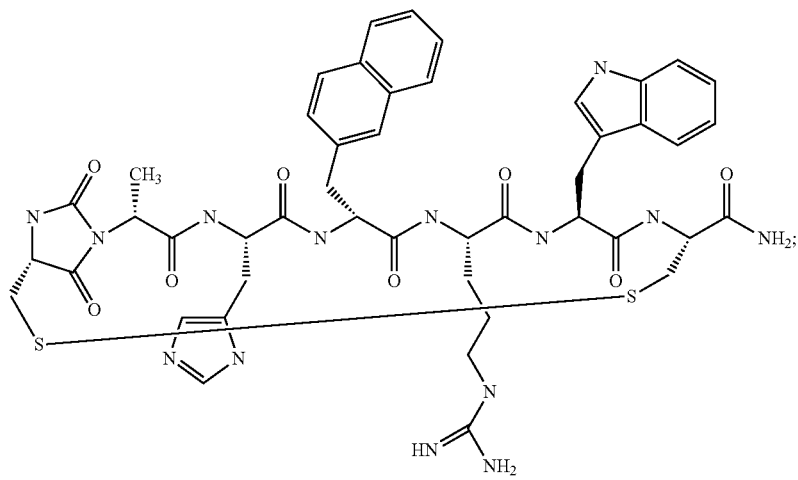 [SMILES: C[C@@H]1C(=O)N[C@@H](Cc2cnc[nH]2)C(=O)N[C@H](Cc2ccc3ccccc3c2)C(=O)N[C@@H](CCCNC(=N)N)C(=O)N[C@@H](Cc2c[nH]c3ccccc23)C(=O)N[C@H](C(N)=O)CSSC[C@@H]2NC(=O)N1C2=O]
cyclo[Hydantoin(C(O)-(Glu-D-Ala))-His-D-Phe-Arg-Trp-Lys]-NH$_2$, (SEQ ID NO:68) which has the following structure:
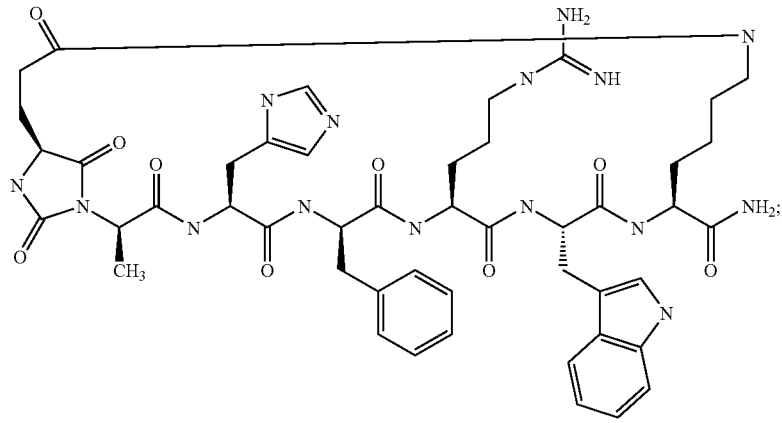 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CCCCNC(=O)CC[C@@H]2NC(=O)N1C2=O]

cyclo[Hydantoin(C(O)-(Glu-D-Ala))-His-D-Phe-Arg-Trp-Orn]-NH$_2$, (SEQ ID NO:11) which has the following structure:
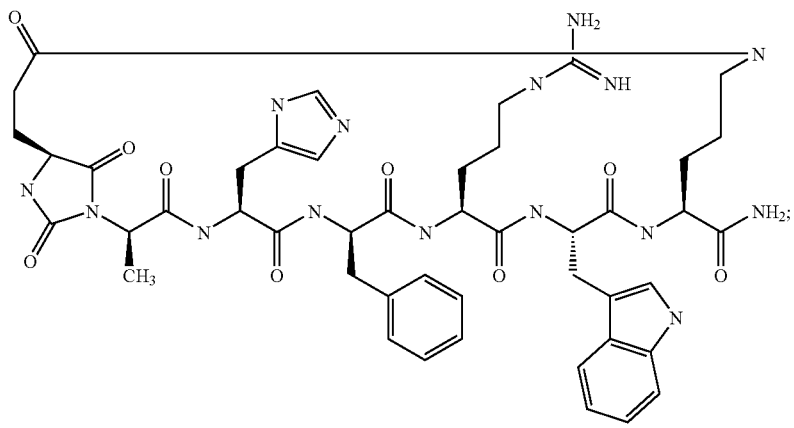 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CCCNC(=O)CC[C@@H]2NC(=O)N1C2=O]
cyclo[Hydantoin(C(O)-(Glu-D-Ala))-His-D-Phe-Arg-Trp-Dab]-NH$_2$, (SEQ ID NO:11) which has the following structure:
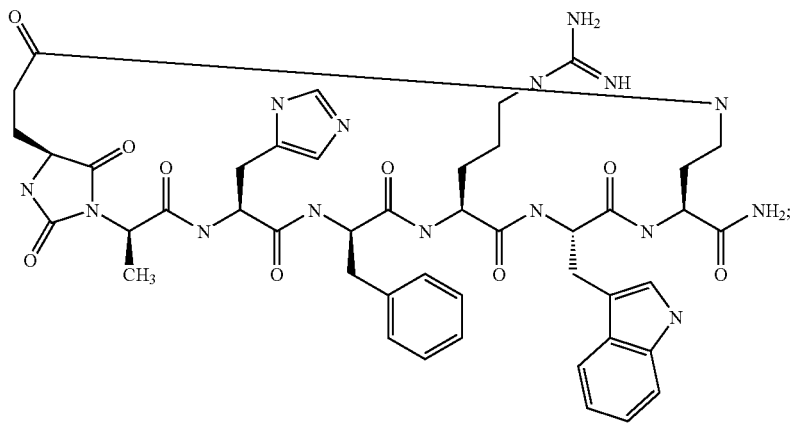 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CCNC(=O)CC[C@@H]2NC(=O)N1C2=O]
cyclo[Hydantoin(C(O)-(Glu-D-Ala))-His-D-Phe-Arg-Trp-Dap]-NH$_2$, (SEQ ID NO:11) which has the following structure:
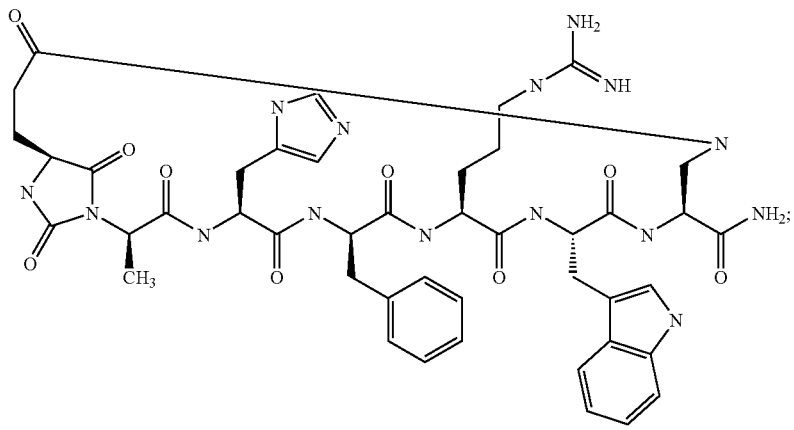 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CNC(=O)CC[C@@H]2NC(=O)N1C2=O]

cyclo[Hydantoin(C(O)-(Asp-D-Ala))-His-D-Phe-Arg-Trp-Lys]-NH$_2$, (SEQ ID NO:3) which has the following structure:
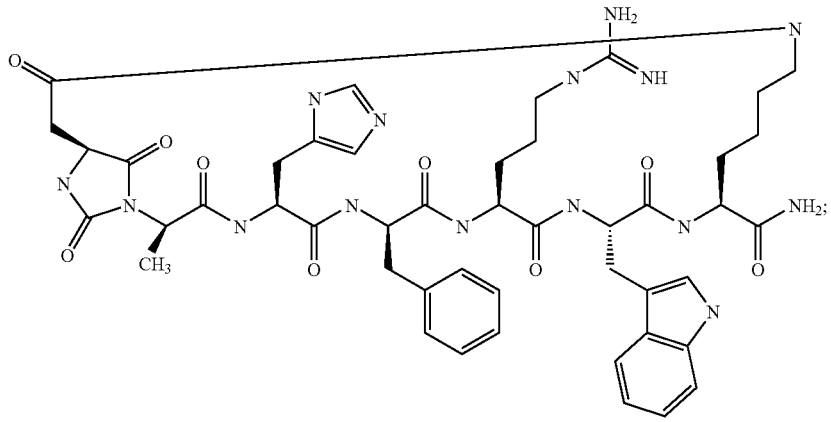 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CCCCNC(=O)C[C@@H]2NC(=O)N1C2=O]
cyclo[Hydantoin(C(O)-(Asp-D-Ala))-His-D-Phe-Arg-Trp-Orn]-NH$_2$, (SEQ ID NO:4) which has the following structure:
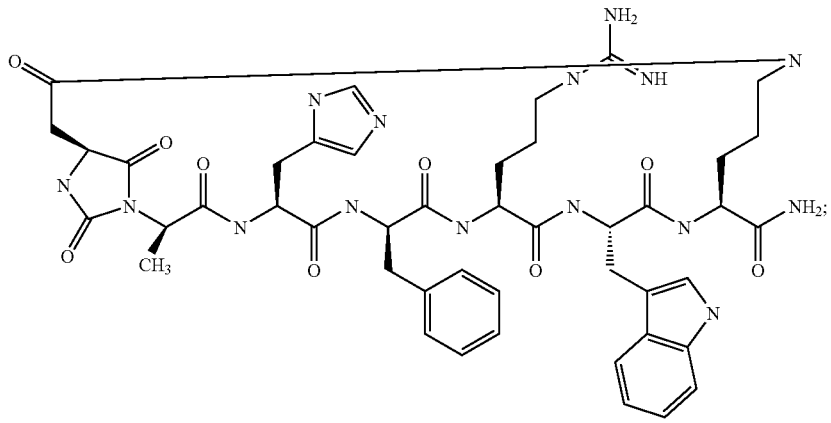 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CCCNC(=O)C[C@@H]2NC(=O)N1C2=O]
cyclo[Hydantoin(C(O)-(Asp-D-Ala))-His-D-Phe-Arg-Trp-Dab]-NH$_2$, (SEQ ID NO:4) which has the following structure:
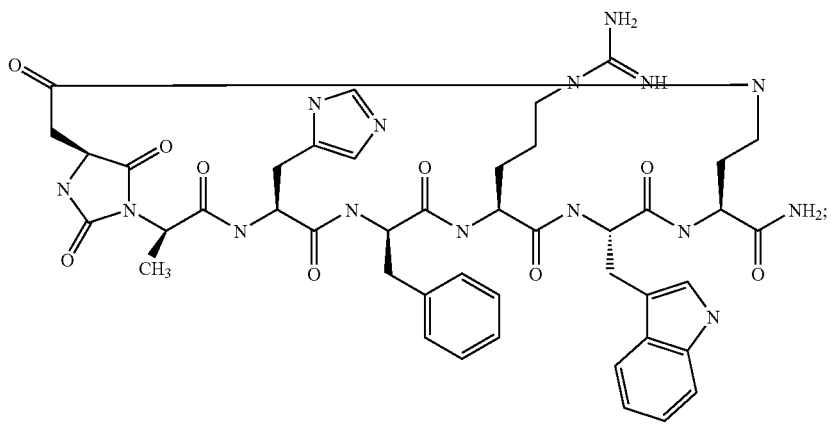 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CCNC(=O)C[C@@H]2NC(=O)N1C2=O]

cyclo[Hydantoin(C(O)-(Asp-D-Ala))-His-D-Phe-Arg-Trp-Dap]-NH₂, (SEQ ID NO:4) which has the following structure:
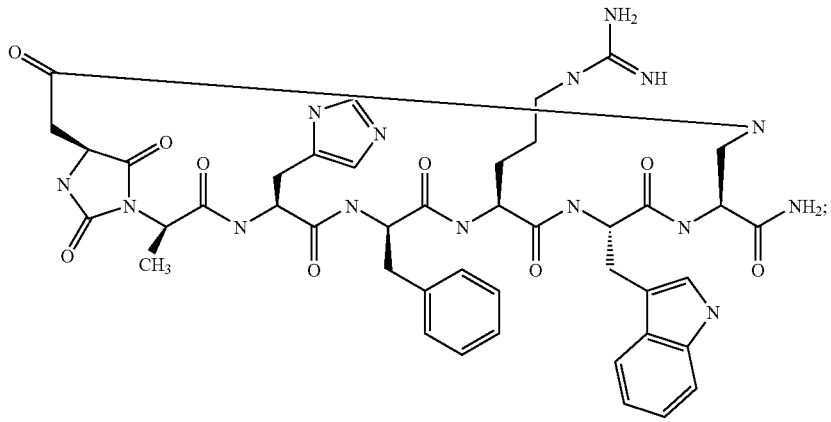 [SMILES: C[C@@H]1C(=O)N[C@@H](Cc2cnc[nH]2)C(=O)N[C@H](Cc2ccccc2)C(=O)N[C@@H](CCCNC(=N)N)C(=O)N[C@@H](Cc2c[nH]c3ccccc23)C(=O)N[C@H](C(N)=O)CNC(=O)C[C@@H]2NC(=O)N1C2=O]
[Hydantoin(C(O)-(A6c-Nle))-cyclo(Cys-D-Ala-His-D-Phe-Arg-Trp-Cys)]-NH₂, (SEQ ID NO:69) which has the following structure:
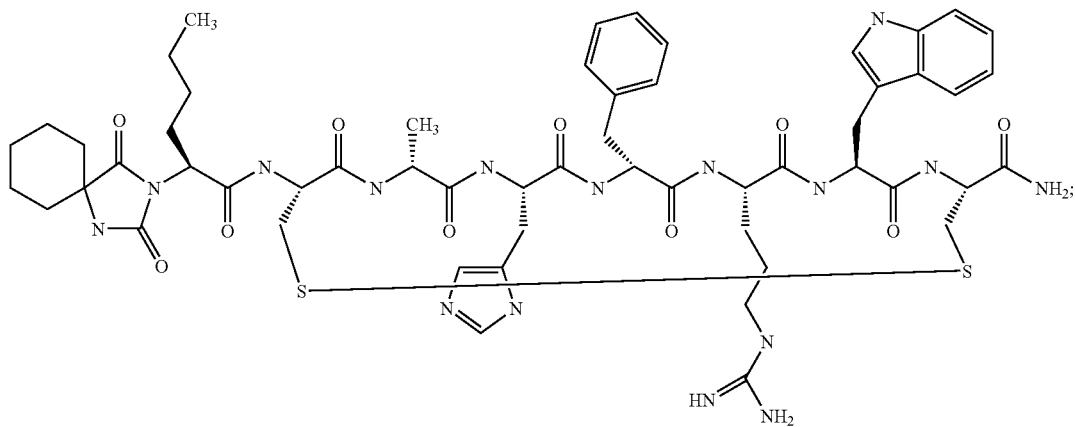 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)NC2(CCCCC2)C1=O]
cyclo[Hydantoin(C(O)-(Nle-Cys))-D-Ala-His-D-Phe-Arg-Trp-Cys]-NH₂, (SEQ ID NO:46) which has the following structure:
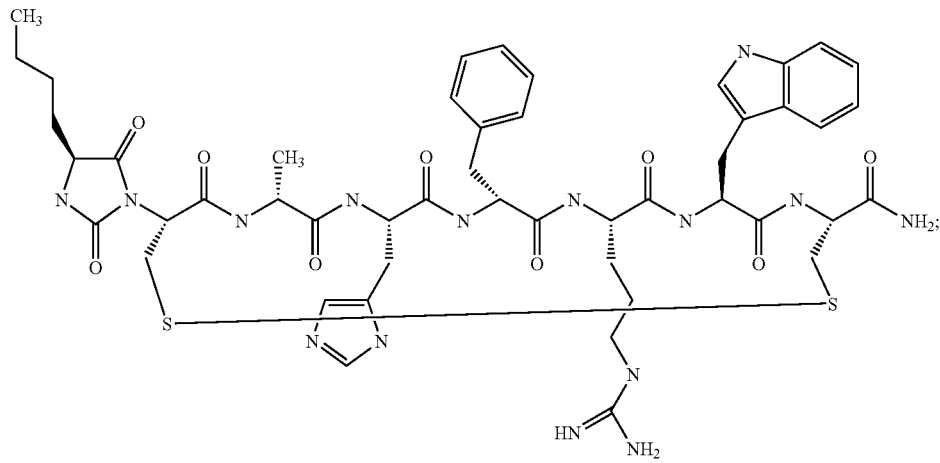 [SMILES: CCCC[C@@H]1NC(=O)N([C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]

cyclo[Hydantoin(C(O)-(Ala-Cys))-D-Ala-His-D-Phe-Arg-Trp-Cys]-NH$_2$, (SEQ ID NO:45) which has the following structure:
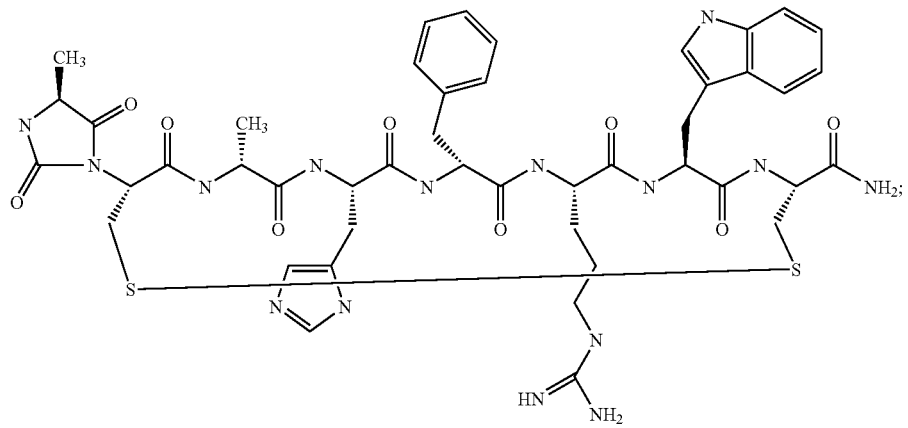 [SMILES: C[C@@H]1NC(=O)N([C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
cyclo[Hydantoin(C(O)-(D-Ala-Cys))-D-Ala-His-D-Phe-Arg-Trp-Cys]-NH$_2$, (SEQ ID NO:47) which has the following structure:
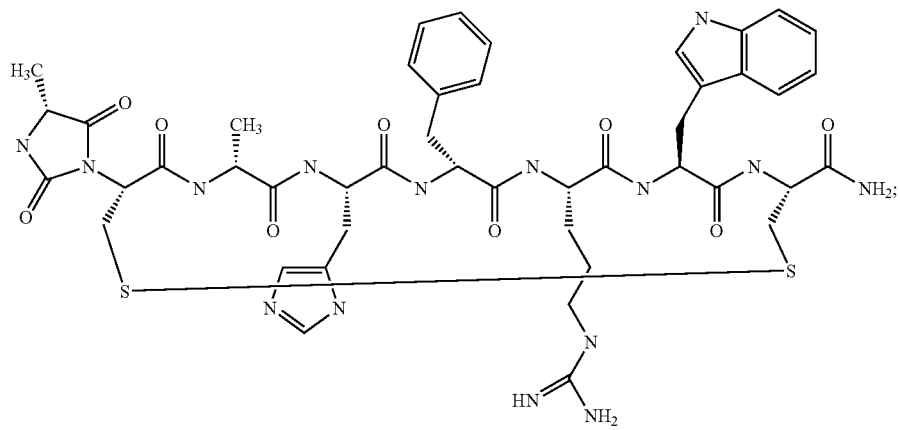 [SMILES: C[C@H]1NC(=O)[C@@H](N2C(=O)N[C@H](C)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
cyclo[Hydantoin(C(O)-(Aib-Cys))-D-Ala-His-D-Phe-Arg-Trp-Cys]-NH$_2$, (SEQ ID NO:48) which has the following structure:
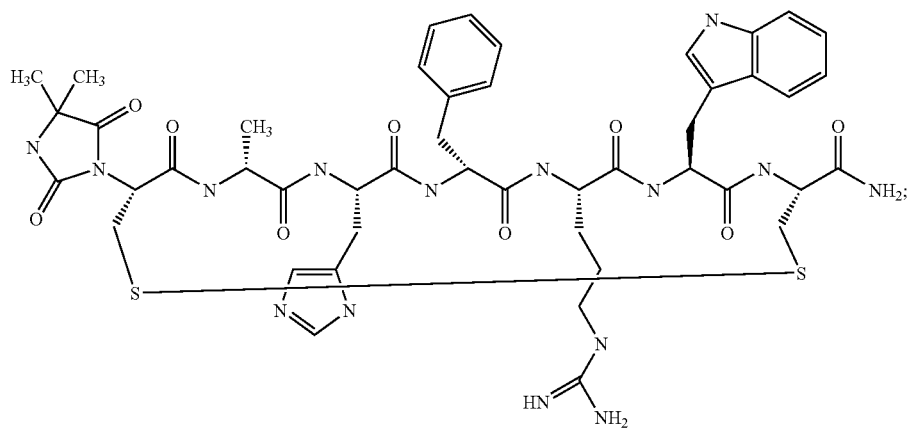 [SMILES: C[C@H]1NC(=O)[C@@H](N2C(=O)NC(C)(C)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]

cyclo[Hydantoin(C(O)-(Val-Cys))-D-Ala-His-D-Phe-Arg-Trp-Cys]-NH₂, (SEQ ID NO:49) which has the following structure:
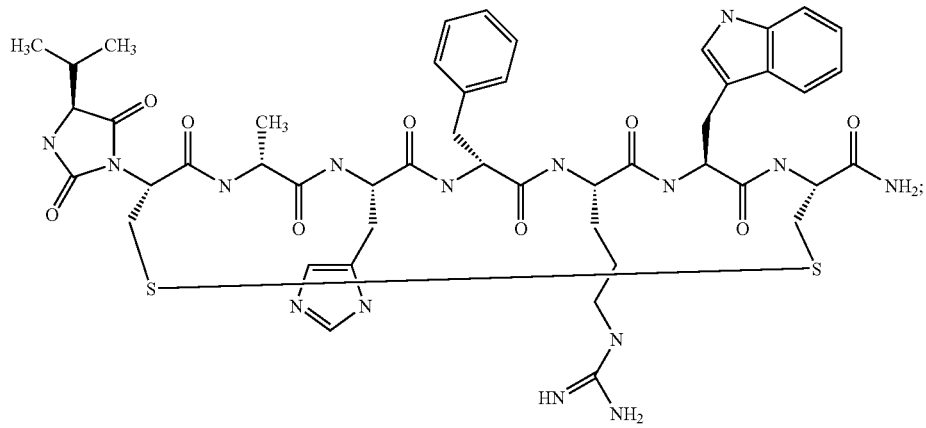 [SMILES: CC(C)[C@@H]1NC(=O)N([C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
cyclo[Hydantoin(C(O)-(Abu-Cys))-D-Ala-His-D-Phe-Arg-Trp-Cys]-NH₂, (SEQ ID NO:50) which has the following structure:
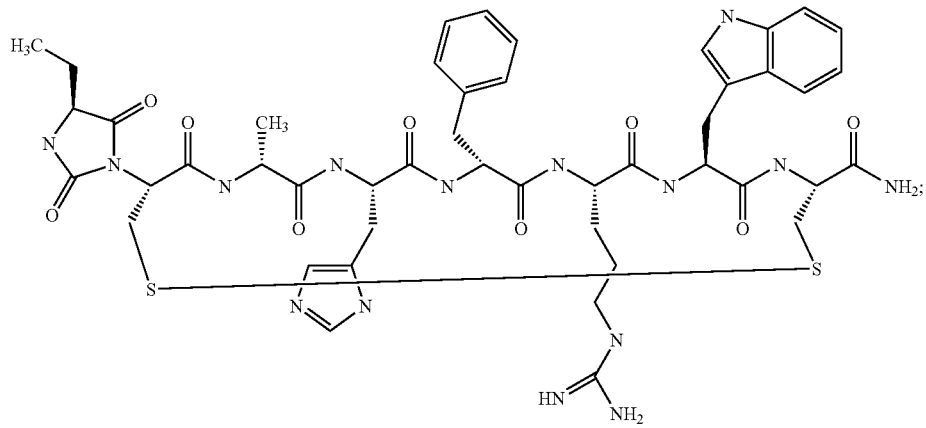 [SMILES: CC[C@@H]1NC(=O)N([C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
cyclo[Hydantoin(C(O)-(Leu-Cys))-D-Ala-His-D-Phe-Arg-Trp-Cys]-NH₂, (SEQ ID NO:51) which has the following structure:
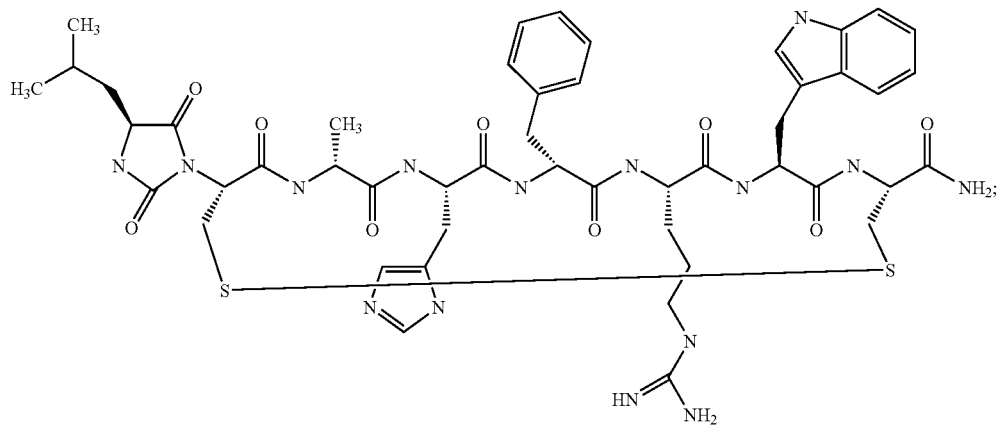 [SMILES: CC(C)C[C@@H]1NC(=O)N([C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]

cyclo[Hydantoin(C(O)-(Ile-Cys))-D-Ala-His-D-Phe-Arg-Trp-Cys]-NH$_2$, (SEQ ID NO:52) which has the following structure:
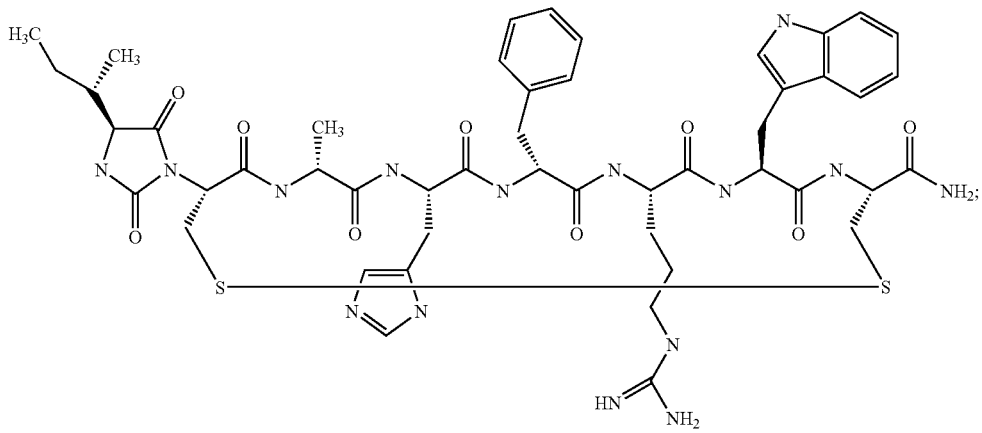 [SMILES: CC[C@H](C)[C@@H]1NC(=O)N([C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
cyclo[Hydantoin(C(O)-(Cha-Cys))-D-Ala-His-D-Phe-Arg-Trp-Cys]-NH$_2$, (SEQ ID NO:53) which has the following structure:
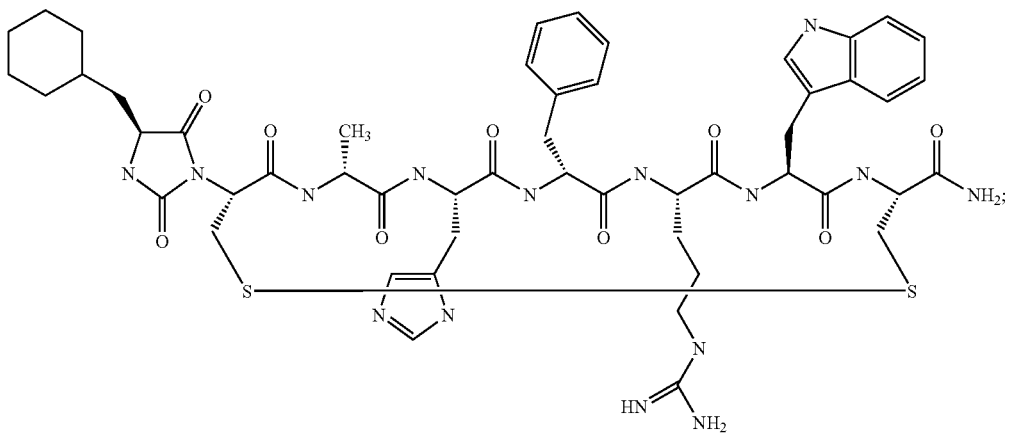 [SMILES: C[C@H]1NC(=O)[C@@H](N2C(=O)N[C@@H](CC3CCCCC3)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
cyclo[Hydantoin(C(O)-(A6c-Cys))-D-Ala-His-D-Phe-Arg-Trp-Cys]-NH$_2$, (SEQ ID NO:54) which has the following structure:
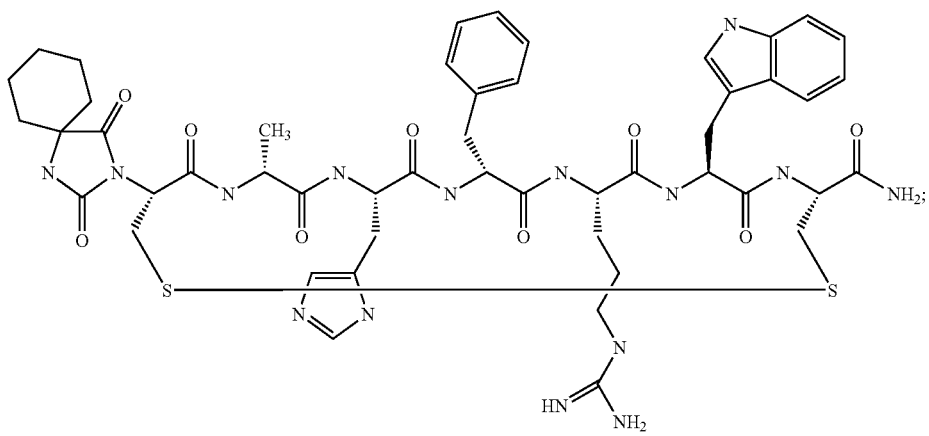 [SMILES: C[C@H]1NC(=O)[C@@H](N2C(=O)NC3(CCCCC3)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]

cyclo[Hydantoin(C(O)-(Phe-Cys))-D-Ala-His-D-Phe-Arg-Trp-Cys]-NH$_2$, (SEQ ID NO:54) which has the following structure:
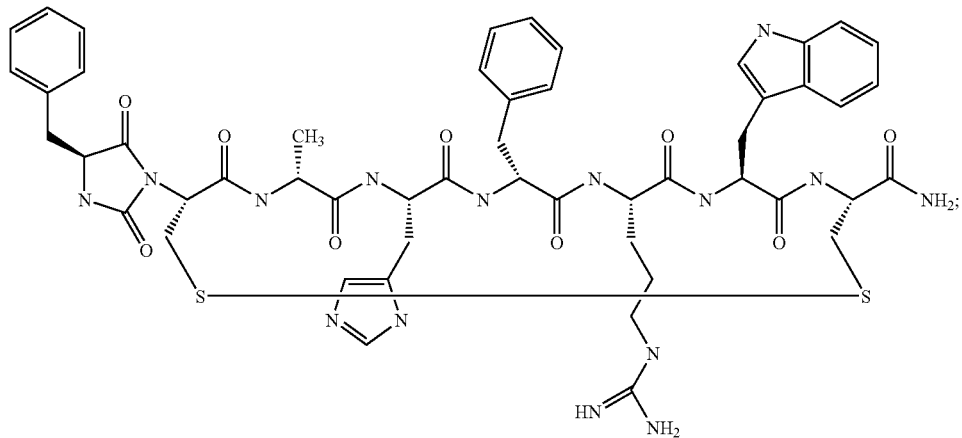 [SMILES: C[C@H]1NC(=O)[C@@H](N2C(=O)N[C@@H](Cc3ccccc3)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
[Hydantoin(C(O)-(Gly-Nle))-cyclo(Cys-D-Ala-His-D-Phe-Arg-Trp-Cys]-NH$_2$, (SEQ ID NO:70) which has the following structure:
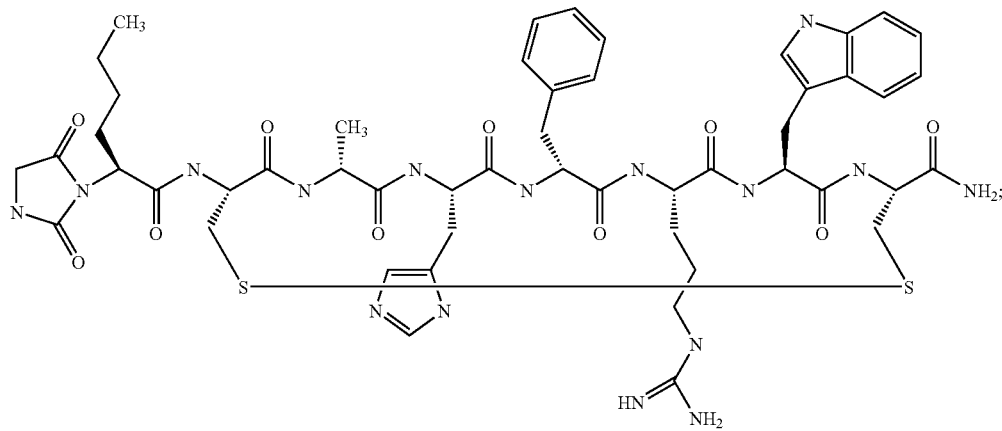 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)CNC1=O]
[Hydantoin(C(O)-(Ala-Nle))-cyclo(Cys-D-Ala-His-D-Phe-Arg-Trp-Cys)]-NH$_2$, (SEQ ID NO:71) which has the following structure:
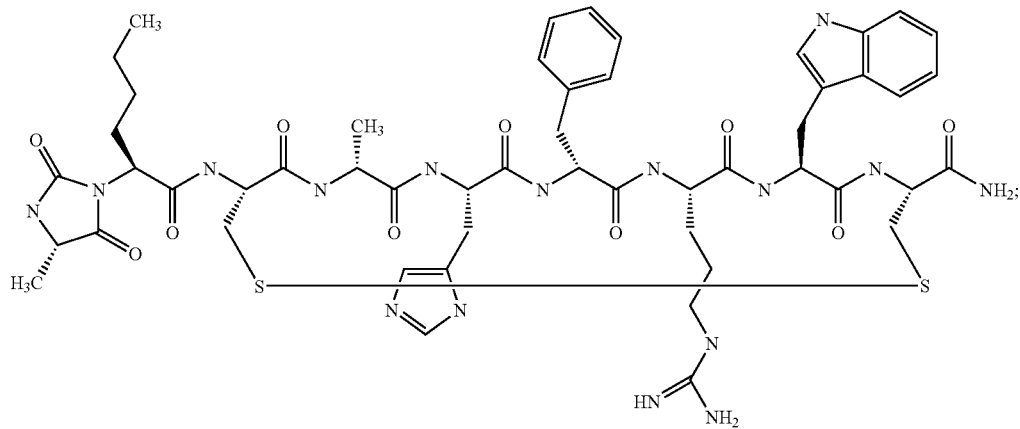 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)N[C@@H](C)C1=O]

[Hydantoin(C(O)-(D-Ala-Nle))-cyclo(Cys-D-Ala-His-D-Phe-Arg-Trp-Cys)]-NH$_2$, (SEQ ID NO:72) which has the following structure:
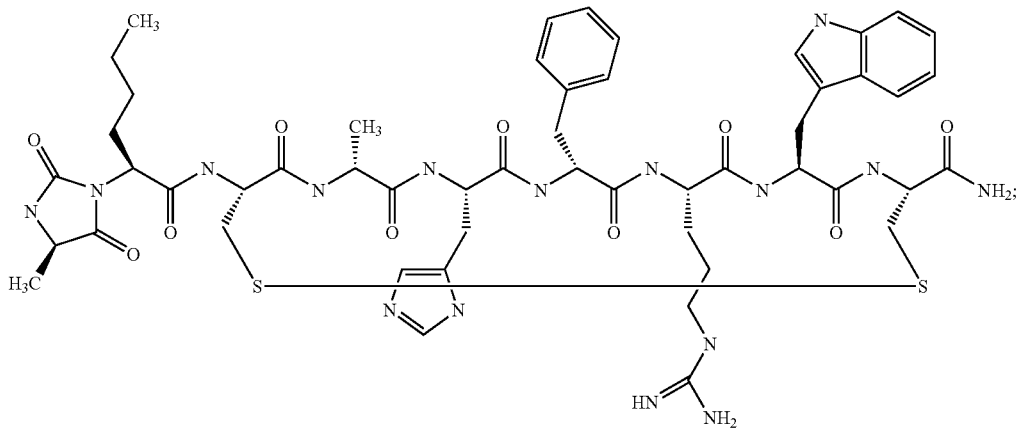 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)N[C@H](C)C1=O]
[Hydantoin(C(O)-(Val-Nle))-cyclo(Cys-D-Ala-His-D-Phe-Arg-Trp-Cys)]-NH$_2$, (SEQ ID NO:73) which has the following structure:
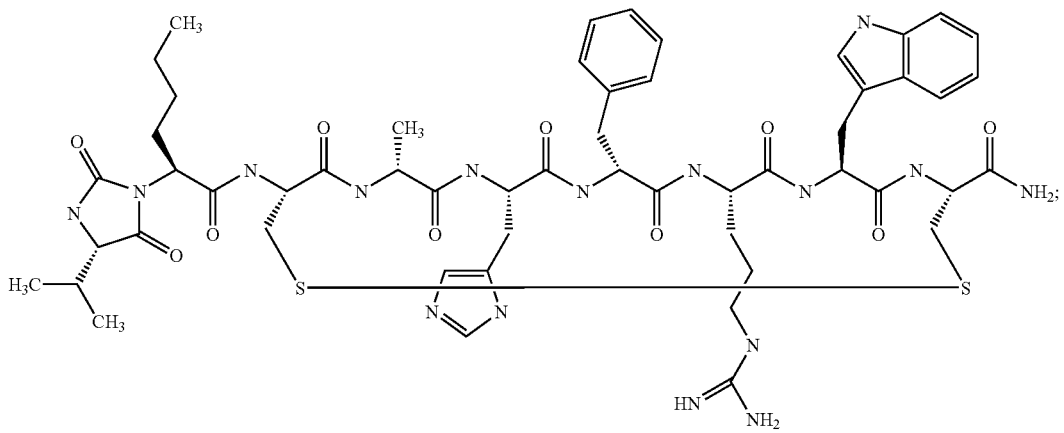 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)N[C@@H](C(C)C)C1=O]
[Hydantoin(C(O)-(Leu-Nle))-cyclo(Cys-D-Ala-His-D-Phe-Arg-Trp-Cys)]-NH$_2$, (SEQ ID NO:74) which has the following structure:
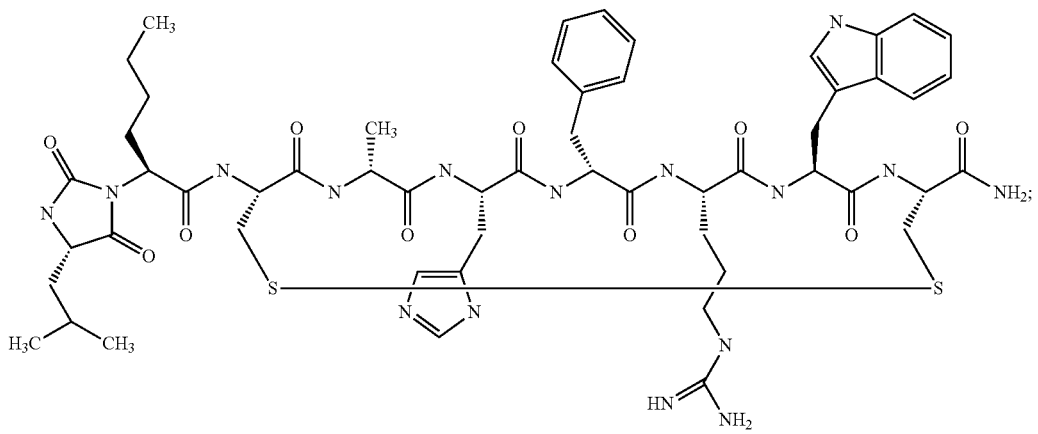 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)N[C@@H](CC(C)C)C1=O]

[Hydantoin(C(O)-(Cha-Nle))-cyclo(Cys-D-Ala-His-D-Phe-Arg-Trp-Cys)]-NH$_2$, (SEQ ID NO:75) which has the following structure:
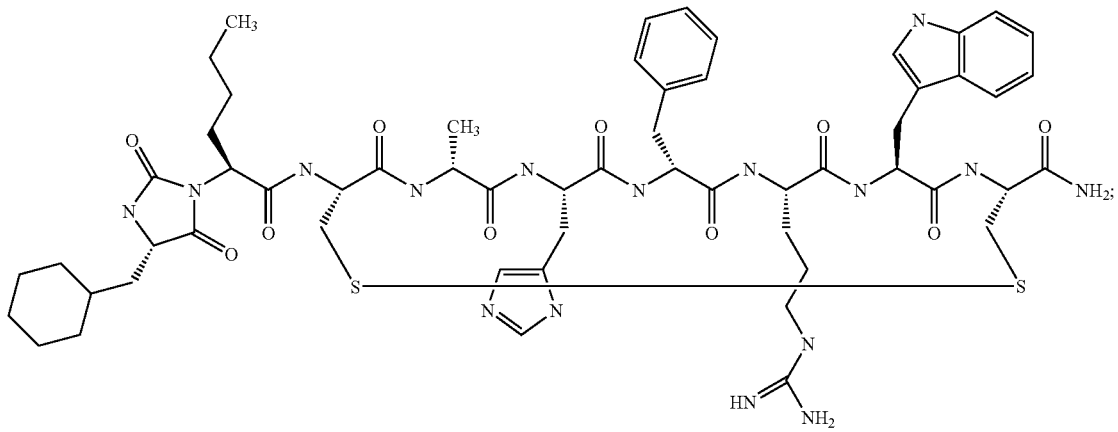 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)N[C@@H](CC2CCCCC2)C1=O]
[Hydantoin(C(O)-(Aib-Nle))-cyclo(Cys-D-Ala-His-D-Phe-Arg-Trp-Cys)]-NH$_2$, (SEQ ID NO:76) which has the following structure:
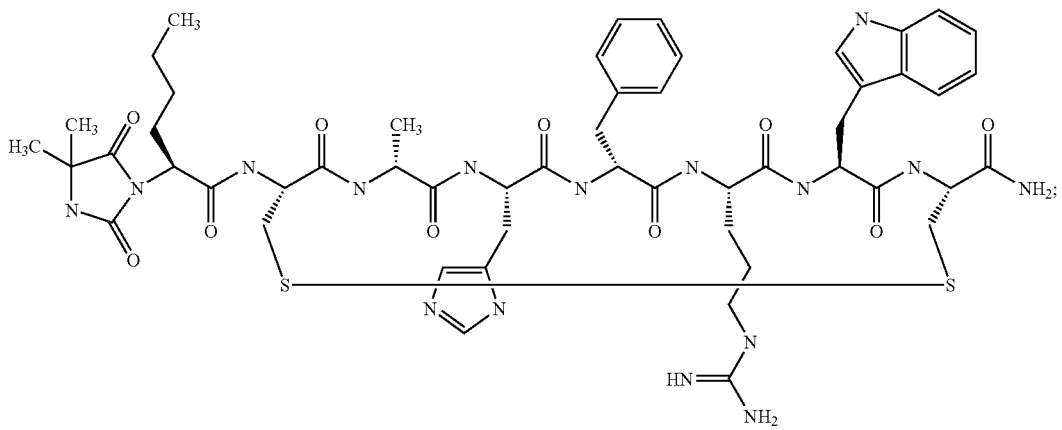 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)NC(C)(C)C1=O]
cyclo[Hydantoin(C(O)-(Gly-Cys))-D-Ala-His-D-Phe-Arg-Trp-Cys)]—NH$_2$, (SEQ ID NO:56) which has the following structure:
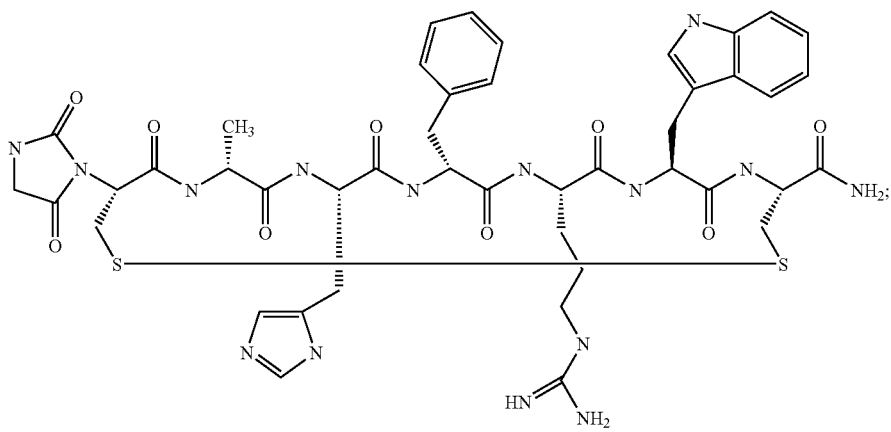 [SMILES: C[C@H]1NC(=O)[C@@H](N2C(=O)CNC2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]

[Hydantoin(C(O)-(Nle-Gly))-cyclo(Cys-D-Ala-His-D-Phe-Arg-Trp-Cys)]-NH$_2$, (SEQ ID NO:77) which has the following structure:
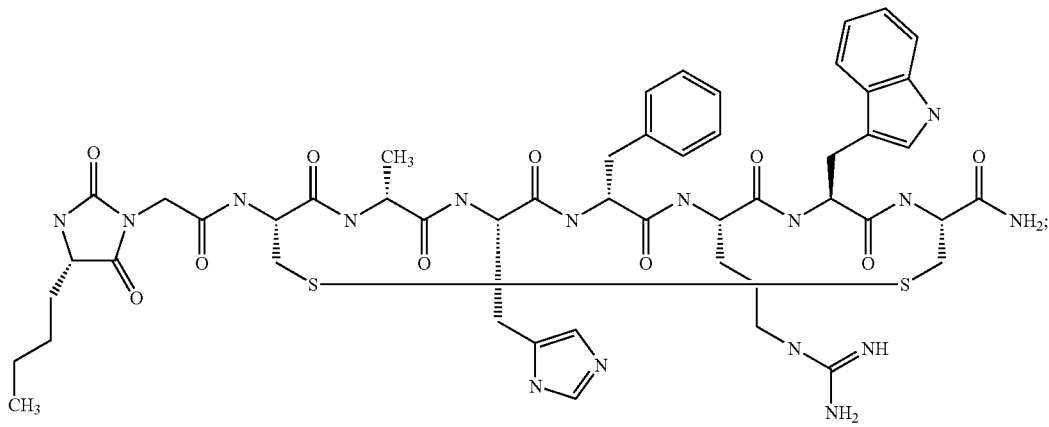 [SMILES: CCCC[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
[Hydantoin(C(O)-(Gly-Gly))-cyclo(Cys-D-Ala-His-D-Phe-Arg-Trp-Cys)]-NH$_2$, (SEQ ID NO:78) which has the following structure:
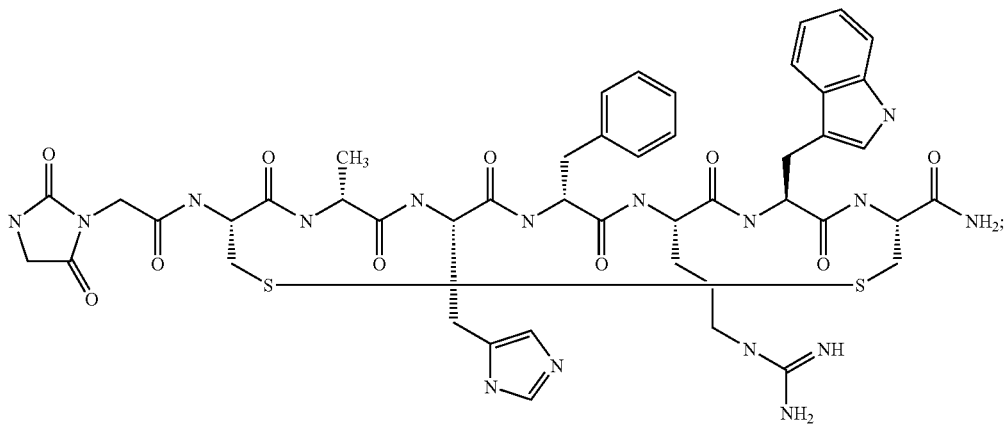 [SMILES: C[C@H]1NC(=O)[C@@H](NC(=O)CN2C(=O)CNC2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
[Hydantoin(C(O)-(Nle-Gly))-cyclo(Cys-D-Ala-His-D-Phe-Arg-Trp-Pen)]-NH$_2$, (SEQ ID NO:79) which has the following structure:
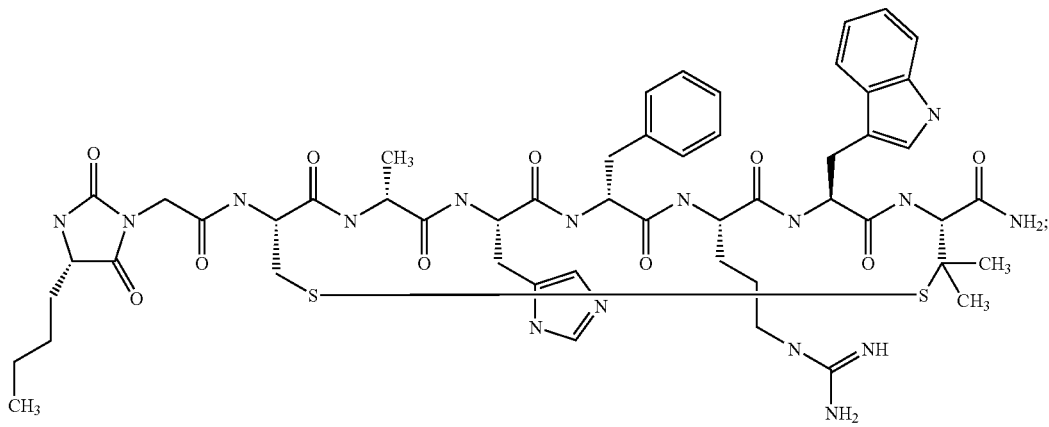 [SMILES: CCCC[C@@H]1NC(=O)N(CC(=O)N[C@H]2CSSC(C)(C)[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]

[Hydantoin(C(O)-(Gly-Gly))-cyclo(Cys-D-Ala-His-D-Phe-Arg-Trp-Pen)]-NH₂, (SEQ ID NO:80) which has the following structure:
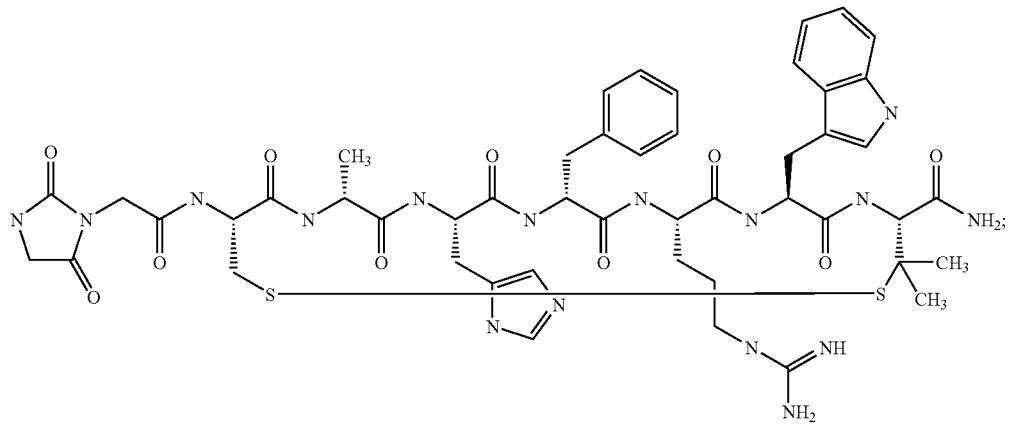 [SMILES: C[C@H]1NC(=O)[C@@H](NC(=O)CN2C(=O)CNC2=O)CSSC(C)(C)[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
[Hydantoin(C(O)-(Ala-Gly))-cyclo(Cys-D-Ala-His-D-Phe-Arg-Trp-Cys)]-NH₂, (SEQ ID NO:81) which has the following structure:
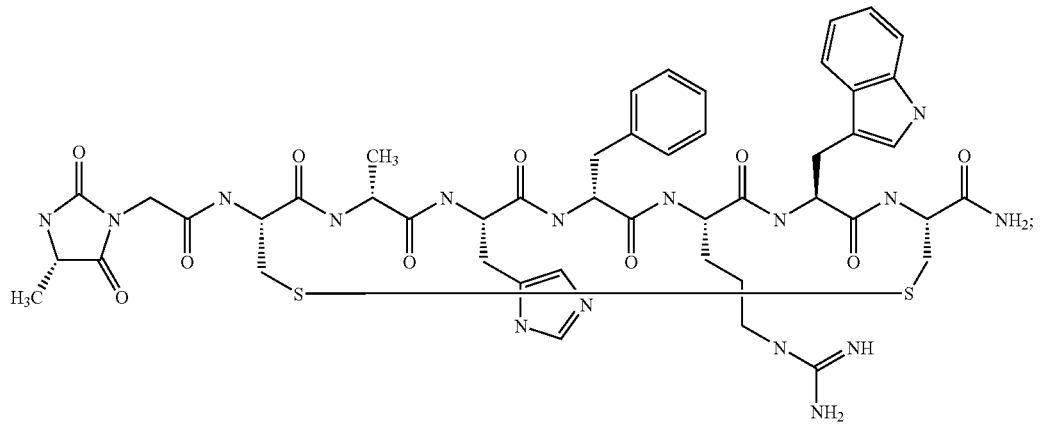 [SMILES: C[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
[Hydantoin(C(O)-(D-Ala-Gly))-cyclo(Cys-D-Ala-His-D-Phe-Arg-Trp-Cys)]-NH₂, (SEQ ID NO:82) which has the following structure:
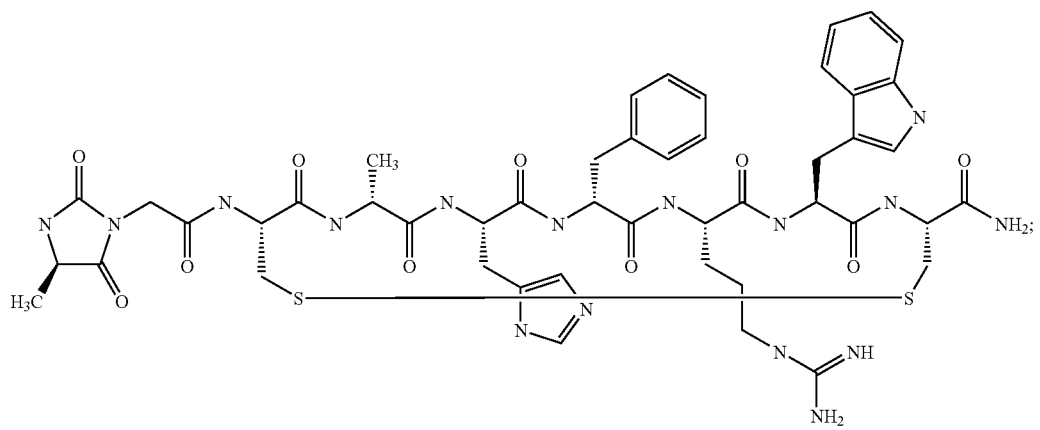 [SMILES: C[C@H]1NC(=O)[C@@H](NC(=O)CN2C(=O)N[C@H](C)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]

[Hydantoin(C(O)-(Aib-Gly))-cyclo(Cys-D-Ala-His-D-Phe-Arg-Trp-Cys)]-NH$_2$, (SEQ ID NO:83) which has the following structure:
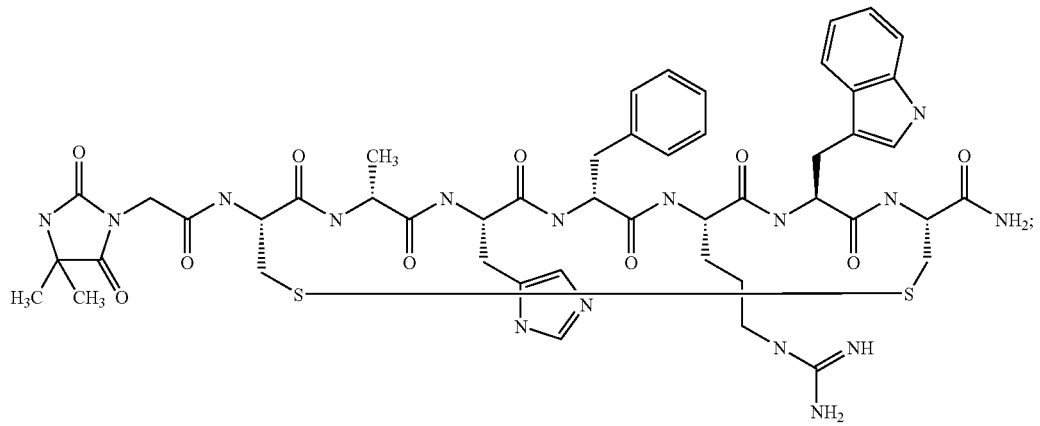 [SMILES: C[C@H]1NC(=O)[C@@H](NC(=O)CN2C(=O)NC(C)(C)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
[Hydantoin(C(O)-(Val-Gly))-cyclo(Cys-D-Ala-His-D-Phe-Arg-Trp-Cys)]-NH$_2$, (SEQ ID NO:84) which has the following structure:
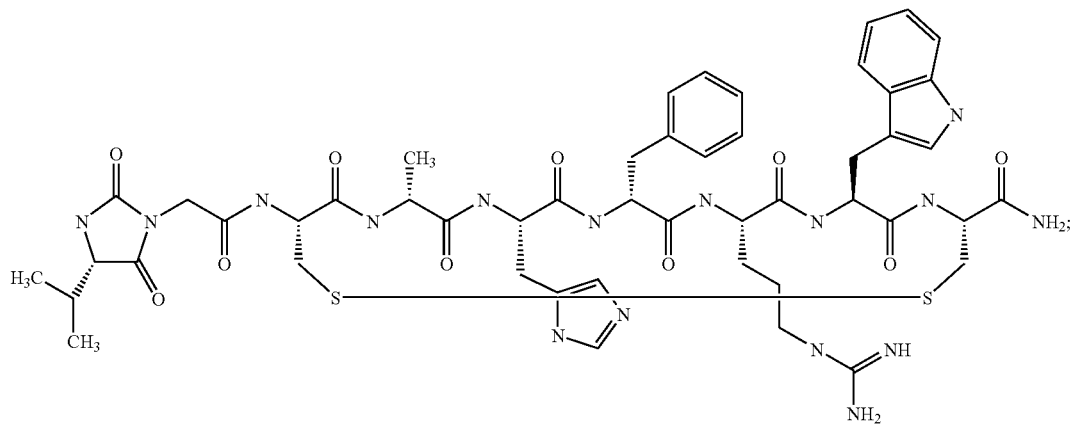 [SMILES: CC(C)[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
[Hydantoin(C(O)-(Ile-Gly))-cyclo(Cys-D-Ala-His-D-Phe-Arg-Trp-Cys)]-NH$_2$, (SEQ ID NO:85) which has the following structure:
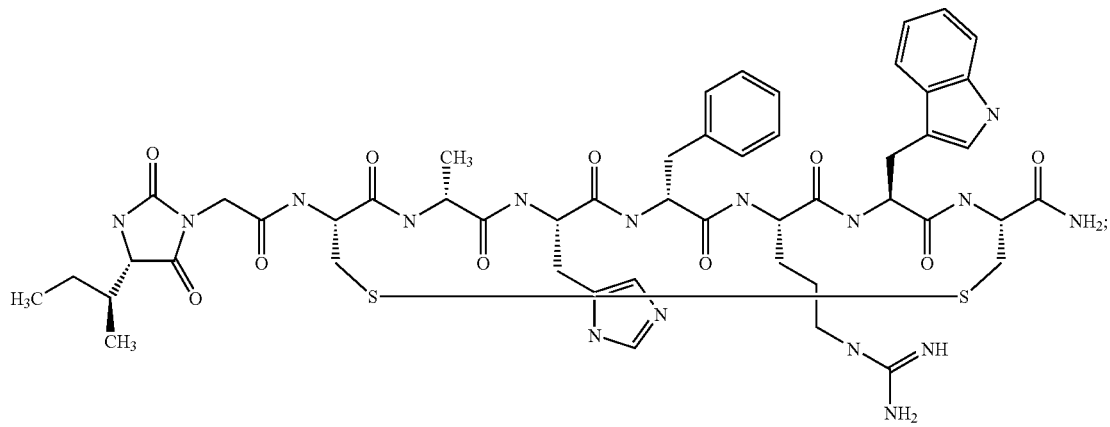 [SMILES: CC[C@H](C)[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]

[Hydantoin(C(O)-(Leu-Gly))-cyclo(Cys-D-Ala-His-D-Phe-Arg-Trp-Cys)]-NH₂, (SEQ ID NO:86) which has the following structure:
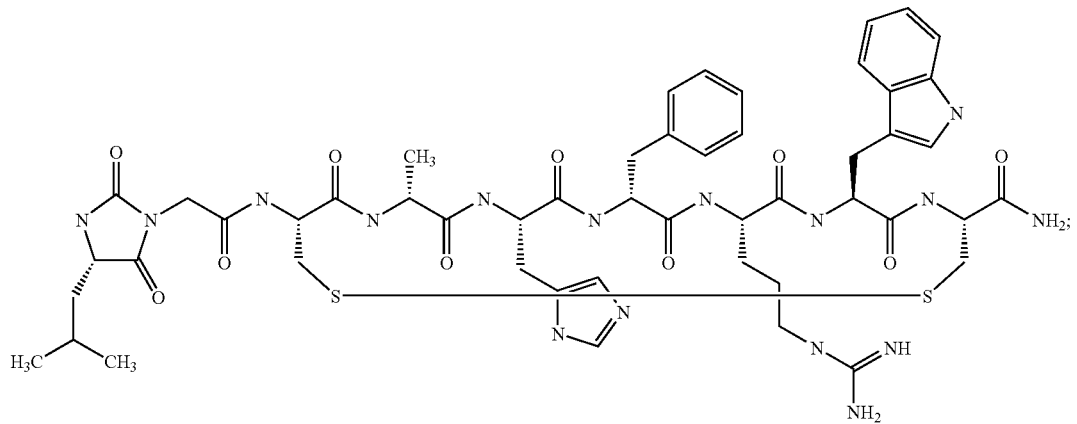 [SMILES: CC(C)C[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccccc3)NC(=O)[C@H](Cc3cnc[nH]3)NC(=O)[C@@H](C)NC2=O)C1=O]
[Hydantoin(C(O)-(Gly-Gly))-cyclo(Cys-Glu-His-D-2-Nal-Arg-Trp-Cys)]-NH₂, (SEQ ID NO:63) which has the following structure:
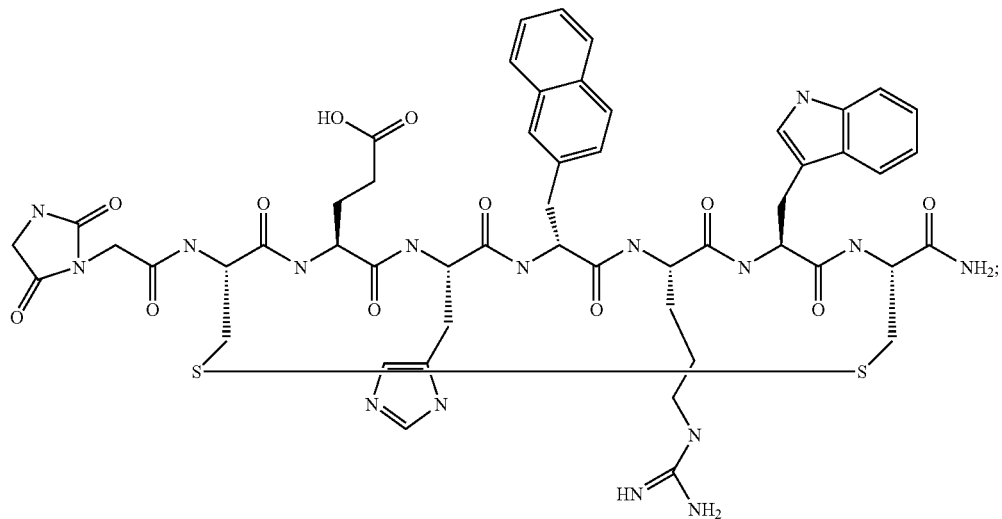 [SMILES: N=C(N)NCCC[C@@H]1NC(=O)[C@@H](Cc2ccc3ccccc3c2)NC(=O)[C@H](Cc2cnc[nH]2)NC(=O)[C@H](CCC(=O)O)NC(=O)[C@@H](NC(=O)CN2C(=O)CNC2=O)CSSC[C@@H](C(N)=O)NC(=O)[C@H](Cc2c[nH]c3ccccc23)NC1=O]

[Hydantoin(C(O)-(Nle-Gly))-cyclo(Cys-Glu-His-D-2-Nal-Arg-Trp-Cys)]-NH$_2$, (SEQ ID NO:62) which has the following structure:
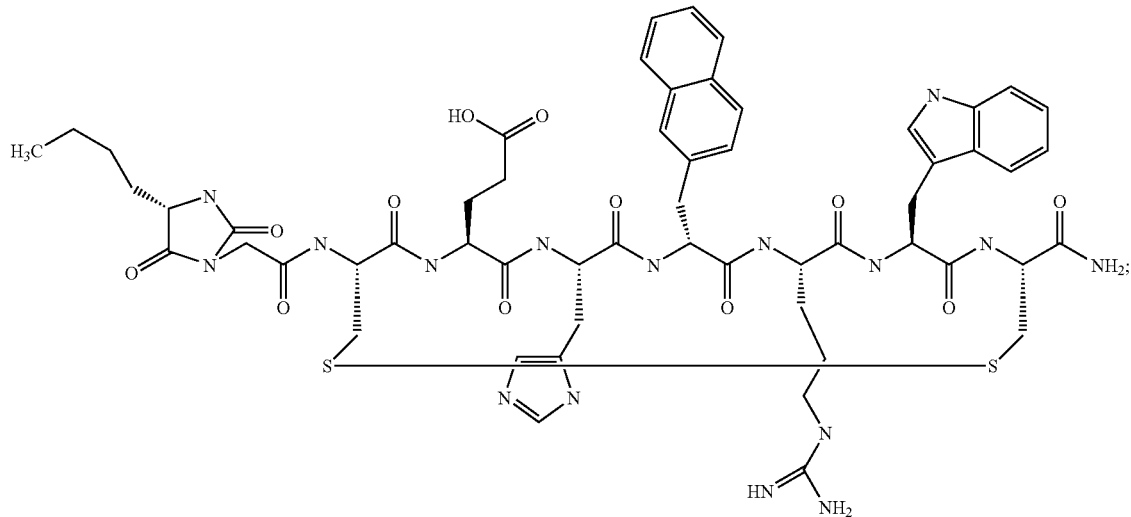 [SMILES: CCCC[C@@H]1NC(=O)N(CC(=O)N[C@H]2CSSC[C@@H](C(N)=O)NC(=O)[C@H](Cc3c[nH]c4ccccc34)NC(=O)[C@H](CCCNC(=N)N)NC(=O)[C@@H](Cc3ccc4ccccc4c3)NC(=O)[C@H](Cc3cnc[nH]3)NC(=O)[C@H](CCC(=O)O)NC2=O)C1=O]
[Hydantoin(C(O)-(D-Arg-Gly))-cyclo(Cys-Glu-His-D-Phe-Arg-Trp-Cys)]-NH$_2$, (SEQ ID NO:87) which has the following structure:
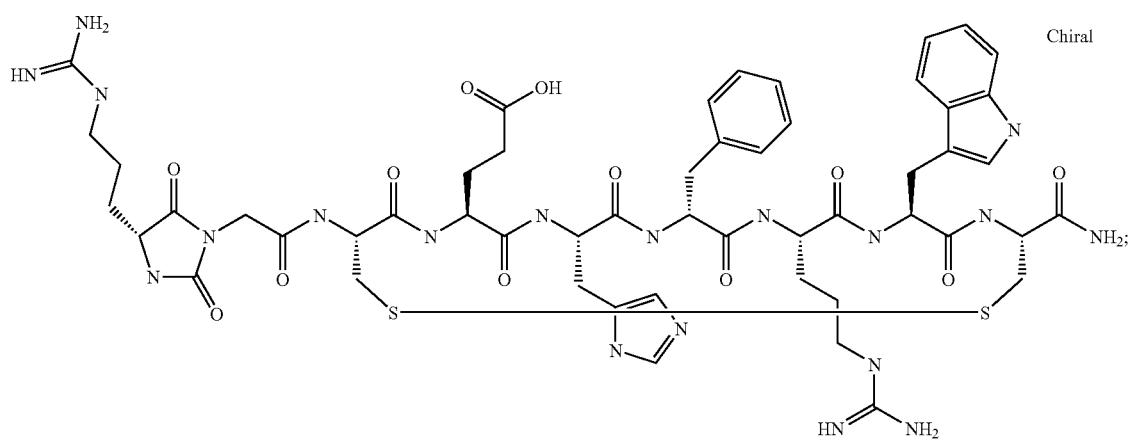 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)CN2C(=O)N[C@H](CCCNC(=N)N)C2=O)CSSC[C@@H](C(N)=O)NC(=O)[C@H](Cc2c[nH]c3ccccc23)NC1=O]
cyclo[Hydantoin(C(O)-(Gly-Cys))-Glu-His-D-Phe-Arg-Trp-Cys]-NH$_2$, (SEQ ID NO:57) which has the following structure:
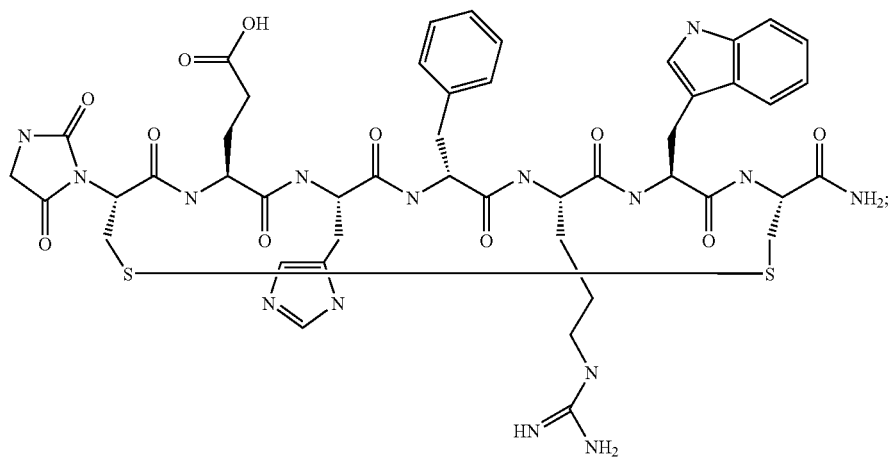 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](N2C(=O)CNC2=O)CSSC[C@@H](C(N)=O)NC(=O)[C@H](Cc2c[nH]c3ccccc23)NC1=O]

[Hydantoin(C(O)-(Gly-D-Arg))-cyclo(Cys-Glu-His-D-Phe-Arg-Trp-Cys)]-NH$_2$, (SEQ ID NO:88) which has the following structure:
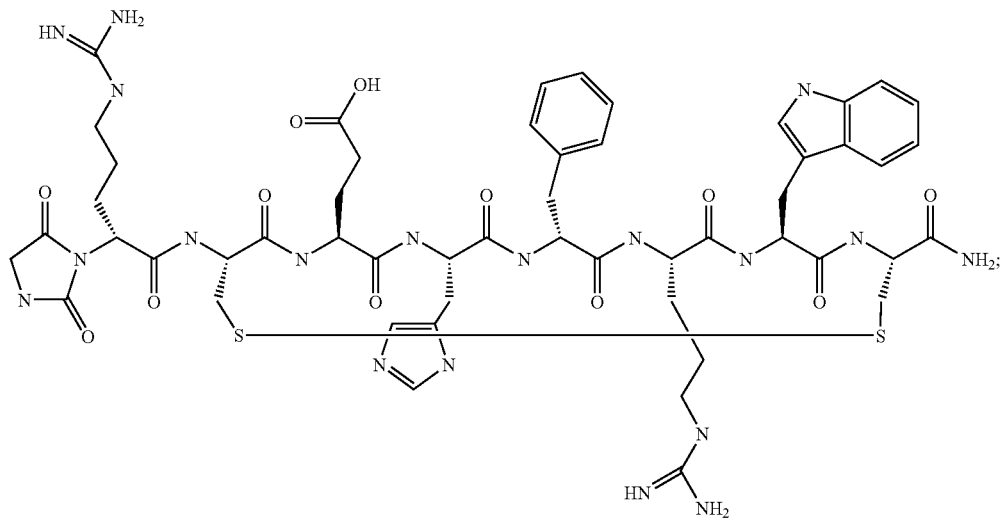 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)[C@@H](CCCNC(=N)N)N2C(=O)CNC2=O)CSSC[C@@H](C(N)=O)NC(=O)[C@H](Cc2c[nH]c3ccccc23)NC1=O]
[Hydantoin(C)(O)-(Arg-Gly))-cyclo(Cys-Glu-His-D-Phe-Arg-Trp-Cys)]-NH$_2$, (SEQ ID NO:89) which has the following structure:
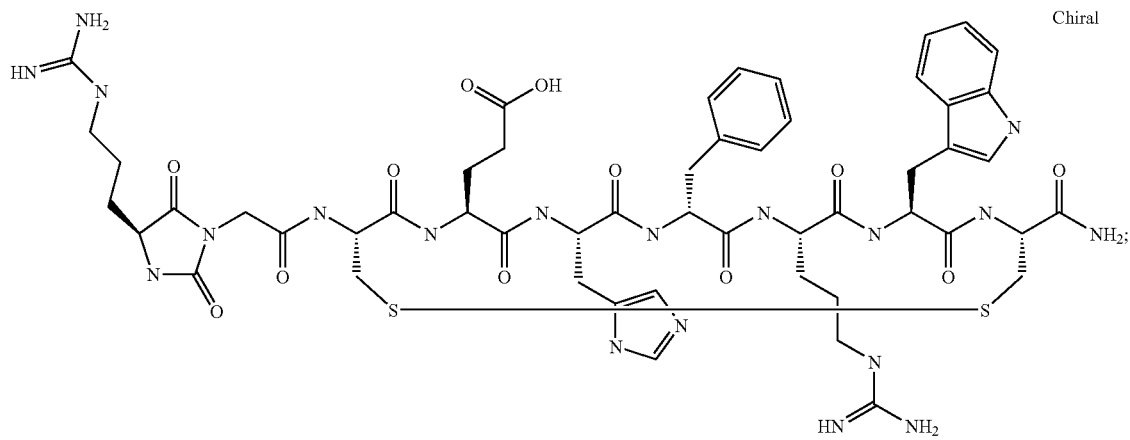 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC1=O]

[Hydantoin(C(O)-(Gly-Arg))-cyclo(Cys-Glu-His-D-Phe-Arg-Trp-Cys)]-NH$_2$, (SEQ ID NO:90) which has the following structure:
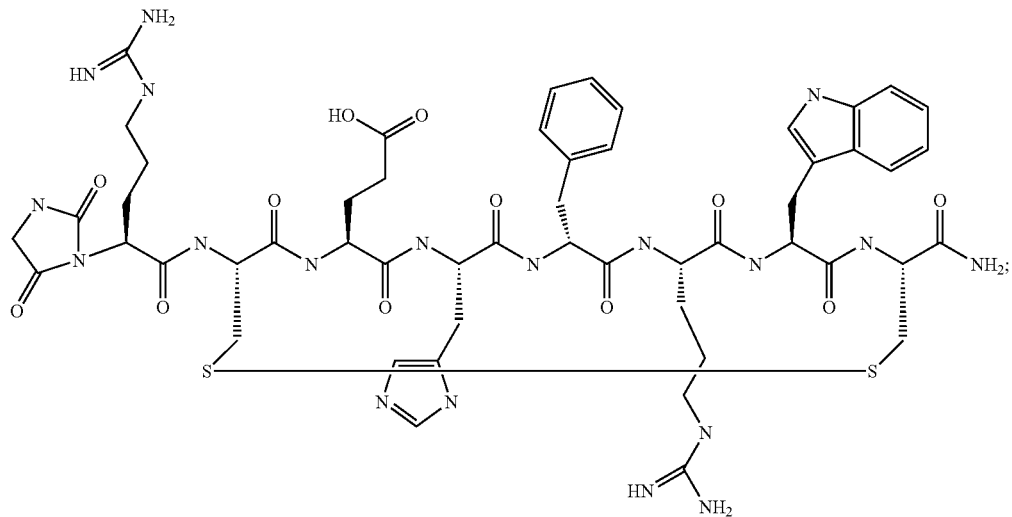 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)[C@H](CCCNC(=N)N)N2C(=O)CNC2=O)CSSC[C@@H](C(N)=O)NC(=O)[C@H](Cc2c[nH]c3ccccc23)NC1=O]
[Hydantoin(C(O)-(Arg-Gly))-cyclo(Cys-D-Ala-His-D-Phe-Arg-Trp-Cys)]-NH$_2$, (SEQ ID NO:91) which has the following structure:
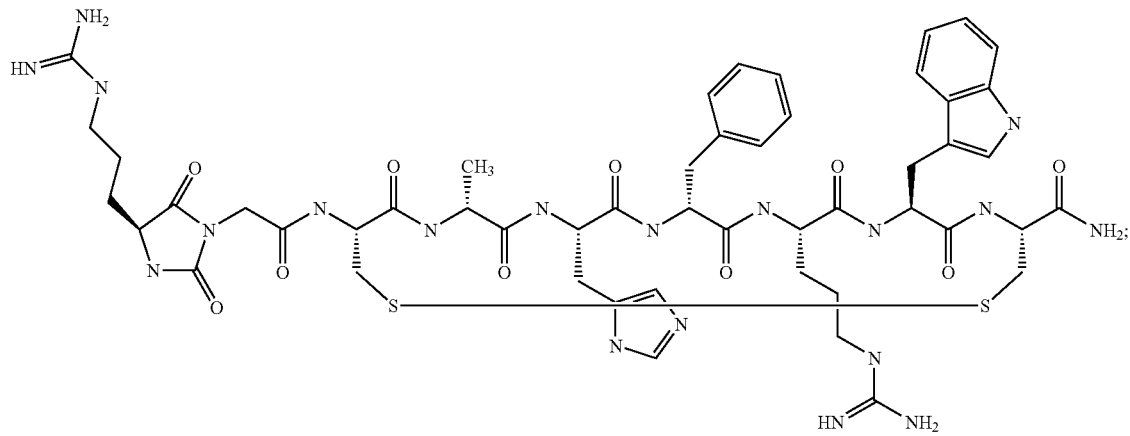 [SMILES: C[C@H]1NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
[Hydantoin(C(O)-(D-Arg-Gly))-cyclo(Cys-D-Ala-His-D-Phe-Arg-Trp-Cys)]-NH$_2$, (SEQ ID NO:92) which has the following structure:
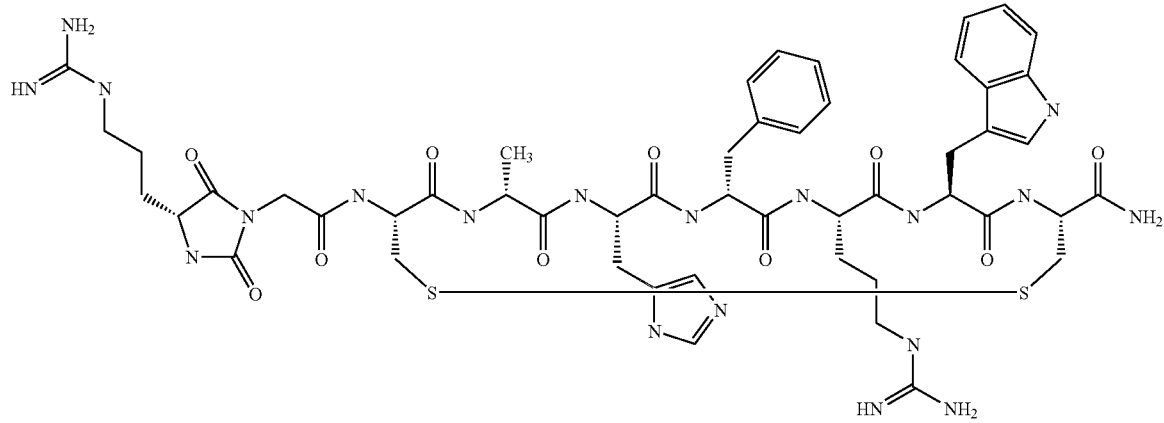 [SMILES: C[C@H]1NC(=O)[C@@H](NC(=O)CN2C(=O)N[C@H](CCCNC(=N)N)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]

[Hydantoin(C(O)-(Gly-D-Arg))-cyclo(Cys-D-Ala-His-D-Phe-Arg-Trp-Cys)]-NH$_2$, (SEQ ID NO:93) which has the following structure:
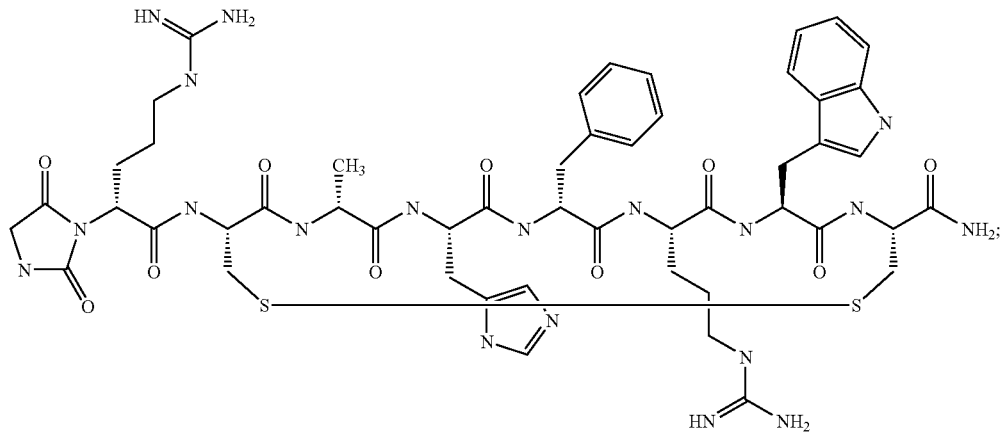 [SMILES: C[C@H]1NC(=O)[C@@H](NC(=O)[C@@H](CCCNC(=N)N)N2C(=O)CNC2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
[Hydantoin(C(O)-(Gly-Arg))-cyclo(Cys-D-Ala-His-D-Phe-Arg-Trp-Cys)]-NH$_2$, (SEQ ID NO:94) which has the following structure:
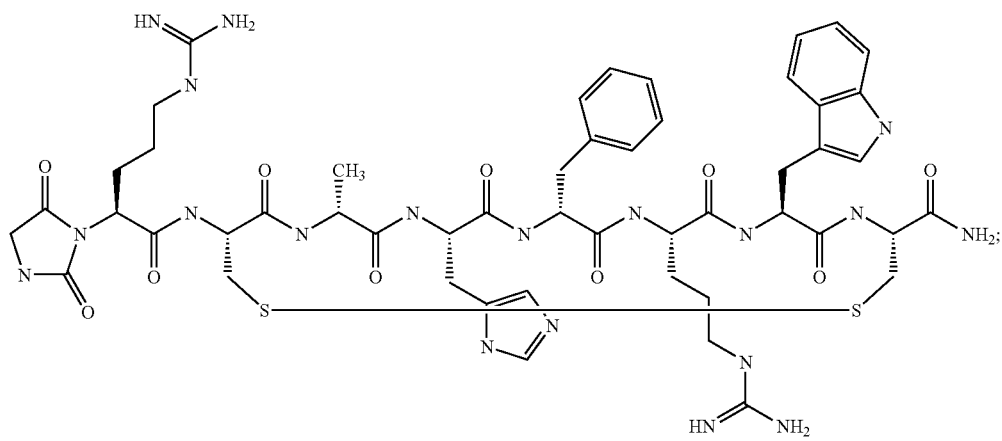 [SMILES: C[C@H]1NC(=O)[C@@H](NC(=O)[C@H](CCCNC(=N)N)N2C(=O)CNC2=O)CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC1=O]
and
[Hydantoin(C(O)-(Arg-Gly))-cyclo(Cys-D-Ala-His-D-2-Nal-Arg-Trp-Cys)]-NH$_2$, (SEQ ID NO:91) which has the following structure:
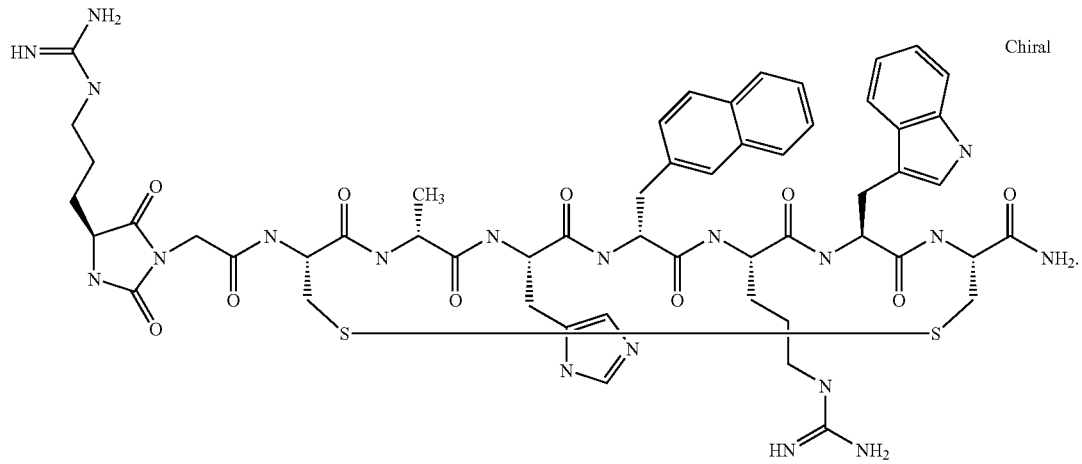 [SMILES: C[C@H]1NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2cnc[nH]2)NC1=O]

A selection of such compounds were subjected to both analytical HPLC and electrospray mass spectrometry for characterization to ensure the identity and purity, the results are provided in Table 1 depicted below.

TABLE 1

Molecular Weight and Purity for Selected Embodiments

| Sequences | Calculated Molecular Weight | Experimental Molecular Weight | Purity |
|---|---|---|---|
| FORMULA I | | | |
| cyclo[Hydantoin(C(O)-(Asp-His))-D-2-Nal-Arg-Trp-Lys]-NH$_2$ (SEQ ID NO: 5) | 945.05 | 944.60 | 96.0% |
| cyclo[Hydantoin(C(O)-(Cys-D-Ala))-His-D-Phe-Arg-Trp-Cys]-NH$_2$ (SEQ ID NO: 1) | 945.1 | 944.5 | 99.9% |
| cyclo[Hydantoin(C(O)-(Glu-D-Ala))-His-D-Phe-Arg-Trp-Lys]-NH$_2$ (SEQ ID NO: 68) | 980.1 | 979.46 | 99.9% |
| cyclo[Hydantoin(C(O)-(Glu-D-Ala))-His-D-Phe-Arg-Trp-Orn]-NH$_2$ (SEQ ID NO: 11) | 966.07 | 965.47 | 99.9% |
| cyclo[Hydantoin(C(O)-(Glu-D-Ala))-His-D-Phe-Arg-Trp-Dab]-NH$_2$ (SEQ ID NO: 11) | 952.04 | 951.55 | 95.5% |
| cyclo[Hydantoin(C(O)-(Glu-D-Ala))-His-D-Phe-Arg-Trp-Dap]-NH$_2$ (SEQ ID NO: 11) | 938.02 | 937.70 | 99.9% |
| cyclo[Hydantoin(C(O)-(Asp-D-Ala))-His-D-Phe-Arg-Trp-Orn]-NH$_2$ (SEQ ID NO: 4) | 952.04 | 951.55 | 98.7% |
| cyclo[Hydantoin(C(O)-(Asp-D-Ala))-His-D-Phe-Arg-Trp-Dap]-NH$_2$ (SEQ ID NO: 4) | 923.99 | 923.40 | 97.0% |
| cyclo[Hydantoin(C(O)-(Asp-Aic))-D-2-Nal-Arg-Trp-Lys]-NH$_2$ (SEQ ID NO: 9) | 967.10 | 966.60 | 99.9% |
| cyclo[Hydantoin(C(O)-(Asp-A5c))-D-2-Nal-Arg-Trp-Lys]-NH$_2$ (SEQ ID NO: 7) | 919.05 | 918.60 | 98.5% |
| cyclo[Hydantoin(C(O)-(Asp-A6c))-D-2-Nal-Arg-Trp-Lys]-NH$_2$ (SEQ ID NO: 8) | 933.08 | 932.50 | 96.3% |
| cyclo[Hydantoin(C(O)-(Asp-Apc))-D-2-Nal-Arg-Trp-Lys]-NH$_2$ (SEQ ID NO: 10) | 934.07 | 933.50 | 98.7% |
| cyclo[Hydantoin(C(O)-(Asp-A3c))-D-2-Nal-Arg-Trp-Lys]-NH$_2$ (SEQ ID NO: 6) | 891.00 | 890.50 | 95.8% |
| FORMULA II | | | |
| Hydantoin(C(O)-(Nle-Gly))-cyclo(Cys-Glu-His-D-Phe-Arg-Trp-Cys)-NH$_2$ (SEQ ID NO: 14) | 1173.34 | 1172.65 | 95.6% |
| Hydantoin(C(O)-(Gly-Gly))-cyclo(Cys-Glu-His-D-Phe-Arg-Trp-Cys)-NH$_2$ (SEQ ID NO: 15) | 1117.23 | 1116.54 | 98.2% |
| Hydantoin(C(O)-(A6c-Nle))-cyclo(Cys-D-Ala-His-D-Phe-Arg-Trp-Cys)-NH$_2$ (SEQ ID NO: 32) | 1183.42 | 1182.58 | 99.9% |
| Hydantoin(C(O)-(D-Ala-Nle))-cyclo(Cys-D-Ala-His-D-Phe-Arg-Trp-Cys)-NH$_2$ (SEQ ID NO: 35) | 1129.33 | 1128.57 | 99.9% |

TABLE 1-continued

Molecular Weight and Purity for Selected Embodiments

| Sequences | Calculated Molecular Weight | Experimental Molecular Weight | Purity |
|---|---|---|---|
| Hydantoin(C(O)-(Val-Nle))-cyclo(Cys-D-Ala-His-D-Phe-Arg-Trp-Cys)-NH$_2$ (SEQ ID NO: 36) | 1157.39 | 1156.61 | 97.9% |
| Hydantoin(C(O)-(Leu-Nle))-cyclo(Cys-D-Ala-His-D-Phe-Arg-Trp-Cys)-NH$_2$ (SEQ ID NO: 37) | 1171.41 | 1170.66 | 95.5% |
| Hydantoin(C(O)-(Cha-Nle))-cyclo(Cys-D-Ala-His-D-Phe-Arg-Trp-Cys)-NH$_2$ (SEQ ID NO: 38) | 1211.48 | 1210.70 | 95.9% |
| Hydantoin(C(O)-(Aib-Nle))-cyclo(Cys-D-Ala-His-D-Phe-Arg-Trp-Cys)-NH$_2$ (SEQ ID NO: 39) | 1143.36 | 1142.80 | 99.9% |
| Hydantoin(C(O)-(Nle-Gly))-cyclo(Cys-D-Ala-His-D-Phe-Arg-Trp-Cys)-NH$_2$ (SEQ ID NO: 16) | 1115.31 | 1114.43 | 95.2% |
| Hydantoin(C(O)-(Gly-Gly))-cyclo(Cys-D-Ala-His-D-Phe-Arg-Trp-Cys)-NH$_2$ (SEQ ID NO: 17) | 1059.20 | 1058.55 | 99.9% |
| Hydantoin(C(O)-(Nle-Gly))-cyclo(Cys-D-Ala-His-D-Phe-Arg-Trp-Pen)-NH$_2$ (SEQ ID NO: 18) | 1143.36 | 1142.55 | 95.9% |
| Hydantoin(C(O)-(Gly-Gly))-cyclo(Cys-D-Ala-His-D-Phe-Arg-Trp-Pen)-NH$_2$ (SEQ ID NO: 19) | 1087.25 | 1086.55 | 99.9% |
| Hydantoin(C(O)-(Ala-Gly))-cyclo(Cys-D-Ala-His-D-Phe-Arg-Trp-Cys)-NH$_2$ (SEQ ID NO: 20) | 1073.22 | 1072.55 | 99.9% |
| Hydantoin(C(O)-(D-Ala-Gly))-cyclo(Cys-D-Ala-His-D-Phe-Arg-Trp-Cys)-NH$_2$ (SEQ ID NO: 21) | 1073.22 | 1073.00 | 98.2% |
| Hydantoin(C(O)-(Aib-Gly))-cyclo(Cys-D-Ala-His-D-Phe-Arg-Trp-Cys)-NH$_2$ (SEQ ID NO: 22) | 1087.25 | 1086.55 | 99.9% |
| Hydantoin(C(O)-(Val-Gly))-cyclo(Cys-D-Ala-His-D-Phe-Arg-Trp-Cys)-NH$_2$ (SEQ ID NO: 23) | 1101.28 | 1100.65 | 96.9% |
| Hydantoin(C(O)-(Ile-Gly))-cyclo(Cys-D-Ala-His-D-Phe-Arg-Trp-Cys)-NH$_2$ (SEQ ID NO: 24) | 1115.31 | 1114.55 | 98.7% |
| Hydantoin(C(O)-(Leu-Gly))-cyclo(Cys-D-Ala-His-D-Phe-Arg-Trp-Cys)-NH$_2$ (SEQ ID NO: 25) | 1115.31 | 1114.75 | 98.0% |
| Hydantoin(C(O)-(D-Arg-Gly))-cyclo(Cys-Glu-His-D-Phe-Arg-Trp-Cys)-NH$_2$ (SEQ ID NO: 26) | 1216.37 | 1216.10 | 97.7% |
| Hydantoin(C(O)-(Gly-D-Arg))-cyclo(Cys-Glu-His-D-Phe-Arg-Trp-Cys)-NH$_2$ (SEQ ID NO: 42) | 1216.37 | 1216.30 | 95.2% |
| Hydantoin(C(O)-(Arg-Gly))-cyclo(Cys-Glu-His-D-Phe-Arg-Trp-Cys)-NH$_2$ (SEQ ID NO: 13) | 1216.37 | 1216.20 | 99.9% |
| Hydantoin(C(O)-(Gly-Arg))-cyclo(Cys-Glu-His-D-Phe-Arg-Trp-Cys)-NH$_2$ (SEQ ID NO: 40) | 1216.37 | 1216.10 | 99.0% |

TABLE 1-continued

Molecular Weight and Purity for Selected Embodiments

| Sequences | Calculated Molecular Weight | Experimental Molecular Weight | Purity |
|---|---|---|---|
| Hydantoin(C(O)-(Arg-Gly))-cyclo(Cys-D-Ala-His-D-Phe-Arg-Trp-Cys)-NH$_2$ (SEQ ID NO: 28) | 1158.33 | 1158.70 | 99.0% |
| Hydantoin(C(O)-(D-Arg-Gly))-cyclo(Cys-D-Ala-His-D-Phe-Arg-Trp-Cys)-NH$_2$ (SEQ ID NO: 27) | 1158.33 | 1158.70 | 97.0% |
| Hydantoin(C(O)-(Gly-D-Arg))-cyclo(Cys-D-Ala-His-D-Phe-Arg-Trp-Cys)-NH$_2$ (SEQ ID NO: 43) | 1158.33 | 1158.70 | 95.0% |
| Hydantoin(C(O)-(Gly-Arg))-cyclo(Cys-D-Ala-His-D-Phe-Arg-Trp-Cys)-NH$_2$ (SEQ ID NO: 41) | 1158.33 | 1158.70 | 98.0% |
| Hydantoin(C(O)-(Arg-Gly))-cyclo(Cys-D-Ala-His-D-2-Nal-Arg-Trp-Cys)-NH$_2$ (SEQ ID NO: 28) | 1208.39 | 1208.00 | 99.9% |
| FORMULA III | | | |
| cyclo[Hydantoin(C(O)-(Aib-Cys))-D-Ala-His-D-Phe-Arg-Trp-Cys]-NH$_2$ (SEQ ID NO: 48) | 1030.20 | 1029.43 | 99.9% |
| cyclo[Hydantoin(C(O)-(Val-Cys))-D-Ala-His-D-Phe-Arg-Trp-Cys]-NH$_2$ (SEQ ID NO: 49) | 1044.23 | 1043.46 | 95.4% |
| cyclo[Hydantoin(C(O)-(Leu-Cys))-D-Ala-His-D-Phe-Arg-Trp-Cys]-NH$_2$ (SEQ ID NO: 51) | 1058.25 | 1057.52 | 99.9% |
| cyclo[Hydantoin(C(O)-(Ile-Cys))-D-Ala-His-D-Phe-Arg-Trp-Cys]-NH$_2$ (SEQ ID NO: 52) | 1058.25 | 1057.46 | 99.9% |
| cyclo[Hydantoin(C(O)-(A6c-Cys))-D-Ala-His-D-Phe-Arg-Trp-Cys]-NH$_2$ (SEQ ID NO: 54) | 1070.26 | 1069.60 | 99.9% |
| cyclo[Hydantoin(C(O)-(Gly-Cys))-Glu-His-D-Phe-Arg-Trp-Cys]-NH$_2$ (SEQ ID NO: 57) | 1060.18 | 1059.70 | 99.9% |

Melanocortin Functional Activity and Selectivity

The compounds of the present invention will interact preferentially (i.e., selectively) to MC-4 relative to the other melanocortin receptors. Selectivity is particularly important when the compounds are administered to humans or other animals to minimize the number of side effects associated with their administration. MC-4 selectivity of a compound is defined herein as the ratio of the $EC_{50}$ of the compound for an MC-1 receptor ($EC_{50}$–MC-1) over the $EC_{50}$ of the compound for the MC-3 ($EC_{50}$–MC-3)/MC-4 ($EC_{50}$–MC-4) receptor, the $EC_{50}$ values being measured as described above. The formulas are as follows:

MC-3 selectivity=$[EC_{50}$–MC-1$]/[EC_{50}$–MC-3$]$

MC-4 selectivity=$[EC_{50}$–MC-1$]/[EC_{50}$–MC-4$]$

A compound is defined herein as being "selective for the MC-3 receptor" when the above mentioned ratio "MC-3-selectivity" is at least about 10, preferably at least about 100, and more preferably at least about 500.

A compound is defined herein as being "selective for the MC-4 receptor" when the above mentioned ratio "MC-4-selectivity" is at least about 10, preferably at least about 100, and more preferably at least about 500.

One skilled in the art would know that procedures similar to those described herein may be used to assay the binding activities of the compounds of the invention to melanocortin receptor molecules.

Cyclic AMP Bioassay

Intracellular cyclic AMP (cAMP) levels were determined by an electrochemiluminescence (ECL) assay (Meso Scale Discovery®, Gaithersburg, Md.; referred to hereinafter as "MSD"). CHO-K1 cells stably expressing the hMC receptor subtypes were suspended in RMPI 1640® assay buffer (RMPI 1640 buffer contains 0.5 mM isobutylmethylxanthine (IBMX) and 0.2% protein cocktail (MSD blocker A)). Transgenic CHO-K1 cells stably expressing hMC receptor subtypes 1, 3, 4 or 5 were dispensed at a density of approximately 7,000 cells/well in 384-well Multi-Array® plates (MSD) containing integrated carbon electrodes and coated with anti-cAMP antibody. Increasing concentrations of the test compounds were added and the cells were incubated for approximately 40 minutes at approximately 37° C. Following this incubation, lysis buffer (HEPES-buffered saline solution with $MgCl_2$ and Triton X-100® at ph 7.3) containing 0.2% protein cocktail and 2.5 nM TAG™ ruthenium-labeled cAMP (MSD) was added and the cells were incubated for approximately 90 minutes at room temperature. At the end of the second incubation period read buffer (Tris-buffered solution containing an ECL co-reactant and Triton X-100 at ph 7.8) was added and the cAMP levels in the cell lysates were immediately determined by ECL detection with a Sector Imager 6000 Reader® (MSD). Data was analyzed using a computer-assisted non-linear regression analysis (XL fit; IDBS) and reported as either an $EC_{50}$ value or a Kb value.

$EC_{50}$ represents the concentration of an agonist compound needed to obtain 50% of the maximum reaction response, e.g., 50% of the maximum level of cAMP as determined using the assay described above.

A selection of compounds was tested using the above-discussed assays and the cAMP bioassay data for selected compounds are reported in Tables 2A, 2B and 2C.

TABLE 2A

Intracellular Cyclic AMP (cAMP) Levels for Formula (I) Examples

| Formula (I) Compounds | $EC_{50}$ hMC1 | $EC_{50}$ hMC3 | $EC_{50}$ hMC4 | $EC_{50}$ hMC5 |
|---|---|---|---|---|
| cyclo[Hydantoin(C(O)-(Cys-D-Ala))-His-D-Phe-Arg-Trp-Cys]-NH$_2$ (SEQ ID NO: 1) | — | 218 | 5.42 | — |
| cyclo[Hydantoin(C(O)-(Glu-D-Ala))-His-D-Phe-Arg-Trp-Lys]-NH$_2$ (SEQ ID NO: 68) | — | 22.3 | 3.62 | — |
| cyclo[Hydantoin(C(O)-(Glu-D-Ala))-His-D-Phe-Arg-Trp-Orn]-NH$_2$ (SEQ ID NO: 11) | — | 39.2 | 4.94 | — |
| cyclo[Hydantoin(C(O)-(Glu-D-Ala))-His-D-Phe-Arg-Trp-Dap]-NH$_2$ (SEQ ID NO: 11) | 56.7 | 18.2 | 0.182 | >10000 |
| cyclo[Hydantoin(C(O)-(Asp-D-Ala))-His-D-Phe-Arg-Trp-Orn]-NH$_2$ (SEQ ID NO: 4) | 56.6 | 88.6 | 4.50 | 9300 |
| cyclo[Hydantoin(C(O)-(Asp-D-Ala))-His-D-Phe-Arg-Trp-Dap]-NH$_2$ (SEQ ID NO: 4) | — | 49.3 | 2.12 | — |

TABLE 2B

Intracellular Cyclic AMP (cAMP) Levels for Formula (II) Examples

| Formula (II) Compounds | $EC_{50}$ hMC1 | $EC_{50}$ hMC3 | $EC_{50}$ hMC4 | $EC_{50}$ hMC5 |
|---|---|---|---|---|
| Hydantoin(C(O)-(Nle-Gly))-cyclo(Cys-Glu-His-D-Phe-Arg-Trp-Cys)-NH$_2$ (SEQ ID NO: 14) | 54.3 | 12.2 | 0.177 | >10000 |
| Hydantoin(C(O)-(Gly-Gly))-cyclo(Cys-Glu-His-D-Phe-Arg-Trp-Cys)-NH$_2$ (SEQ ID NO: 15) | 124 | 8.05 | 0.214 | >10000 |
| Hydantoin(C(O)-(A6c-Nle))-cyclo(Cys-D-Ala-His-D-Phe-Arg-Trp-Cys)-NH$_2$ (SEQ ID NO: 32) | — | 4.89 | 1.80 | — |
| Hydantoin(C(O)-(D-Ala-Nle))-cyclo(Cys-D-Ala-His-D-Phe-Arg-Trp-Cys)-NH$_2$ (SEQ ID NO: 35) | — | 2.56 | 1.47 | — |
| Hydantoin(C(O)-(Val-Nle))-cyclo(Cys-D-Ala-His-D-Phe-Arg-Trp-Cys)-NH$_2$ (SEQ ID NO: 36) | — | 4.61 | 0.977 | — |
| Hydantoin(C(O)-(Leu-Nle))-cyclo(Cys-D-Ala-His-D-Phe-Arg-Trp-Cys)-NH$_2$ (SEQ ID NO: 37) | — | 9.68 | 1.83 | — |
| Hydantoin(C(O)-(Cha-Nle))-cyclo(Cys-D-Ala-His-D-Phe-Arg-Trp-Cys)-NH$_2$ (SEQ ID NO: 38) | — | 9.97 | 13.9 | — |
| Hydantoin(C(O)-(Gly-Gly))-cyclo(Cys-D-Ala-His-D-Phe-Arg-Trp-Cys)-NH$_2$ (SEQ ID NO: 17) | 14.2 | 2.46 | 0.336 | 201 |
| Hydantoin(C(O)-(Nle-Gly))-cyclo(Cys-D-Ala-His-D-Phe-Arg-Trp-Pen)-NH$_2$ (SEQ ID NO: 18) | 17.0 | 21.5 | 0.584 | 352 |
| Hydantoin(C(O)-(Gly-Gly))-cyclo(Cys-D-Ala-His-D-Phe-Arg-Trp-Pen)-NH$_2$ (SEQ ID NO: 19) | 40.2 | 8.90 | 0.495 | 8300 |
| Hydantoin(C(O)-(Ala-Gly))-cyclo(Cys-D-Ala-His-D-Phe-Arg-Trp-Cys)-NH$_2$ (SEQ ID NO: 20) | 17.6 | 2.23 | 0.241 | 516 |

TABLE 2B-continued

Intracellular Cyclic AMP (cAMP) Levels for Formula (II) Examples

| Formula (II) Compounds | $EC_{50}$ hMC1 | $EC_{50}$ hMC3 | $EC_{50}$ hMC4 | $EC_{50}$ hMC5 |
|---|---|---|---|---|
| Hydantoin(C(O)-(D-Ala-Gly))-cyclo(Cys-D-Ala-His-D-Phe-Arg-Trp-Cys)-NH$_2$ (SEQ ID NO: 21) | 4.70 | 2.22 | 0.309 | 355 |
| Hydantoin(C(O)-(D-Arg-Gly))-cyclo(Cys-Glu-His-D-Phe-Arg-Trp-Cys)-NH$_2$ (SEQ ID NO: 26) | 18.0 | 17.1 | 0.160 | 2710 |
| Hydantoin(C(O)-(Gly-D-Arg))-cyclo(Cys-Glu-His-D-Phe-Arg-Trp-Cys)-NH$_2$ (SEQ ID NO: 42) | 12.9 | 10.3 | 0.125 | 7440 |
| Hydantoin(C(O)-(Arg-Gly))-cyclo(Cys-Glu-His-D-Phe-Arg-Trp-Cys)-NH$_2$ (SEQ ID NO: 13) | 8.83 | 7.86 | 0.0979 | 4010 |
| Hydantoin(C(O)-(Gly-Arg))-cyclo(Cys-Glu-His-D-Phe-Arg-Trp-Cys)-NH$_2$ (SEQ ID NO: 40) | 9.97 | 3.63 | 0.0687 | 335 |
| Hydantoin(C(O)-(Arg-Gly))-cyclo(Cys-D-Ala-His-D-Phe-Arg-Trp-Cys)-NH$_2$ (SEQ ID NO: 28) | 8.81 | 18.2 | 0.503 | 3560 |
| Hydantoin(C(O)-(D-Arg-Gly))-cyclo(Cys-D-Ala-His-D-Phe-Arg-Trp-Cys)-NH$_2$ (SEQ ID NO: 27) | 11.5 | 23.2 | 0.513 | 3950 |
| Hydantoin(C(O)-(Gly-D-Arg))-cyclo(Cys-D-Ala-His-D-Phe-Arg-Trp-Cys)-NH$_2$ (SEQ ID NO: 43) | 7.53 | 11.6 | 0.435 | 9840 |
| Hydantoin(C(O)-(Gly-Arg))-cyclo(Cys-D-Ala-His-D-Phe-Arg-Trp-Cys)-NH$_2$ (SEQ ID NO: 41) | 8.85 | 5.17 | 0.599 | 3610 |
| Hydantoin(C(O)-(Arg-Gly))-cyclo(Cys-D-Ala-His-D-2-Nal-Arg-Trp-Cys)-NH$_2$ (SEQ ID NO: 28) | 96.6 | 13.1 | 21.2 | 103 |

TABLE 2C

Intracellular Cyclic AMP (cAMP) Levels for Formula (III) Examples

| Formula (III) Compounds | $EC_{50}$ hMC1 | $EC_{50}$ hMC3 | $EC_{50}$ hMC4 | $EC_{50}$ hMC5 |
|---|---|---|---|---|
| cyclo[Hydantoin(C(O)-(Aib-Cys))-D-Ala-His-D-Phe-Arg-Trp-Cys]-NH$_2$ (SEQ ID NO: 48) | — | 6.28 | 0.407 | — |
| cyclo[Hydantoin(C(O)-(Val-Cys))-D-Ala-His-D-Phe-Arg-Trp-Cys]-NH$_2$ (SEQ ID NO: 49) | — | 3.77 | 0.214 | — |
| cyclo[Hydantoin(C(O)-(Leu-Cys))-D-Ala-His-D-Phe-Arg-Trp-Cys]-NH$_2$ (SEQ ID NO: 51) | — | 4.72 | 0.428 | — |
| cyclo[Hydantoin(C(O)-(Ile-Cys))-D-Ala-His-D-Phe-Arg-Trp-Cys]-NH$_2$ (SEQ ID NO: 52) | — | 8.51 | 1.85 | — |
| cyclo[Hydantoin(C(O)-(A6c-Cys))-D-Ala-His-D-Phe-Arg-Trp-Cys]-NH$_2$ (SEQ ID NO: 54) | — | 5.66 | 1.72 | — |
| cyclo[Hydantoin(C(O)-(Gly-Cys))-Glu-His-D-Phe-Arg-Trp-Cys]-NH$_2$ (SEQ ID NO: 57) | 14.5 | 21.8 | 0.576 | 1780 |

Radioligand Binding Assays

Cellular membranes used for the in vitro receptor binding assays were obtained from transgenic CHO-K1 cells stably expressing hMC-R receptor subtypes 1, 3, 4 or 5. The CHO-K1 cells expressing the desired hMC-R receptor type were sonicated (Branson® setting 7, approximately 30 sec) in ice-cold 50 mM Tris-HCl at pH 7.4 and then centrifuged at 39,000 g for 10 minutes at approximately 4° C. The pellets were re-suspended in the same buffer and centrifuged at 50,000 g for 10 minutes at approximately 4° C. The washed pellets containing the cellular membranes were stored at approximately −80° C.

Competitive inhibition of [$^{125}$I](Tyr$^2$)-(Nle$^4$-D-Phe$^7$)α-MSH ([$^{125}$I]-NDP-α-MSH, Amersham Biosciences®) binding was carried out in polypropylene 96 well plates. Cell membranes (1-10 µg protein/well) prepared as described above were incubated in 50 mM Tris-HCl at pH 7.4 containing 0.2% bovine serum albumin (BSA), 5 mM MgCl$_2$, 1 mM CaCl$_2$ and 0.1 mg/mL bacitracin, with increasing concentrations of the test compound and 0.1-0.3 nM [$^{125}$I]-NDP-α-MSH for approximately 90-120 minutes at approximately 37° C. Bound [$^{125}$I]-NDP-α-MSH ligand was separated from free [$^{125}$I]-NDP-α-MSH by filtration through GF/C glass fiber filter plates (Unifilter®; Packard) presoaked with 0.1% (w/v) polyethylenimine (PEI), using a Packard Filtermate° harvester. Filters were washed three times with 50 mM Tris-HCl at pH 7.4 at a temperature of approximately 0-4° C. and then assayed for radioactivity using a Packard Topcount® scintillation counter. Binding data were analyzed by computer-assisted non-linear regression analysis (XL fit; IDBS).

A selection of the preferred embodiments was tested using the above-discussed assay and the binding constants (Ki in nM) are reported in Tables 3A, 3B and 3C.

TABLE 3A

Binding Constants for Formula (I) Examples

| Formula (I) Compounds | Ki hMC1 | Ki hMC3 | Ki hMC4 | Ki hMC5 |
|---|---|---|---|---|
| cyclo[Hydantoin(C(O)-(Cys-D-Ala))-His-D-Phe-Arg-Trp-Cys]-NH$_2$ (SEQ ID NO: 1) | 230 | 7590 | 126 | 7020 |
| cyclo[Hydantoin(C(O)-(Glu-D-Ala))-His-D-Phe-Arg-Trp-Lys]-NH$_2$ (SEQ ID NO: 68) | 72.6 | 1920 | 45.2 | >10000 |
| cyclo[Hydantoin(C(O)-(Glu-D-Ala))-His-D-Phe-Arg-Trp-Orn]-NH$_2$ (SEQ ID NO: 11) | 60.4 | 2840 | 52.4 | >10000 |
| cyclo[Hydantoin(C(O)-(Glu-D-Ala))-His-D-Phe-Arg-Trp-Dab]-NH$_2$ (SEQ ID NO: 11) | 28 | 90.5 | 12.7 | 877 |
| cyclo[Hydantoin(C(O)-(Glu-D-Ala))-His-D-Phe-Arg-Trp-Dap]-NH$_2$ (SEQ ID NO: 11) | 16.4 | 863 | 4.97 | >10000 |
| cyclo[Hydantoin(C(O)-(Asp-D-Ala))-His-D-Phe-Arg-Trp-Orn]-NH$_2$ (SEQ ID NO: 4) | 37.7 | 576 | 7.81 | 6400 |
| cyclo[Hydantoin(C(O)-(Asp-D-Ala))-His-D-Phe-Arg-Trp-Dap]-NH$_2$ (SEQ ID NO: 4) | 66.6 | 1820 | 19.9 | >10000 |
| cyclo[Hydantoin(C(O)-(Asp-His))-D-2-Nal-Arg-Trp-Lys]-NH$_2$ (SEQ ID NO: 5) | 200 | 68.8 | 6.63 | 142 |
| cyclo[Hydantoin(C(O)-(Asp-Aic))-D-2-Nal-Arg-Trp-Lys]-NH$_2$ (SEQ ID NO: 9) | 9028 | 2628 | 35.8 | 1156 |
| cyclo[Hydantoin(C(O)-(Asp-A5c))-D-2-Nal-Arg-Trp-Lys]-NH$_2$ (SEQ ID NO: 7) | 9938 | 2390 | 44.6 | 1103 |
| cyclo[Hydantoin(C(O)-(Asp-A6c))-D-2-Nal-Arg-Trp-Lys]-NH$_2$ (SEQ ID NO: 8) | 2170 | 1479 | 16.5 | 451 |
| cyclo[Hydantoin(C(O)-(Asp-Apc))-D-2-Nal-Arg-Trp-Lys]-NH$_2$ (SEQ ID NO: 10) | 1276 | 2756 | 266 | 1096 |
| cyclo[Hydantoin(C(O)-(Asp-A3c))-D-2-Nal-Arg-Trp-Lys]-NH$_2$ (SEQ ID NO: 6) | 7567 | 1922 | 420 | 2879 |

TABLE 3B

Binding Constants for Formula (II) Examples

| Formula (II) Compounds | Ki hMC1 | Ki hMC3 | Ki hMC4 | Ki hMC5 |
|---|---|---|---|---|
| Hydantoin(C(O)-(Nle-Gly))-cyclo(Cys-Glu-His-D-Phe-Arg-Trp-Cys)-NH$_2$ (SEQ ID NO: 14) | 14.3 | 198 | 5.76 | 67.8 |
| Hydantoin(C(O)-(Gly-Gly))-cyclo(Cys-Glu-His-D-Phe-Arg-Trp-Cys)-NH$_2$ (SEQ ID NO: 15) | 11.9 | 311 | 5.41 | 73.9 |
| Hydantoin(C(O)-(A6c-Nle))-cyclo(Cys-D-Ala-His-D-Phe-Arg-Trp-Cys)-NH$_2$ (SEQ ID NO: 32) | 31.6 | 224 | 19.6 | 2500 |
| Hydantoin(C(O)-(D-Ala-Nle))-cyclo(Cys-D-Ala-His-D-Phe-Arg-Trp-Cys)-NH$_2$ (SEQ ID NO: 35) | 16.0 | 63.9 | 8.64 | 1820 |
| Hydantoin(C(O)-(Val-Nle))-cyclo(Cys-D-Ala-His-D-Phe-Arg-Trp-Cys)-NH$_2$ (SEQ ID NO: 36) | 33.7 | 132 | 40.2 | 3210 |

TABLE 3B-continued

Binding Constants for Formula (II) Examples

| Formula (II) Compounds | Ki hMC1 | Ki hMC3 | Ki hMC4 | Ki hMC5 |
|---|---|---|---|---|
| Hydantoin(C(O)-(Leu-Nle))-cyclo(Cys-D-Ala-His-D-Phe-Arg-Trp-Cys)-NH$_2$ (SEQ ID NO: 37) | 48.3 | 534 | 74.1 | 3290 |
| Hydantoin(C(O)-(Cha-Nle))-cyclo(Cys-D-Ala-His-D-Phe-Arg-Trp-Cys)-NH$_2$ (SEQ ID NO: 38) | 40.8 | 870 | 137 | 3560 |
| Hydantoin(C(O)-(Aib-Nle))-cyclo(Cys-D-Ala-His-D-Phe-Arg-Trp-Cys)-NH$_2$ (SEQ ID NO: 39) | 17.7 | 73.6 | 8.40 | 2120 |
| Hydantoin(C(O)-(Nle-Gly))-cyclo(Cys-D-Ala-His-D-Phe-Arg-Trp-Cys)-NH$_2$ (SEQ ID NO: 16) | 7.92 | 46.4 | 6.70 | 21.3 |
| Hydantoin(C(O)-(Gly-Gly))-cyclo(Cys-D-Ala-His-D-Phe-Arg-Trp-Cys)-NH$_2$ (SEQ ID NO: 17) | 20.9 | 69.7 | 8.32 | 50.0 |
| Hydantoin(C(O)-(Nle-Gly))-cyclo(Cys-D-Ala-His-D-Phe-Arg-Trp-Pen)-NH$_2$ (SEQ ID NO: 18) | 12.9 | 38.5 | 3.53 | 27.1 |
| Hydantoin(C(O)-(Gly-Gly))-cyclo(Cys-D-Ala-His-D-Phe-Arg-Trp-Pen)-NH$_2$ (SEQ ID NO: 19) | 127 | 811 | 10.4 | 381 |
| Hydantoin(C(O)-(Ala-Gly))-cyclo(Cys-D-Ala-His-D-Phe-Arg-Trp-Cys)-NH$_2$ (SEQ ID NO: 20) | 13.9 | 38.4 | 5.73 | 18.9 |
| Hydantoin(C(O)-(D-Ala-Gly))-cyclo(Cys-D-Ala-His-D-Phe-Arg-Trp-Cys)-NH$_2$ (SEQ ID NO: 21) | 11.7 | 73.1 | 4.28 | 34.7 |
| Hydantoin(C(O)-(Aib-Gly))-cyclo(Cys-D-Ala-His-D-Phe-Arg-Trp-Cys)-NH$_2$ (SEQ ID NO: 22) | 36.8 | 290 | 13.7 | 133 |
| Hydantoin(C(O)-(Val-Gly))-cyclo(Cys-D-Ala-His-D-Phe-Arg-Trp-Cys)-NH$_2$ (SEQ ID NO: 23) | 15.3 | 160 | 8.66 | 33.4 |
| Hydantoin(C(O)-(Ile-Gly))-cyclo(Cys-D-Ala-His-D-Phe-Arg-Trp-Cys)-NH$_2$ (SEQ ID NO: 24) | 11.6 | 194 | 11.5 | 28.9 |
| Hydantoin(C(O)-(Leu-Gly))-cyclo(Cys-D-Ala-His-D-Phe-Arg-Trp-Cys)-NH$_2$ (SEQ ID NO: 25) | 19.3 | 331 | 26.7 | 44.6 |
| Hydantoin(C(O)-(D-Arg-Gly))-cyclo(Cys-Glu-His-D-Phe-Arg-Trp-Cys)-NH$_2$ (SEQ ID NO: 26) | 9.49 | 124 | 2.95 | 2260 |
| Hydantoin(C(O)-(Gly-D-Arg))-cyclo(Cys-Glu-His-D-Phe-Arg-Trp-Cys)-NH$_2$ (SEQ ID NO: 42) | 4.30 | 78.0 | 1.77 | 4540 |
| Hydantoin(C(O)-(Arg-Gly))-cyclo(Cys-Glu-His-D-Phe-Arg-Trp-Cys)-NH$_2$ (SEQ ID NO: 13) | 8.59 | 94.1 | 2.44 | 7760 |
| Hydantoin(C(O)-(Gly-Arg))-cyclo(Cys-Glu-His-D-Phe-Arg-Trp-Cys)-NH$_2$ (SEQ ID NO: 40) | 5.68 | 55.5 | 2.44 | 4220 |
| Hydantoin(C(O)-(Arg-Gly))-cyclo(Cys-D-Ala-His-D-Phe-Arg-Trp-Cys)-NH$_2$ (SEQ ID NO: 28) | 2.65 | 41.3 | 4.17 | 650 |
| Hydantoin(C(O)-(D-Arg-Gly))-cyclo(Cys-D-Ala-His-D-Phe-Arg-Trp-Cys)-NH$_2$ (SEQ ID NO: 27) | 3.52 | 48.7 | 5.78 | 872 |
| Hydantoin(C(O)-(Gly-D-Arg))-cyclo(Cys-D-Ala-His-D-Phe-Arg-Trp-Cys)-NH$_2$ (SEQ ID NO: 43) | 3.51 | 29.2 | 6.04 | 914 |
| Hydantoin(C(O)-(Gly-Arg))-cyclo(Cys-D-Ala-His-D-Phe-Arg-Trp-Cys)-NH$_2$ (SEQ ID NO: 41) | 1.14 | 01.7 | 4.53 | 783 |
| Hydantoin(C(O)-(Arg-Gly))-cyclo(Cys-D-Ala-His-D-2-Nal-Arg-Trp-Cys)-NH$_2$ (SEQ ID NO: 28) | 11.9 | 7.43 | 0.195 | 14.6 |

TABLE 3C

Binding Constants for Formula (III) Examples

| Formula (III) Compounds | Ki hMC1 | Ki hMC3 | Ki hMC4 | Ki hMC5 |
|---|---|---|---|---|
| cyclo[Hydantoin(C(O)-(Aib-Cys))-D-Ala-His-D-Phe-Arg-Trp-Cys]-NH$_2$ (SEQ ID NO: 48) | 47.6 | 1100 | 47.1 | >10000 |
| cyclo[Hydantoin(C(O)-(Val-Cys))-D-Ala-His-D-Phe-Arg-Trp-Cys]-NH$_2$ (SEQ ID NO: 49) | 21.2 | 730 | 34.5 | >10000 |
| cyclo[Hydantoin(C(O)-(Leu-Cys))-D-Ala-His-D-Phe-Arg-Trp-Cys]-NH$_2$ (SEQ ID NO: 51) | 47.4 | 1550 | 27.9 | >10000 |
| cyclo[Hydantoin(C(O)-(Ile-Cys))-D-Ala-His-D-Phe-Arg-Trp-Cys]-NH$_2$ (SEQ ID NO: 52) | 53.4 | 1760 | 41.6 | >10000 |
| cyclo[Hydantoin(C(O)-(A6c-Cys))-D-Ala-His-D-Phe-Arg-Trp-Cys]-NH$_2$ (SEQ ID NO: 54) | 38.5 | 1760 | 53.2 | 9270 |
| cyclo[Hydantoin(C(O)-(Gly-Cys))-Glu-His-D-Phe-Arg-Trp-Cys]-NH$_2$ (SEQ ID NO: 57) | 15.6 | 305 | 8.92 | 3070 |

In Vivo Assays

Ligands for melanocortin receptors of the present invention can be and were tested for an effect upon food intake and/or body weight according to the following procedures. One skilled in the art would know that procedures similar to those described herein may be used to assay the effect of the compounds of the invention upon food intake and/or body weight.

Acute Feeding Experiments (Fasting)

Male Sprague Dawley rats (250 g) are housed in individual cages and maintained under 12:12 hour light:dark conditions. The rats are fasted for 18 hours prior to the start of the experiment with water available ad libitum. At time 0, the rats are injected subcutaneously (sc) with selected compounds at selected doses, for example, 500 or 100 nmole/kg, or with vehicle, and are provided with food. Individual food consumption is measured at about 1, 2, 3, 4, 5 and 6 hours after injection.

Acute Feeding Experiments (Non Fasting)

Male Sprague Dawley rats (250 g) were housed in individual cages and maintained under 12:12 hour light:dark conditions. Food and water was available ad libitum throughout the experiment. At time 0, the rats were injected sc with compound at doses of either 8 μmole/kg, or with vehicle. Individual food consumption was measured at about 0.5, 1, 1.5, 2, 3 and 4 hours after injection. Data for selected compounds of the invention are reported in FIG. 1.

Chronic Feeding Experiments

Male Sprague Dawley rats (250 g) were housed in individual cages and maintained under 12:12 hour light:dark conditions with both food and water available ad libitum. The rats were injected 3×/day (0800, 1200, and 1600 h), sc, with compound at various doses or with vehicle for 7 days. Individual body weight and food consumption were measured daily. Data for selected compounds of the invention are reported in FIGS. 2A, 2B, 3A, 3B, 4A and 4B.

Methods of Use and Compositions

Based on their ability to agonize or antagonize the MC-4 and/or MC-3 receptor, the present inventions also relates to the use of the ligands of the present invention in methods for treating obesity as well as other body weight disorders (e.g., anorexia, bulimia, AIDS wasting, wasting in frail elderly, Prader-Willi syndrome) and cachexia (e.g., cancer cachexia, renal cachexia, cardiac cachexia). The invention further relates to the treatment of disorders relating to behavior (e.g., motivation, anxiety, depression, neuropathic pain), memory (including learning), cardiovascular function (e.g. cardiac cachexia), pulmonary disorders (e.g., acute respiratory distress syndrome, pulmonary fibrosis, chronic obstructive pulmonary disease, asthma), inflammation (e.g., rheumatoid arthritis, gouty arthritis, multiple sclerosis), sepsis and septic, cardiogenic and hypovolemic shock, sexual dysfunction (e.g., endometriosis, uterine bleeding), penile erection, muscle atrophy, bone development, nerve growth, protection and repair (spinal cord injuries), intrauterine fetal growth, and the like. In addition, formula (I), (II) or (III) compounds may ameliorate insult to a patient (e.g., organ transplant rejection, ischemia and reperfusion injury, wounding) or weight loss cause by a medicinal regimen (e.g., chemotherapy, radiation therapy, temporary or permanent immobilization, dialysis). Modulation of normal body functions (e.g., ovarian and placental development, prolactin and FSH secretion, parturition, spermatogenesis, thyroxin release, aldosterone synthesis, body temperature, blood pressure, heart rate, vascular tone, brain blood flow, blood glucose levels, sebum and pheromone secretion) is possible with the claimed compounds.

The present invention provides a method of inhibiting alcohol consumption, for reducing alcohol consumption, for treating alcoholism, or for treating alcohol abuse by eliciting an agonist or antagonist effect from a melanocortin receptor by administering an effective amount of a compound of formula (I), (II) or (III), or a pharmaceutically acceptable salt thereof. The formula (I), (II) or (III) compounds are useful for inhibiting alcohol consumption is a selective melanocortin-4 receptor agonist, or a pharmaceutically acceptable salt thereof, with a functional activity characterized by an $EC_{50}$ at least 15-fold more, at least 17-fold more, at least 90-fold more, at least 200-fold more or at least 3000-fold more selective for the human melanocortin-4 receptor than for the human melanocortin-1 receptor, the human melanocortin-3 receptor and the human melanocortin-5 receptor.

The terms treating and treatment are used herein to mean that, at a minimum, administration of a compound of the present invention mitigates a disease state by acting via the MC-3 or MC-4 receptor. Thus, the terms include: preventing a disease state from occurring in a mammal, particularly when the mammal is predisposed to acquiring the disease, but has not yet been diagnosed with the disease; inhibiting progression of the disease state; and/or alleviating or reversing the disease state.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition and *Peptide and Protein Drug Delivery*, Marcel Dekker, N.Y., 1991.

The compositions of the invention comprise:
a. a safe and effective amount of a compound of formula (I), (II) or (III); and
b. a pharmaceutically-acceptable excipient.

A "safe and effective amount" of a formula (I), (II) or (III) compound is an amount that is effective to interact with the MC-4 and/or MC-3 receptor, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the excipient employed, the solubility of the formula (I), (II) or (III) compound therein, and the dosage regimen desired for the composition.

In addition to the subject compound, the compositions of the subject invention contain one or more pharmaceutically-acceptable excipients. The term "pharmaceutically-acceptable excipient", as used herein, means one or more compatible solid or liquid ingredients which are suitable for administration to an animal, preferably a mammal, more preferably a human. The term "compatible", as used herein, means that the components of the composition are capable of being comingled with the subject compound, and with each other, in a manner such that there is no interaction which would substantially reduce the pharmaceutical efficacy of the composition under ordinary use situations. Pharmaceutically-acceptable excipients must, of course, be of sufficiently high purity and sufficiently low toxicity to render them suitable for administration to the animal, preferably a mammal, more preferably a human being treated.

Some examples of substances which can serve as pharmaceutically-acceptable excipients or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; wetting agents and lubricants, such as sodium lauryl sulfate; coloring agents; flavoring agents; tableting agents, stabilizers; antioxidants; preservatives; pyrogen-free water; isotonic saline; and buffers, such as phosphate, citrate and acetate.

The choice of pharmaceutically-acceptable excipients to be used in conjunction with the subject compound is basically determined by the way the compound is to be administered. If the subject compound is to be injected, the preferred pharmaceutically-acceptable excipient is sterile water, physiological saline, or mixtures thereof, the pH of which has preferably been adjusted to about 4-10 with a pharmaceutical buffer; a compatible suspending agent may also be desirable.

In particular, pharmaceutically-acceptable excipients for systemic administration include sugars, starches, cellulose and its derivatives, malt, gelatin, talc, calcium sulfate, lactose, vegetable oils, synthetic oils, polyols, alginic acid, phosphate, acetate and citrate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight of the total composition.

The compositions of this invention are preferably provided in unit dosage form. As used herein, a "unit dosage form" is a composition of this invention containing an amount of a formula (I), (II) or (III) compound that is suitable for administration to an animal, preferably a mammal, more preferably a human subject, in a single dose, according to good medical practice. These compositions preferably contain from about 1 mg to about 750 mg, more preferably from about 3 mg to about 500 mg, still more preferably from about 5 mg to about 300 mg, of a formula (I), (II) or (III) compound.

The compositions of this invention may be in any of a variety of forms, suitable (for example) for oral, rectal, topical, nasal, ocular, transdermal, pulmonary or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the inhibitory activity of the formula (I), (II) or (III) compound. The amount of excipient employed in conjunction with the formula (I), (II) or (III) compounds is sufficient to provide a practical quantity of material for administration per unit dose of the compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, multi-particulars, gels, films, ovules, elixirs, granules and bulk powders. These oral forms comprise a safe and effective amount, usually at least about 5%, and preferably from about 25% to about 50%, of the formula (I), (II) or (III) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable excipient suitable for the preparation of unit dosage forms for peroral administration are well-known in the art. Tablets typically comprise conventional pharmaceutically-compatible adjuvants as inert diluents, such as calcium carbonate, dibasic calcium phosphate, sodium carbonate, sodium citrate, mannitol, lactose and cellulose; binders such as starch, gelatin, polyvinyl pyrrolidone, hydroxypropylmethylcellulose (HPMC), hydroxypropylcellulose (HPC), acacia and sucrose; disintegrants such as starch (preferably corn, potato or tapioca), sodium starch, glycollate, alginic acid, complex silicates and croscarmelose; lubricants such as magnesium stearate, stearic acid, glyceryl behenate and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of excipient components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable excipients suitable for preparation of such compositions are well known in the art. Typical components of excipients for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth and sodium alginate; typical wetting agents include lecithin and polysorbate 80; and typical preservatives include methyl paraben, propyl paraben and sodium benzoate. Peroral liquid compositions may also contain one or more components such as sweeteners, flavoring agents and colorants disclosed above.

Modified release and pulsatile release dosage forms may contain excipients such as those detailed for immediate-, delayed-, modified-, sustained-, pulsed- or controlled-released in the gastrointestinal tract in the vicinity of the desired topical application, or at various times to extend the desired action, together with additional excipients that act as release rate modifiers, these being coated by conventional methods, typically with pH or time-dependent coatings, on and/or included in the body of the device. Release rate modifiers include, but are not exclusively limited to, hydroxypropyl methyl cellulose, hydroxypropyl methyl cellulose phthalate, methyl cellulose, sodium carboxymethylcellulose, ethyl cellulose, cellulose acetate, cellulose acetate phthalate, polyvinylacetate phthalate, polyethylene oxide, xanthan gum, carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

The compounds of the invention may also be administered as fast-dispersing or fast-dissolving dosage forms (FDDFs). Such formulations may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, fumed silica, silicon dioxide, sodium starch glycolate, sodium stearyl fumarate, sorbitol, xylitol. The terms "dispersing" or "dissolving" as used herein to describe FDDFs, are dependent upon the solubility of the drug substance used, i.e., where the drug substance is insoluble a fast dispersing dosage form can be prepared and where the drug substance is soluble a fast dissolving dosage form can be prepared.

Because the compounds of the present invention are peptides in nature, a preferred mode of administration is parenteral (more preferably intravenous injection) in the form of a unit dose form. Preferred unit dose forms include suspensions and solutions, comprising a safe and effective amount of a formula I, (II) or (III) compound. For such parenteral administration, they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included. When administered intranasally or by inhalation, compounds of formula (I), (II) or (III) are conveniently delivered in the form of a dry powder inhaler or an aerosol spray presentation from a pressurized container, pump, spray, atomizer or nebulae, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A®) or 1,1,1,2,3,3,3-heptafluoropropane (HFA 227EA®), carbon dioxide or other suitable gas. In the case of a pressurized aerosol, the dosage unit may be determined by providing a valve to deliver a metered amount. The pressurized container, pump, spray, atomizer or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the pulmonary, vaginal or rectal routes.

They may also be administered by the ocular route, particularly for treating disorders of the eye. For ophthalmic use, the compounds can be formulated as micronized suspensions in isotonic, pH-adjusted, sterile saline, or, preferably, as solutions in isotonic, pH-adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g., as a carrier, diluent or solubilizer. Alpha-, beta- and gamma-cyclodextrins are most commonly used and suitable examples are described in WO 91/11172 (Stella et al., 1991), WO 94/02518 (Stella et al., 1994) and WO 98/55148 (Vandecruys, 1998).

For treating cardiovascular disorders, particular hypertension, the compounds of the invention may be combined with one or more active ingredient selected from the list:

a) angiotensin receptor blockers (ARB), such as losartan, valsartan, telmisartan, candesartan, irbesartan, eprosartan and olmesartan;

b) calcium channel blockers (CCB) such as amlodipine;

c) statins, such as atorvastatin;

d) PDE5 inhibitors, such as sildenafil, tadalafil, vardenafil, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-di-hydro-7H-pyrazolo[4,3-d]pyrimidin-7-one and; the pyrazolo[4,3-d]pyrimidin-4-ones disclosed in WO 00/27848 particularly N-[[3-(4,7-dihydro-1-methyl-7-oxo-3-propyl-1H-pyrazolo[4,3-d]-pyrimidin-5-1-yl)-4-propxyphenyl]sulfonyl]-1-methyl2-pyrrolidinepropanamide[DA-8159 (Example 68 of WO 00/27848 (Yoo et al., 2000))];

e) beta blockers, such as atenolol or carvedilol;

f) ACE inhibitors, such as quinapril, enalapril and lisinopril;

g) alpha-blockers such as doxazosin;

h) selective aldosterone receptor antagonists (SARA), such as eplerenone or spironolactone;

i) imidazoline $I_1$ agonists, such as rilmenidine or monoxidine; and j) endothelin receptor antagonists and endothelin converting enzyme inhibitors.

Compositions of the subject invention may optionally include other drug actives. If a combination of active agents are administered, then they may be administered simultaneously, separately or sequentially.

Methods of Administration

As indicated, compositions of this invention can be administered topically or systemically. Systemic application includes any method of introducing a formula (I), (II) or (III) compound into the tissues of the body, e.g., intra-articular, intrathecal, epidural, intramuscular, transdermal, intravenous, intraperitoneal, subcutaneous, sublingual, rectal, nasal, pulmonary, and oral administration. The formula (I), (II) or (III) compounds of the present invention are preferably administered systemically, more preferably parenterally and most preferably via intravenous injection.

The specific dosage of compound to be administered, as well as the duration of treatment, and whether the treatment is topical or systemic are interdependent. The dosage and treatment regimen will also depend upon such factors as the specific formula (I), (II) or (III) compound used, the treatment indication, the ability of the formula (I), (II) or (III) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 0.003 mg to about 300 mg, more preferably from about 0.03 mg to about 100 mg, of formula (I), (II) or (III) compound are administered per day for systemic administration. It is understood that these dosage ranges are by way of example only, and that daily administration can be adjusted depending on the factors listed above.

As is known and practiced in the art, all formulations for parenteral administration must be sterile. For mammals, especially humans, (assuming an approximate body weight of 70 kilograms) individual doses of from about 0.001 mg. to about 100 mg are preferred.

A preferred method of systemic administration is intravenous delivery. Individual doses of from about 0.01 mg to about 100 mg, preferably from about 0.1 mg to about 100 mg, are preferred when using this mode of delivery.

In all of the foregoing, of course, the compounds of the invention can be administered alone or as mixtures, and the compositions may further include additional drugs or excipients as appropriate for the indication.

The compound of the invention can be delivered to the preferred site in the body by using a suitable drug delivery system. Drug delivery systems are well known in the art. For example, a drug delivery technique useful for the compounds of the present invention is the conjugation of the compound to an active molecule capable of being transported through a biological barrier (Zlokovic, B. V., *Pharma. Res.*, 12:1395-406 (1995)). A specific example constitutes the coupling of the compound of the invention to fragments of insulin to achieve transport across the blood brain barrier (Fukuta, M. et al., *Pharma. Res.*, 11:1681-8 (1994)). For general reviews of technologies for drug delivery suitable for the compounds of the invention (Zlokovic, B. V., *Pharma. Res.*, 12:1395-406 (1995) and Pardridge, W. M., *Pharmacol. Toxicol.*, 71:3-10 (1992).

The invention claimed is:
1. A compound of formula (II)

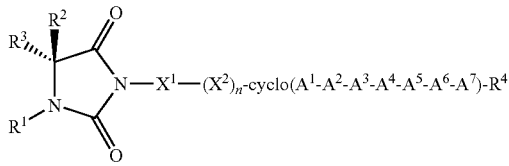

wherein
X1 is

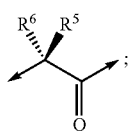

X2 is

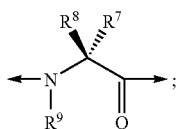

A1 is Asp, Cys, D-Cys, Dab, Dap, Glu, Lys, Orn, Pen or D-Pen;
A2 is an L- or D-amino acid;
A3 is His, 2-Pal, 3-Pal, 4-Pal, Phe, Taz, 2-Thi or 3-Thi;
A4 is D-Bal, D-1-Nal, D-2-Nal, D-Phe;
A5 is Arg, hArg, Dab, Dap, Lys or Orn;
A6 is Bal, 1-Nal, 2-Nal, Phe or Trp;
A7 is Asp, Cys, D-Cys, Dab, Dap, Glu, Lys, Orn, Pen or D-Pen;
R1 is H, (C1-C10)alkyl or substituted (C1-C10)alkyl;
R2 and R3 each is, independently, H, (C1-C10)alkyl, (C1-C10)heteroalkyl, aryl(C1-C5)alkyl, substituted (C1-C10)alkyl, substituted (C1-C10)heteroalkyl or substituted aryl(C1-C5)alkyl or R2 and R3 may be joined together form a cyclic moiety;
R4 is OH or NH2;
R5 and R6 each is, independently, H, (C1-C10)alkyl, or R5 and R6 may be joined together form a cyclic moiety;
R7 and R8 each is, independently, H, (C1-C10)alkyl, (C1-C10)heteroalkyl, aryl(C1-C5)alkyl, substituted (C1-C10)alkyl, substituted (C1-C10)heteroalkyl or substituted aryl(C1-C5)alkyl; or R7 and $R^8$ may be joined together form a cyclic moiety;
$R^9$ is H, $(C_1$-$C_{10})$alkyl or substituted $(C_1$-$C_{10})$alkyl; and
n is 0 ; or
a pharmaceutically acceptable salt thereof.
2. A compound of the formula:

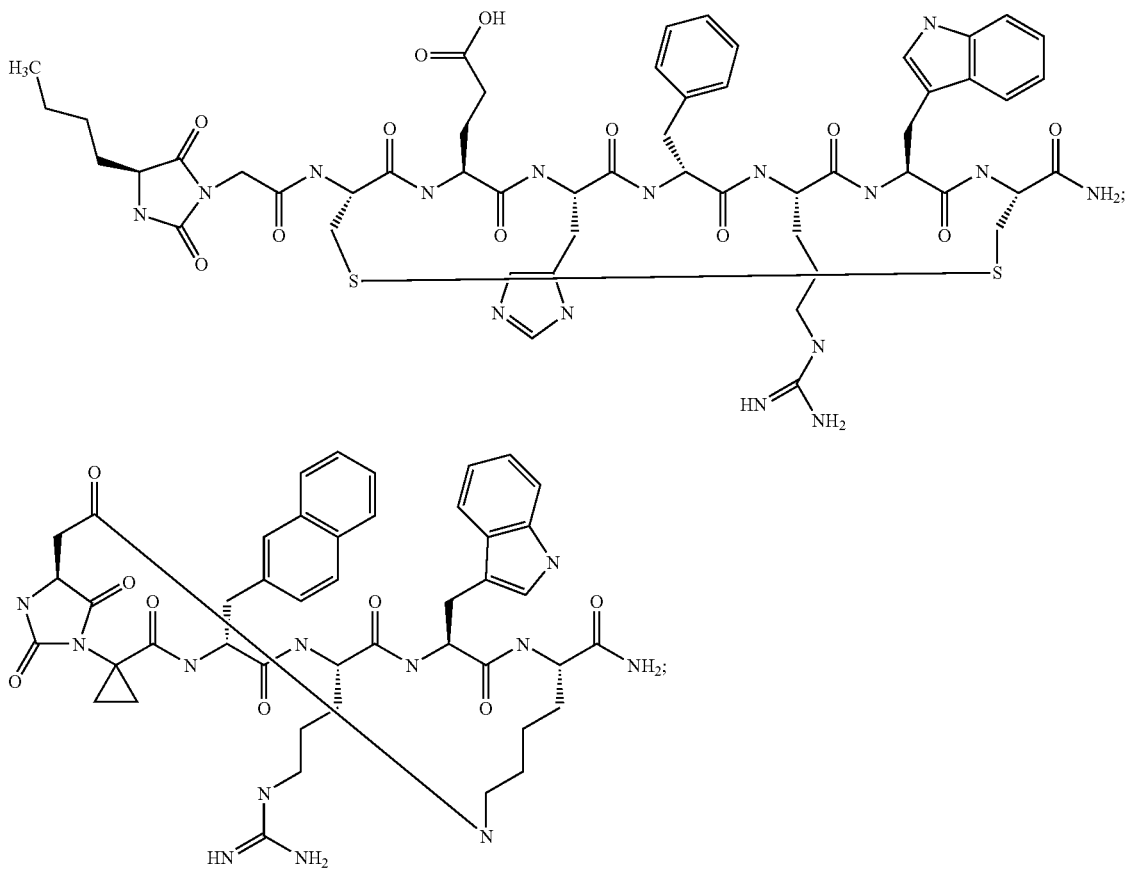

-continued
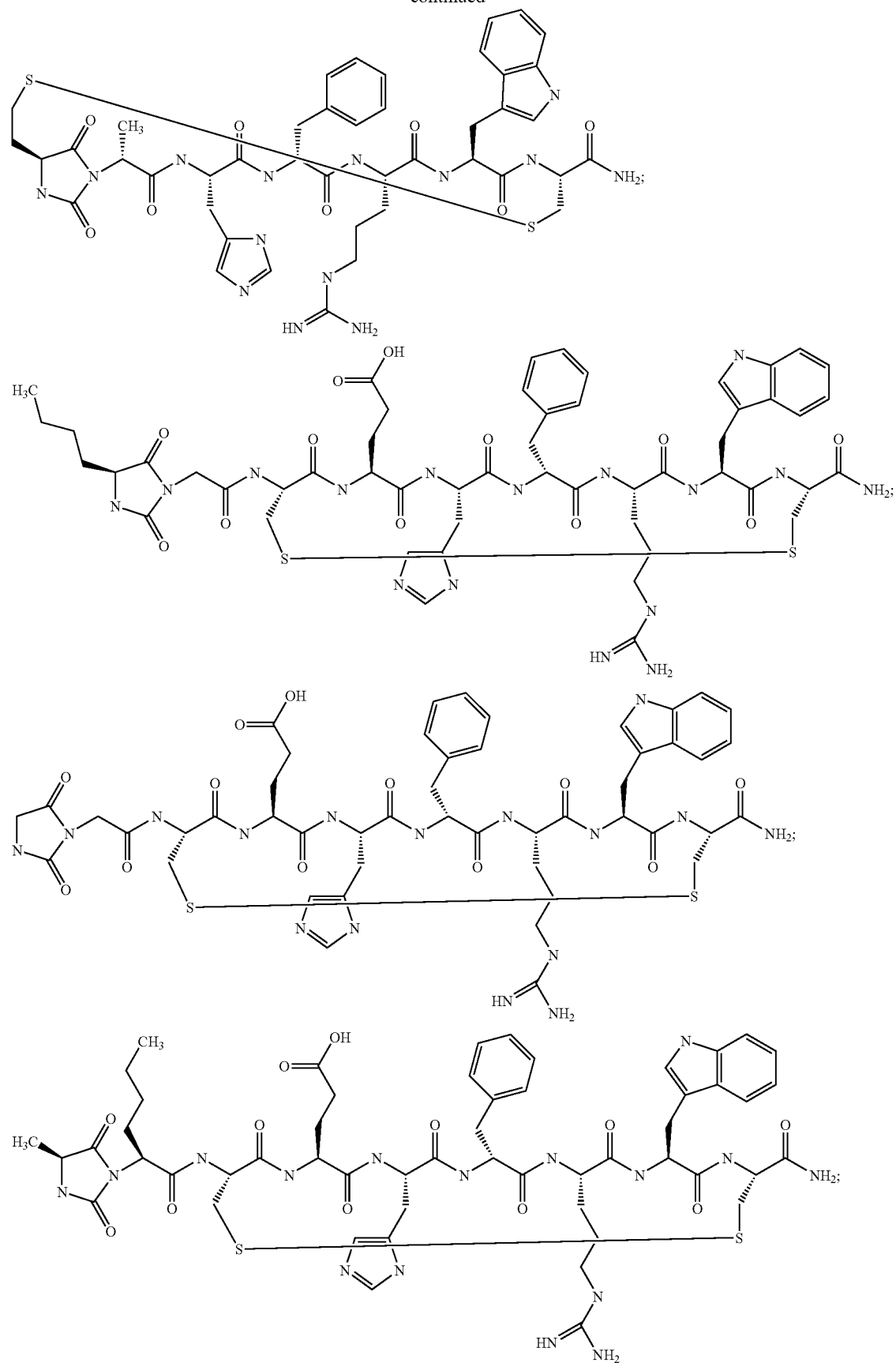

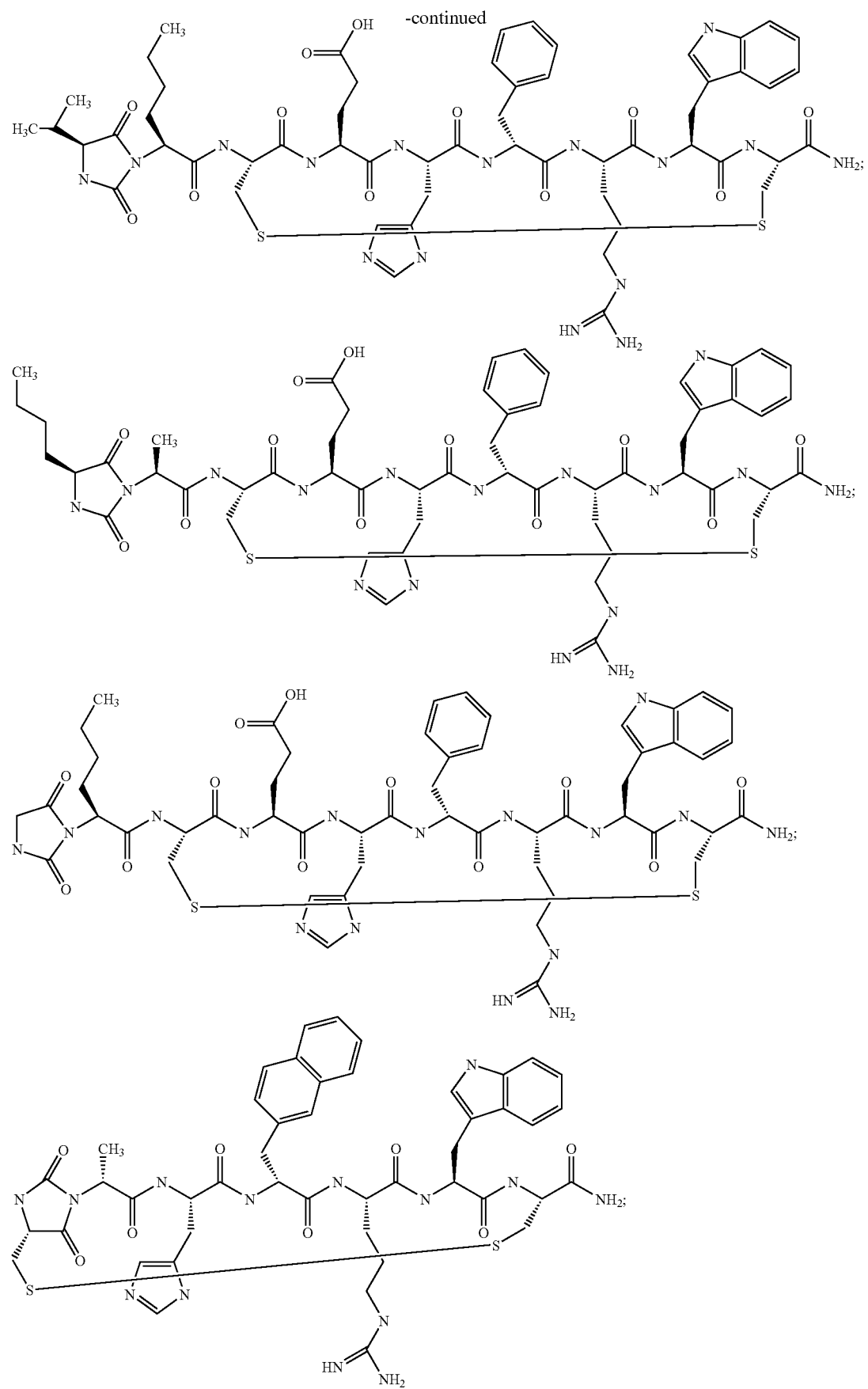

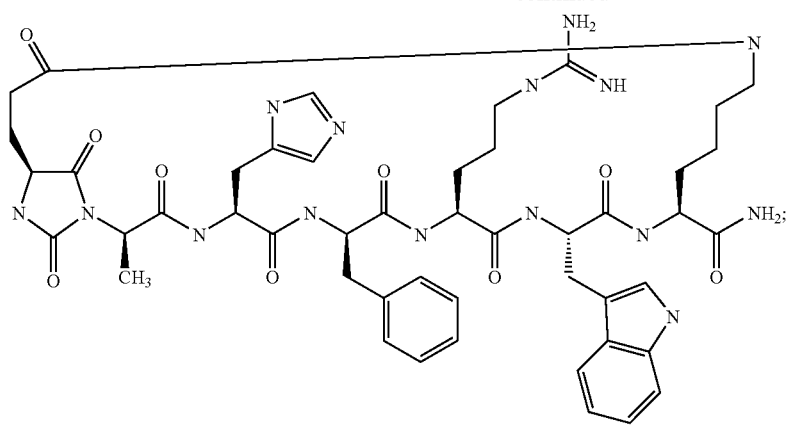
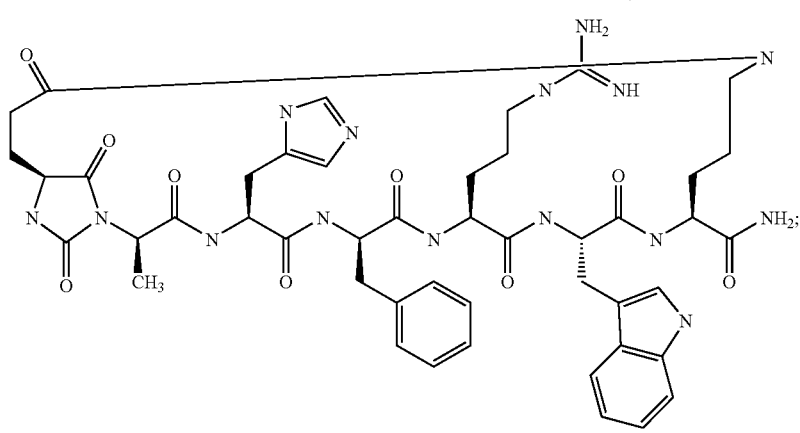
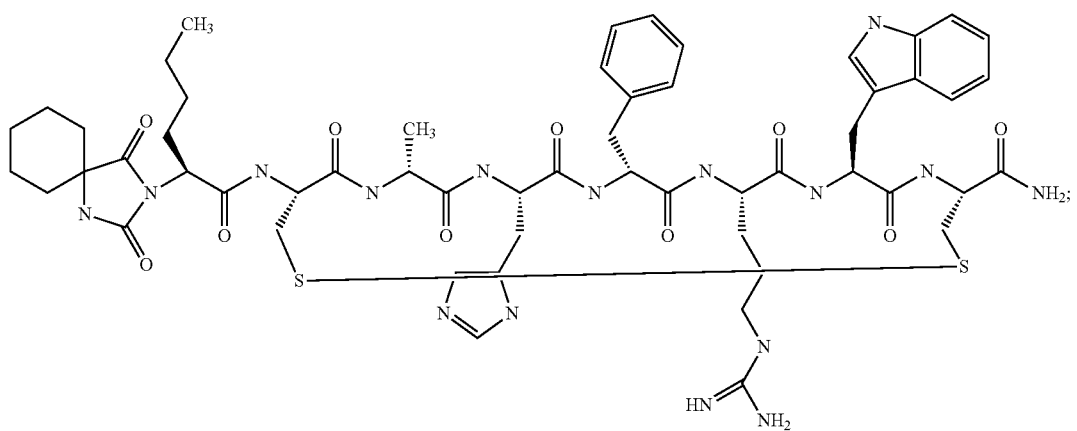 [SMILES: CCCC[C@@H](C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O)N1C(=O)NC2(CCCCC2)C1=O]
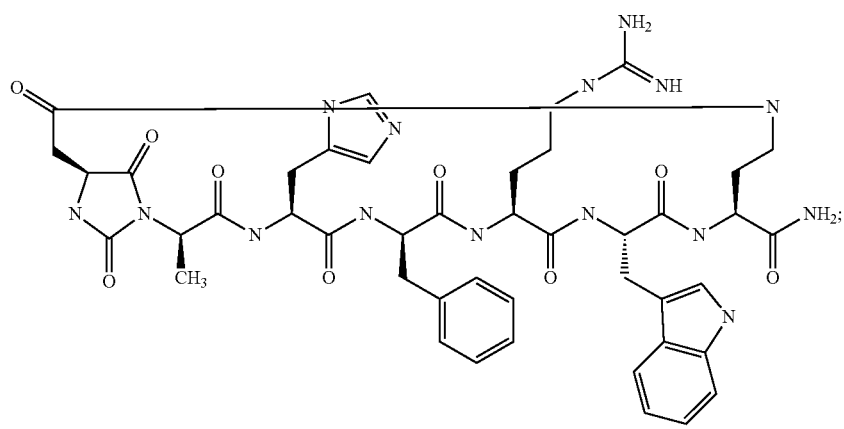

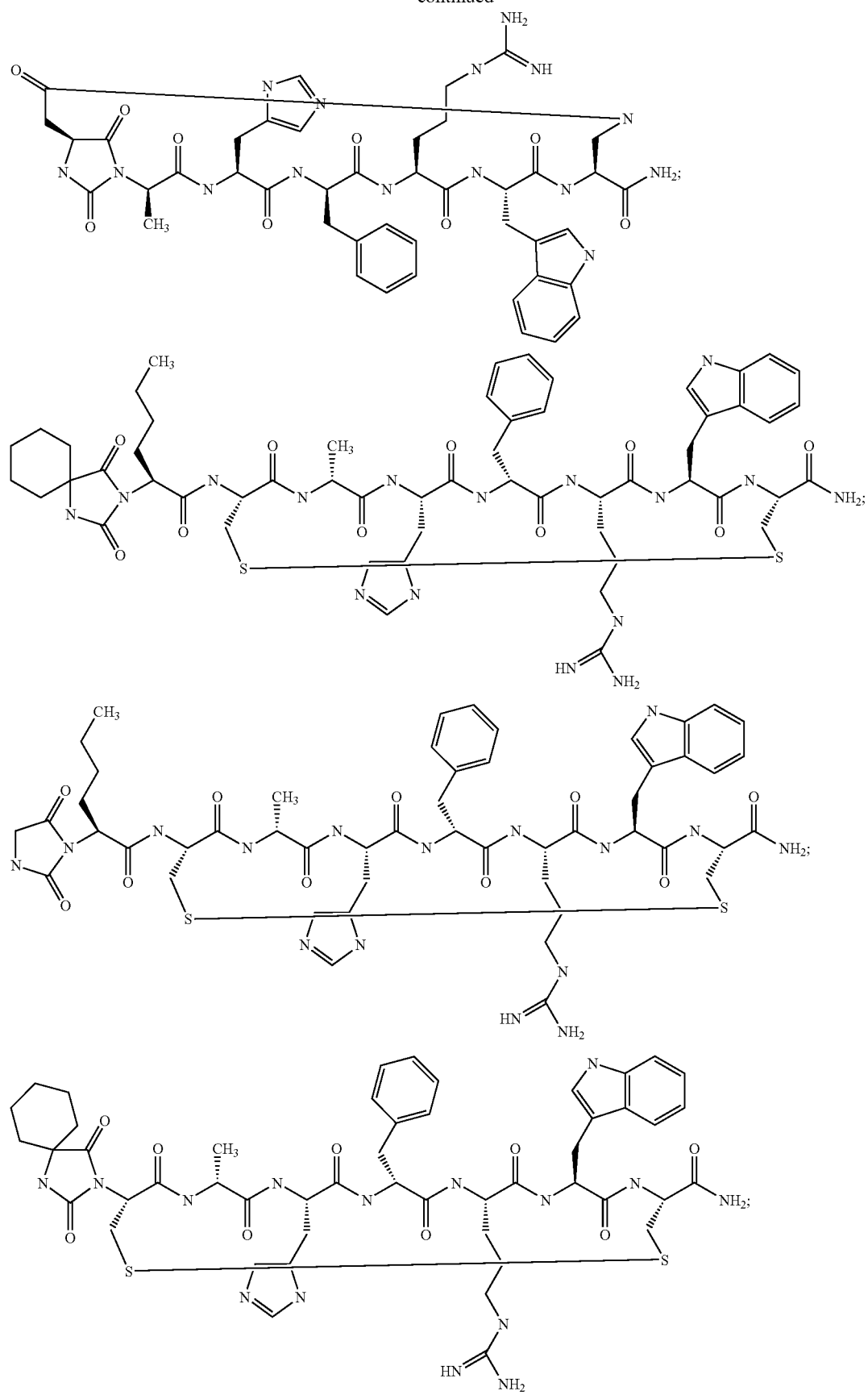

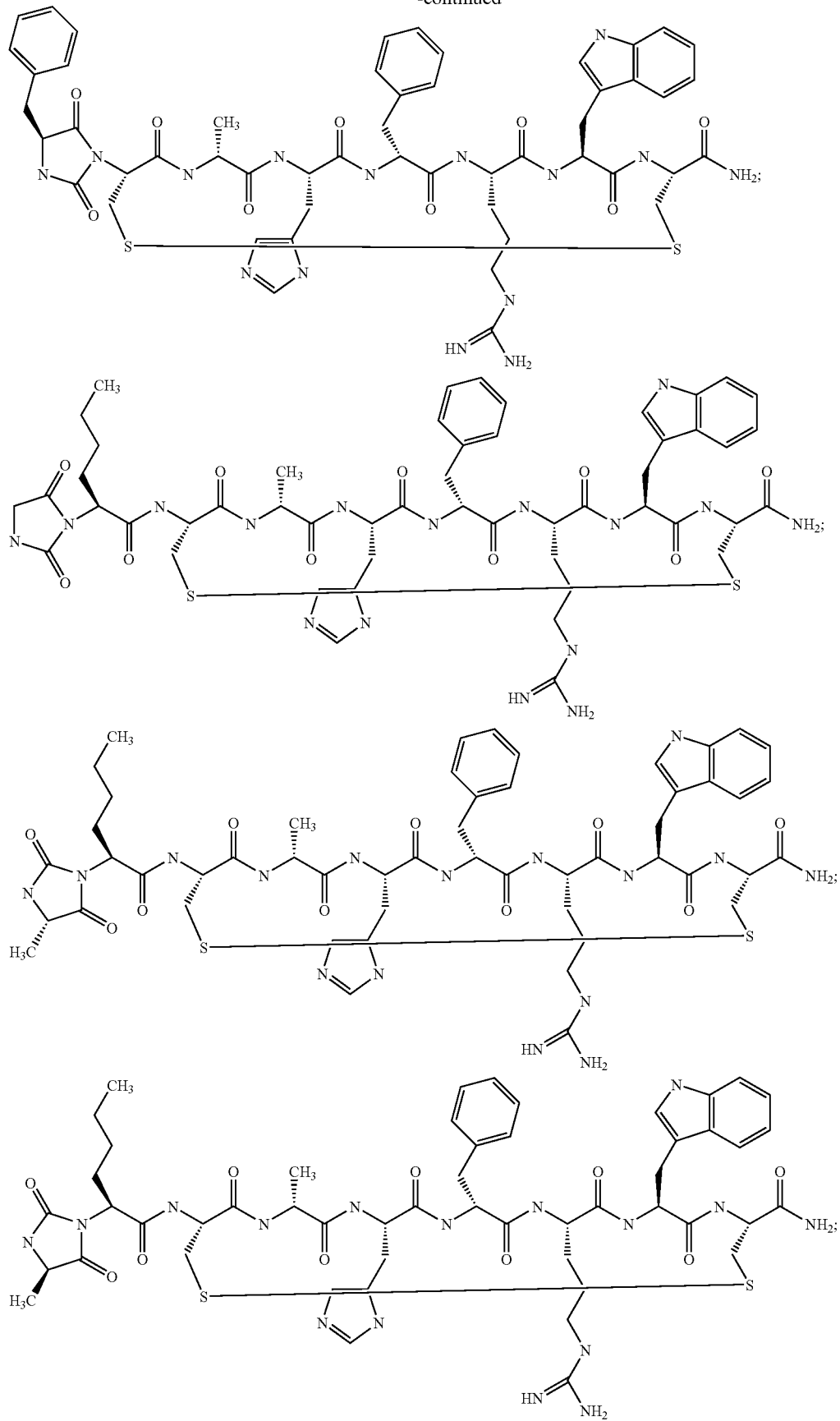

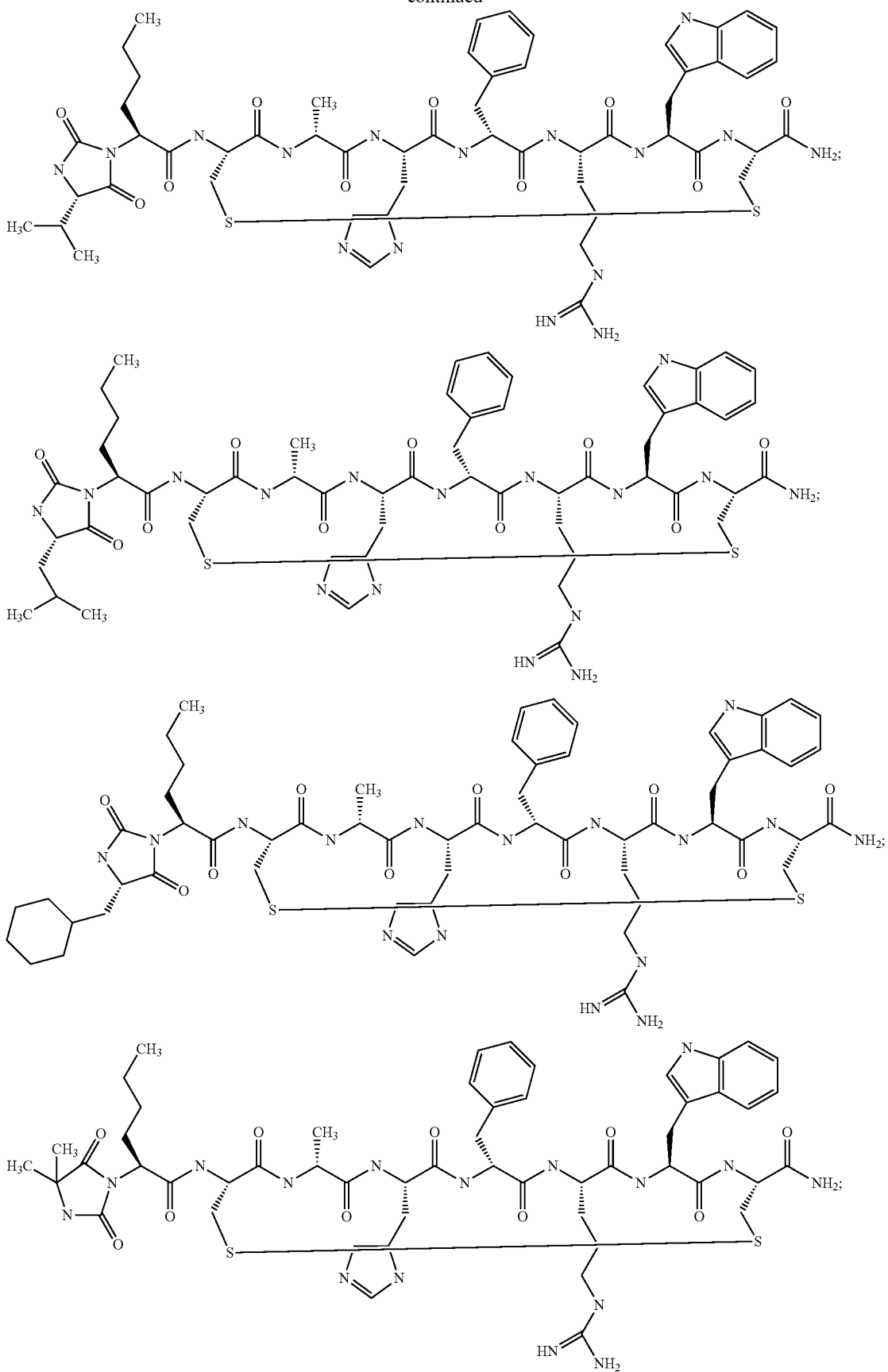

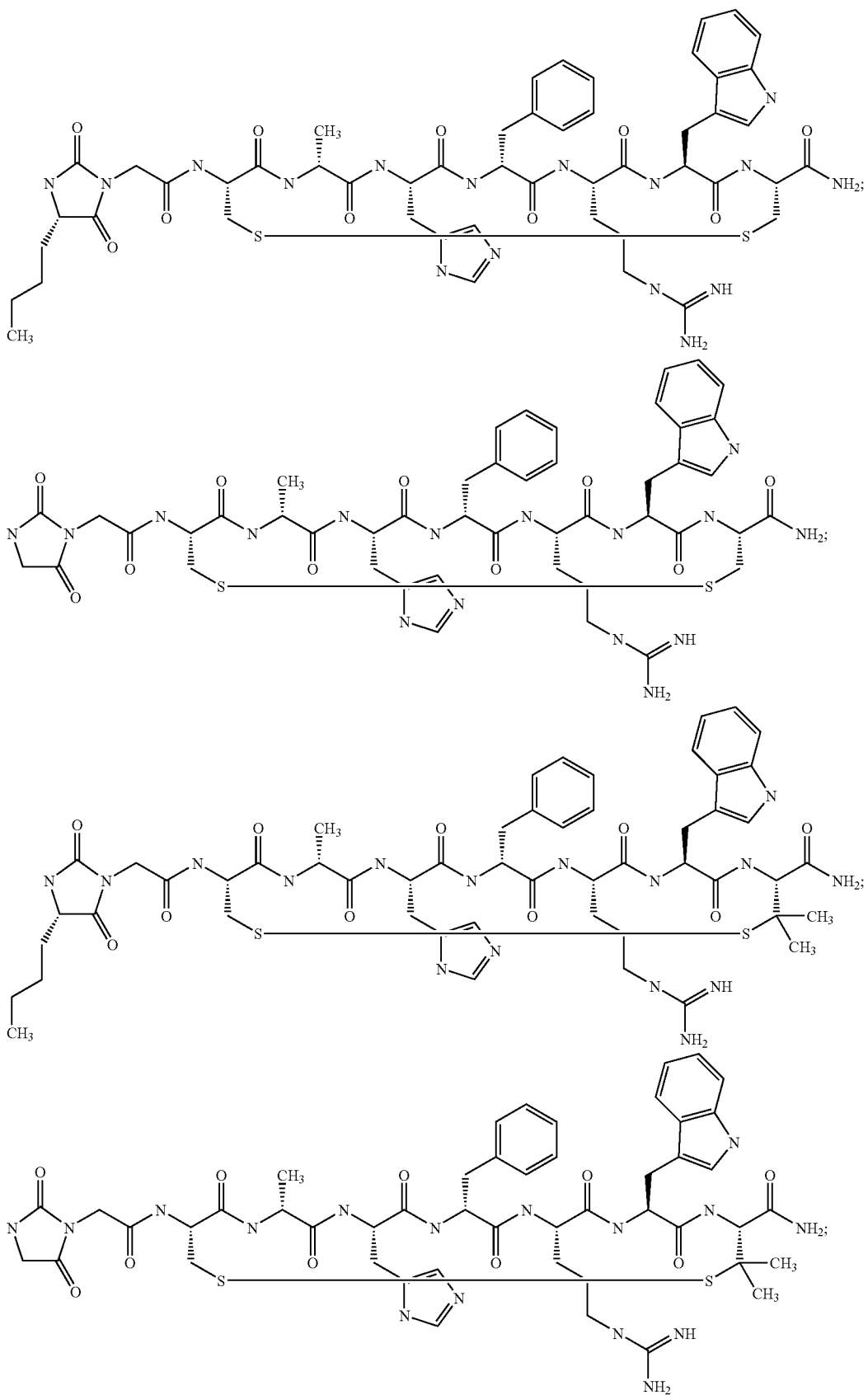

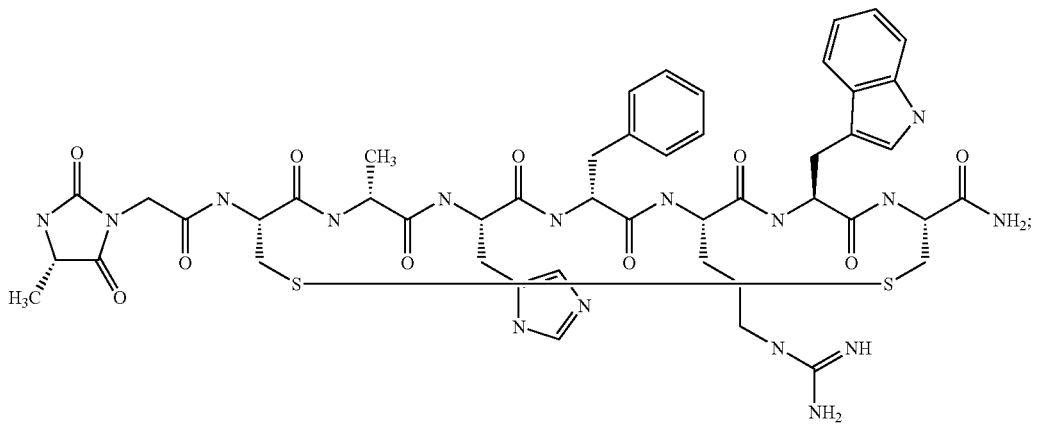
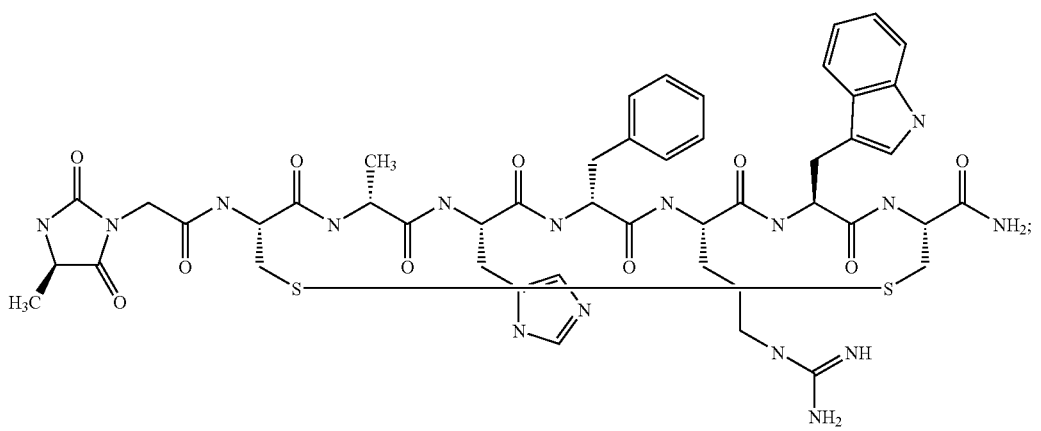
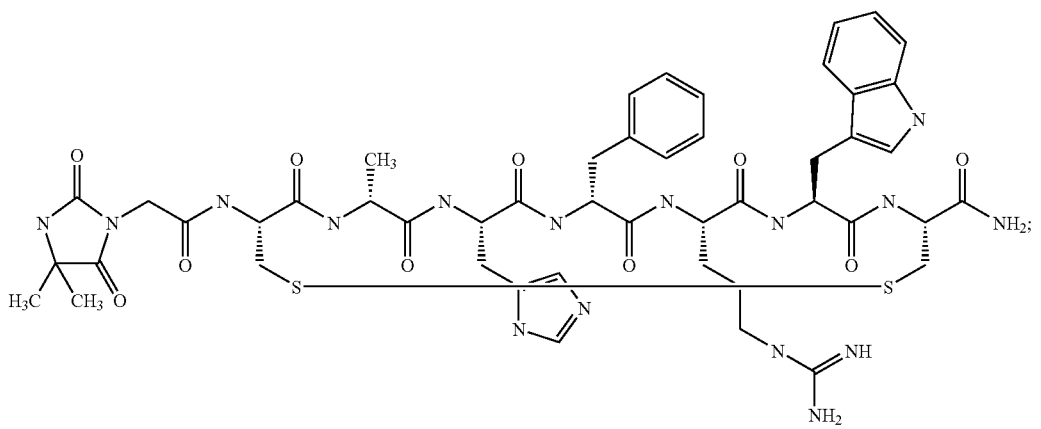
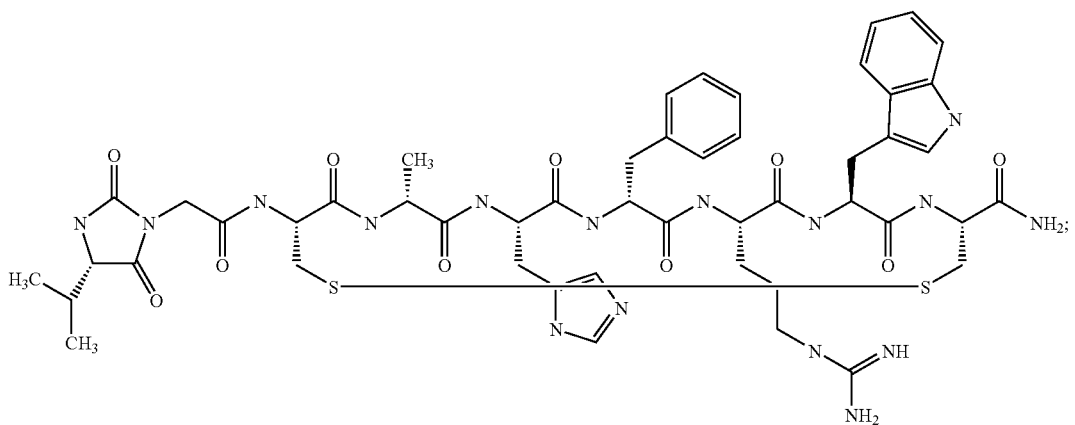

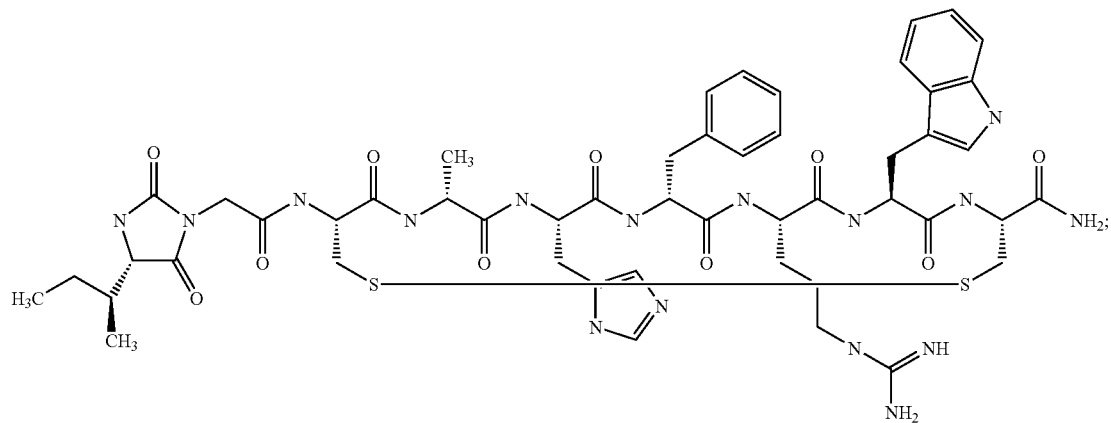
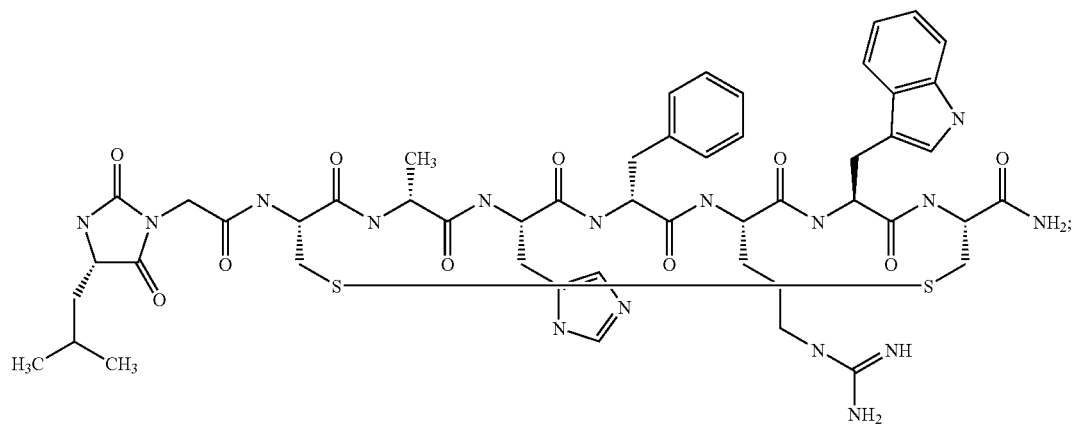
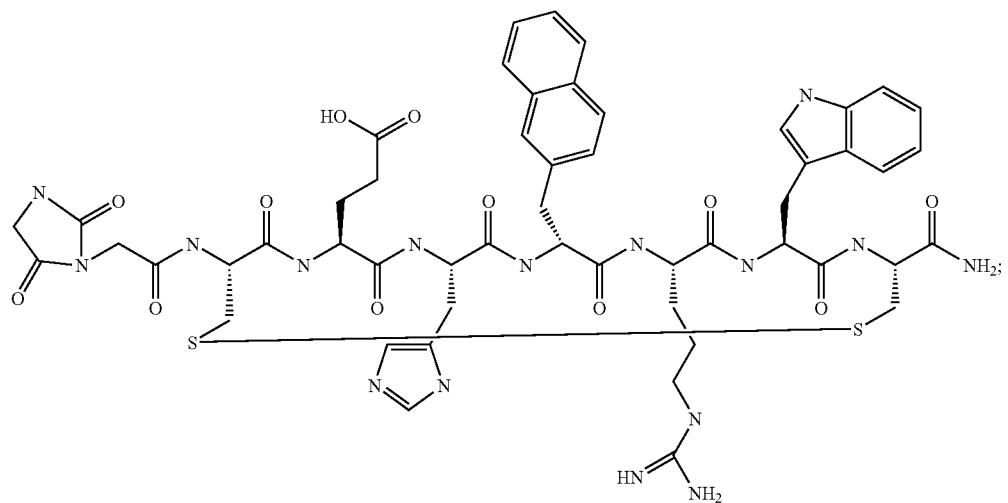

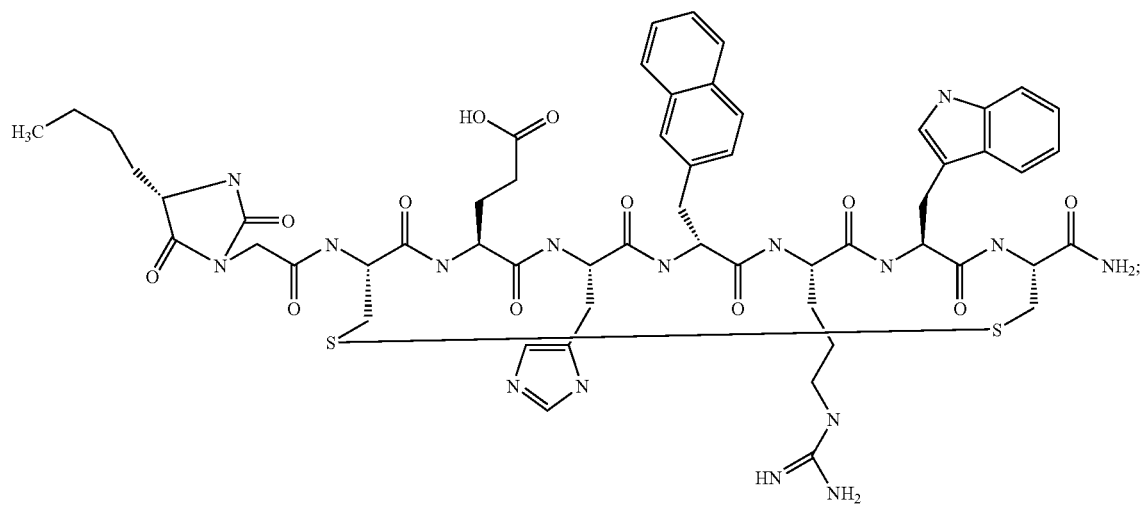
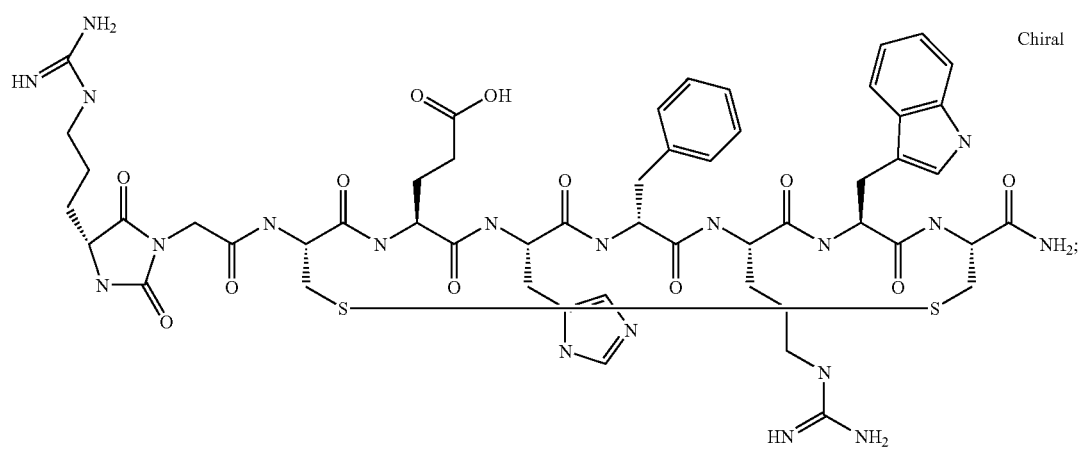
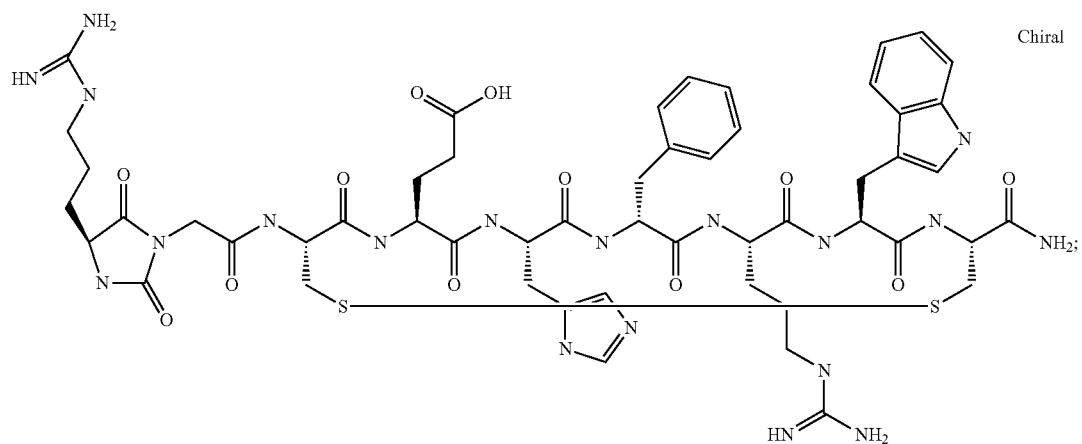

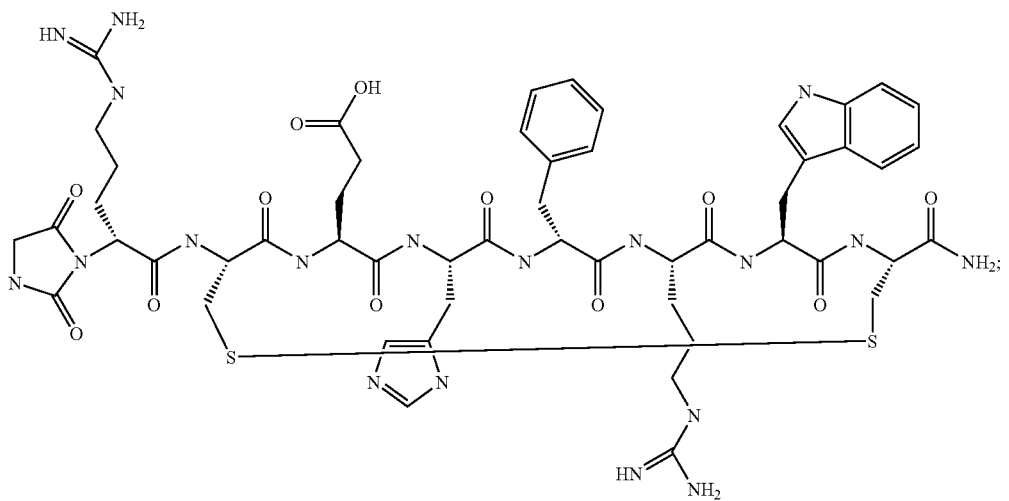
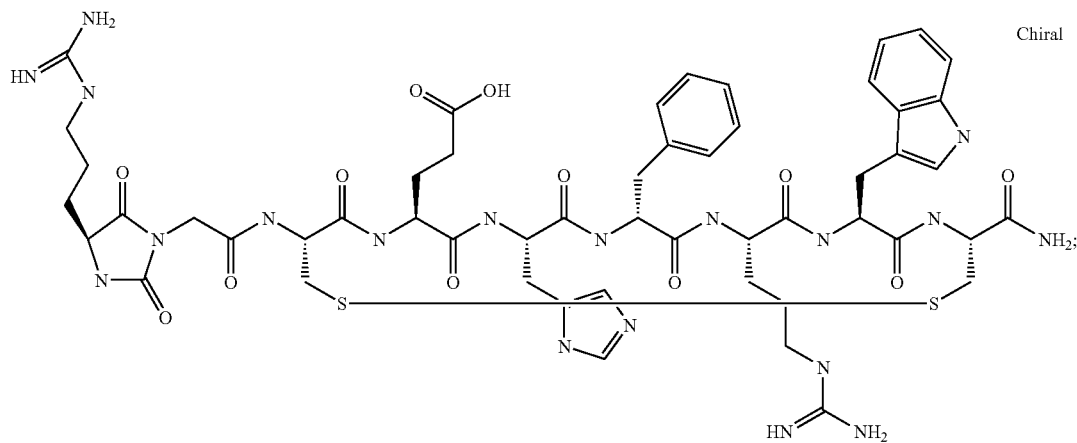 [SMILES: N=C(N)NCCC[C@@H]1NC(=O)[C@@H](Cc2ccccc2)NC(=O)[C@H](Cc2cnc[nH]2)NC(=O)[C@H](CCC(=O)O)NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC1=O]
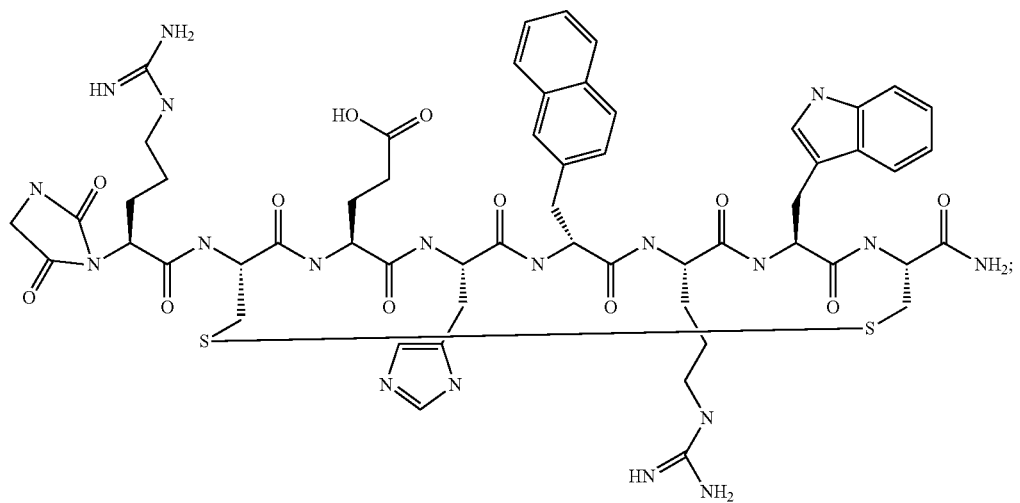

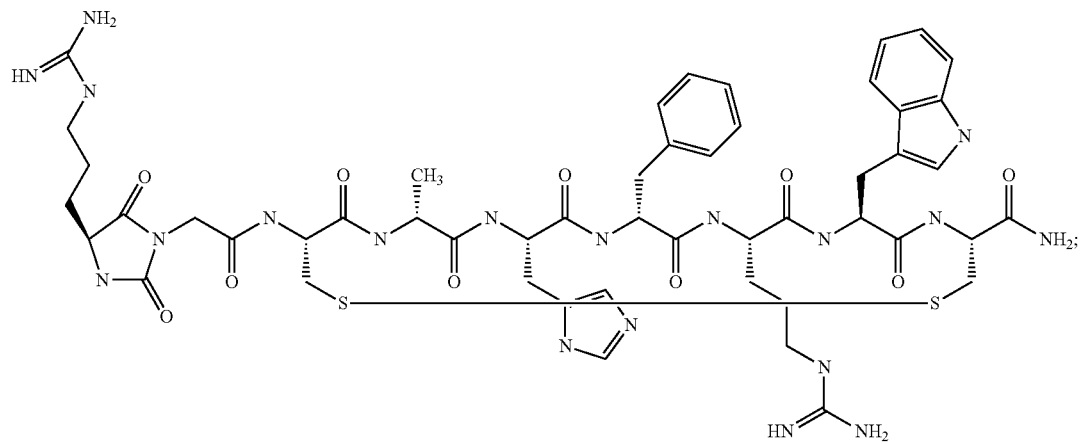
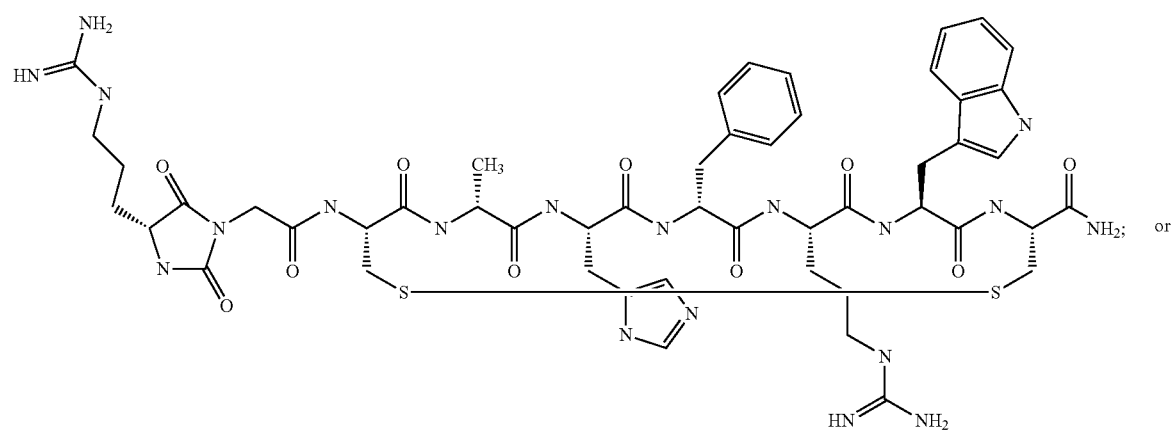
or
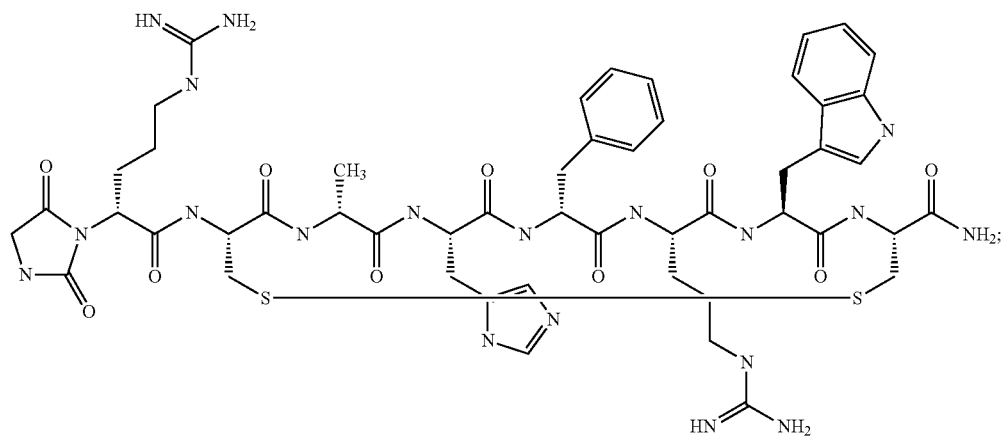

-continued

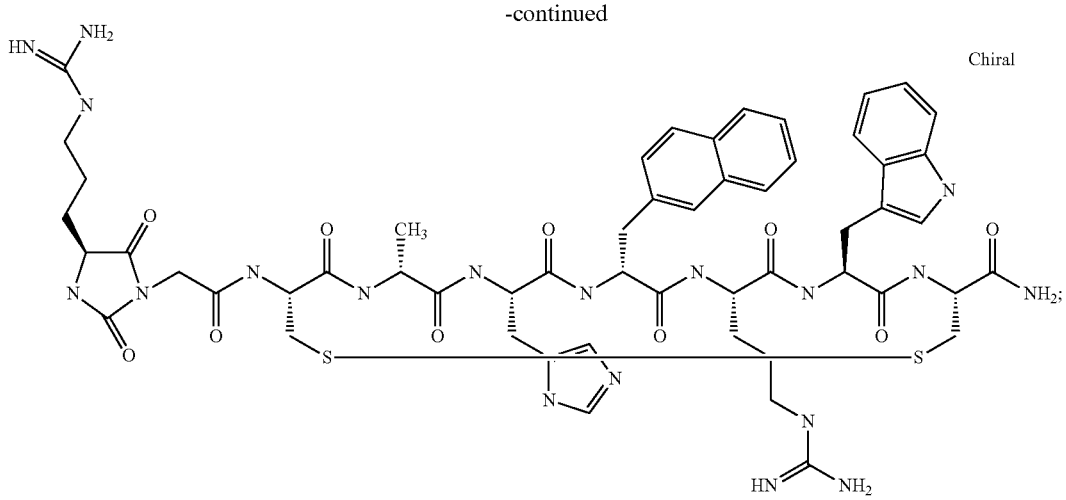

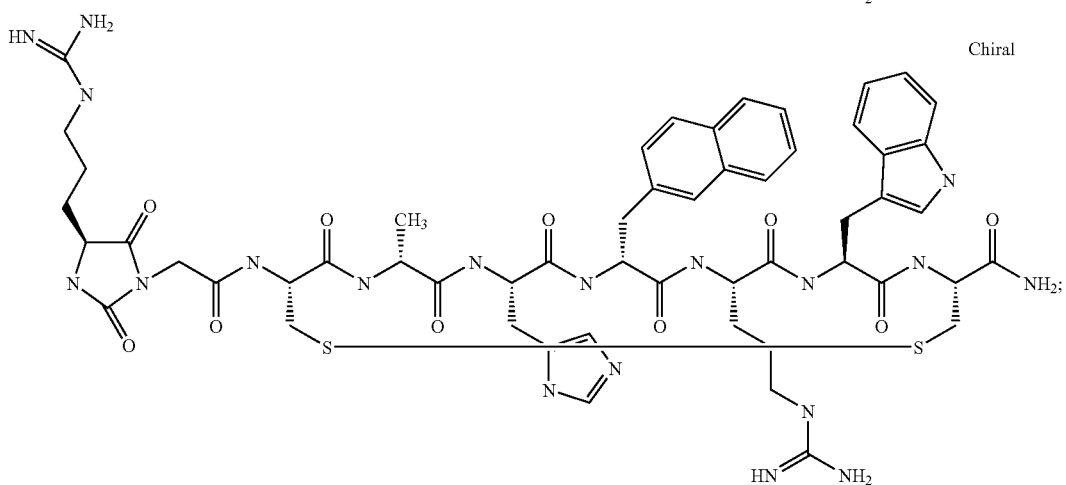

or a pharmaceutically acceptable salt thereof.

3. A compound according to claim 1 wherein said compound is

Hydantoin(C(O)-(Arg-Gly))-cyclo(Cys-Glu-His-D-Phe-Arg-Trp-Cys)-NH2;
(SEQ ID NO:13);

Hydantoin(C(O)-(Nle-Gly))-cyclo(Cys-Glu-His-D-Phe-Arg-Trp-Cys)-NH2;
(SEQ ID NO:14); or Hydantoin(C(O)-(D-Arg-Gly))-cyclo(Cys-Glu-His-D-Phe-Arg-Trp-Cys)-NH2; (SEQ ID NO:26);

or a pharmaceutically acceptable salt thereof.

4. A compound represented by the formula

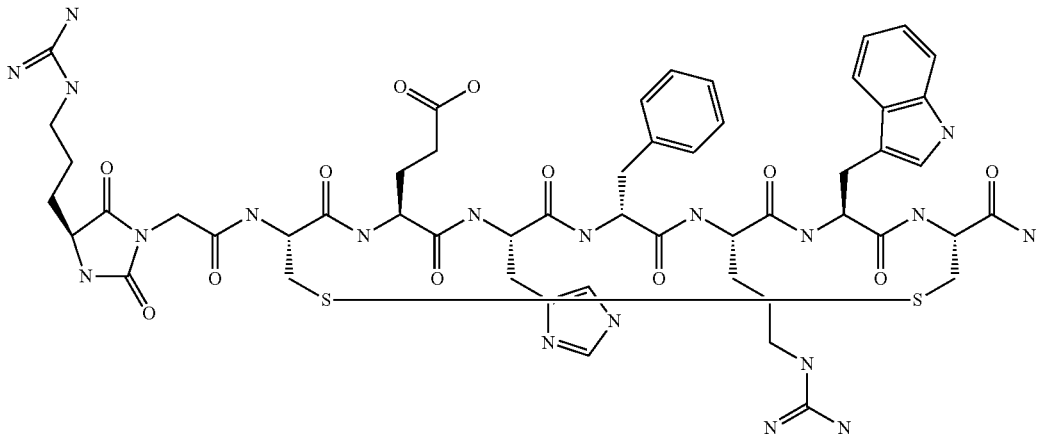 [SMILES: N=C(N)NCCC[C@@H]1NC(=O)[C@@H](Cc2ccccc2)NC(=O)[C@H](Cc2c[nH]cn2)NC(=O)[C@H](CCC(=O)O)NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC1=O]

or a pharmaceutically acceptable salt thereof.

5. A pharmaceutical composition comprising a compound according to claim 3 and a pharmaceutically acceptable carrier or diluent; or a pharmaceutically acceptable salt thereof.

6. A pharmaceutical composition comprising a compound according to claim 4 and a pharmaceutically acceptable carrier or diluent; or a pharmaceutically acceptable salt thereof.

7. A pharmaceutical composition comprising a compound according to claim 1 and a pharmaceutically acceptable carrier or diluent; wherein said compound is a selective melanocortin-4 receptor agonist; or a pharmaceutically acceptable salt thereof.

8. A compound according to claim 1, wherein
$A^1$ is Cys;
$A^2$ is Glu or D-Ala;
$A^3$ is His;
$A^4$ is D2-Nal or D-Phe;
$A^5$ is Arg;
$A^6$ is Trp;
$A^7$ is Cys or Pen; or
a pharmaceutically acceptable salt thereof.

9. A method of treating a metabolic disease or medical condition accompanied by weight gain selected from obesity, feeding disorders and Prader-Willi Syndrome comprising administering a therapeutically effective amount of the compound or salt thereof of claim 4.

10. The method of claim 9, wherein the metabolic disease or medical condition is obesity.

11. A method of decreasing appetite, decreasing body weight or a combination thereof comprising administering a therapeutically effective amount of a compound or salt thereof of claim 4.

12. A method of treating a disease or medical condition in a subject in need thereof which comprises administering to said subject a therapeutically effective amount of a compound according to claim 3, wherein said disease or condition is selected from the group consisting of:
general inflammation, inflammatory bowel disease, brain inflammation, sepsis and septic shock;
rheumatoid arthritis, gouty arthritis and multiple sclerosis;
a metabolic disease or medical condition accompanied by weight gain, obesity, feeding disorders and Prader-Willi Syndrome;
a metabolic disease or medical condition accompanied by weight loss, anorexia, bulimia, AIDS wasting, cachexia, cancer cachexia and wasting in frail elderly;
skin cancer and cancer cachexia;
endometriosis, uterine bleeding, sexual dysfunction, erectile dysfunction and decreased sexual response in females;
organ transplant rejection, ischemia and reperfusion injury, wounding and spinal cord injury, and weight loss due to a medical procedure selected from the group consisting of chemotherapy, radiation therapy, temporary or permanent immobilization and dialysis;
hemorrhagic shock, cardiogenic shock, hypovolemic shock, cardiovascular disorders and cardiac cachexia;
acute respiratory distress syndrome, pulmonary fibrosis, chronic obstructive pulmonary disease and asthma;
enhanced immune tolerance;
allergies;
psoriasis, skin pigmentation depletion, acne and keloid formation;
anxiety, depression, memory dysfunction and neuropathic pain; and
renal cachexia and natriuresis.

13. A method of treating a disease or medical in a subject in need thereof which comprises administering to said subject a therapeutically effective amount of a compound according to claim 4, wherein said disease or condition is selected from the group consisting of:
general inflammation, inflammatory bowel disease, brain inflammation, sepsis and septic shock;
rheumatoid arthritis, gouty arthritis and multiple sclerosis;
a metabolic disease or medical condition accompanied by weight gain, obesity, feeding disorders and Prader-Willi Syndrome;
a metabolic disease or medical condition accompanied by weight loss, anorexia, bulimia, AIDS wasting, cachexia, cancer cachexia and wasting in frail elderly;
skin cancer and cancer cachexia;
endometriosis, uterine bleeding, sexual dysfunction, erectile dysfunction and decreased sexual response in females;
organ transplant rejection, ischemia and reperfusion injury, wounding and spinal cord injury, and weight loss due to a medical procedure selected from the group consisting of chemotherapy, radiation therapy, temporary or permanent immobilization and dialysis;
hemorrhagic shock, cardiogenic shock, hypovolemic shock, cardiovascular disorders and cardiac cachexia;
acute respiratory distress syndrome, pulmonary fibrosis, chronic obstructive pulmonary disease and asthma;
enhanced immune tolerance;
allergies;
psoriasis, skin pigmentation depletion, acne and keloid formation;
anxiety, depression, memory dysfunction and neuropathic pain; and
renal cachexia and natriuresis.

14. A method according to claim 13, wherein obesity is treated.

15. A method according to claim 13, wherein a feeding disorder is treated.

16. A method of decreasing appetite and body weight according to claim 13.

17. A method according to claim 15, wherein anorexia, bulimia, AIDS wasting, wasting in frail elderly, cachexia or cancer cachexia is treated.

18. A method of modulating ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection, nerve growth, bone metabolism, bone formation and bone development in a subject in need thereof which comprises administering to said subject a therapeutically effective amount of a compound according to claim 1.

19. A method of inhibiting alcohol consumption, reducing alcohol consumption, treating alcoholism, or treating alcohol abuse in a subject in need thereof which comprises administering to said subject a therapeutically effective amount of a compound according to claim 1.

* * * * *

UNITED STATES PATENT AND TRADEMARK OFFICE
CERTIFICATE OF CORRECTION

PATENT NO. : 8,563,000 B2
APPLICATION NO. : 12/602010
DATED : October 22, 2013
INVENTOR(S) : Zheng Xin Dong, Daniel B. DeOliveira and Jeanne Mary Comstock It is certified that error appears in the above-identified patent and that said Letters Patent is hereby corrected as shown below:

In the claims

Claim 2, Column 208, Line 31 through Column 233, Line 41 are replaced with the following:

2. A compound of the formula:

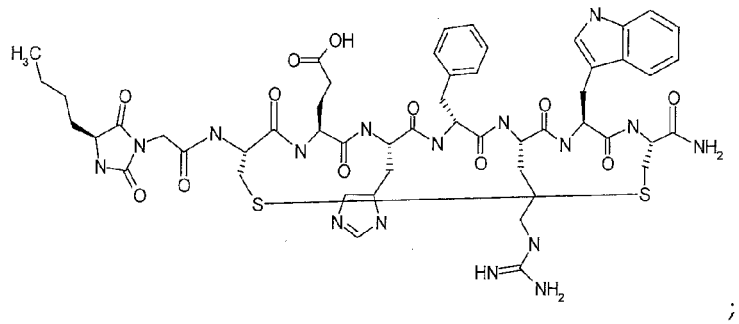

;

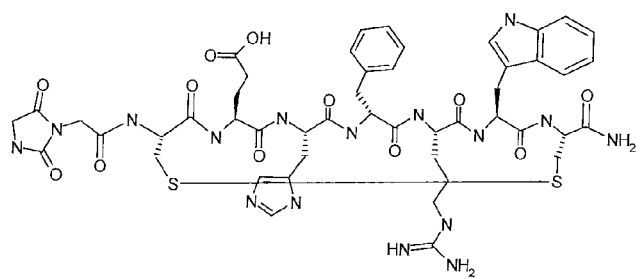

;

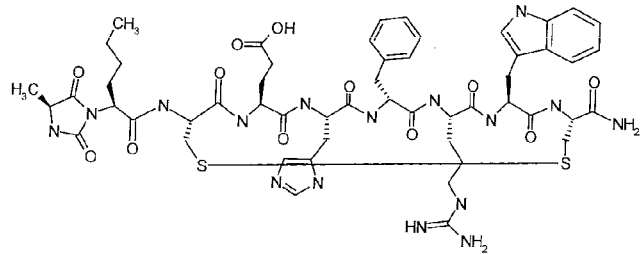

;

Signed and Sealed this
First Day of March, 2016

Michelle K. Lee
*Director of the United States Patent and Trademark Office*

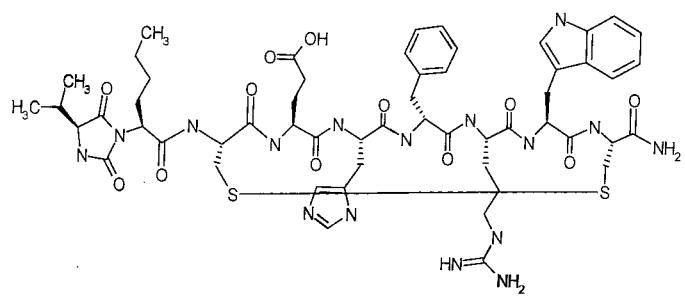
;
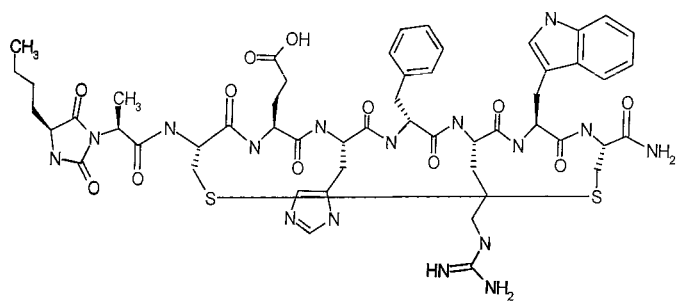
;
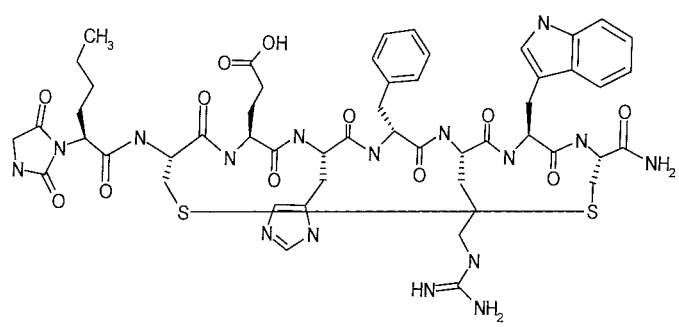
;
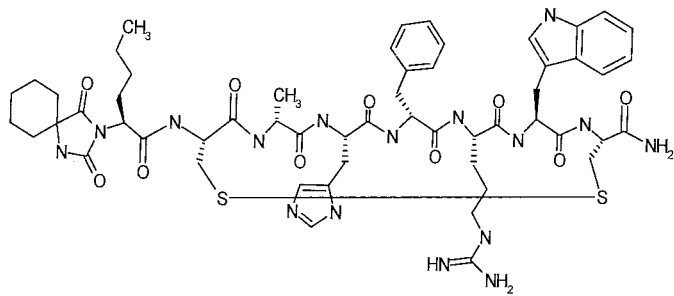
;

CERTIFICATE OF CORRECTION (continued)
U.S. Pat. No. 8,563,000 B2

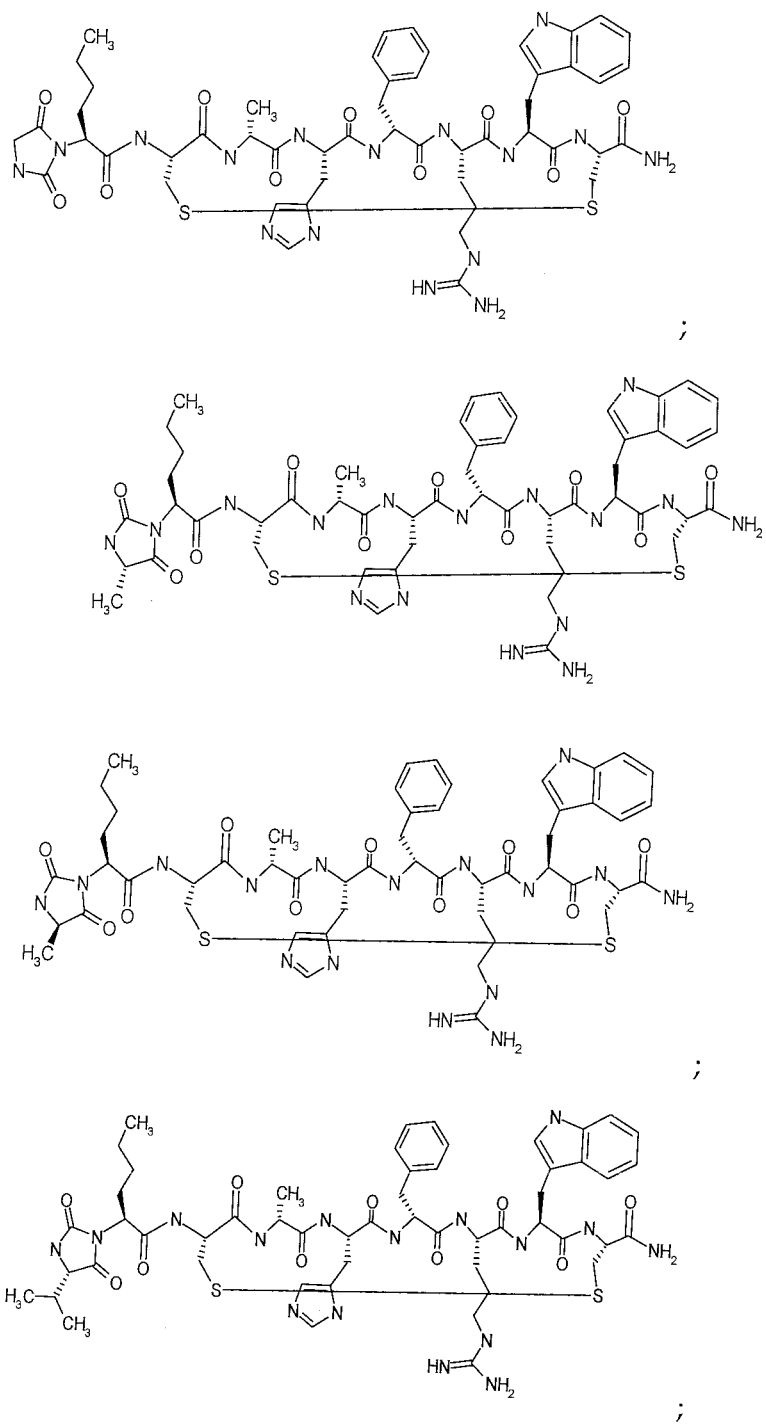

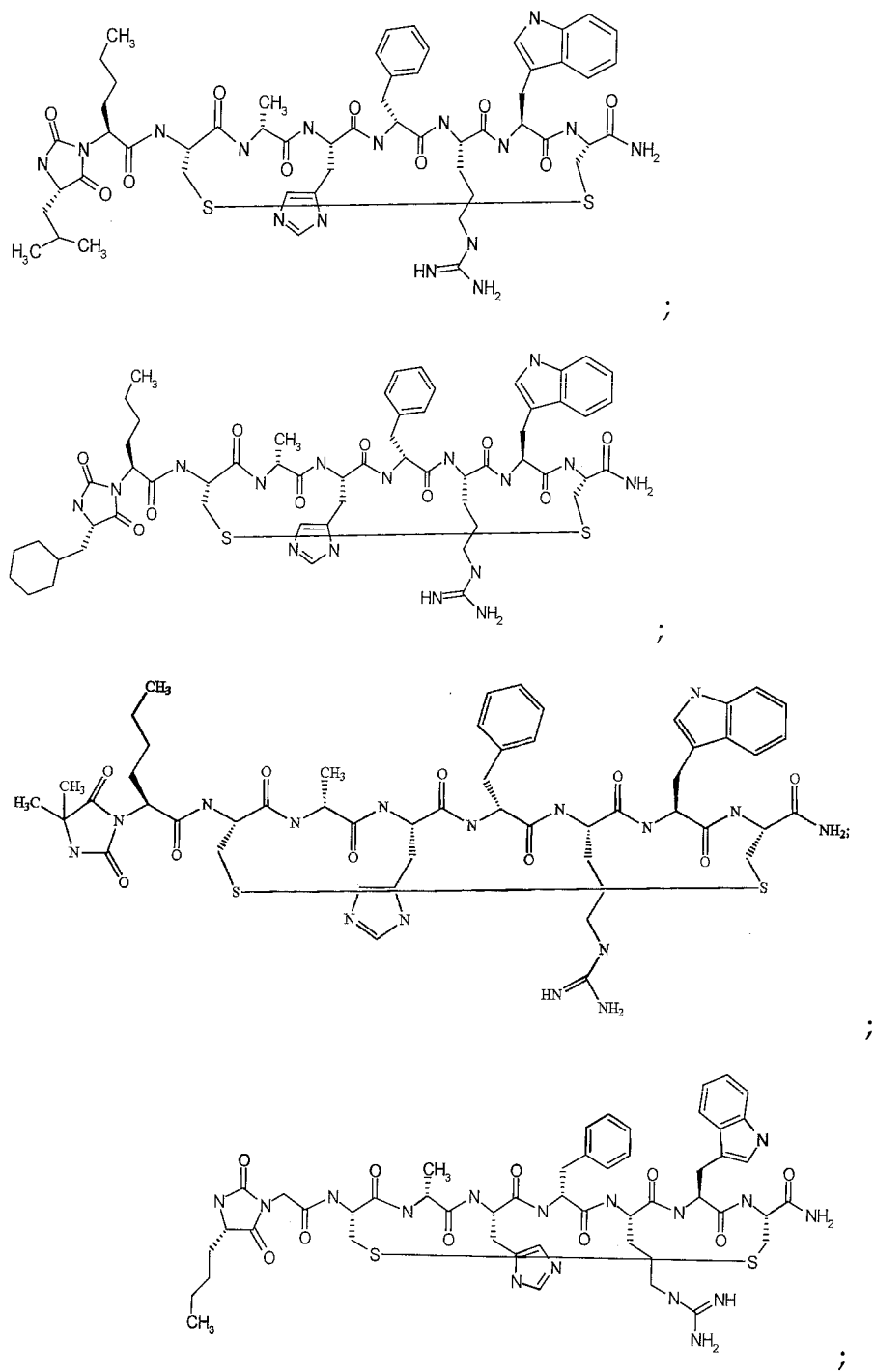

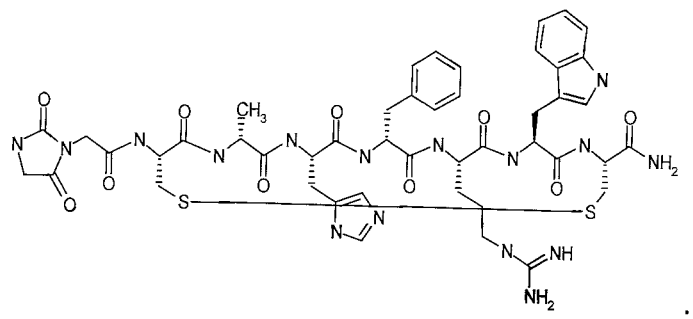
;
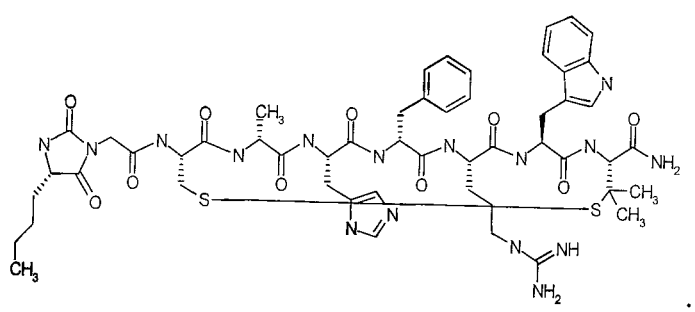
;
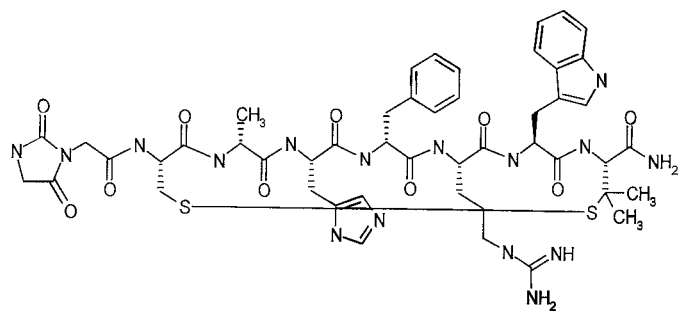
;
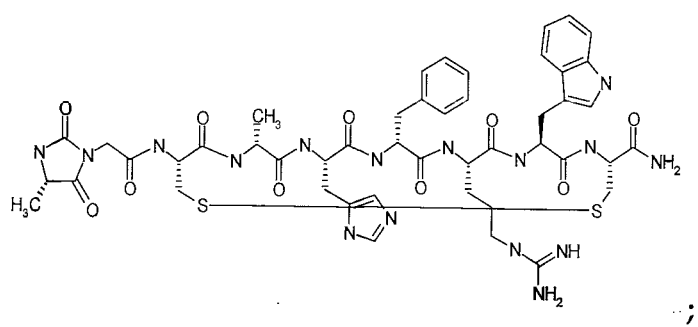
;

CERTIFICATE OF CORRECTION (continued)
U.S. Pat. No. 8,563,000 B2

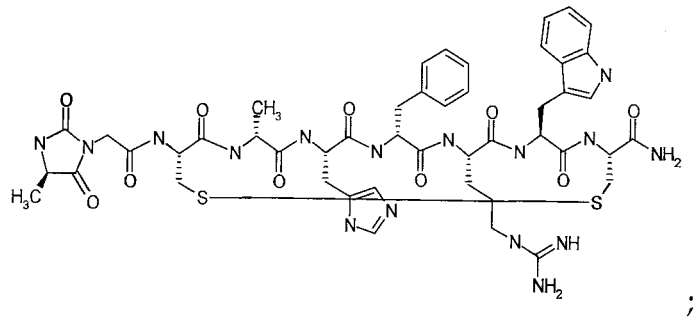

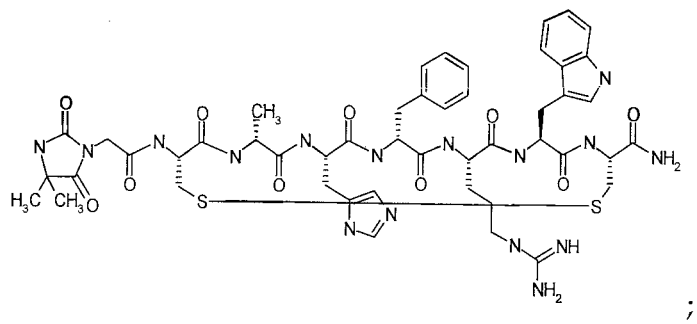

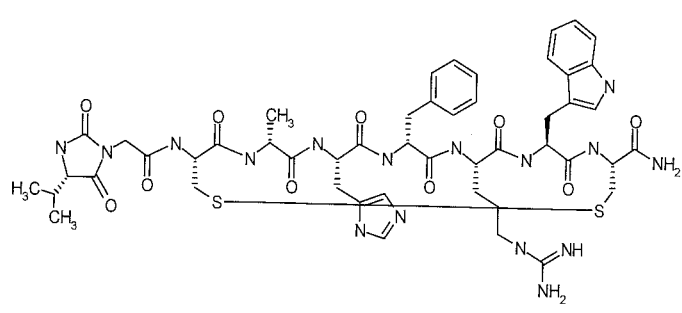

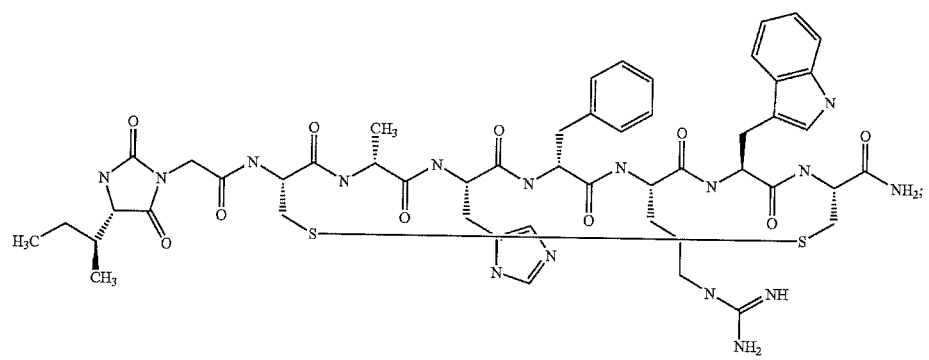

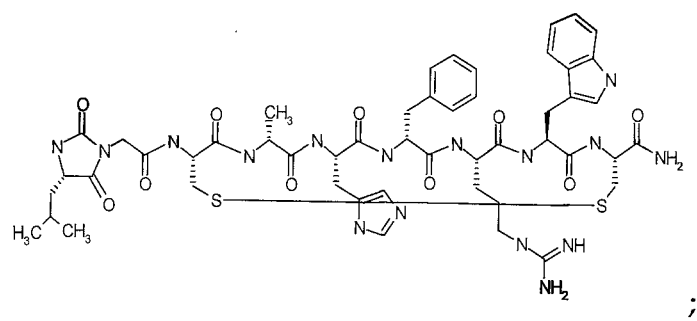;
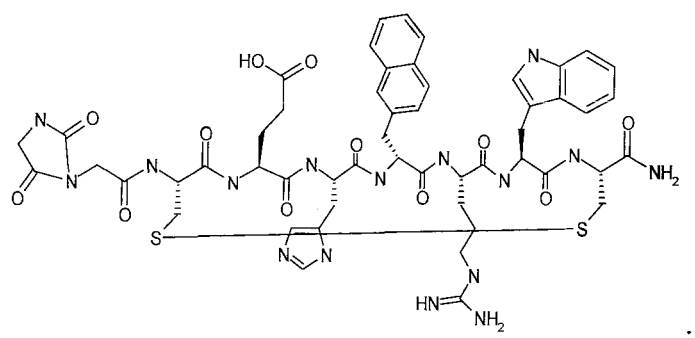;
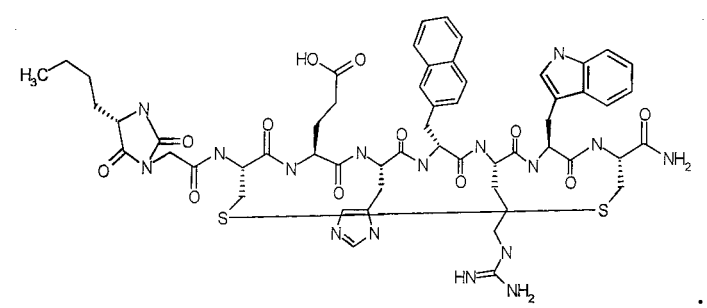;
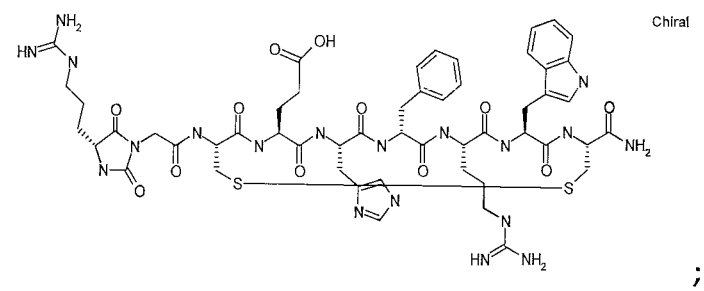;

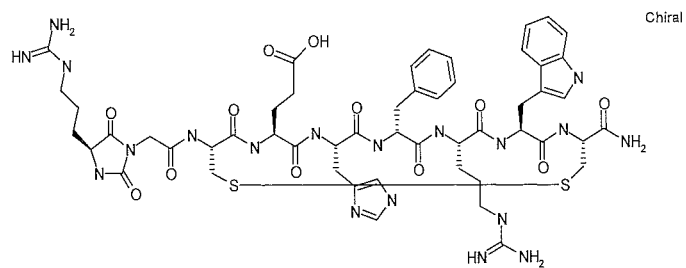
;
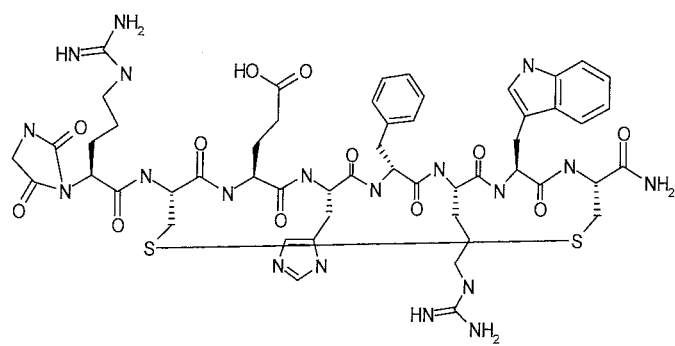
;
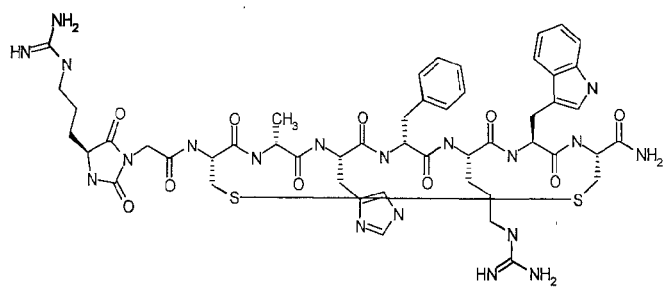
;
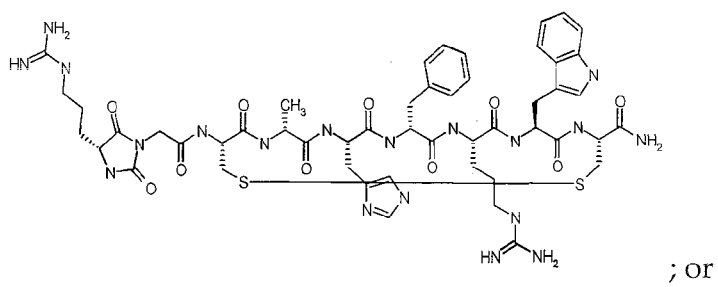
; or

CERTIFICATE OF CORRECTION (continued)
U.S. Pat. No. 8,563,000 B2

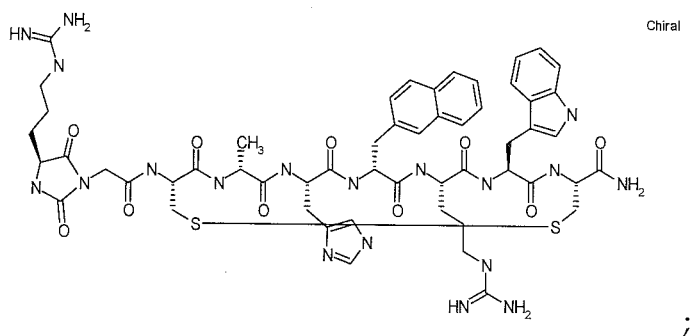

or a pharmaceutically acceptable salt thereof.

Claim 4, Column 234, Line 47 replace the structure with the following:

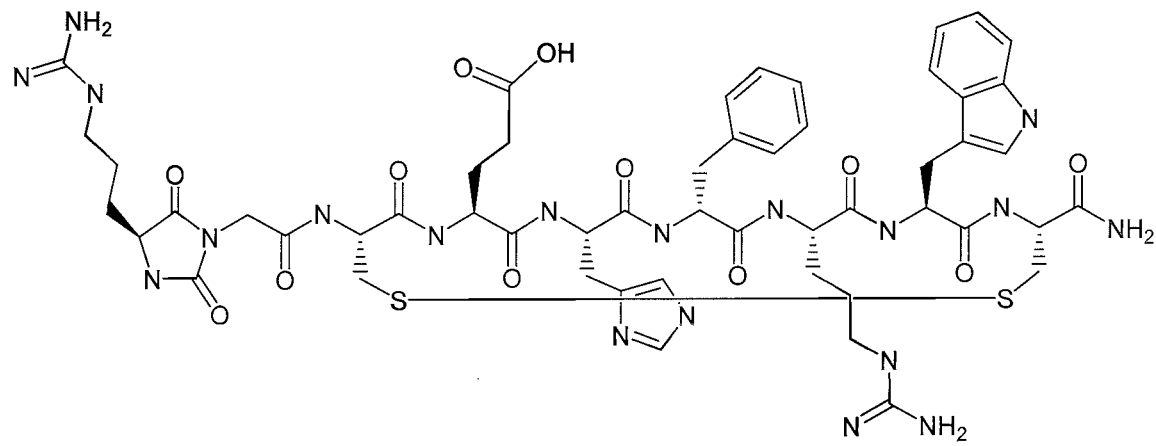

Claim 13, Column 236, Line 4 is replaced with the following:

13. A method of treating a disease or medical condition in a subject in

SEQUENCE LISTING

<160> NUMBER OF SEQ ID NOS: 94

<210> SEQ ID NO 1
<211> LENGTH: 5
<212> TYPE: PRT
<213> ORGANISM: Artificial
<220> FEATURE:
<223> OTHER INFORMATION: Melanocortin receptor ligand modified with hydantoin

```
<220> FEATURE:
<221> NAME/KEY: MOD_RES
<222> LOCATION: (1)..(1)
<223> OTHER INFORMATION: Hydantoin(C(O)-(Cys-D-Ala))
<220> FEATURE:
<221> NAME/KEY: DOMAIN
<222> LOCATION: (1)..(5)
<223> OTHER INFORMATION: cyclic with the hydantoin moiety included
<220> FEATURE:
<221> NAME/KEY: MISC_FEATURE
<222> LOCATION: (2)..(2)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (5)..(5)
<223> OTHER INFORMATION: AMIDATION

<400> SEQUENCE: 1

His Xaa Arg Trp Cys
1               5

<210> SEQ ID NO 2
<211> LENGTH: 5
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(hCys-D-Ala))
<220> FEATURE:
<221> NAME/KEY: DOMAIN
<222> LOCATION: (1)..(5)
<223> OTHER INFORMATION: cyclic with the hydantoin moiety included
<220> FEATURE:
<221> NAME/KEY: MISC_FEATURE
<222> LOCATION: (2)..(2)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (5)..(5)
<223> OTHER INFORMATION: AMIDATION

<400> SEQUENCE: 2

His Xaa Arg Trp Cys
1               5

<210> SEQ ID NO 3
<211> LENGTH: 5
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Asp-D-Ala))
<220> FEATURE:
<221> NAME/KEY: DOMAIN
<222> LOCATION: (1)..(5)
<223> OTHER INFORMATION: cyclic with the hydantoin moiety included
<220> FEATURE:
<221> NAME/KEY: MISC_FEATURE
<222> LOCATION: (2)..(2)
<223> OTHER INFORMATION: Xaa = D-Phe
<220> FEATURE:
<221> NAME/KEY: MOD_RES
<222> LOCATION: (5)..(5)
<223> OTHER INFORMATION: AMIDATION

<400> SEQUENCE: 3
```

```
His Xaa Arg Trp Lys
1               5

<210> SEQ ID NO 4
<211> LENGTH: 5
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Asp-D-Ala))
<220> FEATURE:
<221> NAME/KEY: DOMAIN
<222> LOCATION: (1)..(5)
<223> OTHER INFORMATION: cyclic with the hydantoin moiety included
<220> FEATURE:
<221> NAME/KEY: MISC_FEATURE
<222> LOCATION: (2)..(2)
<223> OTHER INFORMATION: Xaa = D-Phe
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = ornithine (Orn), 2,4-diaminobutyric
      acid (Dab), or 2,3-diaminopropionic acid (Dap)

<400> SEQUENCE: 4

His Xaa Arg Trp Xaa
1               5

<210> SEQ ID NO 5
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-beta-(2-naphthyl)alanine (D-2-Nal)
      or D-Phe
<220> FEATURE:
<221> NAME/KEY: MOD_RES
<222> LOCATION: (1)..(1)
<223> OTHER INFORMATION: Hydantoin(C(O)-(Asp-His))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 5

Xaa Arg Trp Lys
1

<210> SEQ ID NO 6
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
```

```
-continued

<222> LOCATION: (1)..(1)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (1)..(1)
<223> OTHER INFORMATION: Hydantoin(C(O)-(Asp-A3c))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 6

Xaa Arg Trp Lys
1

<210> SEQ ID NO 7
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (1)..(1)
<223> OTHER INFORMATION: Hydantoin(C(O)-(Asp-A5c))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 7

Xaa Arg Trp Lys
1

<210> SEQ ID NO 8
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (1)..(1)
<223> OTHER INFORMATION: Hydantoin(C(O)-(Asp-A6c))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 8
```

```
Xaa Arg Trp Lys
1

<210> SEQ ID NO 9
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (1)..(1)
<223> OTHER INFORMATION: Hydantoin(C(O)-(Asp-Aic))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 9

Xaa Arg Trp Lys
1

<210> SEQ ID NO 10
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (1)..(1)
<223> OTHER INFORMATION: Hydantoin(C(O)-(Asp-Apc))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 10

Xaa Arg Trp Lys
1

<210> SEQ ID NO 11
<211> LENGTH: 5
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Glu-D-Ala))
<220> FEATURE:
<221> NAME/KEY: DOMAIN
<222> LOCATION: (1)..(5)
```

```
-continued

<223> OTHER INFORMATION: cyclic with the hydantoin moiety included
<220> FEATURE:
<221> NAME/KEY: MISC_FEATURE
<222> LOCATION: (2)..(2)
<223> OTHER INFORMATION: Xaa = D-Phe
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = ornithine (Orn), 2,4-diaminobutyric
      acid (Dab), or 2,3-diaminopropionic acid (Dap)

<400> SEQUENCE: 11

His Xaa Arg Trp Xaa
1               5

<210> SEQ ID NO 12
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: MOD_RES
<222> LOCATION: (1)..(1)
<223> OTHER INFORMATION: Hydantoin(C(O)-(Glu-His))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = 2,3-diaminopropionic acid (Dap)

<400> SEQUENCE: 12

Xaa Arg Trp Xaa
1

<210> SEQ ID NO 13
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Arg-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 13
```

-continued

```
Cys Glu His Xaa Arg Trp Cys
1               5

<210> SEQ ID NO 14
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 14

Cys Glu His Xaa Arg Trp Cys
1               5

<210> SEQ ID NO 15
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 15

Cys Glu His Xaa Arg Trp Cys
1               5

<210> SEQ ID NO 16
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Gly))
<220> FEATURE:
<221> NAME/KEY: DOMAIN
```

```
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 16

Cys Xaa His Xaa Arg Trp Cys
1               5

<210> SEQ ID NO 17
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 17

Cys Xaa His Xaa Arg Trp Cys
1               5

<210> SEQ ID NO 18
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
```

```
<222> LOCATION: (7)..(7)
<223> OTHER INFORMATION: AMIDATION
<220> FEATURE:
<221> NAME/KEY: MISC_FEATURE
<222> LOCATION: (7)..(7)
<223> OTHER INFORMATION: Xaa = penicillamine (Pen)

<400> SEQUENCE: 18

Cys Xaa His Xaa Arg Trp Xaa
1               5

<210> SEQ ID NO 19
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION
<220> FEATURE:
<221> NAME/KEY: MISC_FEATURE
<222> LOCATION: (7)..(7)
<223> OTHER INFORMATION: Xaa = penicillamine (Pen)

<400> SEQUENCE: 19

Cys Xaa His Xaa Arg Trp Xaa
1               5

<210> SEQ ID NO 20
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ala-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 20
```

```
Cys Xaa His Xaa Arg Trp Cys
1               5

<210> SEQ ID NO 21
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(D-Ala-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 21

Cys Xaa His Xaa Arg Trp Cys
1               5

<210> SEQ ID NO 22
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Aib-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 22

Cys Xaa His Xaa Arg Trp Cys
1               5

<210> SEQ ID NO 23
<211> LENGTH: 7
<212> TYPE: PRT
<213> ORGANISM: Artificial
<220> FEATURE:
<223> OTHER INFORMATION: Melanocortin receptor ligand modified with
      hydantoin
```

```
<220> FEATURE:
<221> NAME/KEY: MOD_RES
<222> LOCATION: (1)..(1)
<223> OTHER INFORMATION: Hydantoin(C(O)-(Val-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 23

Cys Xaa His Xaa Arg Trp Cys
1               5

<210> SEQ ID NO 24
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ile-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 24

Cys Xaa His Xaa Arg Trp Cys
1               5

<210> SEQ ID NO 25
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Leu-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
```

```
<220> FEATURE:
<221> NAME/KEY: MISC_FEATURE
<222> LOCATION: (4)..(4)
<223> OTHER INFORMATION: Xaa = D-Phe
<220> FEATURE:
<221>

```
<210> SEQ ID NO 28
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Arg-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 28

Cys Xaa His Xaa Arg Trp Cys
1               5

<210> SEQ ID NO 29
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ala-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 29

Cys Glu His Xaa Arg Trp Cys
1               5

<210> SEQ ID NO 30
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Val-Nle))
<220> FEATURE:
<221> NAME/KEY: DOMAIN
<222> LOCATION: (1)..(7)
<223> OTHER INFORMATION: cyclic
```

```
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 30

Cys Glu His Xaa Arg Trp Cys
1               5

<210> SEQ ID NO 31
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 31

Cys Glu His Xaa Arg Trp Cys
1               5

<210> SEQ ID NO 32
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(A6c-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 32

Cys Xaa His Xaa Arg Trp Cys
1               5

<210> SEQ ID NO 33
```

-continued

```
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 33

Cys Xaa His Xaa Arg Trp Cys
1               5

<210> SEQ ID NO 34
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ala-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 34

Cys Xaa His Xaa Arg Trp Cys
1               5

<210> SEQ ID NO 35
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(D-Ala-Nle))
<220> FEATURE:
<221> NAME/KEY: DOMAIN
```

```
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 35

Cys Xaa His Xaa Arg Trp Cys
1               5

<210> SEQ ID NO 36
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Val-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 36

Cys Xaa His Xaa Arg Trp Cys
1               5

<210> SEQ ID NO 37
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Leu-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
```

```
<222> LOCATION: (7)..(7)
<223> OTHER INFORMATION: AMIDATION

<400> SEQUENCE: 37

Cys Xaa His Xaa Arg Trp Cys
1               5

<210> SEQ ID NO 38
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Cha-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 38

Cys Xaa His Xaa Arg Trp Cys
1               5

<210> SEQ ID NO 39
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Aib-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 39

Cys Xaa His Xaa Arg Trp Cys
1               5

<210> SEQ ID NO 40
<211> LENGTH: 7
<212> TYPE: PRT
```

```
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 40

Cys Glu His Xaa Arg Trp Cys
1               5

<210> SEQ ID NO 41
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 41

Cys Xaa His Xaa Arg Trp Cys
1               5

<210> SEQ ID NO 42
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-D-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
```

```
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 42

Cys Glu His Xaa Arg Trp Cys
1               5

<210> SEQ ID NO 43
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-D-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 43

Cys Xaa His Xaa Arg Trp Cys
1               5

<210> SEQ ID NO 44
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Ala))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 44

Cys Glu His Xaa Arg Trp Cys
1               5

<210> SEQ ID NO 45
<211> LENGTH: 6
```

```
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Ala-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa= D-Phe
<220> FEATURE:
<221> NAME/KEY: MOD_RES
<222> LOCATION: (6)..(6)
<223> OTHER INFORMATION: AMIDATION

<400> SEQUENCE: 45

Xaa His Xaa Arg Trp Cys
1               5

<210> SEQ ID NO 46
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa - D-Ala
<220> FEATURE:
<221> NAME/KEY: MOD_RES
<222> LOCATION: (1)..(1)
<223> OTHER INFORMATION: Hydantoin(C(O)-(Nle-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 46

Xaa His Xaa Arg Trp Cys
1               5

<210> SEQ ID NO 47
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
```

```
<223> OTHER INFORMATION: Hydantoin(C(O)-(D-Ala-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 47

Xaa His Xaa Arg Trp Cys
1               5

<210> SEQ ID NO 48
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Aib-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 48

Xaa His Xaa Arg Trp Cys
1               5

<210> SEQ ID NO 49
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Val-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
```

```
<223> OTHER INFORMATION: AMIDATION

<400> SEQUENCE: 49

Xaa His Xaa Arg Trp Cys
1               5

<210> SEQ ID NO 50
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Abu-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 50

Xaa His Xaa Arg Trp Cys
1               5

<210> SEQ ID NO 51
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Leu-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 51

Xaa His Xaa Arg Trp Cys
1               5

<210> SEQ ID NO 52
<211> LENGTH: 6
<212> TYPE: PRT
<213> ORGANISM: Artificial
```

```
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Ile-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 52

Xaa His Xaa Arg Trp Cys
1               5

<210> SEQ ID NO 53
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Cha-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 53

Xaa His Xaa Arg Trp Cys
1               5

<210> SEQ ID NO 54
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(A6c-Cys))
<220> FEATURE:
```

```
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 54

Xaa His Xaa Arg Trp Cys
1               5

<210> SEQ ID NO 55
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Phe-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 55

Xaa His Xaa Arg Trp Cys
1               5

<210> SEQ ID NO 56
<211> LENGTH: 6
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MOD_RES
<222> LOCATION: (1)..(1)
<223> OTHER INFORMATION: Hydantoin(C(O)-(Gly-Cys))
<220> FEATURE:
<221> NAME/KEY: DOMAIN
<222> LOCATION: (1)..(6)
<223> OTHER INFORMATION: cyclic with the hydantoin moiety included
<220> FEATURE:
<221> NAME/KEY: MISC_FEATURE
<222> LOCATION: (3)..(3)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION
```

-continued

```
<400> SEQUENCE: 56

Xaa His Xaa Arg Trp Cys
1               5

<210> S

```
            hydantoin
<220> FEATURE:
<221> NAME/KEY: MOD_RES
<222> LOCATION: (1)..(1)
<223> OTHER INFORMATION: Ac (acyl)
<220> FEATURE:
<221> NAME/KEY: MISC_FEATURE
<222> LOCATION: (1)..(1)
<223> OTHER INFORMATION: Xaa = norleucine (Nle)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: C-terminus is the free acid

<400> SEQUENCE: 59

Xaa Cys Xaa His Xaa Arg Trp Cys
1               5

<210> SEQ ID NO 60
<211> LENGTH: 8
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
<223> OTHER INFORMATION: Xaa = norleucine (Nle)
<220> FEATURE:
<221> NAME/KEY: MOD_RES
<222> LOCATION: (1)..(1)
<223> OTHER INFORMATION: Ac (acyl)
<220> FEATURE:
<221> NAME/KEY: DOMAIN
<222> LOCATION: (2)..(8)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: C-terminus is the free acid

<400> SEQUENCE: 60

Xaa Cys Xaa His Xaa Arg Trp Cys
1               5

<210> SEQ ID NO 61
<211> LENGTH: 4
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MISC_FEATURE
<222> LOCATION: (1)..(1)
```

```
<223> OTHER INFORMATION: Xaa = D-Phe
<220> FEATURE:
<221> NAME/KEY: MOD_RES
<222> LOCATION: (1)..(1)
<223> OTHER INFORMATION: Hydantoin(C(O)-(Glu-His))
<220> FEATURE:
<221> NAME/KEY: DOMAIN
<222> LOCATION: (1)..(4)
<223> OTHER INFORMATION: cyclic with the hydantoin moiety included
<220> FEATURE:
<221> NAME/KEY: MOD_RES
<222> LOCATION: (4)..(4)
<223> OTHER INFORMATION: AMIDATION

<400> SEQUENCE: 61

Xaa Arg Trp Lys
1

<210> SEQ ID NO 62
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: DOMAIN
<222> LOCATION: (1)..(7)
<223> OTHER INFORMATION: cyclic
<220> FEATURE:
<221> NAME/KEY: MOD_RES
<222> LOCATION: (1)..(1)
<223> OTHER INFORMATION: Hydantoin(C(O)-(Nle-Gly))
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 62

Cys Glu His Xaa Arg Trp Cys
1               5

<210> SEQ ID NO 63
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 63

Cys Glu His Xaa Arg Trp Cys
1               5
```

```
<210> SEQ ID NO 64
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ala-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 64

Cys Glu His Xaa Arg Trp Cys
1               5

<210> SEQ ID NO 65
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Val-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 65

Cys Glu His Xaa Arg Trp Cys
1               5

<210> SEQ ID NO 66
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Ala))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
```

```
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 66

Cys Glu His Xaa Arg Trp Cys
1               5

<210> SEQ ID NO 67
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 67

Cys Glu His Xaa Arg Trp Cys
1               5

<210> SEQ ID NO 68
<211> LENGTH: 5
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Glu-D-Ala))
<220> FEATURE:
<221> NAME/KEY: DOMAIN
<222> LOCATION: (1)..(5)
<223> OTHER INFORMATION: cyclic with the hydantoin moiety included
<220> FEATURE:
<221> NAME/KEY: MISC_FEATURE
<222> LOCATION: (2)..(2)
<223> OTHER INFORMATION: Xaa = D-Phe
<220> FEATURE:
<221> NAME/KEY: MOD_RES
<222> LOCATION: (5)..(5)
<223> OTHER INFORMATION: AMIDATION

<400> SEQUENCE: 68

His Xaa Arg Trp Lys
1               5

<210> SEQ ID NO 69
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
```

-continued

```
<221> NAME/KEY: MOD_RES
<222> LOCATION: (1)..(1)
<223> OTHER INFORMATION: Hydantoin(C(O)-(A6c-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 69

Cys Xaa His Xaa Arg Trp Cys
1               5

<210> SEQ ID NO 70
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Nle))
<220> FEATURE:
<221> NAME/KEY: DOMAIN
<222> LOCATION: (1)..(6)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 70

Cys Xaa His Xaa Arg Trp Cys
1               5

<210> SEQ ID NO 71
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ala-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
```

```
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 71

Cys Xaa His Xaa Arg Trp Cys
1               5

<210> SEQ ID NO 72
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(D-Ala-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 72

Cys Xaa His Xaa Arg Trp Cys
1               5

<210> SEQ ID NO 73
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Val-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 73

Cys Xaa His Xaa Arg Trp Cys
1               5
```

```
<210> SEQ ID NO 74
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Leu-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 74

Cys Xaa His Xaa Arg Trp Cys
1               5

<210> SEQ ID NO 75
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Cha-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 75

Cys Xaa His Xaa Arg Trp Cys
1               5

<210> SEQ ID NO 76
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
```

```
<223> OTHER INFORMATION: Hydantoin(C(O)-(Aib-Nle))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 76

Cys Xaa His Xaa Arg Trp Cys
1               5

<210> SEQ ID NO 77
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 77

Cys Xaa His Xaa Arg Trp Cys
1               5

<210> SEQ ID NO 78
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
```

```
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 78

Cys Xaa His Xaa Arg Trp Cys
1               5

<210> SEQ ID NO 79
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Nle-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION
<220> FEATURE:
<221> NAME/KEY: MISC_FEATURE
<222> LOCATION: (7)..(7)
<223> OTHER INFORMATION: Xaa = penicillamine (Pen)

<400> SEQUENCE: 79

Cys Xaa His Xaa Arg Trp Xaa
1               5

<210> SEQ ID NO 80
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION
<220> FEATURE:
<221> NAME/KEY: MISC_FEATURE
<222> LOCATION: (7)..(7)
```

```
<223> OTHER INFORMATION: Xaa = penicillamine (Pen)

<400> SEQUENCE: 80

Cys Xaa His Xaa Arg Trp Xaa
1               5

<210> SEQ ID NO 81
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ala-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 81

Cys Xaa His Xaa Arg Trp Cys
1               5

<210> SEQ ID NO 82
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(D-Ala-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 82

Cys Xaa His Xaa Arg Trp Cys
1               5

<210> SEQ ID NO 83
<211> LENGTH: 7
<212> TYPE: PRT
<213> ORGANISM: Artificial
```

```
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Aib-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 83

Cys Xaa His Xaa Arg Trp Cys
1               5

<210> SEQ ID NO 84
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Val-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 84

Cys Xaa His Xaa Arg Trp Cys
1               5

<210> SEQ ID NO 85
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Ile-Gly))
<220> FEATURE:
<221> NAME/KEY: DOMAIN
<222> LOCATION: (1)..(7)
<223> OTHER INFORMATION: cyclic
<220> FEATURE:
```

```
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 85

Cys Xaa His Xaa Arg Trp Cys
1               5

<210> SEQ ID NO 86
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Leu-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 86

Cys Xaa His Xaa Arg Trp Cys
1               5

<210> SEQ ID NO 87
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: DOMAIN
<222> LOCATION: (1)..(7)
<223> OTHER INFORMATION: cyclic, and cyclic with the hydantoin moiety
      included
<220> FEATURE:
<221> NAME/KEY: MOD_RES
<222> LOCATION: (1)..(1)
<223> OTHER INFORMATION: Hydantoin(C(O)-(D-Arg-Gly))
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 87

Cys Glu His Xaa Arg Trp Cys
```

```
<210> SEQ ID NO 88
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-D-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 88

Cys Glu His Xaa Arg Trp Cys
1               5

<210> SEQ ID NO 89
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C)(O)-(Arg-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 89

Cys Glu His Xaa Arg Trp Cys
1               5

<210> SEQ ID NO 90
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
```

```
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 90

Cys Glu His Xaa Arg Trp Cys
1               5

<210> SEQ ID NO 91
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Arg-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe or D-beta-(2-naphthyl)alanine
      (D-2-Nal)
<220> FEATURE:
<221> NAME/KEY: MOD_RES
<222> LOCATION: (7)..(7)
<223> OTHER INFORMATION: AMIDATION

<400> SEQUENCE: 91

Cys Xaa His Xaa Arg Trp Cys
1               5

<210> SEQ ID NO 92
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(D-Arg-Gly))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 92

Cys Xaa His Xaa Arg Trp Cys
1               5
```

```
<210> SEQ ID NO 93
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-D-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 93

Cys Xaa His Xaa Arg Trp Cys
1               5

<210> SEQ ID NO 94
<211> LENGTH: 7
<212> TYPE: PRT
<213> ORGANISM: Artificial
<220> FEATURE:
<223> OTHER INFORMATION: Melanocortin receptor ligand modified with
      hydantoin
<220> FEATURE:
<221> NAME/KEY: MOD_RES
<222> LOCATION: (1)..(1)
<223> OTHER INFORMATION: Hydantoin(C(O)-(Gly-Arg))
<220> FEATURE:
<221> NAME/KEY: DOMAIN
<222> LOCATION: (1)..(7)
<223> OTHER INFORMATION: cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 94

Cys Xaa His Xaa Arg Trp Cys
1               5
```